US010130622B2

(12) United States Patent
Akkari et al.

(10) Patent No.: US 10,130,622 B2
(45) Date of Patent: *Nov. 20, 2018

(54) COMPOUNDS FOR TREATMENT OF CYSTIC FIBROSIS

(71) Applicants: AbbVie S.à.r.l., Luxembourg (LU); Galapagos NV, Mechelen (BE)

(72) Inventors: Rhalid Akkari, Pantin (FR); Luke Jonathan Alvey, Versailles (FR); Xavier Marie Bock, Romainville (FR); Brian S. Brown, Evanston, IL (US); Pieter Isabelle Roger Claes, Gentbrugge (BE); Marlon D. Cowart, Round Lake Beach, IL (US); Katja E. Conrath, Mechelen (BE); Douglas Cyr, Chapel Hill, NC (US); Elsa De Lemos, Paris (FR); Gert Jules Hector De Wilde, Mechelen (BE); Nicolas Desroy, Massy (FR); Béranger Duthion, Paris (FR); Gregory A. Gfesser, Lindenhurst, IL (US); Romain Luc Marie Gosmini, Savigny-sur-Orge (FR); Christopher Gaëtan Housseman, Montreuil (FR); Koen Karel Jansen, Turnhout (BE); Jianguo Ji, Libertyville, IL (US); Philip R. Kym, Libertyville, IL (US); Jean-Michel Lefrancois, Le Raincy (FR); Oscar Mammoliti, Mechelen (BE); Christel Jeanne Marie Menet, Brussels (BE); Nuria Merayo Merayo, Paris (FR); Gregory John Robert Newsome, Neuilly Plaisance (FR); Adeline Marie Elise Palisse, Brussels (BE); Sachin V. Patel, Round Lake, IL (US); Mathieu Rafaël Pizzonero, Voisins le Bretonneux (FR); Anurupa Shrestha, Vernon Hills, IL (US); Elizabeth C. Swift, Highland Park, IL (US); Chris Tse, Libertyville, IL (US); Steven Emiel Van der Plas, Steenhuffel (BE); Xueqing Wang, Northbrook, IL (US)

(73) Assignees: AbbVie S.à.r.l., Luxembourg (LU); Galapagos NV, Mechelen (BE)

(*) Notice: Subject to any disclaimer, the term of this patent is extended or adjusted under 35 U.S.C. 154(b) by 0 days.

This patent is subject to a terminal disclaimer.

(21) Appl. No.: 15/288,400

(22) Filed: Oct. 7, 2016

(65) Prior Publication Data
US 2017/0100386 A1 Apr. 13, 2017

Related U.S. Application Data

(60) Provisional application No. 62/239,699, filed on Oct. 9, 2015.

(51) Int. Cl.
| A61K 31/437 | (2006.01) |
| A61K 31/4545 | (2006.01) |
| C07D 471/04 | (2006.01) |
| C07D 519/00 | (2006.01) |
| A61K 45/06 | (2006.01) |
| G01N 33/50 | (2006.01) |

(52) U.S. Cl.
CPC .......... A61K 31/4545 (2013.01); A61K 45/06 (2013.01); C07D 471/04 (2013.01); C07D 519/00 (2013.01); G01N 33/5023 (2013.01); G01N 2800/382 (2013.01)

(58) Field of Classification Search
CPC .......................... C07D 471/04; A61K 31/437
USPC ............................................ 546/82; 514/293
See application file for complete search history.

(56) References Cited

U.S. PATENT DOCUMENTS

| 2015/0005275 A1 | 1/2015 | Van der Plas et al. |
| 2015/0045327 A1 | 2/2015 | Van der Plas et al. |
| 2016/0120841 A1 | 5/2016 | Kym et al. |
| 2016/0122331 A1 | 5/2016 | Kym et al. |

FOREIGN PATENT DOCUMENTS

| WO | 2005120497 A2 | 12/2005 |
| WO | 2006002421 A3 | 1/2006 |
| WO | 2008147952 A1 | 4/2008 |
| WO | 2009076593 A1 | 6/2009 |
| WO | 2009074575 A3 | 8/2009 |
| WO | 2010048573 A1 | 4/2010 |
| WO | 2011113894 A1 | 9/2011 |
| WO | 2011072241 A9 | 6/2012 |
| WO | 2012048181 A4 | 6/2012 |
| WO | 2013038373 A1 | 3/2013 |
| WO | 2013038378 A1 | 3/2013 |
| WO | 2013038381 A1 | 3/2013 |
| WO | 2013038386 A1 | 3/2013 |
| WO | 2013038390 A1 | 3/2013 |
| WO | 2013043720 A1 | 3/2013 |
| WO | 2014/081820 A1 | 5/2014 |

(Continued)

OTHER PUBLICATIONS

Kerem, B. et al, "Identification of the cystic fibrosis gene: genetic analysis." Science, 1989. 245(4922): 1073-1080.

(Continued)

Primary Examiner — Charanjit Aulakh
(74) Attorney, Agent, or Firm — Quarles & Brady LLP

(57) ABSTRACT

A corrector agent capable of stabilizing a newly synthesized cystic fibrosis transmembrane conductance regulator (CFTR) protein, useful in the treatment of cystic fibrosis.

33 Claims, 9 Drawing Sheets
Specification includes a Sequence Listing.

(56) References Cited

FOREIGN PATENT DOCUMENTS

| WO | 2014180562 A1 | 11/2014 |
| WO | 2015018823 A1 | 2/2015 |
| WO | 2015138909 A1 | 9/2015 |
| WO | 2015138934 A1 | 9/2015 |

OTHER PUBLICATIONS

PubChem Compound AKOS023808392; Open Chemistry Database, U. S. National Library of Medicine, created Oct. 20, 2014, 5 pages.
Database Registry, Chemical Abstracts Service, Columbus, OH, Jun. 17, 2015, 1 page.
Database Registry, Chemical Abstracts Service, Columbus, OH, Jun. 18, 2015, 1 page.
PubChem Compound 1,3-dimethyl-4-oxo-1H, 4H, 7H-pyrazolo[3,4-b]pyridine-6-carboxylic acid; Open Chemistry Database, U. S. National Library of Medicine, created Nov. 1, 2013, 5 pages.
Partial International Search Report issued in corresponding PCT Application No. PCT/IB2016/056035, dated Jan. 23, 2017, 4 pages.

SEQUENCE LISTING

```
<160> NUMBER OF SEQ ID NOS: 1

<210> SEQ ID NO 1
<211> LENGTH: 1480
<212> TYPE: PRT
<213> ORGANISM: Homo sapiens

<400> SEQUENCE: 1

Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240
```

```
Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Met Glu Lys Met Ile Glu Asn Leu
        275                 280                 285

Arg Gln Thr Glu Leu Lys Leu Thr Arg Lys Ala Ala Tyr Val Arg Tyr
        290                 295                 300

Phe Asn Ser Ser Ala Phe Phe Phe Ser Gly Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
                340                 345                 350

Gln Phe Pro Trp Ala Val Gln Thr Trp Tyr Asp Ser Leu Gly Ala Ile
            355                 360                 365

Asn Lys Ile Gln Asp Phe Leu Gln Lys Gln Glu Tyr Lys Thr Leu Glu
        370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Val Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
                500                 505                 510

Asp Glu Tyr Arg Tyr Arg Ser Val Ile Lys Ala Cys Gln Leu Glu Glu
            515                 520                 525

Asp Ile Ser Lys Phe Ala Glu Lys Asp Asn Ile Val Leu Gly Glu Gly
        530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu His Glu Gly Ser Ser
    610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
```

-continued

```
                660                 665                 670
Gly Asp Ala Pro Val Ser Trp Thr Glu Thr Lys Lys Gln Ser Phe Lys
            675                 680                 685

Gln Thr Gly Glu Phe Gly Glu Lys Arg Lys Asn Ser Ile Leu Asn Pro
            690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
            755                 760                 765

Val Leu Asn Leu Met Thr His Ser Val Asn Gln Gly Gln Asn Ile His
            770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
            820                 825                 830

Phe Phe Asp Asp Met Glu Ser Ile Pro Ala Val Thr Thr Trp Asn Thr
            835                 840                 845

Tyr Leu Arg Tyr Ile Thr Val His Lys Ser Leu Ile Phe Val Leu Ile
            850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
                900                 905                 910

Tyr Tyr Val Phe Tyr Ile Tyr Val Gly Val Ala Asp Thr Leu Leu Ala
            915                 920                 925

Met Gly Phe Phe Arg Gly Leu Pro Leu Val His Thr Leu Ile Thr Val
            930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile Val Ile Gly Ala Ile Ala Val Val
            995                 1000                1005

Ala Val Leu Gln Pro Tyr Ile Phe Val Ala Thr Val Pro Val Ile
            1010                1015                1020

Val Ala Phe Ile Met Leu Arg Ala Tyr Phe Leu Gln Thr Ser Gln
            1025                1030                1035

Gln Leu Lys Gln Leu Glu Ser Glu Gly Arg Ser Pro Ile Phe Thr
            1040                1045                1050

His Leu Val Thr Ser Leu Lys Gly Leu Trp Thr Leu Arg Ala Phe
            1055                1060                1065

Gly Arg Gln Pro Tyr Phe Glu Thr Leu Phe His Lys Ala Leu Asn
            1070                1075                1080
```

-continued

```
Leu His Thr Ala Asn Trp Phe Leu Tyr Leu Ser Thr Leu Arg Trp
    1085                1090                1095

Phe Gln Met Arg Ile Glu Met Ile Phe Val Ile Phe Phe Ile Ala
    1100                1105                1110

Val Thr Phe Ile Ser Ile Leu Thr Thr Gly Glu Gly Glu Gly Arg
    1115                1120                1125

Val Gly Ile Ile Leu Thr Leu Ala Met Asn Ile Met Ser Thr Leu
    1130                1135                1140

Gln Trp Ala Val Asn Ser Ser Ile Asp Val Asp Ser Leu Met Arg
    1145                1150                1155

Ser Val Ser Arg Val Phe Lys Phe Ile Asp Met Pro Thr Glu Gly
    1160                1165                1170

Lys Pro Thr Lys Ser Thr Lys Pro Tyr Lys Asn Gly Gln Leu Ser
    1175                1180                1185

Lys Val Met Ile Ile Glu Asn Ser His Val Lys Lys Asp Asp Ile
    1190                1195                1200

Trp Pro Ser Gly Gly Gln Met Thr Val Lys Asp Leu Thr Ala Lys
    1205                1210                1215

Tyr Thr Glu Gly Gly Asn Ala Ile Leu Glu Asn Ile Ser Phe Ser
    1220                1225                1230

Ile Ser Pro Gly Gln Arg Val Gly Leu Leu Gly Arg Thr Gly Ser
    1235                1240                1245

Gly Lys Ser Thr Leu Leu Ser Ala Phe Leu Arg Leu Leu Asn Thr
    1250                1255                1260

Glu Gly Glu Ile Gln Ile Asp Gly Val Ser Trp Asp Ser Ile Thr
    1265                1270                1275

Leu Gln Gln Trp Arg Lys Ala Phe Gly Val Ile Pro Gln Lys Val
    1280                1285                1290

Phe Ile Phe Ser Gly Thr Phe Arg Lys Asn Leu Asp Pro Tyr Glu
    1295                1300                1305

Gln Trp Ser Asp Gln Glu Ile Trp Lys Val Ala Asp Glu Val Gly
    1310                1315                1320

Leu Arg Ser Val Ile Glu Gln Phe Pro Gly Lys Leu Asp Phe Val
    1325                1330                1335

Leu Val Asp Gly Gly Cys Val Leu Ser His Gly His Lys Gln Leu
    1340                1345                1350

Met Cys Leu Ala Arg Ser Val Leu Ser Lys Ala Lys Ile Leu Leu
    1355                1360                1365

Leu Asp Glu Pro Ser Ala His Leu Asp Pro Val Thr Tyr Gln Ile
    1370                1375                1380

Ile Arg Arg Thr Leu Lys Gln Ala Phe Ala Asp Cys Thr Val Ile
    1385                1390                1395

Leu Cys Glu His Arg Ile Glu Ala Met Leu Glu Cys Gln Gln Phe
    1400                1405                1410

Leu Val Ile Glu Glu Asn Lys Val Arg Gln Tyr Asp Ser Ile Gln
    1415                1420                1425

Lys Leu Leu Asn Glu Arg Ser Leu Phe Arg Gln Ala Ile Ser Pro
    1430                1435                1440
```

| Ser | Asp | Arg | Val | Lys | Leu | Phe | Pro | His | Arg | Asn | Ser | Ser | Lys | Cys |
| --- | --- | --- | --- | --- | --- | --- | --- | --- | --- | --- | --- | --- | --- | --- |
| 1445 | | | | | 1450 | | | | | 1455 | | | | |

| Lys | Ser | Lys | Pro | Gln | Ile | Ala | Ala | Leu | Lys | Glu | Glu | Thr | Glu | Glu |
| --- | --- | --- | --- | --- | --- | --- | --- | --- | --- | --- | --- | --- | --- | --- |
| 1460 | | | | | 1465 | | | | | 1470 | | | | |

| Glu | Val | Gln | Asp | Thr | Arg | Leu |
| --- | --- | --- | --- | --- | --- | --- |
| 1475 | | | | | 1480 | |

COMPOUNDS FOR TREATMENT OF CYSTIC FIBROSIS

CROSS REFERENCE TO RELATED APPLICATIONS

This application claims priority to U.S. Provisional Application No. 62/239,699, filed Oct. 9, 2015, which is incorporated herein by reference for all purposes.

BACKGROUND OF THE INVENTION

Cystic fibrosis (CF) is a disease caused by mutations in the cftr gene which induces defects in the CFTR protein, its production and/or its function. Cystic fibrosis is the most common fatal genetic disease in humans, and affects ~0.04% of white individuals. For example, in the United States, about one in every 2,500 infants is affected, and up to 10 million people carry a single copy of the defective gene without apparent ill effects; moreover subjects bearing a single copy of the gene exhibit increased resistance to cholera and to dehydration resulting from diarrhea. In contrast, individuals with two copies of the CF associated gene suffer from the debilitating and fatal effects of CF, including chronic lung infections.

In cystic fibrosis patients, mutations in endogenous respiratory epithelial CFTR lead to a failure to confer chloride and bicarbonate permeability to epithelial cells in lung and other tissues, thus leading to reduced apical anion secretion and disruptions of the ion and fluid transport. This decrease in anion transport causes an enhanced mucus and pathogenic agent accumulation in the lung triggering microbial infections that ultimately cause death in CF patients.

Beyond respiratory disease, CF patients also suffer from gastrointestinal problems and pancreatic insufficiency that result in death if left untreated. Furthermore, female subjects with cystic fibrosis suffer from decreased fertility, whilst males with cystic fibrosis are infertile.

A variety of disease causing mutations has been identified through sequence analysis of the CFTR gene of CF chromosomes. ΔF508-CFTR, the most common CF mutation (present in at least 1 allele in ~90% of CF patients) and occurring in approximately 70% of the cases of cystic fibrosis, contains a single amino acid deletion of phenylalanine 508. The F508del misfolding originates in the first nucleotide-binding domain (NBD1), which induces a global conformational change in CFTR through NBD1's interactions with other domains. This deletion prevents the nascent protein from folding correctly, whereby the protein in turn cannot exit the endoplasmic reticulum (ER) and being transported to the plasma membrane, and then is rapidly degraded. As a result, the number of channels present in the membrane is far less than in cells expressing wild-type CFTR. In addition to impaired trafficking, the mutation results in defective channel gating.

Currently there are no effective therapies for cystic fibrosis patients. Therefore, there is a need for novel compounds able to modulate CFTR.

SUMMARY OF THE DISCLOSURE

The present invention is based on an unexpected discovery that a corrector agent for cystic fibrosis may be designed, made and identified to stabilize a newly synthesized Cystic fibrosis transmembrane conductance regulator (CFTR) protein while it does not stabilize the biogenic intermediates of the CFTR protein during the biosynthesis.

In one aspect, the present invention relates to a corrector agent that is capable of stabilizing a newly synthesized Cystic fibrosis transmembrane conductance regulator (CFTR) protein.

In some embodiments, the CFTR protein is a mutant CFTR protein. In some embodiments, the CFTR protein comprises a mutation selected from a group consisting of Class I, Class II, Class III, Class IV, Class V and Class VI mutations. Preferably, the CFTR comprises a Class I mutation or Class III mutation. More preferably, the CFTR comprises a CFTRΔF508 mutation.

In some embodiments, the CFTR protein is a wild-type CFTR protein.

In some embodiments, the CFTR protein is synthesized in full length and prior to post-translational modifications. In some embodiments, the post-translation modification is glycosylation or ubiquitination in Golgi complex.

In some embodiments, the corrector agent is capable of stabilizing the defective CFTR protein to at least about 15% of CFTR from healthy cells In some embodiments, the corrector agent does not stabilize biogenic intermediate CFTR380, CFTR837 or CFTR837-1480 during the biosynthesis of the CFTR protein.

In some embodiments, the corrector agent reduces the channel activity of the CFTR protein.

In some embodiments, the corrector agent of the present invention is capable of stabilizing a CFTR protein, wherein said CFTR comprises a CFTRΔF508 mutation and the plasma membrane levels of said CFTR in the presence of said agent are at least 300% of the level obtainable with a type I corrector with said CFTR protein.

In some embodiments, the corrector agent of the present invention is capable of stabilizing a CFTR protein, wherein the CFTR comprises a CFTRΔF508 mutation and plasma membrane levels of said CFTR protein in the presence of said agent and a type I corrector are at least 50% of the level of wild-type CFTR in healthy cells.

In some embodiments, the corrector agent of the present invention directly binds to CFTR protein.

In some embodiments, the corrector agent of the present invention is capable of stabilizing a CFTR protein, wherein said CFTR protein comprises NBD1 domain, wherein said domain comprises a CFTRΔF508 mutation, and wherein said NBD1 domain is not produced in a correctly folded form in the presence of said agent.

In some embodiments, the corrector agent of the present invention is capable of stabilizing a CFTR protein, wherein the corrector agent decreases the CFTR channel gating activity.

In some embodiments, the corrector agent of the present invention is capable of stabilizing a CFTR protein, wherein the corrector agent decreases the CFTR channel gating activity by at least 25%.

In some embodiments, the corrector agent of the present invention decreases the CFTR channel gating activity in a dose dependent manner. In more specific embodiments, the corrector agent decreases the CFTR channel gating activity and said activity is reversed in the presence of a potentiator agent.

In some embodiments the corrector agent of the present invention is capable of stabilizing a CFTR protein, wherein the corrector agent reduces the forkolin dependent CFTR channel activity by at least 25%.

In some embodiments, the corrector agent is a compound of formula (I) or a pharmaceutically acceptable salt thereof,

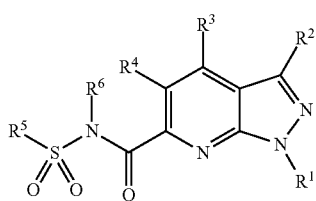

(I)

In some embodiments, the corrector agent is a compound of formula (II) or a pharmaceutically acceptable salt thereof,

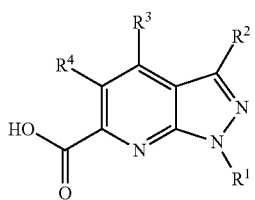

(II)

In another aspect, the present invention relates to a pharmaceutical composition for treating cystic fibrosis comprising a first corrector agent and a pharmaceutically acceptable carrier, wherein the first corrector agent is an agent described herein.

In some embodiments, the composition further comprises a potentiator agent.

In some embodiments, the composition further comprises a second corrector agent, wherein the second corrector agent works through a different correction mechanisms as the first corrector agent.

In some embodiments, the second corrector stabilizes at least one of biogenic intermediates selected from a group consisting of CFTR375, CFTR380, CFTR430, CFTR653, CFTR837 and CFTR837-1480 during the biosynthesis of the CFTR protein.

In another aspect, the present invention relates to a method of treating cystic fibrosis in a patient comprising the step of administering to the patient an effective amount of a first corrector agent, wherein the first corrector agent is an agent described herein.

In some embodiments, the first corrector agent is co-administered with an effective amount of a second corrector agent, wherein the second corrector agent works through a different correction mechanism as compared to the first corrector agent.

In some embodiments, the second corrector is a type I corrector.

In some embodiments, the first corrector agent is co-administered with an effective amount of a potentiator agent.

In another aspect, the present invention relates to a method of screening for a candidate corrector agent for cystic fibrosis comprising the steps of: i) contacting a test agent with a cell expressing at least one of the CFTR biogenic intermediates selected from group consisting of CFTR380, CFTR837 and CFTR837-1480 and a CFTR protein, ii) measuring the accumulation of the CFTR biogenic intermediate and CFTR protein, iii) comparing the accumulation of the CFTR biogenic intermediate and the CFTR protein in the cell with the accumulation of the CFTR biogenic intermediate and the CFTR protein in a cell that is not contacted with the test agent, wherein if the accumulation of the CFTR biogenic intermediates in the cell contacted with the test agent is not greater than the accumulation of the respective CFTR biogenic intermediate in the cell not contacted with the test agent, and if the accumulation of the CFTR protein in the cell contacted with the test agent is greater than the accumulation of the CFTR protein in the cell not contacted with the test agent, the test agent is a candidate corrector agent.

In another aspect, the present invention relates to a kit for screening for a candidate corrector agent comprising a cell expressing one or more CFTR biogenic intermediates selected from group consisting of CFTR380, CFTR837 and CFTR837-1480 and a CFTR protein. The kit may further comprise a test agent.

DETAILED DESCRIPTION OF THE INVENTION

Figure 1:
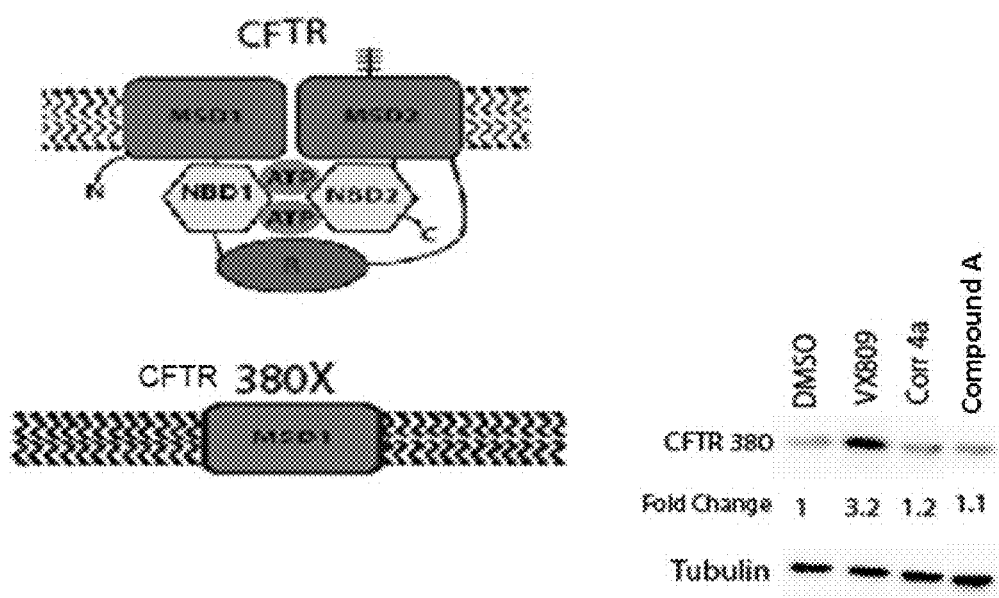
FIG. 1 is a western blot showing the effect of VX-809, Corr-4a and Compound A on the accumulation of CFTR380.

The present invention is based on an unexpected discovery of a molecule that can improve maturation, stability and functionality of a CFTR protein through stabilization of a CFTR protein when it is newly synthesized and prior to post-translational modifications.

Definitions

As used in the specification and the appended claims, unless specified to the contrary, the following terms have the meaning indicated:

The term "CFTR" as used herein means cystic fibrosis transmembrane regulator or a mutation thereof, including, but not limited to, a mutation in Class I, II, III, IV and V. The gene encoding CFTR has been identified and sequenced (Kerem, B., Rommens, J. M., Buchanan, J. A., Markiewicz, D., Cox, T. K., Chakravarti, A., Buchwald, M., Tsui, L. C., 1989. Identification of the cystic fibrosis gene: genetic analysis. Science 245, 1073-1080). CFTR comprises about 1480 amino acids that encode a protein made up of a tandem repeat of transmembrane domains, each containing six transmembrane helices and a nucleotide binding domain. The pair of transmembrane domains is linked by a large, polar, regulatory (R)-domain with multiple phosphorylation sites that regulate channel activity and cellular trafficking In some embodiments, a CFTR protein has a sequence of SEQ ID NO:1 or a sequence that substantially identical to SEQ ID NO:1. In some embodiments, a CFTR protein has a sequence of SEQ ID NO:1 or a sequence that is at least 80%, 85%, 90%, 91%, 92%, 93%, 94%, 95%, 96%. 97%, 98%, 98%, 99% or 100% identical to SEQ ID NO:1.

In some embodiments, a CFTR protein is an assembly of several fragments or biogenic intermediates produced during biosynthesis of the CFTR protein. Examples of the biogenic intermediates include, but are not limited to, CFTR375, CFTR380, CFTR430, CFTR653, CFTR837 and CFTR837-1480.

The term "CFTR375" means a polypeptide consisting of the N-terminal 375 amino acids or residues 1-375 of a CFTR protein having a sequence of SEQ ID NO:1 or a sequence that substantially identical to SEQ ID NO:1. In some embodiments, a CFTR375 is a polypeptide consisting of the N-terminal 375 amino acids or residues 1-375 of a CFTR protein having a sequence of SEQ ID NO:1 or a sequence that is at least 80%, 85%, 90%, 91%, 92%, 93%, 94%, 95%, 96%. 97%, 98%, 98%, 99% or 100% identical to SEQ ID NO:1.

The term "CFTR380" means a polypeptide consisting of the N-terminal 380 amino acids or residues 1-380 of a CFTR protein having a sequence of SEQ ID NO:1 or a sequence that is substantially identical to SEQ ID NO:1. In some embodiments, a CFTR380 is a polypeptide consisting of the N-terminal 380 amino acids or residues 1-380 of a CFTR protein having a sequence of SEQ ID NO:1 or a sequence that is at least 80%, 85%, 90%, 91%, 92%, 93%, 94%, 95%, 96%. 97%, 98%, 98%, 99% or 100% identical to SEQ ID NO:1.

The term "CFTR430" means a polypeptide consisting of the N-terminal 430 amino acids or residues 1-430 of a CFTR protein having a sequence of SEQ ID NO:1 or a sequence that is substantially identical to SEQ ID NO:1. In some embodiments, a CFTR430 is a polypeptide consisting of the N-terminal 430 amino acids or residues 1-430 of a CFTR protein having a sequence of SEQ ID NO:1 or a sequence that is at least 80%, 85%, 90%, 91%, 92%, 93%, 94%, 95%, 96%. 97%, 98%, 98%, 99% or 100% identical to SEQ ID NO:1.

The term "CFTR653" means a polypeptide consisting of the N-terminal 653 amino acids or residues 1-653 of a CFTR protein having a sequence of SEQ ID NO:1 or a sequence that is substantially identical to SEQ ID NO:1. In some embodiments, a CFTR653 is a polypeptide consisting of the N-terminal 653 amino acids or residues 1-653 of a CFTR protein having a sequence of SEQ ID NO:1 or a sequence that is at least 80%, 85%, 90%, 91%, 92%, 93%, 94%, 95%, 96%. 97%, 98%, 98%, 99% or 100% identical to SEQ ID NO:1.

The term "CFTR837" means a polypeptide consisting of the N-terminal 837 amino acids or residues 1-837 of a CFTR protein having a sequence of SEQ ID NO:1 or a sequence that is substantially identical to SEQ ID NO:1. In some embodiments, a CFTR837 is a polypeptide consisting of the N-terminal 837 amino acids or residues 1-837 of a CFTR protein having a sequence of SEQ ID NO:1 or a sequence that is at least 80%, 85%, 90%, 91%, 92%, 93%, 94%, 95%, 96%. 97%, 98%, 98%, 99% or 100% identical to SEQ ID NO:1.

The term "CFTR837-1480" means a polypeptide consisting of the residues 837-1480 of a CFTR protein having a sequence of SEQ ID NO:1 or a sequence that is substantially identical to SEQ ID NO:1. In some embodiments, a CFTR837-1480 is a polypeptide consisting of the residues 837-1480 of a CFTR protein having a sequence of SEQ ID NO:1 or a sequence that is at least 80%, 85%, 90%, 91%, 92%, 93%, 94%, 95%, 96%. 97%, 98%, 98%, 99% or 100% identical to SEQ ID NO:1.

The term "R (regulator) domain" refers to a domain that keeps a chloride channel closed at rest and which opens the channel when phosphorylated (e.g. by cAMP-dependent protein kinase (PKA) or protein kinase C (PKC)).

The term "NBD or Nucleotide Binding Domain" refers to a domain that binds nucleotides (e.g. adenosine triphosphate (ATP)).

The term "MSD or Membrane Spanning Domain" refers to a domain that forms a chloride channel The term "sequence identity" as used herein refers to the extent that sequences are identical on a nucleotide-by-nucleotide basis or an amino acid-by-amino acid basis over a window of comparison. Nucleic acid and protein sequence identities can be evaluated by using any method known in the art. For example, the identities can be evaluated by using the Basic Local Alignment Search Tool ("BLAST"). The BLAST programs identity homologous sequences by identifying similar segments between a query amino or nucleic acid sequence and a test sequence which is preferably obtained from protein or nuclei acid sequence database. The BLAST program can be used with the default parameters or with modified parameters provided by the user.

The term "corrector agent" or "corrector" used herein means a small or large molecule that is capable of correcting the defective cellular processing of CFTR, or inducing the amount of functional CFTR, or increasing the amount of CFTR in a cell membrane. Preferably, the corrector agent means a molecule that is capable of modulating a wild type or mutant CFTR protein to decrease proteolytic sensitivity of the CFTR protein, to increase transportation or trafficking of the CFTR out of endoplasmic reticulum (ER), and/or to increase the number of the CFTR protein in the cell membrane or on cell surface.

The term "type I corrector agent" or "type I corrector" used herein means a corrector that works through a different correction mechanism as compared to the corrector agents of the present invention. In particular, the type I corrector is an agent that restores the function of a CFTR protein comprising a CFTRΔF508 mutation by only acting on MSD1 of the CFTR protein.

The term "potentiator" as used herein means a compound that increases the gating activity of CFTR in a membrane of a cell. In particular, the potentiators exhibit improvement in channel activity of a mutant CFTR protein.

The term "stabilizing" or "stabilization" used herein means any improvement on physical, chemical or biological function of a defective CFTR protein or fragments thereof where the defectiveness is caused by, associated with or induced by improper protein translation, synthesis, conformation and/or folding of the CFTR protein or fragments thereof due to genetic defects in its gene. In some embodiments, the corrector agent stabilizes a CFTR protein by preventing or decreasing the degradation of the CFTR protein. In some embodiments, the corrector agent stabilizes a CFTR protein by increasing the amount of CFTR protein that is trafficked to the cell surface. In some embodiments, the corrector agent stabilizes a CFTR protein by increasing the amount of CFTR proteins on the cell surface. In some embodiments, the corrector agent stabilizes a CFTR protein by a combination of any two or more of the above-mentioned effects.

The term "newly synthesized CFTR" used herein means a form of CFTR protein that has been produced, synthesized or assembled but has not undergone partial or complete post-translational process or modification within a cell.

The term "post-translational modification" or "PTM" as used herein means any type of chemical modifications of a CFTR protein and/or peptide that takes place after completion of CFTR protein translation. Examples of such modifications include inter alfa phosphorylation, ubiquitinylation, acetylation, glycosylation, alkylation, isoprenylation, and lipoylation, with glycosylation or ubiquitinylation being particularly preferred. The term is also to be understood not to be limited with regard to the numbers and/or types of post-translational modifications being comprised in a CFTR protein and/or peptide. Thus, a given CFTR protein may comprise in its sequence one, two or more modifications such as glycosylated amino acids or phosphorylated amino acids residues.

The term "glycosylation" used herein means a process or a reaction where a carbohydrate is attached to a hydroxyl or other functional group of a CFTR protein so the CFTR protein comprises in their primary sequence one or more glycosylated amino acid residues.

The term "ubiquitination" used herein means an enzymatic process that involves the bonding of an ubiquitin protein to a substrate CFTR protein or fragments thereof.

The terms "treat", "treating", and "treatment" refer to a method of alleviating a disease and/or its attendant symptoms. In certain embodiments, "treat," "treating," and "treatment" refer to ameliorating at least one physical parameter, which may not be discernible by the subject. In yet another embodiment, "treat", "treating", and "treatment" refer to modulating the disease or disorder, either physically (for example, stabilization of a discernible symptom), physiologically (for example, stabilization of a physical parameter), or both. In a further embodiment, "treat", "treating", and "treatment" refer to slowing the progression of the disease or disorder.

Preventing' or 'prevention' refers to a reduction in risk of acquiring or developing a disease or disorder (i.e. causing at least one of the clinical symptoms of the disease not to develop in a subject that may be exposed to a disease-causing agent, or predisposed to the disease in advance of disease onset.

The phrase "therapeutically effective amount" or "effective amount" means an amount of a compound, or a pharmaceutically acceptable salt thereof, sufficient to prevent the development of or to alleviate to some extent one or more of the symptoms of the condition or disorder being treated when administered alone or in conjunction with another therapeutic agent for treatment in a particular subject or subject population. The "therapeutically effective amount" may vary depending on the compound, the disease and its severity, and the age, weight, health, etc., of the subject to be treated. For example in a human or other mammal, a therapeutically effective amount may be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, pigs, horses, dogs, cats, rabbits, rats, mice and the like. In one embodiment, the subject is a human. The terms "human," "patient," and "subject" are used interchangeably herein.

The term 'one or more' refers to one to four. In one embodiment it refers to one or three. In another embodiment it refers to one to three. In a further embodiment it refers to one to two. In yet other embodiment it refers to two. In yet other further embodiment it refers to one.

The term "Class I mutation(s)" refers to mutations which interfere with protein synthesis. They result in the introduction of a premature signal of termination of translation (stop codon) in the mRNA. The truncated CFTR proteins are unstable and rapidly degraded, so, the net effect is that there is no protein at the apical membrane. In particular, Class I mutation(s) refers to p.Gly542X (G542X), W1282X, c.489+1G>T (621+1G>T), or c.579+1G>T (711+1G>T) mutation. More particularly, Class I mutation(s) refers to G542X; or W1282X mutations.

The term "Class II mutation(s)" refers to mutations which affect protein maturation. These lead to the production of a CFTR protein that cannot be correctly folded and/or trafficked to its site of function on the apical membrane. In particular, Class II mutation(s) refers to p.Phe508del (F508del), p.Ile507del, or p.Asn1303Lys (N1303K) mutations. More particularly, Class II mutation(s) refers to F508del or N1303K mutations.

The term "Class III mutation(s)" refers to mutations which alter the regulation of the CFTR channel. The mutated CFTR protein is properly trafficked and localized to the plasma membrane but cannot be activated, or it cannot function as a chloride channel. In particular, Class III mutation(s) refers to p.Gly551Asp (G551D), G551S, R553G; G1349D; S1251N, G178R, S549N mutations. More particularly, Class III mutation(s) refers to G551D, R553G, G1349D, S1251N, G178R, or S549N mutations.

The term "Class IV mutation(s)" refers to mutations which affect chloride conductance. The CFTR protein is correctly trafficked to the cell membrane but generates reduced chloride flow or a "gating defect" (most are missense mutations located within the membrane-spanning domain). In particular, Class IV mutation(s) refers to p.Arg117His (R117H), R347P, or p.Arg334Trp (R334W) mutations.

The term "Class V mutation(s)" refers to mutations which reduce the level of normally functioning CFTR at the apical membrane or result in a "conductance defect" (for example partially aberrant splicing mutations or inefficient trafficking missense mutations). In particular, Class V mutation(s) refers to c.1210-12T[5] (5T allele), c.S3140-26A>G (3272-26A>G), c.3850-2477C>T (3849+10kbC>T) mutations.

The term "Class VI mutation(s)" refers to mutations which decrease the stability of the CFTR which is present or which affect the regulation of other channels, resulting in inherent instability of the CFTR protein. In effect, although functional, the CFTR protein is unstable at the cell surface and it is rapidly removed and degraded by cell machinery. In particular, Class VI mutation(s) refers to Rescued F508del, 120del23, N287Y, 4326dellTC, or 4279insA mutations. More particularly, Class VI mutation(s) refers to Rescued F508del mutations.

The term "alkenyl" as used herein, means a straight or branched hydrocarbon chain containing from 2 to 10 carbons and containing at least one carbon-carbon double bond. The term "C2-C6 alkenyl" means an alkenyl group containing 2-6 carbon atoms. Non-limiting examples of C2-C6 alkenyl include buta-1,3-dienyl, ethenyl, 2-propenyl, 2-methyl-2-propenyl, 3-butenyl, 4-pentenyl, and 5-hexenyl.

The term "C1-C3 alkoxy" as used herein, means a C1-C3 alkyl group, as defined herein, appended to the parent molecular moiety through an oxygen atom. Examples of C1-C3 alkoxy include, but are not limited to, methoxy, ethoxy, propoxy, and 2-propoxy.

The term "alkyl" as used herein, means a saturated, straight or branched hydrocarbon chain radical. In some instances, the number of carbon atoms in an alkyl moiety is indicated by the prefix "Cx-Cy", wherein x is the minimum and y is the maximum number of carbon atoms in the substituent. Thus, for example, "C1-C6 alkyl" means an alkyl substituent containing from 1 to 6 carbon atoms and "C1-C3 alkyl" means an alkyl substituent containing from 1 to 3 carbon atoms. Representative examples of C1-C6 alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 3,3-dimethylbutyl, 1,1-dimethylpropyl, 1,2-dimethylpropyl, 2,2-dimethylpropyl, 1-methylpropyl, 2-methylpropyl, 1-ethylpropyl, and 1,2,2-trimethylpropyl.

The term "alkylene" or "alkylenyl" means a divalent radical derived from a straight or branched, saturated hydrocarbon chain, for example, of 1 to 10 carbon atoms or of 1 to 6 carbon atoms (C1-C6 alkylenyl) or of 1 to 4 carbon atoms or of 1 to 3 carbon atoms (C1-C3 alkylenyl) or of 2 to 6 carbon atoms (C2-C6 alkylenyl). Examples of C1-C6 alkylenyl include, but are not limited to, —CH$_2$—, CH$_2$CH$_2$—, —C((CH$_3$)$_2$)—CH$_2$CH$_2$CH$_2$—, —C((CH$_3$)$_2$)CH$_2$CH$_2$—, —CH$_2$CH$_2$CH$_2$CH$_2$—, and —CH$_2$CH(CH$_3$)CH$_2$—.

The term "C2-C6 alkynyl" as used herein, means a straight or branched chain hydrocarbon radical containing from 2 to 6 carbon atoms and containing at least one carbon-carbon triple bond. Representative examples of C2-C6 alkynyl include, but are not limited, to acetylenyl, 1-propynyl, 2-propynyl, 3-butynyl, 2-pentynyl, and 1-butynyl.

The term "cycloalkyl" as used herein, means a C3-C6 cycloalkyl as defined herein, wherein the C3-C6 cycloalkyl may further contain one or two alkylene bridges of 1, 2, 3, or 4 carbon atoms, and each links two non-adjacent carbon atoms of the ring. Examples of such bridged ring system include, but are not limited to, bicyclo[2.2.1]heptyl, bicyclo[2.1.1]hexyl, and bicyclo[3.1.1]heptyl. The cycloalkyl ring systems (including the exemplary rings) are optionally substituted unless otherwise indicated.

The term "C3-C6 cycloalkyl" as used herein, means cyclopropyl, cyclobutyl, cyclopentyl, and cyclohexyl, each of which is optionally substituted unless otherwise indicated.

The term "C4-C6 cycloalkenyl" as used herein, means cyclobutenyl, cyclopentenyl, and cyclohexenyl, each of which is optionally substituted unless otherwise indicated.

The term "halo" or "halogen" as used herein, means Cl, Br, I, and F.

The term "C1-C3 haloalkoxy" as used herein, means a C1-C3 haloalkyl group, as defined herein, appended to the parent molecular moiety through an oxygen atom. Examples of C1-C3 haloalkoxy include, but are not limited to, trifluoromethoxy, difluoromethoxy, and 2-fluoroethoxy.

The term "haloalkyl" as used herein, means an alkyl group, as defined herein, in which one, two, three, four, five or six hydrogen atoms are replaced by halogen. The term "C1-C6 haloalkyl" means a C1-C6 alkyl group, as defined herein, in which one, two, three, four, five, or six hydrogen atoms are replaced by halogen. The term "C1-C3 haloalkyl" means a C1-C3 alkyl group, as defined herein, in which one, two, three, four, or five hydrogen atoms are replaced by halogen. Representative examples of haloalkyl include, but are not limited to, chloromethyl, 2-fluoroethyl, 2,2-difluoroethyl, fluoromethyl, 2,2,2-trifluoroethyl, trifluoromethyl, difluoromethyl, pentafluoroethyl, 2-chloro-3-fluoropentyl, trifluorobutyl, and trifluoropropyl.

The term "heterocycle" or "heterocyclic" as used herein, means a radical of a monocyclic heterocycle, a bicyclic heterocycle, or a spiro heterocycle. A monocyclic heterocycle is a three-, four-, five-, six-, seven-, or eight-membered carbocyclic ring wherein at least one carbon atom is replaced by heteroatom independently selected from the group consisting of O, N, and S. A three- or four-membered ring contains zero or one double bond, and one heteroatom selected from the group consisting of O, N, and S. A five-membered ring contains zero or one double bond and one, two, or three heteroatoms selected from the group consisting of O, N, and S. Examples of five-membered heterocyclic rings include those containing in the ring: 1 O; 1 S; 1 N; 2 N; 3 N; 1 S and 1 N; 1 S, and 2 N; 1 O and 1 N; or 1 O and 2 N. Non limiting examples of 5-membered heterocyclic groups include 1,3-dioxolanyl, tetrahydrofuranyl, dihydrofuranyl, tetrahydrothienyl, dihydrothienyl, imidazolidinyl, oxazolidinyl, imidazolinyl, isoxazolidinyl, pyrazolidinyl, pyrazolinyl, pyrrolidinyl, 2-pyrrolinyl, 3-pyrrolinyl, thiazolinyl, and thiazolidinyl. A six-membered ring contains zero, one, or two double bonds and one, two, or three heteroatoms selected from the group consisting of O, N, and S. Examples of six-membered heterocyclic rings include those containing in the ring: 1 O; 2 O; 1 S; 2 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Examples of 6-membered heterocyclic groups include tetrahydropyranyl, dihydropyranyl, dioxanyl, 1,4-dithianyl, hexahydropyrimidine, morpholinyl, piperazinyl, piperidinyl, 1,2,3,6-tetrahydropyridinyl, tetrahydrothiopyranyl, thiomorpholinyl, thioxanyl, and trithianyl. Seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3 dithiolanyl, 1,3 dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyridinyl, tetrahydropyranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is a monocyclic heterocycle fused to a phenyl group, or a monocyclic heterocycle fused to a C3-C6 cycloalkyl, or a monocyclic heterocycle fused to a C4-C6 cycloalkenyl, or a monocyclic heterocycle fused to a monocyclic heterocycle. Representative examples of bicyclic heterocycles include, but are not limited to, benzopyranyl, benzothiopyranyl, 2,3-dihydrobenzofuranyl, 2,3-dihydrobenzothienyl, 2,3-dihydro-1H-indolyl, 3,4-dihydroisoquinolin-2(1H)-yl, 2,3,4,6-tetrahydro-1H-pyrido[1,2-a]pyrazin-2-yl, hexahydropyrano[3,4-b][1,4]oxazin-1(5H)-yl, hexahydropyrrolo[3,4-c]pyrrol-2(1H)-yl, and hexahydrocyclopenta[c]pyrrol-3a(1H)-yl. The monocyclic heterocycle and the bicyclic heterocycle may further contain one or two alkylene bridges, each consisting of 1, 2, 3, or 4 carbon atoms and each linking two non-adjacent atoms of the ring system. Examples of such bridged heterocycles include, but are not limited to, azabicyclo[2.2.1]heptyl (including 2-azabicyclo[2.2.1]hept-2-yl), 8-azabicyclo[3.2.1] oct-8-yl, octahydro-2,5-epoxypentalene, hexahydro-2H-2,5-methanocyclopenta[b]furan, hexahydro-1H-1,4-methanocyclopenta[c]furan, aza-admantane (1 azatricyclo [3.3.1.13,7]decane), and oxa-adamantane (2-oxatricyclo [3.3.1.1ic3,7]decane). The term "spiro heterocycle" as used herein, means a monocyclic heterocycle as defined herein wherein two substituents on the same carbon atom of the monocyclic heterocycle ring together with said carbon atom form a second monocyclic heterocycle or a C3-C6 cycloalkyl ring. Non-limiting examples of the spiro heterocycle include 6-azaspiro[3.4]octane, 2-oxa-6-azaspiro[3.4] octan-6-yl, and 2,7-diazaspiro[4.4]nonane. The monocyclic, the bicyclic, and the spiro heterocycles, including exemplary rings, are optionally substituted unless otherwise indicated. The monocyclic, the bicyclic, and the spiro heterocycles are connected to the parent molecular moiety through any carbon atom or any nitrogen atom contained within the ring systems. The nitrogen and sulfur heteroatoms in the heterocycle rings may optionally be oxidized (e.g., 1,1-dioxido-tetrahydrothienyl, 1,1-dioxido-1,2-thiazolidinyl, 1,1-dioxidothiomorpholinyl)) and the nitrogen atoms may optionally be quarternized.

The term "4-6 membered monocyclic heterocycle" or "4-6 membered monocyclic heterocyclic" as used herein, means a 4-, 5-, or 6-membered monocyclic heterocycle as defined herein above. Examples of 4-6 membered monocyclic heterocycle include azetidinyl, dihydropyranyl, pyrrolidinyl, tetrahydrofuranyl, tetrahydropyranyl, piperazinyl, piperidinyl, thiomorpholinyl, and morpholinyl. The 4-6 membered monocyclic heterocycles, including exemplary rings, are optionally substituted unless indicated otherwise.

The term "monocyclic heteroaryl" as used herein, means a 5- or 6-membered monocyclic aromatic ring. The five-membered ring contains two double bonds. The five-membered ring may contain one heteroatom selected from the group consisting of O and S; or one, two, three, or four nitrogen atoms and optionally one oxygen or one sulfur atom. The six-membered ring contains three double bonds and one, two, three, or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The monocyclic heteroaryls, including exemplary rings, are optionally substituted unless otherwise indicated. The monocyclic heteroaryls are connected to the parent molecular moiety through any substitutable carbon atom or any substitutable nitrogen atom contained within the ring systems. The nitrogen atom in the heteroaryl rings may optionally be oxidized and may optionally be quarternized.

The term "heteroatom" as used herein, means a nitrogen, oxygen, and sulfur.

The term "oxo" as used herein, means a =O group.

The term "radiolabel" means a compound of the invention in which at least one of the atoms is a radioactive atom or a radioactive isotope, wherein the radioactive atom or isotope spontaneously emits gamma rays or energetic particles, for example alpha particles or beta particles, or positrons. Examples of such radioactive atoms include, but are not limited to, $^3$H (tritium), $^{14}$C, $^{11}$C, $^{15}$O, $^{18}$F, $^{35}$S, $^{123}$I, and $^{125}$I.

A moiety is described as "substituted" when a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

Corrector Agents of the Present Invention

In its first aspect, the present invention relates to a corrector agent for the treatment of Cystic Fibrosis. The corrector agent includes, but not limited to, a small molecule, a peptide, a protein and a polymer. Preferably, the corrector agent of the present invention is a small molecule.

In some embodiments, the corrector agent of the present invention is capable of stabilizing a wild type CFTR protein. In some embodiments, the corrector agent of the present invention is capable of stabilizing a mutant CFTR protein. In some embodiments, the corrector agent of the present invention is capable of stabilizing a combination of a wild type CFTR protein and a mutant CFTR protein.

In some embodiments, the corrector agent of the present invention is capable of stabilizing a mutant CFTR protein comprising one or more mutations selected from a group consisting of Class I, Class II, Class III, Class IV and Class V CFTR mutations. Preferably, the corrector agent of the present invention is capable of stabilizing a mutant CFTR protein comprising one or more Class II mutations or one or more Class III mutations. More preferably, the corrector agent of the present invention is capable of stabilizing a mutant CFTR protein comprising one or more Class II mutations. Most preferably, the corrector agent of the present invention is capable of stabilizing a mutant CFTR protein comprising one CFTRΔF508 mutation in its sequence.

In some embodiments, the corrector agent of the present invention is capable of stabilizing a CFTR protein when the CFTR protein is newly and fully synthesized.

In some embodiments, a newly and fully synthesized CFTR protein has a full length of a CFTR protein comprising two membrane-spanning domains (MSD1 and MSD2), two nucleotide-binding domains (NBD1 and NBD2) and a regulatory domain (R). In some embodiments, a newly and fully synthesized CFTR protein comprises the residues 1-1480 of a CFTR protein having a sequence of SEQ ID NO:1 or a sequence that is substantially identical to SEQ ID NO:1, preferably a sequence that is at least 80%, 85%, 90%, 91%, 92%, 93%, 94%, 95%, 96%. 97%, 98%, 98%, 99% or 100% identical to SEQ ID NO:1. In some embodiments, a newly and fully synthesized CFTR protein consists the residues 1-1480 of a CFTR protein having a sequence of SEQ ID NO:1 or a sequence that is substantially identical to SEQ ID NO:1, preferably a sequence that is at least 80%, 85%, 90%, 91%, 92%, 93%, 94%, 95%, 96%. 97%, 98%, 98%, 99% or 100% identical to SEQ ID NO:1.

In some embodiments, the corrector agent of the present invention is capable of stabilizing a fully and newly synthesized CFTR protein prior to post-translational modifications by at least 5%, 6%, 7%, 8%, 9%, 10%, 11%, 12%, 13%, 14% or 15% as compared to the stability of a CFTR protein in the absence of a corrector agent or the corrector agent of the present invention. Preferably, the corrector agent of the present invention is capable of stabilizing the CFTR protein by at least 15%. The stabilization can be measured by any methods known in the art or characterized by any methods known in the art. In some embodiments, the corrector agent of the present invention stabilizes a CFTR protein by increasing the accumulation of the CFTR protein in vivo. In some embodiments such accumulation is increased by at least 15%, at least 20%, at least 30%, and at least 50% when compared to the accumulation in the absence of the corrector agent.

In some embodiments, the corrector agent of the present invention does not stabilize any one of the biogenic intermediates selected from a group consisting of CFTR380, CFTR837 and CFTR837-1480 during the biosynthesis of the CFTR protein.

In some embodiments, the corrector agent of the present invention does not stabilize any one of the biogenic intermediates selected from a group consisting of MSD1, MSD1-NBD1 and MSD2-NBD2 during the biosynthesis of the CFTR protein.

In some embodiments, the capability of the corrector agent on stabilizing a biogenic intermediate during the biosynthesis or a fully synthesized protein is measured by accumulation of the biogenic intermediate and the full length protein. In some embodiments, the corrector agent is considered incapable of stabilizing a biogenic intermediate if it does not change the accumulation of the biogenic intermediate as compared to that in the absence of the corrector agent. In some embodiments, the corrector agent is considered incapable of stabilizing a biogenic intermediate if it decreases the accumulation of the biogenic intermediate. In some embodiments, the corrector agent is incapable of stabilizing a biogenic intermediate as described above if it increases the accumulation of the biogenic intermediate by no more than 5% as compared to that in the absence of the corrector agent.

In some embodiments, the corrector agent of the present invention does not increase the gating activity of a CFTR protein. In some embodiments, the corrector agent of the present invention reduces the gating activity of a CFTR protein. In some embodiments, the corrector agent of the present invention reduces the gating activity of a CFTR protein by at least 5% as compared to that in the absence of the corrector agent. Measurements of a gating activity of a CFTR protein are known in the art. The term gating activity used herein refers to changes in channel opening and closing of a CFTR protein or an activity in which a conducting channel of the CFTR protein becomes either physically available or unavailable.

In some embodiments, the corrector agent of the present invention is capable of stabilizing a CFTR protein, wherein said CFTR comprises a CFTRAF508 mutation and the plasma membrane levels of said CFTR in the presence of said agent are at least 300% of the level obtainable with a type I corrector with said CFTR protein.

In some embodiments, non-limiting examples of the type I correctors include Lumacaftor (VX-809), 1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661), VX-983, GLPG2222, GLPG2665, GLPG2851, VX-152, VX-440, FDL169, FDL304, FD2052160, and FD2035659. Examples of correctors are also disclosed in U.S. application Ser. Nos. 14/925,649; 14/926,727; and 15/205,512.

In more specific embodiment said type I corrector is selected from a group consisting of VX809, VX-661, VX-983, GLPG2222, GLPG2665, GLPG2851, VX-152, VX-440, FDL169, FDL304, FD2052160, and FD2035659.

In a more particular embodiment, said membrane level of said CFTR is measured in a Cell Surface Expression assay as disclosed herein.

In some embodiments, the corrector agent of the present invention is capable of stabilizing a CFTR protein, wherein the CFTR comprises a CFTRAF508 mutation and plasma membrane levels of said CFTR protein in the presence of said agent are at least 50, 60, 70, 80, 90, 100% of the level of wild-type CFTR in healthy cells.

In some embodiments, the corrector agent of the present invention directly binds to CFTR protein. More particularly said binding is measured using patch clamp and Back scattering technology as described herein.

In some embodiments, the corrector agent of the present invention is capable of stabilizing a CFTR protein, wherein said CFTR protein comprises NBD1 domain, wherein said domain comprises a CFTRAF508 mutation. In a more specific embodiment said NBD1 domain is not produced in a correctly folded form in the presence of said agent.

In some embodiments, the corrector agent of the present invention is capable of stabilizing a CFTR protein, wherein the corrector agent is capable of stabilizing CFTRAF508 mutation containing CFTR protein by at least 15% compared to wild-type CFTR levels in healthy cells.

In some embodiments, the corrector agent of the present invention is capable of stabilizing a CFTR protein, wherein the corrector agent reduces the open probability of the channel formed by said CFTR protein by at least 25, 30, 35, 40, 45, 50, 55, 60, 65, 70 75, 80, 85, 90, and 95%.

In some embodiments, the corrector agent of the present invention is capable of stabilizing a CFTR protein, wherein the corrector agent decreases the CFTR channel gating activity. In a particular embodiment the corrector agent decreases the CFTR channel gating activity in a dose dependent manner. In a more specific embodiment the reduced ability of opening of the CFTR channel is reversed in the presence of a potentiator agent.

In some embodiments the corrector agent of the present invention is capable of stabilizing a CFTR protein, wherein the corrector agent reduces the forkolin dependent CFTR channel activity by at least 25, 30, 35, 40, 45, 50, 55, 60, 65, 70 75, 80, 85, 90, and 95%.

In some embodiments, the corrector agent of the present invention is a compound described in the U.S. patent application Ser. No. 15/287,911 and the U.S. patent application Ser. No. 15/287,922 which are incorporated by reference herein in their entirety.

In some embodiments, the corrector agent of the present invention is a compound of formula (I) or a pharmaceutically acceptable salt thereof, (I)

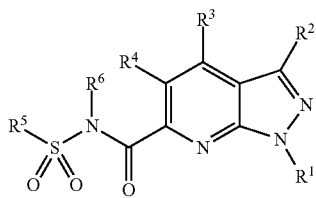

wherein
R¹ is G$^{1A}$, C$_1$-C$_6$ haloalkyl, or C$_1$-C$_6$ alkyl; wherein the C$_1$-C$_6$ haloalkyl and the C$_1$-C$_6$ alkyl are each optionally substituted with one G$^{1A}$;
G$^{1A}$, at each occurrence, is independently phenyl, 5-6 membered monocyclic heteroaryl, 4-7 membered monocyclic heterocycle, 5-11 membered fused bicyclic heterocycle, or C$_3$-C$_6$ monocyclic cycloalkyl; wherein each G$^{1A}$ is optionally substituted with 1, 2, 3, or 4 substituents independently selected from the group consisting of R$^{1a}$ and G$^{1B}$;
G$^{1B}$, at each occurrence, is independently 4-7 membered monocyclic heterocycle which is optionally substituted with 1, 2, 3, or 4 independently selected R$^{1b}$ groups;
R² is hydrogen, C$_2$-C$_4$ alkenyl, C$_1$-C$_6$ alkyl, C$_1$-C$_6$ haloalkyl, —OR$^{2xa}$, —N(R$^{2xa}$)(R$^{2xb}$), or G$^{2A}$;
R$^{2xa}$, at each occurrence, is independently C$_1$-C$_6$ alkyl, C$_1$-C$_6$ haloalkyl, or G$^{2B}$;
R$^{2xb}$ is hydrogen, C$_1$-C$_3$ alkyl, or C$_1$-C$_3$ haloalkyl;
G$^{2A}$ and G$^{2B}$ are each independently a 4-7 membered monocyclic heterocycle or a C$_3$-C$_6$ monocyclic cycloalkyl; wherein G$^{2A}$ and G$^{2B}$ are each optionally substituted with 1, 2, or 3 independently selected R$^{2a}$ groups;
R³ is G$^{3A}$, -G$^{3B}$-L$^1$-G$^{3C}$, -G$^{3B}$-L$^3$-G$^{3C}$-G$^{3E}$, alkylenyl)-G$^{3D}$, —OR$^{3a}$, or —N(R$^{3a}$)(R$^{3b}$);
R$^{3a}$, at each occurrence, is independently G$^{3D}$, C$_1$-C$_6$ haloalkyl, or C$_1$-C$_6$ alkyl; wherein the C$_1$-C$_6$ haloalkyl and the C$_1$-C$_6$ alkyl are each optionally substituted with one or two substituents independently selected from the group consisting of G$^{3D}$, —OR$^{3xa}$, and —N(R$^{3xb}$)$_2$;
R$^{3xa}$ and R$^{3xb}$, at each occurrence, are each independently hydrogen, C$_1$-C$_6$ haloalkyl, C$_1$-C$_6$ alkyl, or G$^{3D}$;
R$^{3b}$ is hydrogen, C$_1$-C$_6$ alkyl, or C$_1$-C$_6$ haloalkyl;
L¹ is a bond, C$_1$-C$_6$ alkylenyl, (C$_1$-C$_6$ alkylenyl)$_r$-L²-(C$_1$-C$_6$ alkylenyl) or O—(C$_1$-C$_6$ alkylenyl)-C(O), wherein the left end of the L¹ moiety is attached to G$^{3B}$;
L² is O, N(R$^x$), C(O), N(R$^x$)C(O), or C(O)N(R$^x$); wherein each R$^x$ is independently hydrogen, C$_1$-C$_6$ alkyl, or C$_1$-C$_6$ haloalkyl;
L³ is a bond or C$_1$-C$_6$ alkylenyl;
r is 0 or 1;
s is 0 or 1;
G$^{3A}$, G$^{3B}$, and G$^{3C}$ and each independently C$_3$-C$_{11}$ cycloalkyl, phenyl, 5-6 membered monocyclic heteroaryl, or 4-11 membered heterocycle; wherein G$^{3A}$, G$^{3B}$, and G$^{3C}$ are each optionally substituted with 1, 2, 3, or 4 independently selected R$^e$ groups;
G$^{3D}$, at each occurrence, is independently C$_3$-C$_8$ monocyclic cycloalkyl, 4-7 membered monocyclic heterocycle, a 5-11 membered fused bicyclic heterocycle, or a 5-11 membered spiro heterocycle; wherein each G$^{3D}$ is optionally substituted with 1, 2, 3, or 4 substituents independently selected from the group consisting of R$^e$ and G$^{3E}$;
G$^{3E}$, at each occurrence, is independently C$_3$-C$_8$ monocyclic cycloalkyl or 4-7 membered monocyclic heterocycle;

wherein each G$^{3E}$ is optionally substituted with 1, 2, 3, or 4 independently selected R$^e$ groups;
R⁴ is hydrogen, C$_1$-C$_3$ alkyl, or C$_1$-C$_3$ haloalkyl;
R⁵ is C$_1$-C$_6$ alkyl, C$_2$-C$_6$ alkenyl, C$_2$-C$_6$ alkynyl, C$_1$-C$_6$ haloalkyl, —N(R$^{5ax}$)(R$^{5bx}$), —OR$^{5dx}$, or G$^{5A}$;
wherein the C$_1$-C$_6$ alkyl and the C$_1$-C$_6$ haloalkyl are each optionally substituted with one or two substituents independently selected from the group consisting of G$^{5A}$, —CN, —N$_3$, —OR$^{5ax}$, —S(O)$_2$R$^{5ax}$, —S(O)$_2$N(R$^{5ax}$)(R$^{5bx}$), —N(R$^{5ax}$)(R$^{5bx}$), —N(R$^{5bx}$)S(O)$_2$R$^{5cx}$, —N(R$^{5bx}$)C(O)R$^{5cx}$, —(R$^{5bx}$)C(O)N(R$^{5ax}$)(R$^{5bx}$), —N(R$^{5bx}$)C(O)OR$^{5cx}$, —C(O)R$^{5ax}$, —C(O)OR$^{5ax}$, —C(O)N(R$^{5bx}$)S(O)$_2$R$^{5cx}$, and —C(O)N(R$^{5ax}$)(R$^{5bx}$);
R$^{5ax}$ and R$^{5bx}$, at each occurrence, are each independently hydrogen, C$_1$-C$_6$ alkyl, C$_1$-C$_6$ haloalkyl, —OR$^{5ex}$, —(C$_1$-C$_6$ alkylenyl)-OR$^{5ex}$, G$^{5A}$, or —(C$_1$-C$_6$ alkylenyl)-G$^{5A}$;
R$^{5cx}$, at each occurrence, is independently C$_1$-C$_6$ alkyl, C$_1$-C$_6$ haloalkyl, G$^{5A}$, or —(C$_1$-C$_6$ alkylenyl)-G$^{5A}$;
R$^{5dx}$ is C$_1$-C$_6$ alkyl, or C$_1$-C$_6$ haloalkyl;
R$^{5ex}$ is hydrogen, C$_1$-C$_6$ alkyl, or C$_1$-C$_6$ haloalkyl;
G$^{5A}$, at each occurrence, is independently C$_3$-C$_{11}$ cycloalkyl, phenyl, 5-6 membered monocyclic heteroaryl, or 4-11 membered heterocycle; wherein each G$^{5A}$ is optionally substituted with 1, 2, 3, or 4 independently selected R$^{5a}$ groups;
R$^{5a}$, at each occurrence, is independently C$_1$-C$_6$ alkyl, C$_2$-C$_6$ alkenyl, C$_2$-C$_6$ alkynyl, halogen, C$_1$-C$_6$ haloalkyl, oxo, G$^{5B}$, —CN, NO$_2$, —OR$^b$, —OC(O)R$^c$, —OC(O)N(R$^d$)$_2$, —SR$^b$, —S(O)$_2$R$^b$, —S(O)$_2$N(R$^d$)$_2$, —C(O)R$^b$, —C(O)OR$^b$, —C(O)N(R$^d$)$_2$, —C(O)N(R$^d$)S(O)$_2$R$^c$, —N(R$^d$)$_2$, —N(R$^d$)C(O)R$^c$, —N(R$^d$)S(O)$_2$R$^c$, —N(R$^d$)C(O)OR$^b$), —N(R$^d$)C(O)N(R$^d$)$_2$, —N(R$^d$)S(O)$_2$N(R$^d$)$_2$, —(C$_1$-C$_6$ alkylenyl)-CN, —(C$_1$-C$_6$ alkylenyl)-G$^{5B}$, —(C$_1$-C$_6$ alkylenyl)-OR$^b$, —(C$_1$-C$_6$ alkylenyl)-OC(O)R$^c$, —(C$_1$-C$_6$ alkylenyl)-OC(O)N(R$^d$)$_2$, —(C$_1$-C$_6$ alkylenyl)-SR$^b$, —(C$_1$-C$_6$ alkylenyl)-S(O)$_2$R$^b$, —(C$_1$-C$_6$ alkylenyl)-S(O)$_2$N(R$^d$)$_2$, —(C$_1$-C$_6$ alkylenyl)-C(O)R$^b$, —(C$_1$-C$_6$ alkylenyl)-C(O)OR$^b$, —(C$_1$-C$_6$ alkylenyl)-C(O)N(R$^d$)$_2$, —(C$_1$-C$_6$ alkylenyl)-C(O)N(R$^d$)S(O)$_2$R$^c$, —(C$_1$-C$_6$ alkylenyl)-N(R$^d$)$_2$, —(C$_1$-C$_6$ alkylenyl)-N(R$^d$)C(O)R$^c$, —(C$_1$-C$_6$ alkylenyl)-N(R$^d$)S(O)$_2$R$^c$, —(C$_1$-C$_6$ alkylenyl)-N(R$^d$)C(O)O(R$^c$), —(C$_1$-C$_6$ alkylenyl)-N(R$^d$)C(O)N(R$^d$)$_2$, or —(C$_1$-C$_6$ alkylenyl)-N(R$^d$)S(O)$_2$N(R$^d$)$_2$;
R$^b$ and R$^d$, at each occurrence, are each independently hydrogen, C$_1$-C$_6$ alkyl, C$_1$-C$_6$ haloalkyl, alkoxyalkyl, G$^{5B}$, or —(C$_1$-C$_6$ alkylenyl)-G$^{5B}$;
R$^c$, at each occurrence, is independently C$_1$-C$_6$ alkyl, C$_1$-C$_6$ haloalkyl, alkoxyalkyl, G$^{5B}$, or —(C$_1$-C$_6$ alkylenyl)-G$^{5B}$;
G$^{5B}$, at each occurrence, is independently C$_3$-C$_6$ monocyclic cycloalkyl, phenyl, 5-6 membered monocyclic heteroaryl, or 4-7 membered monocyclic heterocycle; wherein each G$^{5B}$ is optionally substituted with 1, 2, 3, or 4 independently selected R$^{5b}$ groups;
R$^e$, at each occurrence, is independently C$_2$-C$_6$ alkenyl, C$_2$-C$_6$ alkynyl, C$_1$-C$_6$ alkyl, C$_1$-C$_6$ haloalkyl, halogen, oxo, —CN, —N$_3$, NO$_2$, —OR$^f$, —OC(O)R$^g$, —OC(O)NR$^f$R$^h$, —SR$^f$, —S(O)$_2$R$^f$, —S(O)$_2$NR$^f$R$^h$, —C(O)R$^f$, —C(O)OR$^f$, —C(O)NR$^f$R$^h$, —C(O)N(R$^h$)S(O)$_2$R$^f$, —N(R$^f$)$_2$, —N(R$^h$)C(O)R$^h$, —N(R$^h$)S(O)$_2$R$^g$, —N(R$^h$)C(O)O(R$^g$), —N(R$^h$)C(O)NR$^f$R$^h$, or —N(R$^h$)S(O)$_2$NR$^f$R$^h$;
wherein the C$_1$-C$_6$ haloalkyl and the C$_1$-C$_6$ alkyl are each optionally substituted with 1 or 2 substituents independently selected from the group consisting of —CN, NO$_2$, —OR$^f$, —OC(O)R$^g$, —OC(O)NR$^f$R$^h$, —SR$^f$, —S(O)$_2$R$^f$, —S(O)$_2$NR$^f$R$^h$, —C(O)R$^f$, —C(O)OR$^f$, —C(O)NR$^f$R$^h$, —C(O)N(R$^h$)S(O)$_2$R$^f$, —N(R$^f$)$_2$, —N(R$^h$)C(O)R$^g$, —N(R$^h$)S(O)$_2$R$^g$, —N(R$^h$)C(O)O(R$^g$), —N(R$^h$)C(O)NR$^f$R$^h$, and —N(R$^h$)S(O)$_2$NR$^f$R$^h$;

R$^f$, at each occurrence, is independently hydrogen, C$_1$-C$_6$ alkyl, C$_2$-C$_6$ alkenyl, C$_2$-C$_6$ alkynyl, C$_1$-C$_6$ haloalkyl, —(C$_1$-C$_6$ alkylenyl)-CN, —(C$_1$-C$_6$ alkylenyl)-OR$^m$, —(C$_1$-C$_6$ alkylenyl)-OC(O)R$^n$, —(C$_1$-C$_6$ alkylenyl)-OC(O)N(R$^m$)$_2$, —(C$_1$-C$_6$ alkylenyl)-SR$^m$, —(C$_1$-C$_6$ alkylenyl)-S(O)$_2$R$^m$, —(C$_1$-C$_6$ alkylenyl)-S(O)$_2$N(R$^m$)$_2$, —(C$_1$-C$_6$ alkylenyl)-C(O)R$^m$, —(C$_1$-C$_6$ alkylenyl)-C(O)OR$^m$, —(C$_1$-C$_6$ alkylenyl)-C(O)N(R$^m$)$_2$, —(C$_1$-C$_6$ alkylenyl)-C(O)N(R$^m$)S(O)$_2$R$^n$, —(C$_1$-C$_6$ alkylenyl)-N(R$^m$)$_2$, —(C$_1$-C$_6$ alkylenyl)-N(R$^m$)C(O)R$^n$, —(C$_1$-C$_6$ alkylenyl)-N(R$^m$)S(O)$_2$R$^n$, —(C$_1$-C$_6$ alkylenyl)-N(R$^m$)C(O)O(R$^n$), —(C$_1$-C$_6$ alkylenyl)-N(R$^m$)C(O)N(R$^m$)$_2$, or —(C$_1$-C$_6$ alkylenyl)-N(R$^m$)S(O)$_2$N(R$^m$)$_2$;

R$^g$, at each occurrence, is independently C$_1$-C$_6$ alkyl, C$_2$-C$_6$ alkenyl, C$_2$-C$_6$ alkynyl, C$_1$-C$_6$ haloalkyl, —(C$_1$-C$_6$ alkylenyl)-CN, —(C$_1$-C$_6$ alkylenyl)-OR$^m$, —(C$_1$-C$_6$ alkylenyl)-OC(O)R$^n$, —(C$_1$-C$_6$ alkylenyl)-OC(O)N(R$^m$)$_2$, —(C$_1$-C$_6$ alkylenyl)-SR$^m$, —(C$_1$-C$_6$ alkylenyl)-S(O)$_2$R$^m$, —(C$_1$-C$_6$ alkylenyl)-S(O)$_2$N(R$^m$)$_2$, —(C$_1$-C$_6$ alkylenyl)-C(O)R$^m$, —(C$_1$-C$_6$ alkylenyl)-C(O)OR$^m$, —(C$_1$-C$_6$ alkylenyl)-C(O)N(R$^m$)$_2$, —(C$_1$-C$_6$ alkylenyl)-C(O)N(R$^m$)S(O)$_2$R$^n$, —(C$_1$-C$_6$ alkylenyl)-N(R$^m$)$_2$, —(C$_1$-C$_6$ alkylenyl)-N(R$^m$)C(O)R$^n$, —(C$_1$-C$_6$ alkylenyl)-N(R$^m$)S(O)$_2$R$^n$, —(C$_1$-C$_6$ alkylenyl)-N(R$^m$)C(O)O(R$^n$)—(C$_1$-C$_6$ alkylenyl)-N(R$^m$)C(O)N(R$^m$)$_2$, or —(C$_1$-C$_6$ alkylenyl)-N(R$^m$)S(O)$_2$N(R$^m$)$_2$;

R$^h$, at each occurrence, is independently hydrogen, C$_1$-C$_6$ alkyl, C$_1$-C$_6$ haloalkyl, or —(C$_1$-C$_6$ alkylenyl)-OR$^m$;

R$^{1a}$, R$^{1b}$, R$^{2a}$, and R$^{5b}$, at each occurrence, are each independently C$_1$-C$_6$ alkyl, C$_2$-C$_6$ alkenyl, C$_2$-C$_6$ alkynyl, halogen, C$_1$-C$_6$ haloalkyl, oxo, —CN, NO$_2$, —OR$^m$, —OC(O)R$^n$, —OC(O)N(R$^m$)$_2$, —SR$^m$, —S(O)$_2$R$^m$, —S(O)$_2$N(R$^m$)$_2$, —C(O)R$^m$, —C(O)OR$^m$, —C(O)O(benzyl), —C(O)N(R$^m$)$_2$, —C(O)N(R$^m$)S(O)$_2$R$^n$, —N(R$^m$)$_2$, —N(R$^m$)(alkoxyalkyl), —N(alkoxyalkyl)$_2$, —N(R$^m$)C(O)R$^n$, —N(R$^m$)S(O)$_2$R$^n$, —N(R$^m$)C(O)O(R$^n$), —N(R$^m$)C(O)N(R$^m$)$_2$, —N(R$^m$)S(O)$_2$N(R$^m$)$_2$, —(C$_1$-C$_6$ alkylenyl)-CN, —(C$_1$-C$_6$ alkylenyl)-OR$^m$, —(C$_1$-C$_6$ alkylenyl)-OC(O)R$^n$, —(C$_1$-C$_6$ alkylenyl)-OC(O)N(R$^m$)$_2$, —(C$_1$-C$_6$ alkylenyl)-SR$^m$, —(C$_1$-C$_6$ alkylenyl)-S(O)$_2$R$^m$, —(C$_1$-C$_6$ alkylenyl)-S(O)$_2$N(R$^m$)$_2$, —(C$_1$-C$_6$ alkylenyl)-C(O)R$^m$, —(C$_1$-C$_6$ alkylenyl)-C(O)OR$^m$, —(C$_1$-C$_6$ alkylenyl)-C(O)N(R$^m$)$_2$, —(C$_1$-C$_6$ alkylenyl)-C(O)N(R$^m$)S(O)$_2$R$^n$, —(C$_1$-C$_6$ alkylenyl)-N(R$^m$)$_2$, —(C$_1$-C$_6$ alkylenyl)-N(R$^m$)C(O)R$^n$, —(C$_1$-C$_6$ alkylenyl)-N(R$^m$)S(O)$_2$R$^n$, —(C$_1$-C$_6$ alkylenyl)-N(R$^m$)C(O)O(R$^n$), —(C$_1$-C$_6$ alkylenyl)-N(R$^m$)C(O)N(R$^n$)$_2$, or —(C$_1$-C$_6$ alkylenyl)-N(R$^m$)S(O)$_2$N(R$^n$)$_2$;

R$^m$, at each occurrence, is independently hydrogen, C$_1$-C$_6$ alkyl, or C$_1$-C$_6$ haloalkyl;

R$^n$, at each occurrence, is independently C$_1$-C$_6$ alkyl or C$_1$-C$_6$ haloalkyl;

R$^6$ is hydrogen, C$_1$-C$_6$ alkyl, or C$_1$-C$_6$ haloalkyl; or

R$^5$ and R$^6$ together form a C$_1$-C$_6$ alkylenyl or —N(R$^z$)—(C$_1$-C$_6$ alkylenyl)- wherein the N(R$^z$) is attached to the S(O)$_2$ moiety of formula (I); and R$^z$ is hydrogen, C$_1$-C$_6$ alkyl, or C$_1$-C$_6$ haloalkyl.

In some embodiments, the corrector agent of the present invention is a compound of formula (II) or a pharmaceutically acceptable salt thereof,

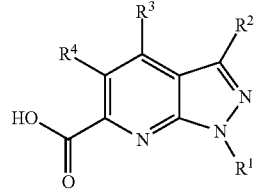

(II)

wherein

R$^1$ is G$^{1A}$, -G$^{1B}$-G$^{1C}$, -G$^{1B}$-L$^{1A}$-G$^{1C}$, C$_1$-C$_6$ haloalkyl, C$_1$-C$_6$ alkyl, —(C$_1$-C$_6$alkylenyl)-CN, —(C$_1$-C$_6$ alkylenyl)-G$^{1D}$, or -G$^{1D}$-O-benzyl;

L$^{1A}$ is —O— or —O—(C$_1$-C$_3$ alkylenyl)-; wherein the left end of the L$^{1A}$ moiety is attached to G$^{1B}$;

G$^{1A}$ is phenyl, aryl, 5-6 membered monocyclic heteroaryl, 4-7 membered monocyclic heterocycle, fused bicyclic heterocycle, or C$_3$-C$_6$ monocyclic cycloalkyl; wherein each G$^{1A}$ is optionally substituted with 1, 2, 3, or 4 independently selected R$^{1a}$ groups;

G$^{1B}$ is phenyl or 5-6 membered monocyclic heteroaryl; wherein each G$^{1B}$ is optionally substituted with 1, 2, 3, or 4 independently selected R$^{1b}$ groups;

G$^{1C}$ is 4-7 membered monocyclic heterocycle which is optionally substituted with 1, 2, 3, or 4 independently selected R$^{1c}$ groups;

G$^{1D}$, at each occurrence, is a 4-7 membered monocyclic heterocycle, 5-6 membered monocyclic heteroaryl, or a C$_3$-C$_6$ monocyclic cycloalkyl; wherein each G$^{1D}$ is optionally substituted with 1, 2, 3, or 4 independently selected R$^{1d}$ groups;

R$^2$ is C$_2$-C$_4$ alkenyl, C$_1$-C$_6$ alkyl, C$_1$-C$_6$ haloalkyl, —OR$^{2xa}$, —(C$_1$-C$_6$ alkylenyl)-OR$^{2xb}$, —(C$_1$-C$_6$ alkylenyl)-N(R$^{2xb}$)$_2$, —C(O)OR$^{2xb}$, —C(O)N(R$^{2xb}$)$_2$, or -G$^{2A}$;

R$^{2xa}$ is hydrogen, C$_1$-C$_6$ alkyl, C$_1$-C$_6$ haloalkyl, or G$^{2B}$;

R$^{2xb}$, at each occurrence, is independently hydrogen, C$_1$-C$_6$ alkyl, or C$_1$-C$_6$ haloalkyl;

G$^{2A}$ and G$^{2B}$ are each independently 4-7 membered monocyclic heterocycle or C$_3$-C$_6$ monocyclic cycloalkyl; wherein G$^{2A}$ and G$^{2B}$ are each optionally substituted with 1, 2, or 3 independently selected R$^{2a}$ groups;

R$^3$ is halogen, G$^{3A}$, -G$^{3B}$-L$^1$-G$^{3C}$, -G$^{3B}$-L$^3$-G$^{3C}$-L$^4$-G$^{3F}$, —(C$_1$-C$_6$ alkylenyl)-G$^{3E}$, —OR$^{3a}$, —N(R$^{3a}$)(R$^{3b}$), —N(R$^{3b}$)C(O)G$^{3D}$, or —C(O)G$^{3D}$;

R$^{3a}$, at each occurrence, is independently G$^{3E}$, C$_1$-C$_6$ haloalkyl, or C$_1$-C$_6$ alkyl; wherein the C$_1$-C$_6$ haloalkyl and the C$_1$-C$_6$ alkyl are each optionally substituted with one or two substituents independently selected from the group consisting of G$^{3E}$, —OR$^{3xa}$, —C(O)G$^{3D}$, —N(R$^{3xb}$)$_2$, and —S(O)$_2$R$^{3xc}$;

R$^{3xa}$, R$^{3xb}$, and R$^{3xc}$, at each occurrence, are each independently hydrogen, C$_1$-C$_6$ haloalkyl, C$_1$-C$_6$ alkyl, G$^{3E}$, —(C$_1$-C$_6$ alkylenyl)-OR$^{3ya}$, or —(C$_1$-C$_6$ alkylenyl)-N(R$^{3ya}$)$_2$; wherein R$^{3ya}$, at each occurrence, is independently hydrogen, C$_1$-C$_6$ alkyl, or C$_1$-C$_6$ haloalkyl;

R$^{3b}$, at each occurrence, is hydrogen, C$_1$-C$_6$ alkyl, or C$_1$-C$_6$ haloalkyl;

L$^1$ is a bond, C$_1$-C$_6$ alkylenyl, (C$_1$-C$_6$ alkylenyl)$_r$-L$^2$-(C$_1$-C$_6$ alkylenyl)$_s$, or O—(C$_1$-C$_6$ alkylenyl)-C(O), wherein the left end of the L$^1$ moiety is attached to G$^{3B}$;

L$^2$ is O, N(R$^x$), C(O), N(R$^x$)C(O), or C(O)N(R$^x$); wherein each R$^x$ is independently hydrogen, C$_1$-C$_6$ alkyl, or C$_1$-C$_6$ haloalkyl;

L$^3$ is a bond or C$_1$-C$_6$ alkylenyl;

L$^4$ is a bond, C$_1$-C$_6$ alkylenyl, O, N(R$^{2x}$), C(O), N(R$^{2x}$)C(O), or C(O)N(R$^{2x}$); wherein each R$^{2x}$ is independently hydrogen, C$_1$-C$_6$ alkyl, or C$_1$-C$_6$ haloalkyl;

r is 0 or 1;

s is 0 or 1;

G$^{3A}$, G$^{3B}$, and G$^{3C}$, are each independently C$_3$-C$_{11}$ cycloalkyl, phenyl, 5-6 membered monocyclic heteroaryl, or 4-11 membered heterocycle, wherein G$^{3A}$, G$^{3B}$, and G$^{3C}$ are each optionally substituted with 1, 2, 3, or 4 independently selected R$^e$ groups;

G$^{3D}$, at each occurrence, is 4-7 membered monocyclic heterocycle which is optionally substituted with 1, 2, 3, or 4 independently selected R$^e$ groups;

G$^{3E}$, at each occurrence, is independently C$_3$-C$_8$ monocyclic cycloalkyl or 4-11 membered heterocycle; wherein each G$^{3E}$ is optionally substituted with 1, 2, 3, or 4 substituents independently selected from the group consisting of R$^e$ and G$^{3F}$;

G$^{3F}$, at each occurrence, is independently a 4-7 membered monocyclic heterocycle or a C$_3$-C$_6$ monocyclic cycloalkyl; wherein each G$^{3F}$ is optionally substituted with 1, 2, 3, or 4 independently selected R$^e$ groups;

R$^e$, at each occurrence, is independently C$_2$-C$_6$ alkenyl, C$_2$-C$_6$ alkynyl, C$_1$-C$_6$ alkyl, C$_1$-C$_6$ haloalkyl, halogen, oxo, —CN, —N$_3$, NO$_2$, —OR$^f$, —OC(O)R$^g$, —OC(O)NR$^f$R$^h$, —SR$^f$, —S(O)$_2$R$^f$, —S(O)$_2$NR$^f$R$^h$, —C(O)R$^f$, —C(O)OR$^f$, —C(O)NR$^f$R$^h$, —C(O)N(R$^h$)S(O)$_2$R$^f$, —N(R$^f$)$_2$, —N(R$^h$)C(O)R$^f$, —N(R$^h$)S(O)$_2$R$^g$, —N(R$^h$)C(O)O(R$^g$), —N(R$^h$)C(O)NR$^f$R$^h$, or —N(R$^h$)S(O)$_2$NR$^f$R$^h$; wherein the C$_1$-C$_6$ haloalkyl and the C$_1$-C$_6$ alkyl are each optionally substituted with 1 or 2 substituents independently selected from the group consisting of halogen, —CN, NO$_2$, —OR$^f$, —OC(O)R$^g$, —OC(O)NR$^f$R$^h$, —SR$^f$, —S(O)$_2$R$^f$, —S(O)$_2$NR$^f$R$^h$, —C(O)R$^f$, —C(O)OR$^f$, —C(O)NR$^f$R$^h$, —C(O)N(R$^h$)S(O)$_2$R$^f$, —N(R$^f$)$_2$, —N(R$^h$)C(O)R$^f$, —N(R$^h$)S(O)$_2$R$^g$, —N(R$^h$)C(O)O(R$^g$), —N(R$^h$)C(O)NR$^f$R$^h$, and —N(R$^h$)S(O)$_2$NR$^f$R$^h$;

R$^f$, at each occurrence, is independently hydrogen, C$_1$-C$_6$ alkyl, C$_2$-C$_6$ alkenyl, C$_2$-C$_6$ alkynyl, C$_1$-C$_6$ haloalkyl, —(C$_1$-C$_6$ alkylenyl)-CN, —(C$_1$-C$_6$ alkylenyl)-OR$^m$, —(C$_1$-C$_6$ alkylenyl)-OC(O)R$^n$, —(C$_1$-C$_6$ alkylenyl)-OC(O)N(R$^m$)$_2$, —(C$_1$-C$_6$ alkylenyl)-SR$^m$, —(C$_1$-C$_6$ alkylenyl)-S(O)$_2$R$^m$, —(C$_1$-C$_6$ alkylenyl)-S(O)$_2$N(R$^m$)$_2$, —(C$_1$-C$_6$ alkylenyl)-C(O)R$^m$, —(C$_1$-C$_6$ alkylenyl)-C(O)OR$^m$, —(C$_1$-C$_6$ alkylenyl)-C(O)N(R$^m$)$_2$, —(C$_1$-C$_6$ alkylenyl)-C(O)N(R$^m$)S(O)$_2$R$^n$, —(C$_1$-C$_6$ alkylenyl)-N(R$^m$)$_2$, —(C$_1$-C$_6$ alkylenyl)-N(R$^m$)C(O)R$^n$, —(C$_1$-C$_6$ alkylenyl)-N(R$^m$)S(O)$_2$R$^n$, —(C$_1$-C$_6$ alkylenyl)-N(R$^m$)C(O)O(R$^n$), —(C$_1$-C$_6$ alkylenyl)-N(R$^m$)C(O)N(R$^m$)$_2$, or —(C$_1$-C$_6$ alkylenyl)-N(R$^m$)S(O)$_2$N(R$^m$)$_2$;

R$^g$, at each occurrence, is independently C$_1$-C$_6$ alkyl, C$_2$-C$_6$ alkenyl, C$_2$-C$_6$ alkynyl, C$_1$-C$_6$ haloalkyl, —(C$_1$-C$_6$ alkylenyl)-CN, —(C$_1$-C$_6$ alkylenyl)-OR$^m$, —(C$_1$-C$_6$ alkylenyl)-OC(O)R$^n$, —(C$_1$-C$_6$ alkylenyl)-OC(O)N(R$^m$)$_2$, —(C$_1$-C$_6$ alkylenyl)-SR$^m$, —(C$_1$-C$_6$ alkylenyl)-S(O)$_2$R$^m$, —(C$_1$-C$_6$ alkylenyl)-S(O)$_2$N(R$^m$)$_2$, —(C$_1$-C$_6$ alkylenyl)-C(O)R$^m$, —(C$_1$-C$_6$ alkylenyl)-C(O)OR$^m$, —(C$_1$-C$_6$ alkylenyl)-C(O)N(R$^m$)$_2$, —(C$_1$-C$_6$ alkylenyl)-C(O)N(R$^m$)S(O)$_2$R$^n$, —(C$_1$-C$_6$ alkylenyl)-N(R$^m$)$_2$, —(C$_1$-C$_6$ alkylenyl)-N(R$^m$)C(O)R$^n$, —(C$_1$-C$_6$ alkylenyl)-N(R$^m$)S(O)$_2$R$^n$, —(C$_1$-C$_6$ alkylenyl)-N(R$^m$)C(O)O(R$^n$), —(C$_1$-C$_6$ alkylenyl)-N(R$^m$)C(O)N(R$^m$)$_2$, or —(C$_1$-C$_6$ alkylenyl)-N(R$^m$)S(O)$_2$N(R$^m$)$_2$;

R$^h$, at each occurrence, is independently hydrogen, C$_1$-C$_6$ alkyl, C$_1$-C$_6$ haloalkyl, or —(C$_1$-C$_6$ alkylenyl)-OR$^m$;

R$^{1a}$, R$^{1b}$, R$^{1c}$, R$^{1d}$, and R$^{2a}$, at each occurrence, are each independently C$_1$-C$_6$ alkyl, C$_2$-C$_6$ alkenyl, C$_2$-C$_6$ alkynyl, halogen, C$_1$-C$_6$ haloalkyl, oxo, —CN, NO$_2$, —OR$^m$, —OC(O)R$^n$, —OC(O)N(R$^m$)$_2$, —SR$^m$, —S(O)$_2$R$^m$, —S(O)$_2$N(R$^m$)$_2$, —C(O)R$^m$, —C(O)OR$^m$, —C(O)N(R$^m$)$_2$, —C(O)N(R$^m$)S(O)$_2$R$^n$, —N(R$^m$)$_2$, —N(R$^m$)(alkoxyalkyl), —N(alkoxyalkyl)$_2$, —N(R$^m$)C(O)R$^n$, —N(R$^m$)S(O)$_2$R$^n$, —N(R$^m$)C(O)O(R$^n$), —N(R$^m$)C(O)N(R$^m$)$_2$, —N(R$^m$)S(O)$_2$N(R$^m$)$_2$, —(C$_1$-C$_6$ alkylenyl)-CN, —(C$_1$-C$_6$ alkylenyl)-OR$^m$, —(C$_1$-C$_6$ alkylenyl)-OC(O)R$^n$, —(C$_1$-C$_6$ alkylenyl)-OC(O)N(R$^m$)$_2$, —(C$_1$-C$_6$ alkylenyl)-SR$^m$, —(C$_1$-C$_6$ alkylenyl)-S(O)$_2$R$^m$, —(C$_1$-C$_6$ alkylenyl)-S(O)$_2$N(R$^m$)$_2$, —(C$_1$-C$_6$ alkylenyl)-C(O)R$^m$, —(C$_1$-C$_6$ alkylenyl)-C(O)OR$^m$, —(C$_1$-C$_6$ alkylenyl)-C(O)N(R$^m$)$_2$, —(C$_1$-C$_6$ alkylenyl)-C(O)N(R$^m$)S(O)$_2$R$^n$, —(C$_1$-C$_6$ alkylenyl)-N(R$^m$)$_2$, —(C$_1$-C$_6$ alkylenyl)-N(R$^m$)C(O)R$^n$, —(C$_1$-C$_6$ alkylenyl)-N(R$^m$)S(O)$_2$R$^n$, —(C$_1$-C$_6$ alkylenyl)-N(R$^m$)C(O)O(R$^n$), —(C$_1$-C$_6$ alkylenyl)-N(R$^m$)C(O)N(R$^n$, or —(C$_1$-C$_6$ alkylenyl)-N(R$^m$)S(O)$_2$N(R$^n$)$_2$;

R$^m$, at each occurrence, is independently hydrogen, C$_1$-C$_6$ alkyl, or C$_1$-C$_6$ haloalkyl;

R$^n$, at each occurrence, is independently C$_1$-C$_6$ alkyl or C$_1$-C$_6$ haloalkyl; and R$^4$ is hydrogen, C$_1$-C$_3$ alkyl, or C$_1$-C$_3$ haloalkyl;

with the proviso that when R$^1$ is C$_1$-C$_6$ alkyl or G$^{1A}$, wherein G$^{1A}$ is optionally substituted phenyl, optionally substituted 5-6 membered monocyclic heteroaryl, or optionally substituted 4-7 membered monocyclic heterocycle, R$^2$ is C$_1$-C$_6$ alkyl, and R$^3$ is G$^{3A}$, then G$^{3A}$ is not optionally substituted phenyl or optionally substituted 5-6 membered monocyclic heteroaryl.

In some embodiments, the corrector agent of the present invention is a compound selected from a group consisting of N-(methanesulfonyl)-3-methyl-4-[4-(morpholin-4-yl)phenyl]-1-phenyl-1H-pyrazolo[3,4-b]pyridine-6-carboxamide;

N-(benzenesulfonyl)-3-methyl-4-[4-(morpholin-4-yl)phenyl]-1-phenyl-1H-pyrazolo[3,4-b]pyridine-6-carboxamide;

3-methyl-4-[4-(morpholin-4-yl)phenyl]-1-phenyl-N-(trifluoromethanesulfonyl)-1H-pyrazolo[3,4-b]pyridine-6-carboxamide;

N-(cyclopropanesulfonyl)-3-methyl-4-[4-(morpholin-4-yl)phenyl]-1-phenyl-1H-pyrazolo[3,4-b]pyridine-6-carboxamide;

N-(ethanesulfonyl)-3-methyl-4-[4-(morpholin-4-yl)phenyl]-1-phenyl-1H-pyrazolo[3,4-b]pyridine-6-carboxamide;

N-(methanesulfonyl)-3-methyl-4-[4-(morpholin-4-yl)phenyl]-1-[3-(trifluoromethoxy)phenyl]-1H-pyrazolo[3,4-b]pyridine-6-carboxamide;

4-[4-(dimethylamino)phenyl]-N-(methanesulfonyl)-1-phenyl-3-(propan-2-yl)-1H-pyrazolo[3,4-b]pyridine-6-carboxamide;

N-(methanesulfonyl)-3-methyl-4-[4-(morpholin-4-yl)phenyl]-1-[3-(trifluoromethyl)phenyl]-1H-pyrazolo[3,4-b]pyridine-6-carboxamide;

1-cyclohexyl-4-[2-(dimethylamino)pyrimidin-5-yl]-N-(methanesulfonyl)-3-(propan-2-yl)-1H-pyrazolo[3,4-b]pyridine-6-carboxamide;

1-[3-(azetidin-1-yl)phenyl]-N-(methanesulfonyl)-4-[4-(morpholin-4-yl)phenyl]-3-(propan-2-yl)-1H-pyrazolo[3,4-b]pyridine-6-carboxamide;

1-cyclohexyl-N-(methanesulfonyl)-4-[2-(morpholin-4-yl)pyrimidin-5-yl]-3-(propan-2-yl)-1H-pyrazolo[3,4-b]pyridine-6-carboxamide;

3-tert-butyl-1-cyclopentyl-N-(methanesulfonyl)-4-[6-(morpholin-4-yl)pyridin-3-yl]-1H-pyrazolo[3,4-b]pyridine-6-carboxamide;

N-(methanesulfonyl)-3-methyl-1-phenyl-4-(piperidin-1-yl)-1H-pyrazolo[3,4-b]pyridine-6-carboxamide;

N-(methanesulfonyl)-4-(4-methoxyphenyl)-3-methyl-1-phenyl-1H-pyrazolo[3,4-b]pyridine-6-carboxamide;

N-(ethanesulfonyl)-4-(4-methoxyphenyl)-3-methyl-1-phenyl-1H-pyrazolo[3,4-b]pyridine-6-carboxamide;

N-(methanesulfonyl)-4-[4-(morpholin-4-yl)phenyl]-3-(propan-2-yl)-1-[3-(pyrrolidin-1-yl)phenyl]-1H-pyrazolo[3,4-b]pyridine-6-carboxamide;

4-[4-(dimethylamino)phenyl]-N-(methanesulfonyl)-1-(6-methoxypyridin-3-yl)-3-(propan-2-yl)-1H-pyrazolo[3,4-b]pyridine-6-carboxamide;

1-(3-chloro-4-methylphenyl)-N-(methanesulfonyl)-4-(4-methoxyphenyl)-3-methyl-1H-pyrazolo[3,4-b]pyridine-6-carboxamide;

N-(ethanesulfonyl)-3-methyl-1-phenyl-4-(piperidin-1-yl)-1H-pyrazolo[3,4-b]pyridine-6-carboxamide;

N-(methanesulfonyl)-4-[2-(morpholin-4-yl)pyrimidin-5-yl]-1-phenyl-3-(propan-2-yl)-1H-pyrazolo[3,4-b]pyridine-6-carboxamide;

1-(2,4-difluorophenyl)-N-(methanesulfonyl)-3-methyl-4-[4-(morpholin-4-yl)phenyl]-1H-pyrazolo[3,4-b]pyridine-6-carboxamide;

1-cyclohexyl-4-[6-(dimethylamino)pyridin-3-yl]-N-(methanesulfonyl)-3-(propan-2-yl)-1H-pyrazolo[3,4-b]pyridine-6-carboxamide;

1-(3,5-difluorophenyl)-N-(methanesulfonyl)-3-methyl-4-[4-(morpholin-4-yl)phenyl]-1H-pyrazolo[3,4-b]pyridine-6-carboxamide;

1-(3,5-dimethylphenyl)-N-(methanesulfonyl)-3-methyl-4-[4-(morpholin-4-yl)phenyl]-1H-pyrazolo[3,4-b]pyridine-6-carboxamide;

1-(3,4-difluorophenyl)-N-(methanesulfonyl)-3-methyl-4-[4-(morpholin-4-yl)phenyl]-1H-pyrazolo[3,4-b]pyridine-6-carboxamide;

4-[4-(dimethyl amino)phenyl]-N-(methanesulfonyl)-3-methyl-1-[3-(trifluoromethyl)phenyl]-1H-pyrazolo[3,4-b]pyridine-6-carboxamide;

N-(methanesulfonyl)-4-(4-methoxyphenyl)-3-methyl-1-(3-methylphenyl)-1H-pyrazolo[3,4-b]pyridine-6-carboxamide;

N-(ethanesulfonyl)-4-(4-methoxyphenyl)-3-methyl-1-(3-methylphenyl)-1H-pyrazolo[3,4-b]pyridine-6-carboxamide;

4-[2-(dimethylamino)pyrimidin-5-yl]-N-(methanesulfonyl)-1-[3-(morpholin-4-yl)phenyl]-3-(propan-2-yl)-1H-pyrazolo[3,4-b]pyridine-6-carboxamide;

4-[2-(dimethylamino)pyrimidin-5-yl]-N-(ethanesulfonyl)-1-[3-(morpholin-4-yl)phenyl]-3-(propan-2-yl)-1H-pyrazolo[3,4-b]pyridine-6-carboxamide;

4-[6-(dimethylamino)pyridin-3-yl]-N-(methanesulfonyl)-1-[3-(morpholin-4-yl)phenyl]-3-(propan-2-yl)-1H-pyrazolo[3,4-b]pyridine-6-carboxamide;

4-[6-(dimethylamino)pyridin-3-yl]-N-(ethanesulfonyl)-1-[3-(morpholin-4-yl)phenyl]-3-(propan-2-yl)-1H-pyrazolo[3,4-b]pyridine-6-carboxamide;

4-[4-(dimethylamino)phenyl]-N-(methanesulfonyl)-3-methyl-1-phenyl-1H-pyrazolo[3,4-b]pyridine-6-carboxamide;

N-(methanesulfonyl)-4-[6-(morpholin-4-yl)pyridin-3-yl]-1-phenyl-3-(propan-2-yl)-1H-pyrazolo[3,4-b]pyridine-6-carboxamide;

N-(ethanesulfonyl)-4-[6-(morpholin-4-yl)pyridin-3-yl]-1-phenyl-3-(propan-2-yl)-1H-pyrazolo[3,4-b]pyridine-6-carboxamide;

N-(methanesulfonyl)-1-[3-(3-methoxyazetidin-1-yl)phenyl]-4-[4-(morpholin-4-yl)phenyl]-3-(propan-2-yl)-1H-pyrazolo[3,4-b]pyridine-6-carboxamide;

N-(methanesulfonyl)-3-methyl-4-[6-(morpholin-4-yl)pyridin-3-yl]-1-phenyl-1H-pyrazolo[3,4-b]pyridine-6-carboxamide;

1-(4,4-difluorocyclohexyl)-N-(methanesulfonyl)-4-[4-(morpholin-4-yl)phenyl]-3-(propan-2-yl)-1H-pyrazolo[3,4-b]pyridine-6-carboxamide;

N-(methanesulfonyl)-4-[4-(morpholin-4-yl)phenyl]-1-(oxan-3-yl)-3-(propan-2-yl)-1H-pyrazolo[3,4-b]pyridine-6-carboxamide;

N-(ethanesulfonyl)-4-[4-(morpholin-4-yl)phenyl]-1-(oxan-3-yl)-3-(propan-2-yl)-1H-pyrazolo[3,4-b]pyridine-6-carboxamide;

4-{4-[3-(dimethylamino)azetidin-1-yl]phenyl}-N-(methanesulfonyl)-3-methyl-1-phenyl-1H-pyrazolo[3,4-b]pyridine-6-carboxamide;

4-{4-[3-(dimethylamino)azetidin-1-yl]phenyl}-N-(ethanesulfonyl)-3-methyl-1-phenyl-1H-pyrazolo[3,4-b]pyridine-6-carboxamide;

1-[3-(3,3-dimethylazetidin-1-yl)phenyl]-N-(methanesulfonyl)-4-[4-(morpholin-4-yl)phenyl]-3-(propan-2-yl)-1H-pyrazolo[3,4-b]pyridine-6-carboxamide;

1-cyclohexyl-N-(methanesulfonyl)-4-[6-(morpholin-4-yl)pyridin-3-yl]-3-(propan-2-yl)-1H-pyrazolo[3,4-b]pyridine-6-carboxamide;

1-cyclohexyl-N-(ethanesulfonyl)-4-[4-(morpholin-4-yl)phenyl]-3-(propan-2-yl)-1H-pyrazolo[3,4-b]pyridine-6-carboxamide;

1-[3-(3-fluoropyrrolidin-1-yl)phenyl]-N-(methanesulfonyl)-4-[4-(morpholin-4-yl)phenyl]-3-(propan-2-yl)-1H-pyrazolo[3,4-b]pyridine-6-carboxamide;

1-cyclohexyl-N-(methanesulfonyl)-3-methyl-4-[6-(morpholin-4-yl)pyridin-3-yl]-1H-pyrazolo[3,4-b]pyridine-6-carboxamide;

1-cyclohexyl-N-(ethanesulfonyl)-3-methyl-4-[6-(morpholin-4-yl)pyridin-3-yl]-1H-pyrazolo[3,4-b]pyridine-6-carboxamide;

1-cyclohexyl-4-[2-(dimethylamino)pyrimidin-5-yl]-N-(methanesulfonyl)-3-methyl-1H-pyrazolo[3,4-b]pyridine-6-carboxamide;

1-cyclohexyl-4-[2-(dimethylamino)pyrimidin-5-yl]-N-(ethanesulfonyl)-3-methyl-1H-pyrazolo[3,4-b]pyridine-6-carboxamide;

1-cyclohexyl-N-(methanesulfonyl)-4-{6-[methyl(oxan-4-yl)amino]pyridin-3-yl}-3-(propan-2-yl)-1H-pyrazolo[3,4-b]pyridine-6-carboxamide;

methyl 3-{1-cyclohexyl-4-[2-(dimethylamino)pyrimidin-5-yl]-6-[(ethanesulfonyl)carbamoyl]-1H-pyrazolo[3,4-b]pyridin-3-yl}azetidine-1-carboxylate;

1-[3-(dimethylamino)phenyl]-N-(methanesulfonyl)-4-[6-(morpholin-4-yl)pyridin-3-yl]-3-(propan-2-yl)-1H-pyrazolo[3,4-b]pyridine-6-carboxamide;

1-[3-(dimethylamino)phenyl]-N-(ethanesulfonyl)-4-[6-(morpholin-4-yl)pyridin-3-yl]-3-(propan-2-yl)-1H-pyrazolo[3,4-b]pyridine-6-carboxamide;

1-cyclopentyl-4-[6-(dimethylamino)pyridin-3-yl]-N-(methanesulfonyl)-3-(propan-2-yl)-1H-pyrazolo[3,4-b]pyridine-6-carboxamide;

1-cyclopentyl-4-[6-(dimethylamino)pyridin-3-yl]-N-(ethanesulfonyl)-3-(propan-2-yl)-1H-pyrazolo[3,4-b]pyridine-6-carboxamide;

N-(methanesulfonyl)-3-methyl-4-[6-(morpholin-4-yl)pyridin-3-yl]-1-[3-(trifluoromethyl)phenyl]-1H-pyrazolo[3,4-b]pyridine-6-carboxamide;

N-(ethanesulfonyl)-3-methyl-4-[6-(morpholin-4-yl)pyridin-3-yl]-1-[3-(trifluoromethyl)phenyl]-1H-pyrazolo[3,4-b]pyridine-6-carboxamide;

1-[3-(dimethylamino)phenyl]-N-(methanesulfonyl)-4-[2-(morpholin-4-yl)pyrimidin-5-yl]-3-(propan-2-yl)-1H-pyrazolo[3,4-b]pyridine-6-carboxamide;

1-(2,4-difluorophenyl)-N-(methanesulfonyl)-3-methyl-4-[6-(morpholin-4-yl)pyridin-3-yl]-1H-pyrazolo[3,4-b]pyridine-6-carboxamide;

1-(2,4-difluorophenyl)-N-(ethanesulfonyl)-3-methyl-4-[6-(morpholin-4-yl)pyridin-3-yl]-1H-pyrazolo[3,4-b]pyridine-6-carboxamide;

1-[3-(dimethylamino)phenyl]-N-(ethanesulfonyl)-4-[2-(morpholin-4-yl)pyrimidin-5-yl]-3-(propan-2-yl)-1H-pyrazolo[3,4-b]pyridine-6-carboxamide;

3-cyclobutyl-N-(methanesulfonyl)-4-{6-[(2-methoxyethyl)(methyl)amino]pyridin-3-yl}-1-phenyl-1H-pyrazolo[3,4-b]pyridine-6-carboxamide;

1-cyclohexyl-4-[6-(3,3-difluoropyrrolidin-1-yl)pyridin-3-yl]-N-(methanesulfonyl)-3-(propan-2-yl)-1H-pyrazolo[3,4-b]pyridine-6-carboxamide;

1-(3-chlorophenyl)-N-(methanesulfonyl)-3-methyl-4-[4-(morpholin-4-yl)phenyl]-1H-pyrazolo[3,4-b]pyridine-6-carboxamide;

1-(3-chlorophenyl)-N-(ethanesulfonyl)-3-methyl-4-[4-(morpholin-4-yl)phenyl]-1H-pyrazolo[3,4-b]pyridine-6-carboxamide;

1-(3-fluorophenyl)-N-(methanesulfonyl)-3-methyl-4-[4-(morpholin-4-yl)phenyl]-1H-pyrazolo[3,4-b]pyridine-6-carboxamide;

N-(ethanesulfonyl)-1-(3-fluorophenyl)-3-methyl-4-[4-(morpholin-4-yl)phenyl]-1H-pyrazolo[3,4-b]pyridine-6-carboxamide;

N-(methanesulfonyl)-3-methyl-4-[4-(morpholin-4-yl)phenyl]-1-[4-(trifluoromethoxy)phenyl]-1H-pyrazolo[3,4-b]pyridine-6-carboxamide;

N-(ethanesulfonyl)-3-methyl-4-[4-(morpholin-4-yl)phenyl]-1-[4-(trifluoromethoxy)phenyl]-1H-pyrazolo[3,4-b]pyridine-6-carboxamide;

4-[6-(4-cyanopiperidin-1-yl)pyridin-3-yl]-3-cyclobutyl-N-(methanesulfonyl)-1-phenyl-1H-pyrazolo[3,4-b]pyridine-6-carboxamide;

N-(methanesulfonyl)-1-(3-methoxyphenyl)-3-methyl-4-[4-(morpholin-4-yl)phenyl]-1H-pyrazolo[3,4-b]pyridine-6-carboxamide;

N-(ethanesulfonyl)-1-(3-methoxyphenyl)-3-methyl-4-[4-(morpholin-4-yl)phenyl]-1H-pyrazolo[3,4-b]pyridine-6-carboxamide;

3-cyclobutyl-N-(methanesulfonyl)-4-{6-[methyl(oxan-4-yl)amino]pyridin-3-yl}-1-phenyl-1H-pyrazolo[3,4-b]pyridine-6-carboxamide;

3-cyclobutyl-N-(methanesulfonyl)-4-{4-[(2-methoxyethyl)(methyl)amino]phenyl}-1-phenyl-1H-pyrazolo[3,4-b]pyridine-6-carboxamide;

N-(methanesulfonyl)-1-{3-[(2-methoxyethyl)(methyl)amino]phenyl}-4-[4-(morpholin-4-yl)phenyl]-3-(propan-2-yl)-1H-pyrazolo[3,4-b]pyridine-6-carboxamide;

1-[3-(dimethylamino)phenyl]-4-[2-(dimethylamino)pyrimidin-5-yl]-N-(methanesulfonyl)-3-(propan-2-yl)-1H-pyrazolo[3,4-b]pyridine-6-carboxamide;

1-[3-(dimethylamino)phenyl]-4-[2-(dimethylamino)pyrimidin-5-yl]-N-(ethanesulfonyl)-3-(propan-2-yl)-1H-pyrazolo[3,4-b]pyridine-6-carboxamide;

4-(4-acetamidophenyl)-1-cyclohexyl-N-(methanesulfonyl)-3-(propan-2-yl)-1H-pyrazolo[3,4-b]pyridine-6-carboxamide;

4-[4-(4-cyanopiperidin-1-yl)phenyl]-1-cyclohexyl-N-(methanesulfonyl)-3-(propan-2-yl)-1H-pyrazolo[3,4-b]pyridine-6-carboxamide;

4-[4-(4-cyanopiperidin-1-yl)phenyl]-1-[3-(dimethylamino)phenyl]-N-(methanesulfonyl)-3-(propan-2-yl)-1H-pyrazolo[3,4-b]pyridine-6-carboxamide;

1-[3-(dimethylamino)phenyl]-N-(methanesulfonyl)-4-{4-[(2-methoxyethyl)(methyl)amino]phenyl}-3-(propan-2-yl)-1H-pyrazolo[3,4-b]pyridine-6-carboxamide;

4-[6-(4-cyanopiperidin-1-yl)pyridin-3-yl]-1-[3-(dimethylamino)phenyl]-N-(methanesulfonyl)-3-(propan-2-yl)-1H-pyrazolo[3,4-b]pyridine-6-carboxamide;

1-[3-(dimethylamino)phenyl]-N-(methanesulfonyl)-4-{6-[(2-methoxyethyl)(methyl)amino]pyridin-3-yl}-3-(propan-2-yl)-1H-pyrazolo[3,4-b]pyridine-6-carboxamide;

4-[6-(4-cyanopiperidin-1-yl)pyridin-3-yl]-N-(methanesulfonyl)-1-[3-(morpholin-4-yl)phenyl]-3-(propan-2-yl)-1H-pyrazolo[3,4-b]pyridine-6-carboxamide;

N-(methanesulfonyl)-4-{6-[(2-methoxyethyl)(methyl)amino]pyridin-3-yl}-1-[3-(morpholin-4-yl)phenyl]-3-(propan-2-yl)-1H-pyrazolo[3,4-b]pyridine-6-carboxamide;

N-(methanesulfonyl)-4-{6-[methyl(oxan-4-yl)amino]pyridin-3-yl}-1-[3-(morpholin-4-yl)phenyl]-3-(propan-2-yl)-1H-pyrazolo[3,4-b]pyridine-6-carboxamide;

N-(methanesulfonyl)-4-{4-[(2-methoxyethyl)(methyl)amino]phenyl}-1-[3-(morpholin-4-yl)phenyl]-3-(propan-2-yl)-1H-pyrazolo[3,4-b]pyridine-6-carboxamide;

1-[3-(dimethylamino)phenyl]-N-(methanesulfonyl)-4-{6-[methyl(oxan-4-yl)amino]pyridin-3-yl}-3-(propan-2-yl)-1H-pyrazolo[3,4-b]pyridine-6-carboxamide;

1-cyclohexyl-N-(ethanesulfonyl)-4-{6-[methyl(oxan-4-yl)amino]pyridin-3-yl}-3-(propan-2-yl)-1H-pyrazolo[3,4-b]pyridine-6-carboxamide;

1-[3-(dimethylamino)phenyl]-N-(methanesulfonyl)-4-{2-[methyl(oxan-4-yl)amino]pyrimidin-5-yl}-3-(propan-2-yl)-1H-pyrazolo[3,4-b]pyridine-6-carboxamide;

1-cyclohexyl-3-cyclopropyl-4-[6-(dimethylamino)pyridin-3-yl]-N-(ethanesulfonyl)-1H-pyrazolo[3,4-b]pyridine-6-carboxamide;

1-cyclohexyl-4-[6-(2,6-dimethylmorpholin-4-yl)pyridin-3-yl]-N-(methanesulfonyl)-3-(propan-2-yl)-1H-pyrazolo[3,4-b]pyridine-6-carboxamide;

1-cyclohexyl-4-[6-(2,2-dimethylmorpholin-4-yl)pyridin-3-yl]-N-(methanesulfonyl)-3-(propan-2-yl)-1H-pyrazolo[3,4-b]pyridine-6-carboxamide;

4-[2-(4-cyanopiperidin-1-yl)pyrimidin-5-yl]-1-[3-(dimethylamino)phenyl]-N-(methanesulfonyl)-3-(propan-2-yl)-1H-pyrazolo[3,4-b]pyridine-6-carboxamide;

1-[3-(dimethylamino)phenyl]-N-(methanesulfonyl)-4-{4-[methyl(oxan-4-yl)amino]phenyl}-3-(propan-2-yl)-1H-pyrazolo[3,4-b]pyridine-6-carboxamide;

N-(methanesulfonyl)-4-{4-[methyl(oxan-4-yl)amino]phenyl}-1-[3-(morpholin-4-yl)phenyl]-3-(propan-2-yl)-1H-pyrazolo[3,4-b]pyridine-6-carboxamide;

4-[6-(4-cyano-4-methylpiperidin-1-yl)pyridin-3-yl]-1-cyclohexyl-N-(methanesulfonyl)-3-(propan-2-yl)-1H-pyrazolo[3,4-b]pyridine-6-carboxamide;

4-[2-(4-cyanopiperidin-1-yl)pyrimidin-5-yl]-N-(methanesulfonyl)-1-[3-(morpholin-4-yl)phenyl]-3-(propan-2-yl)-1H-pyrazolo[3,4-b]pyridine-6-carboxamide;

4-{4-[3-(dimethylamino)pyrrolidin-1-yl]phenyl}-N-(methanesulfonyl)-3-methyl-1-phenyl-1H-pyrazolo[3,4-b]pyridine-6-carboxamide;

N-(methanesulfonyl)-1-(3-methylphenyl)-4-(piperidin-1-yl)-3-(propan-2-yl)-1H-pyrazolo[3,4-b]pyridine-6-carboxamide;

N-(ethanesulfonyl)-1-(3-methylphenyl)-4-(piperidin-1-yl)-3-(propan-2-yl)-1H-pyrazolo[3,4-b]pyridine-6-carboxamide;

4-[4-(4-cyanopiperidin-1-yl)phenyl]-3-cyclobutyl-1-cyclohexyl-N-(methanesulfonyl)-1H-pyrazolo[3,4-b]pyridine-6-carboxamide;

4-[6-(4-cyanopiperidin-1-yl)pyridin-3-yl]-3-cyclobutyl-1-cyclohexyl-N-(methanesulfonyl)-1H-pyrazolo[3,4-b]pyridine-6-carboxamide;

1-[3-(3-hydroxyazetidin-1-yl)phenyl]-N-(methanesulfonyl)-4-[4-(morpholin-4-yl)phenyl]-3-(propan-2-yl)-1H-pyrazolo[3,4-b]pyridine-6-carboxamide;

1-cyclohexyl-N-(methanesulfonyl)-4-[6-(3-methoxypyrrolidin-1-yl)pyridin-3-yl]-3-(propan-2-yl)-1H-pyrazolo[3,4-b]pyridine-6-carboxamide;

methyl 3-{4-(4-acetamidophenyl)-1-(3,5-difluorophenyl)-6-[(methanesulfonyl)carbamoyl]-1H-pyrazolo[3,4-b]pyridin-3-yl}azetidine-1-carboxylate;

1-cyclohexyl-4-[6-(3-fluoropiperidin-1-yl)pyridin-3-yl]-N-(methanesulfonyl)-3-(propan-2-yl)-1H-pyrazolo[3,4-b]pyridine-6-carboxamide;

N-(methanesulfonyl)-4-{4-[(2-methoxyethyl)(methyl)amino]phenyl}-3-(propan-2-yl)-1-[3-(pyrrolidin-1-yl)phenyl]-1H-pyrazolo[3,4-b]pyridine-6-carboxamide;

N-(methanesulfonyl)-4-{4-[methyl(oxan-4-yl)amino]phenyl}-3-(propan-2-yl)-1-[3-(pyrrolidin-1-yl)phenyl]-1H-pyrazolo[3,4-b]pyridine-6-carboxamide;

3-cyclobutyl-N-(methanesulfonyl)-4-{4-[methyl(oxan-4-yl)amino]phenyl}-1-[3-(pyrrolidin-1-yl)phenyl]-1H-pyrazolo[3,4-b]pyridine-6-carboxamide;

N-(ethanesulfonyl)-4-[2-(morpholin-4-yl)pyrimidin-5-yl]-1-phenyl-3-(propan-2-yl)-1H-pyrazolo[3,4-b]pyridine-6-carboxamide;

1-(2,4-difluorophenyl)-N-(ethanesulfonyl)-3-methyl-4-[4-(morpholin-4-yl)phenyl]-1H-pyrazolo[3,4-b]pyridine-6-carboxamide;

1-(3-chloro-4-methylphenyl)-N-(ethane sulfonyl)-4-(4-methoxyphenyl)-3-methyl-1H-pyrazolo[3,4-b]pyridine-6-carboxamide;

1-(3,5-dimethylphenyl)-N-(ethanesulfonyl)-3-methyl-4-[4-(morpholin-4-yl)phenyl]-1H-pyrazolo[3,4-b]pyridine-6-carboxamide;

1-(3,4-difluorophenyl)-N-(ethanesulfonyl)-3-methyl-4-[4-(morpholin-4-yl)phenyl]-1H-pyrazolo[3,4-b]pyridine-6-carboxamide;

N-(methanesulfonyl)-4-(4-methoxypiperidin-1-yl)-1-(3-methylphenyl)-3-(propan-2-yl)-1H-pyrazolo[3,4-b]pyridine-6-carboxamide;

N-(ethanesulfonyl)-4-(4-methoxypiperidin-1-yl)-1-(3-methylphenyl)-3-(propan-2-yl)-1H-pyrazolo[3,4-b]pyridine-6-carboxamide;

4-[2-(4-cyanopiperidin-1-yl)pyrimidin-5-yl]-1-cyclohexyl-N-(methanesulfonyl)-3-(propan-2-yl)-1H-pyrazolo[3,4-b]pyridine-6-carboxamide;

1-cyclohexyl-N-(methanesulfonyl)-4-{2-[(2-methoxyethyl)(methyl)amino]pyrimidin-5-yl}-3-(propan-2-yl)-1H-pyrazolo[3,4-b]pyridine-6-carboxamide;

4-{6-[bis(2-methoxyethyl)amino]pyridin-3-yl}-1-cyclohexyl-N-(methanesulfonyl)-3-(propan-2-yl)-1H-pyrazolo[3,4-b]pyridine-6-carboxamide;

1-cyclohexyl-N-(methanesulfonyl)-4-{6-[methyl(oxolan-3-yl)amino]pyridin-3-yl}-3-(propan-2-yl)-1H-pyrazolo[3,4-b]pyridine-6-carboxamide;

1-cyclohexyl-N-(methanesulfonyl)-4-{2-[methyl(oxan-4-yl)amino]pyrimidin-5-yl}-3-(propan-2-yl)-1H-pyrazolo[3,4-b]pyridine-6-carboxamide;

4-[6-(4-cyanopiperidin-1-yl)pyridin-3-yl]-N-(methanesulfonyl)-3-(propan-2-yl)-1-[3-(trifluoromethyl)phenyl]-1H-pyrazolo[3,4-b]pyridine-6-carboxamide;

1-[6-(dimethylamino)pyridin-2-yl]-N-(methanesulfonyl)-4-[4-(morpholin-4-yl)phenyl]-3-(propan-2-yl)-1H-pyrazolo[3,4-b]pyridine-6-carboxamide;

N-(methanesulfonyl)-4-[4-(morpholin-4-yl)phenyl]-3-(propan-2-yl)-1-[3-(trifluoromethoxy)phenyl]-1H-pyrazolo[3,4-b]pyridine-6-carboxamide;

1-(3,4-difluorophenyl)-N-(methanesulfonyl)-4-[4-(morpholin-4-yl)phenyl]-3-(propan-2-yl)-1H-pyrazolo[3,4-b]pyridine-6-carboxamide;

N-(methanesulfonyl)-4-[4-(morpholin-4-yl)phenyl]-1-[6-(morpholin-4-yl)pyridin-2-yl]-3-(propan-2-yl)-1H-pyrazolo[3,4-b]pyridine-6-carboxamide;

4-(2,6-difluoro-4-methoxyphenyl)-1-(3-fluoro-5-methoxyphenyl)-N-(methanesulfonyl)-3-methyl-1H-pyrazolo[3,4-b]pyridine-6-carboxamide;

4-[4-(4-cyanopiperidin-1-yl)phenyl]-1-(3,5-difluorophenyl)-N-(methanesulfonyl)-3-(propan-2-yl)-1H-pyrazolo[3,4-b]pyridine-6-carboxamide;

4-[4-(4-cyanopiperidin-1-yl)phenyl]-1-(3-fluorophenyl)-N-(methanesulfonyl)-3-(propan-2-yl)-1H-pyrazolo[3,4-b]pyridine-6-carboxamide;

N-(methanesulfonyl)-4-{4-[(2-methoxyethyl)(methyl)amino]phenyl}-3-(propan-2-yl)-1-[3-(trifluoromethyl)phenyl]-1H-pyrazolo[3,4-b]pyridine-6-carboxamide;

N-(methanesulfonyl)-4-{6-[methyl(oxan-4-yl)amino]pyridin-3-yl}-3-(propan-2-yl)-1-[3-(trifluoromethyl)phenyl]-1H-pyrazolo[3,4-b]pyridine-6-carboxamide;

1-(4-fluorophenyl)-N-(methanesulfonyl)-4-{2-[methyl(oxan-4-yl)amino]pyrimidin-5-yl}-3-(propan-2-yl)-1H-pyrazolo[3,4-b]pyridine-6-carboxamide;

4-[4-(4-cyanopiperidin-1-yl)phenyl]-N-(methanesulfonyl)-3-(propan-2-yl)-1-[3-(trifluoromethyl)phenyl]-1H-pyrazolo[3,4-b]pyridine-6-carboxamide;

N-(methanesulfonyl)-4-[4-(morpholin-4-yl)phenyl]-1-[2-(morpholin-4-yl)pyridin-4-yl]-3-(propan-2-yl)-1H-pyrazolo[3,4-b]pyridine-6-carboxamide;

N-(methanesulfonyl)-3-(1-methylcyclobutyl)-4-[4-(morpholin-4-yl)phenyl]-1-phenyl-1H-pyrazolo[3,4-b]pyridine-6-carboxamide;

N-(ethanesulfonyl)-3-(1-methylcyclobutyl)-4-[4-(morpholin-4-yl)phenyl]-1-phenyl-1H-pyrazolo[3,4-b]pyridine-6-carboxamide;

4-[2-(4-cyanopiperidin-1-yl)pyrimidin-5-yl]-1-(2,4-difluorophenyl)-N-(methanesulfonyl)-3-(propan-2-yl)-1H-pyrazolo[3,4-b]pyridine-6-carboxamide;

4-[6-(4-cyanopiperidin-1-yl)pyridin-3-yl]-1-(2,4-difluorophenyl)-N-(methanesulfonyl)-3-(propan-2-yl)-1H-pyrazolo[3,4-b]pyridine-6-carboxamide;

4-[4-(4-cyanopiperidin-1-yl)phenyl]-1-(2,4-difluorophenyl)-N-(methanesulfonyl)-3-(propan-2-yl)-1H-pyrazolo[3,4-b]pyridine-6-carboxamide;

3-cyclobutyl-N-(methanesulfonyl)-4-(4-methoxypiperidin-1-yl)-1-phenyl-1H-pyrazolo[3,4-b]pyridine-6-carboxamide;

3-cyclobutyl-N-(1,1-dioxo-1$\lambda^6$-thiolane-3-sulfonyl)-4-(4-methoxypiperidin-1-yl)-1-phenyl-1H-pyrazolo[3,4-b]pyridine-6-carboxamide;

1-[3-(dimethylamino)phenyl]-N-(methanesulfonyl)-4-[4-(methoxymethyl)piperidin-1-yl]-3-(propan-2-yl)-1H-pyrazolo[3,4-b]pyridine-6-carboxamide;

4-[6-(4-cyanopiperidin-1-yl)pyridin-3-yl]-N-(methanesulfonyl)-1-(oxan-3-yl)-3-(propan-2-yl)-1H-pyrazolo[3,4-b]pyridine-6-carboxamide;

3-cyclobutyl-N-(2-methoxyethanesulfonyl)-4-(4-methoxypiperidin-1-yl)-1-phenyl-1H-pyrazolo[3,4-b]pyridine-6-carboxamide;

3-cyclobutyl-4-(4-methoxypiperidin-1-yl)-1-phenyl-N-(3,3,3-trifluoropropane-1-sulfonyl)-1H-pyrazolo[3,4-b]pyridine-6-carboxamide;

3-cyclobutyl-N-(methanesulfonyl)-4-[4-(morpholin-4-yl)phenyl]-1-phenyl-1H-pyrazolo[3,4-b]pyridine-6-carboxamide;

4-(1,1-difluoro-5-azaspiro[2.4]heptan-5-yl)-N-(methanesulfonyl)-1-(3-methylphenyl)-3-(propan-2-yl)-1H-pyrazolo[3,4-b]pyridine-6-carboxamide;

1-cyclohexyl-N-(methanesulfonyl)-4-(4-methoxypiperidin-1-yl)-3-(propan-2-yl)-1H-pyrazolo[3,4-b]pyridine-6-carboxamide;

3-cyclobutyl-N-(methanesulfonyl)-1-phenyl-4-{4-[(propan-2-yl)oxy]piperidin-1-yl}-1H-pyrazolo[3,4-b]pyridine-6-carboxamide;

3-cyclobutyl-N-(methanesulfonyl)-1-phenyl-4-(4-propoxypiperidin-1-yl)-1H-pyrazolo[3,4-b]pyridine-6-carboxamide;

3-cyclobutyl-N-(methanesulfonyl)-4-[3-(methoxymethyl)piperidin-1-yl]-1-phenyl-1H-pyrazolo[3,4-b]pyridine-6-carboxamide;

3-cyclobutyl-N-(methanesulfonyl)-4-{4-[2-oxo-2-(pyrrolidin-1-yl)ethoxy]piperidin-1-yl}-1-phenyl-1H-pyrazolo[3,4-b]pyridine-6-carboxamide;

1-[3-(dimethylamino)phenyl]-N-(methanesulfonyl)-4-(4-methoxypiperidin-1-yl)-3-(propan-2-yl)-1H-pyrazolo[3,4-b]pyridine-6-carboxamide;

N-(methanesulfonyl)-4-[4-(methoxymethyl)piperidin-1-yl]-1-(3-methylphenyl)-3-(propan-2-yl)-1H-pyrazolo[3,4-b]pyridine-6-carboxamide;

1-[3-(dimethylamino)phenyl]-N-(methanesulfonyl)-4-(piperidin-1-yl)-3-(propan-2-yl)-1H-pyrazolo[3,4-b]pyridine-6-carboxamide;

4-[6-(4-cyanopiperidin-1-yl)pyridin-3-yl]-N-(methanesulfonyl)-3-(propan-2-yl)-1-[2-(pyrrolidin-1-yl)pyridin-4-yl]-1H-pyrazolo[3,4-b]pyridine-6-carboxamide;

3-cyclobutyl-N-(methanesulfonyl)-4-(1-oxa-7-azaspiro[3.5]nonan-7-yl)-1-phenyl-1H-pyrazolo[3,4-b]pyridine-6-carboxamide;

4-(4-cyanopiperidin-1-yl)-1-[3-(dimethylamino)phenyl]-N-(methanesulfonyl)-3-(propan-2-yl)-1H-pyrazolo[3,4-b]pyridine-6-carboxamide;

N-(methanesulfonyl)-4-[4-(2-methoxyethyl)piperidin-1-yl]-1-(3-methylphenyl)-3-(propan-2-yl)-1H-pyrazolo[3,4-b]pyridine-6-carboxamide;

N-(methanesulfonyl)-4-(3-methoxypiperidin-1-yl)-1-(3-methylphenyl)-3-(propan-2-yl)-1H-pyrazolo[3,4-b]pyridine-6-carboxamide;

N-(ethanesulfonyl)-4-(3-methoxypiperidin-1-yl)-1-(3-methylphenyl)-3-(propan-2-yl)-1H-pyrazolo[3,4-b]pyridine-6-carboxamide;

4-[4-(fluoromethyl)piperidin-1-yl]-N-(methanesulfonyl)-1-(3-methylphenyl)-3-(propan-2-yl)-1H-pyrazolo[3,4-b]pyridine-6-carboxamide;

N-(methanesulfonyl)-4-[4-(methanesulfonyl)piperidin-1-yl]-1-(3-methylphenyl)-3-(propan-2-yl)-1H-pyrazolo[3,4-b]pyridine-6-carboxamide;

N-(methanesulfonyl)-4-[4-(morpholin-4-yl)phenyl]-1-phenyl-3-[(propan-2-yl)oxy]-1H-pyrazolo[3,4-b]pyridine-6-carboxamide;

1-(4-fluorophenyl)-N-(methanesulfonyl)-4-(4-methoxypiperidin-1-yl)-3-(propan-2-yl)-1H-pyrazolo[3,4-b]pyridine-6-carboxamide;

1-(4-fluorophenyl)-N-(methanesulfonyl)-4-[4-(methoxymethyl)piperidin-1-yl]-3-(propan-2-yl)-1H-pyrazolo[3,4-b]pyridine-6-carboxamide;

4-[4-(4-cyanopiperidin-1-yl)phenyl]-N-(methanesulfonyl)-3-(propan-2-yl)-1-[2-(pyrrolidin-1-yl)pyridin-4-yl]-1H-pyrazolo[3,4-b]pyridine-6-carboxamide;

N-(methanesulfonyl)-4-[(2-methoxyethyl)(methyl)amino]-1-(3-methylphenyl)-3-(propan-2-yl)-1H-pyrazolo[3,4-b]pyridine-6-carboxamide;

N-(methanesulfonyl)-1-(3-methylphenyl)-4-(8-oxa-2-azaspiro[4.5]decan-2-yl)-3-(propan-2-yl)-1H-pyrazolo[3,4-b]pyridine-6-carboxamide;

4-(4-butoxypiperidin-1-yl)-1-(4-fluorophenyl)-N-(methanesulfonyl)-3-(propan-2-yl)-1H-pyrazolo[3,4-b]pyridine-6-carboxamide;

1-(4-fluorophenyl)-N-(methanesulfonyl)-4-(4-methoxy-4-methylpiperidin-1-yl)-3-(propan-2-yl)-1H-pyrazolo[3,4-b]pyridine-6-carboxamide;

2-[(2-{[3-cyclobutyl-4-(4-methoxypiperidin-1-yl)-1-phenyl-1H-pyrazolo[3,4-b]pyridine-6-carbonyl]sulfamoyl}ethyl)carbamoyl]benzoic acid;

1-(4-fluorophenyl)-N-(methanesulfonyl)-4-[4-(2-methylpropoxy)piperidin-1-yl]-3-(propan-2-yl)-1H-pyrazolo[3,4-b]pyridine-6-carboxamide;

3-cyclobutyl-4-(4-methoxypiperidin-1-yl)-1-phenyl-N-(2,2,2-trifluoroethanesulfonyl)-1H-pyrazolo[3,4-b]pyridine-6-carboxamide;

1-(4-fluorophenyl)-N-(methanesulfonyl)-4-(1-oxa-7-azaspiro[3.5]nonan-7-yl)-3-(propan-2-yl)-1H-pyrazolo[3,4-b]pyridine-6-carboxamide;

4-[3-(difluoromethyl)piperidin-1-yl]-1-(4-fluorophenyl)-N-(methanesulfonyl)-3-(propan-2-yl)-1H-pyrazolo[3,4-b]pyridine-6-carboxamide;

1-(4-fluorophenyl)-N-(methanesulfonyl)-4-(6-oxa-2-azaspiro[3.5]nonan-2-yl)-3-(propan-2-yl)-1H-pyrazolo[3,4-b]pyridine-6-carboxamide;

1-(4-fluorophenyl)-N-(methanesulfonyl)-4-(1-oxa-8-azaspiro[4.5]decan-8-yl)-3-(propan-2-yl)-1H-pyrazolo[3,4-b]pyridine-6-carboxamide;

3-cyclobutyl-4-(cyclohexylmethoxy)-N-(methanesulfonyl)-1-phenyl-1H-pyrazolo[3,4-b]pyridine-6-carboxamide;

3-cyclobutyl-N-(methanesulfonyl)-1-phenyl-4-(piperidin-1-yl)-1H-pyrazolo[3,4-b]pyridine-6-carboxamide;

3-cyclobutyl-N-(methanesulfonyl)-4-[4-(2-methoxyethyl)piperidin-1-yl]-1-phenyl-1H-pyrazolo[3,4-b]pyridine-6-carboxamide;

4-(2-azaspiro[3.4]octan-2-yl)-3-cyclobutyl-N-(methanesulfonyl)-1-phenyl-1H-pyrazolo[3,4-b]pyridine-6-carboxamide;

3-cyclobutyl-N-(methanesulfonyl)-4-[4-(methoxymethyl)piperidin-1-yl]-1-phenyl-1H-pyrazolo[3,4-b]pyridine-6-carboxamide;

4-(3-azabicyclo[3.1.0]hexan-3-yl)-3-cyclobutyl-N-(methanesulfonyl)-1-phenyl-1H-pyrazolo[3,4-b]pyridine-6-carboxamide;

N-(methanesulfonyl)-4-(4-methoxypiperidin-1-yl)-1-[2-(morpholin-4-yl)pyridin-4-yl]-3-(propan-2-yl)-1H-pyrazolo[3,4-b]pyridine-6-carboxamide;

N-(methanesulfonyl)-4-(4-methoxypiperidin-1-yl)-3-(propan-2-yl)-1-[2-(pyrrolidin-1-yl)pyridin-4-yl]-1H-pyrazolo[3,4-b]pyridine-6-carboxamide;

4-[6-(4-cyanopiperidin-1-yl)pyridin-3-yl]-3-cyclobutyl-N-(methanesulfonyl)-1-[2-(pyrrolidin-1-yl)pyridin-4-yl]-1H-pyrazolo[3,4-b]pyridine-6-carboxamide;

3-cyclobutyl-N-(methanesulfonyl)-4-[4-(methanesulfonyl)piperidin-1-yl]-1-phenyl-1H-pyrazolo[3,4-b]pyridine-6-carboxamide;

4-(4-cyanopiperidin-1-yl)-3-cyclobutyl-N-(methanesulfonyl)-1-phenyl-1H-pyrazolo[3,4-b]pyridine-6-carboxamide;

4-(2-azaspiro[3.5]nonan-2-yl)-3-cyclobutyl-N-(methanesulfonyl)-1-phenyl-1H-pyrazolo[3,4-b]pyridine-6-carboxamide;

3-cyclobutyl-N-(methanesulfonyl)-4-[3-(methoxymethyl)azetidin-1-yl]-1-phenyl-1H-pyrazolo[3,4-b]pyridine-6-carboxamide;

4-[6-(4-cyanopiperidin-1-yl)pyridin-3-yl]-N-(methanesulfonyl)-3-(cis-3-methoxycyclobutyl)-1-phenyl-1H-pyrazolo[3,4-b]pyridine-6-carboxamide;

4-[6-(4-cyanopiperidin-1-yl)pyridin-3-yl]-3-(3,3-difluorocyclobutyl)-N-(methanesulfonyl)-1-phenyl-1H-pyrazolo[3,4-b]pyridine-6-carboxamide 4-[6-(4-cyanopiperidin-1-yl)pyridin-3-yl]-3-(3,3-dimethylcyclobutyl)-N-(methanesulfonyl)-1-phenyl-1H-pyrazolo[3,4-b]pyridine-6-carboxamide;

4-[6-(4-cyanopiperidin-1-yl)pyridin-3-yl]-3-(3-fluorocyclobutyl)-N-(methanesulfonyl)-1-phenyl-1H-pyrazolo[3,4-b]pyridine-6-carboxamide;

3-cyclobutyl-N-(methanesulfonyl)-4-[2-(oxan-4-yl)ethoxy]-1-phenyl-1H-pyrazolo[3,4-b]pyridine-6-carboxamide;

3-cyclobutyl-4-[(2S)-2-fluoro-2-(oxan-4-yl)ethoxy]-N-(methanesulfonyl)-1-phenyl-1H-pyrazolo[3,4-b]pyridine-6-carboxamide;

3-cyclobutyl-N-(methanesulfonyl)-4-[(oxan-4-yl)methoxy]-1-phenyl-1H-pyrazolo[3,4-b]pyridine-6-carboxamide;

4-[6-(4-cyanopiperidin-1-yl)pyridin-3-yl]-3-cyclobutyl-N-(methanesulfonyl)-1-[2-(morpholin-4-yl)pyridin-4-yl]-1H-pyrazolo[3,4-b]pyridine-6-carboxamide;

3-cyclobutyl-4-(1,1-difluoro-5-azaspiro[2.4]heptan-5-yl)-N-(methanesulfonyl)-1-phenyl-1H-pyrazolo[3,4-b]pyridine-6-carboxamide;

3-cyclobutyl-N-(methanesulfonyl)-4-(5-oxa-2-azaspiro[3.5]nonan-2-yl)-1-phenyl-1H-pyrazolo[3,4-b]pyridine-6-carboxamide;

3-cyclobutyl-N-(methanesulfonyl)-4-(7-oxa-2-azaspiro[3.5]nonan-2-yl)-1-phenyl-1H-pyrazolo[3,4-b]pyridine-6-carboxamide;

4-(5-azaspiro[2.5]octan-5-yl)-3-cyclobutyl-N-(methanesulfonyl)-1-phenyl-1H-pyrazolo[3,4-b]pyridine-6-carboxamide;

3-cyclobutyl-N-(methanesulfonyl)-4-[(2-methoxyethyl)(methyl)amino]-1-phenyl-1H-pyrazolo[3,4-b]pyridine-6-carboxamide;

3-cyclobutyl-4-(4-methoxypiperidin-1-yl)-N-(oxane-4-sulfonyl)-1-phenyl-1H-pyrazolo[3,4-b]pyridine-6-carboxamide;

benzyl 4-{[3-cyclobutyl-4-(4-methoxypiperidin-1-yl)-1-phenyl-1H-pyrazolo[3,4-b]pyridine-6-carbonyl]sulfamoyl}piperidine-1-carboxylate;

4-[6-(4-cyanopiperidin-1-yl)pyridin-3-yl]-3-(cis-3-fluorocyclobutyl)-N-(methanesulfonyl)-1-phenyl-1H-pyrazolo[3,4-b]pyridine-6-carboxamide;

4-[6-(4-cyanopiperidin-1-yl)pyridin-3-yl]-3-(trans-3-fluorocyclobutyl)-N-(methanesulfonyl)-1-phenyl-1H-pyrazolo[3,4-b]pyridine-6-carboxamide;

3-cyclobutyl-N-(methanesulfonyl)-4-[(cis-4-methoxycyclohexyl)oxy]-1-phenyl-1H-pyrazolo[3,4-b]pyridine-6-carboxamide;

3-cyclobutyl-N-(methanesulfonyl)-4-[(trans-4-methoxycyclohexyl)oxy]-1-phenyl-1H-pyrazolo[3,4-b]pyridine-6-carboxamide;

4-{4-[(benzyloxy)methyl]piperidin-1-yl}-3-cyclobutyl-N-(methanesulfonyl)-1-phenyl-1H-pyrazolo[3,4-b]pyridine-6-carboxamide;

4-(2-azaspiro[3.3]heptan-2-yl)-3-cyclobutyl-N-(methanesulfonyl)-1-phenyl-1H-pyrazolo[3,4-b]pyridine-6-carboxamide;

methyl 5-{3-cyclobutyl-6-[(methanesulfonyl)carbamoyl]-1-phenyl-1H-pyrazolo[3,4-b]pyridin-4-yl}octahydro-1H-pyrrolo[3,2-c]pyridine-1-carboxylate;

4-(1-acetyloctahydro-5H-pyrrolo[3,2-c]pyridin-5-yl)-3-cyclobutyl-N-(methanesulfonyl)-1-phenyl-1H-pyrazolo[3,4-b]pyridine-6-carboxamide;

N-(methanesulfonyl)-4-(4-methoxypiperidin-1-yl)-1-[6-(morpholin-4-yl)pyridin-2-yl]-3-(propan-2-yl)-1H-pyrazolo[3,4-b]pyridine-6-carboxamide;

1-cyclohexyl-N-(methanesulfonyl)-4-[4-(methoxymethyl)piperidin-1-yl]-3-(propan-2-yl)-1H-pyrazolo[3,4-b]pyridine-6-carboxamide;

3-cyclobutyl-4-{4-[(1S)-2-(dimethylamino)-1-fluoroethyl]piperidin-1-yl}-N-(methanesulfonyl)-1-phenyl-1H-pyrazolo[3,4-b]pyridine-6-carboxamide;

3-cyclobutyl-4-[4-(fluoromethyl)piperidin-1-yl]-N-(methanesulfonyl)-1-phenyl-1H-pyrazolo[3,4-b]pyridine-6-carboxamide;

1-(4-fluorophenyl)-N-(methanesulfonyl)-4-[4-(2-methoxypropan-2-yl)piperidin-1-yl]-3-(propan-2-yl)-1H-pyrazolo[3,4-b]pyridine-6-carboxamide;

4-(3-azaspiro[5.5]undecan-3-yl)-3-cyclobutyl-N-(methanesulfonyl)-1-phenyl-1H-pyrazolo[3,4-b]pyridine-6-carboxamide;

1-(3,4-difluorophenyl)-N-(ethanesulfonyl)-4-[4-(morpholin-4-yl)phenyl]-3-(propan-2-yl)-1H-pyrazolo[3,4-b]pyridine-6-carboxamide;

N-(ethanesulfonyl)-1-(3-fluorophenyl)-4-{6-[methyl(oxan-4-yl)amino]pyridin-3-yl}-3-(propan-2-yl)-1H-pyrazolo[3,4-b]pyridine-6-carboxamide;

N-(cyclopropanesulfonyl)-4-[4-(morpholin-4-yl)phenyl]-1-phenyl-3-[(propan-2-yl)oxy]-1H-pyrazolo[3,4-b]pyridine-6-carboxamide;

N-(2-methoxyethanesulfonyl)-4-[4-(morpholin-4-yl)phenyl]-1-phenyl-3-[(propan-2-yl)oxy]-1H-pyrazolo[3,4-b]pyridine-6-carboxamide;

4-[6-(4-cyanopiperidin-1-yl)pyridin-3-yl]-N-(methanesulfonyl)-1-[2-(morpholin-4-yl)pyridin-4-yl]-3-(propan-2-yl)-1H-pyrazolo[3,4-b]pyridine-6-carboxamide;

3-cyclobutyl-4-[4-(cyclopentyloxy)piperidin-1-yl]-N-(methanesulfonyl)-1-phenyl-1H-pyrazolo[3,4-b]pyridine-6-carboxamide;

3-cyclobutyl-4-[4-(cyclohexyloxy)piperidin-1-yl]-N-(methanesulfonyl)-1-phenyl-1H-pyrazolo[3,4-b]pyridine-6-carboxamide;

3-cyclobutyl-4-[4-(cyclopropylmethoxy)piperidin-1-yl]-N-(methanesulfonyl)-1-phenyl-1H-pyrazolo[3,4-b]pyridine-6-carboxamide;

N-(2-methoxyethanesulfonyl)-4-(4-methoxyphenyl)-3-methyl-1-(2-methylpropyl)-1H-pyrazolo[3,4-b]pyridine-6-carboxamide;

N-(2-methoxyethane sulfonyl)-4-[4-(morpholin-4-yl)phenyl]-1-(oxolan-3-yl)-3-(propan-2-yl)-1H-pyrazolo[3,4-b]pyridine-6-carboxamide;

N-(2-methoxyethanesulfonyl)-4-[4-(morpholin-4-yl)phenyl]-1-phenyl-1H-pyrazolo[3,4-b]pyridine-6-carboxamide;

N-(2-methoxyethanesulfonyl)-4-(4-methoxyphenyl)-3-methyl-1-(propan-2-yl)-1H-pyrazolo[3,4-b]pyridine-6-carboxamide;

1-cyclopropyl-N-(2-methoxyethanesulfonyl)-3-methyl-4-[4-(morpholin-4-yl)phenyl]-1H-pyrazolo[3,4-b]pyridine-6-carboxamide;

1-(4-fluorophenyl)-N-(2-methoxyethanesulfonyl)-4-[4-(methoxymethyl)piperidin-1-yl]-3-(propan-2-yl)-1H-pyrazolo[3,4-b]pyridine-6-carboxamide;

3-cyclobutyl-4-[(2R)-2-fluoro-2-(oxan-4-yl)ethoxy]-N-(methanesulfonyl)-1-phenyl-1H-pyrazolo[3,4-b]pyridine-6-carboxamide;

3-cyclobutyl-4-[(3,3-difluorocyclopentyl)methoxy]-N-(methane sulfonyl)-1-phenyl-1H-pyrazolo[3,4-b]pyridine-6-carboxamide;

1-cyclohexyl-N-(cyclopropanesulfonyl)-3-methyl-4-[4-(morpholin-4-yl)phenyl]-1H-pyrazolo[3,4-b]pyridine-6-carboxamide;

4-(4-cyanopiperidin-1-yl)-1-(4-fluorophenyl)-N-(methanesulfonyl)-3-(propan-2-yl)-1H-pyrazolo[3,4-b]pyridine-6-carboxamide;

3-cyclobutyl-N-(methanesulfonyl)-4-[4-(1-methoxyethyl)piperidin-1-yl]-1-phenyl-1H-pyrazolo[3,4-b]pyridine-6-carboxamide;

3-cyclobutyl-N-(methanesulfonyl)-1-phenyl-4-[4-(1,1,1-trifluoro-2-methoxypropan-2-yl)piperidin-1-yl]-1H-pyrazolo[3,4-b]pyridine-6-carboxamide;

3-cyclobutyl-4-[2-(1,1-dioxo-1$\lambda^6$,4-thiazinan-4-yl)ethoxy]-N-(methanesulfonyl)-1-phenyl-1H-pyrazolo[3,4-b]pyridine-6-carboxamide;

3-cyclobutyl-4-[4-(hydroxymethyl)piperidin-1-yl]-N-(methanesulfonyl)-1-phenyl-1H-pyrazolo[3,4-b]pyridine-6-carboxamide;

3-cyclobutyl-4-[4-(methoxymethyl)piperidin-1-yl]-N-(1-methyl-1H-pyrazole-4-sulfonyl)-1-phenyl-1H-pyrazolo[3,4-b]pyridine-6-carboxamide;

4-{6-[bis(2-methoxyethyl)amino]pyridin-3-yl}-3-cyclobutyl-N-(methanesulfonyl)-1-phenyl-1H-pyrazolo[3,4-b]pyridine-6-carboxamide;

3-cyclobutyl-N-(methanesulfonyl)-4-[4-methoxy-4-(methoxymethyl)piperidin-1-yl]-1-phenyl-1H-pyrazolo[3,4-b]pyridine-6-carboxamide;

N-(methanesulfonyl)-4-[4-(methoxymethyl)piperidin-1-yl]-1-[2-(morpholin-4-yl)pyridin-4-yl]-3-(propan-2-yl)-1H-pyrazolo[3,4-b]pyridine-6-carboxamide;

N-(2-methoxyethanesulfonyl)-4-[4-(methoxymethyl)piperidin-1-yl]-1-[2-(morpholin-4-yl)pyridin-4-yl]-3-(propan-2-yl)-1H-pyrazolo[3,4-b]pyridine-6-carboxamide;

3-cyclobutyl-N-(1,2-dimethyl-1H-imidazole-4-sulfonyl)-4-[4-(methoxymethyl)piperidin-1-yl]-1-phenyl-1H-pyrazolo[3,4-b]pyridine-6-carboxamide;

1-cyclohexyl-N-(2-methoxyethanesulfonyl)-4-[4-(methoxymethyl)piperidin-1-yl]-3-(propan-2-yl)-1H-pyrazolo[3,4-b]pyridine-6-carboxamide;

4-{6-[bis(2-methoxyethyl)amino]pyridin-3-yl}-N-(methanesulfonyl)-1-[2-(morpholin-4-yl)pyridin-4-yl]-3-(propan-2-yl)-1H-pyrazolo[3,4-b]pyridine-6-carboxamide;

3-cyclobutyl-4-[4-(methoxymethyl)piperidin-1-yl]-1-phenyl-N-(1H-pyrazole-4-sulfonyl)-1H-pyrazolo[3,4-b]pyridine-6-carboxamide;

3-cyclobutyl-N-(methanesulfonyl)-4-[(3-methyloxetan-3-yl)methoxy]-1-phenyl-1H-pyrazolo[3,4-b]pyridine-6-carboxamide;

3-cyclobutyl-4-{4-[(1,1-dioxo-1$\lambda^6$,4-thiazinan-4-yl)methyl]-4-methoxypiperidin-1-yl}-N-(methanesulfonyl)-1-phenyl-1H-pyrazolo[3,4-b]pyridine-6-carboxamide;

3-cyclobutyl-N-(2-methoxyethanesulfonyl)-4-[4-(methoxymethyl)piperidin-1-yl]-1-phenyl-1H-pyrazolo[3,4-b]pyridine-6-carboxamide;

4-[6-(4-cyanopiperidin-1-yl)pyridin-3-yl]-N-(methanesulfonyl)-3-(trans-3-methylcyclobutyl)-1-phenyl-1H-pyrazolo[3,4-b]pyridine-6-carboxamide;

4-[6-(4-cyanopiperidin-1-yl)pyridin-3-yl]-N-(methanesulfonyl)-1-phenyl-3-[(piperidin-4-yl)oxy]-1H-pyrazolo[3,4-b]pyridine-6-carboxamide;

tert-butyl 4-({4-[6-(4-cyanopiperidin-1-yl)pyridin-3-yl]-6-[(methanesulfonyl)carbamoyl]-1-phenyl-1H-pyrazolo[3,4-b]pyridin-3-yl}oxy)piperidine-1-carboxylate;

3-cyclobutyl-N-[2-(1,3-dioxo-1,3-dihydro-2H-isoindol-2-yl)ethanesulfonyl]-4-[4-(methoxymethyl)piperidin-1-yl]-1-phenyl-1H-pyrazolo[3,4-b]pyridine-6-carboxamide;

N-(2-aminoethanesulfonyl)-3-cyclobutyl-4-[4-(methoxymethyl)piperidin-1-yl]-1-phenyl-1H-pyrazolo[3,4-b]pyridine-6-carboxamide;

1-(cyclobutylmethyl)-N-(methanesulfonyl)-4-[4-(methoxymethyl)piperidin-1-yl]-3-(propan-2-yl)-1H-pyrazolo[3,4-b]pyridine-6-carboxamide;

1-(cyclobutylmethyl)-N-(2-methoxyethanesulfonyl)-4-[4-(methoxymethyl)piperidin-1-yl]-3-(propan-2-yl)-1H-pyrazolo[3,4-b]pyridine-6-carboxamide;

N-(methanesulfonyl)-4-[4-(methoxymethyl)piperidin-1-yl]-1-(2-methylpropyl)-3-(propan-2-yl)-1H-pyrazolo[3,4-b]pyridine-6-carboxamide;

N-(2-methoxyethane sulfonyl)-4-[4-(methoxymethyl)piperidin-1-yl]-1-(2-methylpropyl)-3-(propan-2-yl)-1H-pyrazolo[3,4-b]pyridine-6-carboxamide;

1-(4-fluorophenyl)-N-(methanesulfonyl)-3-(propan-2-yl)-4-[4-(2,2,2-trifluoroethyl)piperazin-1-yl]-1H-pyrazolo[3,4-b]pyridine-6-carboxamide;

3-cyclobutyl-4-[4-(methoxymethyl)piperidin-1-yl]-N-[2-(morpholin-4-yl)ethanesulfonyl]-1-phenyl-1H-pyrazolo[3,4-b]pyridine-6-carboxamide;

N-(methanesulfonyl)-4-[4-(methoxymethyl)piperidin-1-yl]-1-(1-methyl-6-oxo-1,6-dihydropyridazin-3-yl)-3-(propan-2-yl)-1H-pyrazolo[3,4-b]pyridine-6-carboxamide;

3-cyclobutyl-N-(2-methoxyethanesulfonyl)-4-[(3-methyloxetan-3-yl)methoxy]-1-phenyl-1H-pyrazolo[3,4-b]pyridine-6-carboxamide;

3-cyclobutyl-N-(methanesulfonyl)-1-phenyl-4-[(propan-2-yl)piperazin-1-yl]-1H-pyrazolo[3,4-b]pyridine-6-carboxamide;

3-cyclobutyl-N-(2-methoxyethanesulfonyl)-1-phenyl-4-[4-(propan-2-yl)piperazin-1-yl]-1H-pyrazolo[3,4-b]pyridine-6-carboxamide;

1-(4-fluorophenyl)-4-[4-(methoxymethyl)piperidin-1-yl]-N-[3-(morpholin-4-yl)propane-1-sulfonyl]-3-(propan-2-yl)-1H-pyrazolo[3,4-b]pyridine-6-carboxamide;

3-cyclobutyl-N-[2-(dimethylamino)ethanesulfonyl]-4-[4-(methoxymethyl)piperidin-1-yl]-1-phenyl-1H-pyrazolo[3,4-b]pyridine-6-carboxamide;

4-[(1-acetyl-4-fluoropiperidin-4-yl)methoxy]-3-cyclobutyl-N-(methanesulfonyl)-1-phenyl-1H-pyrazolo[3,4-b]pyridine-6-carboxamide;

4-[6-(4-cyanopiperidin-1-yl)pyridin-3-yl]-N-(2-methoxyethanesulfonyl)-3-[(oxolan-3-yl)oxy]-1-phenyl-1H-pyrazolo[3,4-b]pyridine-6-carboxamide;

4-[6-(4-cyanopiperidin-1-yl)pyridin-3-yl]-N-(2-methoxyethanesulfonyl)-3-(trans-3-methylcyclobutyl)-1-phenyl-1H-pyrazolo[3,4-b]pyridine-6-carboxamide;

4-[6-(4-cyanopiperidin-1-yl)pyridin-3-yl]-N-(methanesulfonyl)-3-[(oxolan-3-yl)oxy]-1-phenyl-1H-pyrazolo[3,4-b]pyridine-6-carboxamide;

1-[3-(dimethylamino)phenyl]-N-(methanesulfonyl)-4-[(oxan-4-yl)methoxy]-3-(propan-2-yl)-1H-pyrazolo[3,4-b]pyridine-6-carboxamide;

N-(methanesulfonyl)-4-[4-(methoxymethyl)piperidin-1-yl]-1-[2-(morpholin-4-yl)pyrimidin-4-yl]-3-(propan-2-yl)-1H-pyrazolo[3,4-b]pyridine-6-carboxamide;

4-(4-cyclobutylpiperazin-1-yl)-1-(4-fluorophenyl)-N-(methanesulfonyl)-3-(propan-2-yl)-1H-pyrazolo[3,4-b]pyridine-6-carboxamide;

3-cyclobutyl-N-(methanesulfonyl)-4-[3-(morpholin-4-yl)propoxy]-1-phenyl-1H-pyrazolo[3,4-b]pyridine-6-carboxamide;

3-cyclobutyl-4-[(3,3-difluoro-1-methylcyclobutyl)methoxy]-N-(methanesulfonyl)-1-phenyl-1H-pyrazolo[3,4-b]pyridine-6-carboxamide;

3-cyclobutyl-N-(methanesulfonyl)-4-[(oxolan-2-yl)methoxy]-1-phenyl-1H-pyrazolo[3,4-b]pyridine-6-carboxamide;

1-(4-fluorophenyl)-N-(methanesulfonyl)-4-[(oxan-4-yl)methoxy]-3-(propan-2-yl)-1H-pyrazolo[3,4-b]pyridine-6-carboxamide;

1-(4-fluorophenyl)-N-(methanesulfonyl)-4-[2-(oxan-4-yl)ethoxy]-3-(propan-2-yl)-1H-pyrazolo[3,4-b]pyridine-6-carboxamide;

3-cyclobutyl-4-[4-(methoxymethyl)piperidin-1-yl]-N-(1-methyl-1H-imidazole-4-sulfonyl)-1-phenyl-1H-pyrazolo[3,4-b]pyridine-6-carboxamide;

3-cyclobutyl-N-(3,5-dimethyl-1,2-oxazole-4-sulfonyl)-4-[4-(methoxymethyl)piperidin-1-yl]-1-phenyl-1H-pyrazolo[3,4-b]pyridine-6-carboxamide;

methyl 3-({3-cyclobutyl-4-[4-(methoxymethyl)piperidin-1-yl]-1-phenyl-1H-pyrazolo[3,4-b]pyridine-6-carbonyl}sulfamoyl)propanoate;

3-({3-cyclobutyl-4-[4-(methoxymethyl)piperidin-1-yl]-1-phenyl-1H-pyrazolo[3,4-b]pyridine-6-carbonyl}sulfamoyl)propanoic acid;

N-[3-(dimethylamino)propane-1-sulfonyl]-1-(4-fluorophenyl)-4-[4-(methoxymethyl)piperidin-1-yl]-3-(propan-2-yl)-1H-pyrazolo[3,4-b]pyridine-6-carboxamide;

1-(4-fluorophenyl)-4-[4-(methoxymethyl)piperidin-1-yl]-3-(propan-2-yl)-N-[3-(pyrrolidin-1-yl)propane-1-sulfonyl]-1H-pyrazolo[3,4-b]pyridine-6-carboxamide;

1-(4-fluorophenyl)-N-(methanesulfonyl)-4-[3-(morpholin-4-yl)propoxy]-3-(propan-2-yl)-1H-pyrazolo[3,4-b]pyridine-6-carboxamide;

1-(4-fluorophenyl)-N-(methanesulfonyl)-4-[(3-methyloxetan-3-yl)methoxy]-3-(propan-2-yl)-1H-pyrazolo[3,4-b]pyridine-6-carboxamide;

3-cyclobutyl-N-(methanesulfonyl)-4-[4-(2-methoxypropan-2-yl)piperidin-1-yl]-1-phenyl-1H-pyrazolo[3,4-b]pyridine-6-carboxamide;

1-(4-fluorophenyl)-N-(methanesulfonyl)-4-[(oxolan-2-yl)methoxy]-3-(propan-2-yl)-1H-pyrazolo[3,4-b]pyridine-6-carboxamide;

4-[(1-acetylpiperidin-4-yl)methoxy]-3-cyclobutyl-N-(methanesulfonyl)-1-phenyl-1H-pyrazolo[3,4-b]pyridine-6-carboxamide;

methyl 4-[({3-cyclobutyl-6-[(methanesulfonyl)carbamoyl]-1-phenyl-1H-pyrazolo[3,4-b]pyridin-4-yl}oxy)methyl]piperidine-1-carboxylate;

3-cyclobutyl-N-[3-(dimethylamino)-3-oxopropane-1-sulfonyl]-4-[4-(methoxymethyl)piperidin-1-yl]-1-phenyl-1H-pyrazolo[3,4-b]pyridine-6-carboxamide;

4-[3-(dimethylamino)propoxy]-1-(4-fluorophenyl)-N-(methanesulfonyl)-3-(propan-2-yl)-1H-pyrazolo[3,4-b]pyridine-6-carboxamide;

4-[6-(4-cyanopiperidin-1-yl)pyridin-3-yl]-N-(methanesulfonyl)-3-[(oxetan-3-yl)oxy]-1-phenyl-1H-pyrazolo[3,4-b]pyridine-6-carboxamide;

1-(4-fluorophenyl)-N-(methanesulfonyl)-4-[(2-methoxyethyl)(methyl)amino]-3-(propan-2-yl)-1H-pyrazolo[3,4-b]pyridine-6-carboxamide;

N-[3-(azetidin-1-yl)propane-1-sulfonyl]-1-(4-fluorophenyl)-4-[4-(methoxymethyl)piperidin-1-yl]-3-(propan-2-yl)-1H-pyrazolo[3,4-b]pyridine-6-carboxamide;

3-cyclobutyl-4-[3-(dimethylamino)propoxy]-N-(methanesulfonyl)-1-phenyl-1H-pyrazolo[3,4-b]pyridine-6-carboxamide;

1-(4-fluorophenyl)-4-[4-(2-hydroxypropan-2-yl)piperidin-1-yl]-N-(methanesulfonyl)-3-(propan-2-yl)-1H-pyrazolo[3,4-b]pyridine-6-carboxamide;

1-(4-fluorophenyl)-N-(methanesulfonyl)-4-[2-(1-methylpiperidin-2-yl)ethoxy]-3-(propan-2-yl)-1H-pyrazolo[3,4-b]pyridine-6-carboxamide;

4-[(3,3-difluoro-1-methylcyclobutyl)methoxy]-1-(4-fluorophenyl)-N-(methanesulfonyl)-3-(propan-2-yl)-1H-pyrazolo[3,4-b]pyridine-6-carboxamide;

1-(4-fluorophenyl)-N-(methanesulfonyl)-4-[3-(piperidin-1-yl)propoxy]-3-(propan-2-yl)-1H-pyrazolo[3,4-b]pyridine-6-carboxamide;

4-[(1-acetyl-4-fluoropiperidin-4-yl)methoxy]-1-(4-fluorophenyl)-N-(methanesulfonyl)-3-(propan-2-yl)-1H-pyrazolo[3,4-b]pyridine-6-carboxamide;

1-(4-fluorophenyl)-N-(methanesulfonyl)-4-{2-[(oxetan-3-yl)(propan-2-yl)amino]ethoxy}-3-(propan-2-yl)-1H-pyrazolo[3,4-b]pyridine-6-carboxamide;

1-(4-fluorophenyl)-N-(methanesulfonyl)-3-(propan-2-yl)-4-{[4-(propan-2-yl)morpholin-3-yl]methoxy}-1H-pyrazolo[3,4-b]pyridine-6-carboxamide;

4-[(1,3-dimethoxypropan-2-yl)oxy]-1-(4-fluorophenyl)-N-(methanesulfonyl)-3-(propan-2-yl)-1H-pyrazolo[3,4-b]pyridine-6-carboxamide;

4-[(1,4-dioxan-2-yl)methoxy]-1-(4-fluorophenyl)-N-(methanesulfonyl)-3-(propan-2-yl)-1H-pyrazolo[3,4-b]pyridine-6-carboxamide;

1-(4-fluorophenyl)-N-(methanesulfonyl)-4-{2-[(oxetan-3-yl)oxy]ethoxy}-3-(propan-2-yl)-1H-pyrazolo[3,4-b]pyridine-6-carboxamide;

3-cyclobutyl-N-(methanesulfonyl)-1-phenyl-4-[3-(piperidin-1-yl)propoxy]-1H-pyrazolo[3,4-b]pyridine-6-carboxamide;

3-cyclobutyl-N-(2-methoxyethanesulfonyl)-4-[(oxan-4-yl)methoxy]-1-phenyl-1H-pyrazolo[3,4-b]pyridine-6-carboxamide;

3-cyclobutyl-1-(4-fluorophenyl)-N-(methanesulfonyl)-4-[4-(methoxymethyl)piperidin-1-yl]-1H-pyrazolo[3,4-b]pyridine-6-carboxamide;

3-cyclobutyl-4-[4-(2-hydroxypropan-2-yl)piperidin-1-yl]-N-(methanesulfonyl)-1-phenyl-1H-pyrazolo[3,4-b]pyridine-6-carboxamide;

3-cyclobutyl-1-(4-fluorophenyl)-N-(methanesulfonyl)-4-[(oxan-4-yl)methoxy]-1H-pyrazolo[3,4-b]pyridine-6-carboxamide;

4-[4-(dimethylamino)piperidin-1-yl]-1-(4-fluorophenyl)-N-(methanesulfonyl)-3-(propan-2-yl)-1H-pyrazolo[3,4-b]pyridine-6-carboxamide;

1-(4-fluorophenyl)-N-(methanesulfonyl)-4-(1'-methyl[4,4'-bipiperidin]-1-yl)-3-(propan-2-yl)-1H-pyrazolo[3,4-b]pyridine-6-carboxamide;

4-[(1-acetylpiperidin-4-yl)methoxy]-1-(4-fluorophenyl)-N-(methanesulfonyl)-3-(propan-2-yl)-1H-pyrazolo[3,4-b]pyridine-6-carboxamide;

methyl 4-({[1-(4-fluorophenyl)-6-[(methanesulfonyl)carbamoyl]-3-(propan-2-yl)-1H-pyrazolo[3,4-b]pyridin-4-yl]oxy}methyl)piperidine-1-carboxylate;

3-cyclobutyl-N-(methanesulfonyl)-4-[2-(1-methylpiperidin-2-yl)ethoxy]-1-phenyl-1H-pyrazolo[3,4-b]pyridine-6-carboxamide;

3-cyclobutyl-4-[(1,3-dimethoxypropan-2-yl)oxy]-N-(methanesulfonyl)-1-phenyl-1H-pyrazolo[3,4-b]pyridine-6-carboxamide;

3-cyclobutyl-N-(methanesulfonyl)-4-{2-[(oxetan-3-yl)(propan-2-yl)amino]ethoxy}-1-phenyl-1H-pyrazolo[3,4-b]pyridine-6-carboxamide;

4-[4-(cyanomethyl)-4-hydroxypiperidin-1-yl]-3-cyclobutyl-N-(methanesulfonyl)-1-phenyl-1H-pyrazolo[3,4-b]pyridine-6-carboxamide;

4-(4-azidophenyl)-N-(3-azidopropane-1-sulfonyl)-1-[3-(dimethylamino)phenyl]-3-(propan-2-yl)-1H-pyrazolo[3,4-b]pyridine-6-carboxamide;

3-cyclobutyl-N-(methanesulfonyl)-4-[4-(morpholin-4-yl)piperidin-1-yl]-1-phenyl-1H-pyrazolo[3,4-b]pyridine-6-carboxamide;

3-cyclobutyl-N-(methanesulfonyl)-1-phenyl-4-[4-(2,2,2-trifluoroethyl)piperazin-1-yl]-1H-pyrazolo[3,4-b]pyridine-6-carboxamide;

3-cyclobutyl-N-(2-methoxyethanesulfonyl)-1-phenyl-4-[4-(2,2,2-trifluoroethyl)piperazin-1-yl]-1H-pyrazolo[3,4-b]pyridine-6-carboxamide;

3-cyclobutyl-N-(methanesulfonyl)-4-{4-[2-(morpholin-4-yl)ethyl]piperidin-1-yl}-1-phenyl-1H-pyrazolo[3,4-b]pyridine-6-carboxamide;

rac-4-[(3aR,7aS)-1-acetyloctahydro-5H-pyrrolo[3,2-c]pyridin-5-yl]-3-cyclobutyl-N-[3-(morpholin-4-yl)propane-1-sulfonyl]-1-phenyl-1H-pyrazolo[3,4-b]pyridine-6-carboxamide;

3-cyclobutyl-N-(cyclopropanesulfonyl)-4-[(oxan-4-yl)methoxy]-1-phenyl-1H-pyrazolo[3,4-b]pyridine-6-carboxamide;

3-cyclobutyl-N-(dimethylsulfamoyl)-4-[(oxan-4-yl)methoxy]-1-phenyl-1H-pyrazolo[3,4-b]pyridine-6-carboxamide;

3-cyclobutyl-N-(ethanesulfonyl)-4-[(oxan-4-yl)methoxy]-1-phenyl-1H-pyrazolo[3,4-b]pyridine-6-carboxamide;

N-(methanesulfonyl)-1-[2-(morpholin-4-yl)pyridin-4-yl]-4-[(oxan-4-yl)methoxy]-3-(propan-2-yl)-1H-pyrazolo[3,4-b]pyridine-6-carboxamide;

ethyl 4-[1-(4-fluorophenyl)-6-[(methanesulfonyl)carbamoyl]-3-(propan-2-yl)-1H-pyrazolo[3,4-b]pyridin-4-yl]piperazine-1-carboxylate;

1-(4-fluorophenyl)-N-(methanesulfonyl)-4-(3-methyl-2-oxo-1-oxa-3,8-diazaspiro[4.5]decan-8-yl)-3-(propan-2-yl)-1H-pyrazolo[3,4-b]pyridine-6-carboxamide;

1-(4-fluorophenyl)-N-(methanesulfonyl)-3-(propan-2-yl)-4-[3-(trifluoromethyl)piperazin-1-yl]-1H-pyrazolo[3,4-b]pyridine-6-carboxamide;

1-(4-fluorophenyl)-N-(methanesulfonyl)-4-[4-(2-methoxyethyl)piperazin-1-yl]-3-(propan-2-yl)-1H-pyrazolo[3,4-b]pyridine-6-carboxamide;

4-(2,4-dioxo-1,3,8-triazaspiro[4.5]decan-8-yl)-1-(4-fluorophenyl)-N-(methanesulfonyl)-3-(propan-2-yl)-1H-pyrazolo[3,4-b]pyridine-6-carboxamide;

4-[4-(ethoxymethyl)-4-fluoropiperidin-1-yl]-1-(4-fluorophenyl)-N-(methanesulfonyl)-3-(propan-2-yl)-1H-pyrazolo[3,4-b]pyridine-6-carboxamide;

4-{4-fluoro-4-[(2-methoxyethoxy)methyl]piperidin-1-yl}-1-(4-fluorophenyl)-N-(methanesulfonyl)-3-(propan-2-yl)-1H-pyrazolo[3,4-b]pyridine-6-carboxamide;

4-[(3R,4R)-3-fluoro-4-hydroxypiperidin-1-yl]-1-(4-fluorophenyl)-N-(methanesulfonyl)-3-(propan-2-yl)-1H-pyrazolo[3,4-b]pyridine-6-carboxamide;

4-[4-fluoro-4-(methoxymethyl)piperidin-1-yl]-1-(4-fluorophenyl)-N-(methanesulfonyl)-3-(propan-2-yl)-1H-pyrazolo[3,4-b]pyridine-6-carboxamide;

4-{3-fluoro-3-[(2-methoxyethoxy)methyl]piperidin-1-yl}-1-(4-fluorophenyl)-N-(methanesulfonyl)-3-(propan-2-yl)-1H-pyrazolo[3,4-b]pyridine-6-carboxamide;

3-cyclobutyl-N-[3-(morpholin-4-yl)propane-1-sulfonyl]-4-[(oxan-4-yl)methoxy]-1-phenyl-1H-pyrazolo[3,4-b]pyridine-6-carboxamide;

4-([1,4'-bipiperidin]-1'-yl)-1-(4-fluorophenyl)-N-(methanesulfonyl)-3-(propan-2-yl)-1H-pyrazolo[3,4-b]pyridine-6-carboxamide;

3-cyclobutyl-4-[(3R)-3-(hydroxymethyl)piperidin-1-yl]-N-(methanesulfonyl)-1-phenyl-1H-pyrazolo[3,4-b]pyridine-6-carboxamide;

3-cyclobutyl-4-[(3R)-3-(hydroxymethyl)piperidin-1-yl]-N-[3-(morpholin-4-yl)propane-1-sulfonyl]-1-phenyl-1H-pyrazolo[3,4-b]pyridine-6-carboxamide;

3-cyclobutyl-4-[(oxan-4-yl)methoxy]-1-phenyl-N-[4-(pyrrolidin-1-yl)piperidine-1-sulfonyl]-1H-pyrazolo[3,4-b]pyridine-6-carboxamide;

3-cyclobutyl-N-[(2S)-2-(4-methylpiperazine-1-carbonyl)pyrrolidine-1-sulfonyl]-4-[(oxan-4-yl)methoxy]-1-phenyl-1H-pyrazolo[3,4-b]pyridine-6-carboxamide;

N-([1,4'-bipiperidine]-1'-sulfonyl)-3-cyclobutyl-4-[(oxan-4-yl)methoxy]-1-phenyl-1H-pyrazolo[3,4-b]pyridine-6-carboxamide;

3-cyclobutyl-N-[methyl(propyl)sulfamoyl]-4-[(oxan-4-yl)methoxy]-1-phenyl-1H-pyrazolo[3,4-b]pyridine-6-carboxamide;

3-cyclobutyl-N-[ethyl(propyl)sulfamoyl]-4-[(oxan-4-yl)methoxy]-1-phenyl-1H-pyrazolo[3,4-b]pyridine-6-carboxamide;

ethyl 4-[({3-cyclobutyl-4-[(oxan-4-yl)methoxy]-1-phenyl-1H-pyrazolo[3,4-b]pyridine-6-carbonyl}sulfamoyl)amino]piperidine-1-carboxylate;

N-(4-acetyl-1,4-diazepane-1-sulfonyl)-3-cyclobutyl-4-[(oxan-4-yl)methoxy]-1-phenyl-1H-pyrazolo[3,4-b]pyridine-6-carboxamide;

3-cyclobutyl-N-(morpholine-4-sulfonyl)-4-[(oxan-4-yl)methoxy]-1-phenyl-1H-pyrazolo[3,4-b]pyridine-6-carboxamide;

3-cyclobutyl-N-[4-(morpholin-4-yl)piperidine-1-sulfonyl]-4-[(oxan-4-yl)methoxy]-1-phenyl-1H-pyrazolo[3,4-b]pyridine-6-carboxamide;

3-cyclobutyl-N-[4-(4-methylpiperazine-1-carbonyl)piperidine-1-sulfonyl]-4-[(oxan-4-yl)methoxy]-1-phenyl-1H-pyrazolo[3,4-b]pyridine-6-carboxamide;

3-cyclobutyl-N-(4-methylpiperazine-1-sulfonyl)-4-[(oxan-4-yl)methoxy]-1-phenyl-1H-pyrazolo[3,4-b]pyridine-6-carboxamide;

3-cyclobutyl-N-(2-methylpropane-2-sulfonyl)-4-[(oxan-4-yl)methoxy]-1-phenyl-1H-pyrazolo[3,4-b]pyridine-6-carboxamide;

4-(4-azidophenyl)-N-(but-3-yne-1-sulfonyl)-1-[3-(dimethylamino)phenyl]-3-(propan-2-yl)-1H-pyrazolo[3,4-b]pyridine-6-carboxamide;

N-(cyanomethanesulfonyl)-3-cyclobutyl-4-[4-(methoxymethyl)piperidin-1-yl]-1-phenyl-1H-pyrazolo[3,4-b]pyridine-6-carboxamide;

4-([1,4'-bipiperidin]-1'-yl)-3-cyclobutyl-N-(methanesulfonyl)-1-phenyl-1H-pyrazolo[3,4-b]pyridine-6-carboxamide;

3-cyclobutyl-N-(2-hydroxyethanesulfonyl)-4-[4-(methoxymethyl)piperidin-1-yl]-1-phenyl-1H-pyrazolo[3,4-b]pyridine-6-carboxamide;

3-cyclobutyl-N-(3-hydroxypropane-1-sulfonyl)-4-[4-(methoxymethyl)piperidin-1-yl]-1-phenyl-1H-pyrazolo[3,4-b]pyridine-6-carboxamide;

3-cyclobutyl-4-[4-(methoxymethyl)piperidin-1-yl]-1-phenyl-N-(piperidine-4-sulfonyl)-1H-pyrazolo[3,4-b]pyridine-6-carboxamide;

3-cyclobutyl-4-[4-(methoxymethyl)piperidin-1-yl]-N-(oxolane-3-sulfonyl)-1-phenyl-1H-pyrazolo[3,4-b]pyridine-6-carboxamide;

1-(2,6-dimethylpyridin-4-yl)-N-(methanesulfonyl)-4-[4-(methoxymethyl)piperidin-1-yl]-3-(propan-2-yl)-1H-pyrazolo[3,4-b]pyridine-6-carboxamide;

3-cyclobutyl-4-(1,1-dioxo-1$\lambda^6$,4-thiazinan-4-yl)-N-(methanesulfonyl)-1-phenyl-1H-pyrazolo[3,4-b]pyridine-6-carboxamide;

3-cyclobutyl-4-[4-(methoxymethyl)piperidin-1-yl]-1-phenyl-N-[2-(1H-pyrazol-1-yl)ethanesulfonyl]-1H-pyrazolo[3,4-b]pyridine-6-carboxamide;

benzyl [2-({3-cyclobutyl-4-[4-(methoxymethyl)piperidin-1-yl]-1-phenyl-1H-pyrazolo[3,4-b]pyridine-6-carbonyl}sulfamoyl)ethyl]carbamate;

3-cyclobutyl-4-[4-(methoxymethyl)piperidin-1-yl]-N-(1-methylcyclopropane-1-sulfonyl)-1-phenyl-1H-pyrazolo[3,4-b]pyridine-6-carboxamide;

3-cyclobutyl-4-[4-(methoxymethyl)piperidin-1-yl]-N-(2-methylpropane-1-sulfonyl)-1-phenyl-1H-pyrazolo[3,4-b]pyridine-6-carboxamide;

methyl ({3-cyclobutyl-4-[4-(methoxymethyl)piperidin-1-yl]-1-phenyl-1H-pyrazolo[3,4-b]pyridine-6-carbonyl}sulfamoyl)acetate;

benzyl 3-({3-cyclobutyl-4-[4-(methoxymethyl)piperidin-1-yl]-1-phenyl-1H-pyrazolo[3,4-b]pyridine-6-carbonyl}sulfamoyl)pyrrolidine-1-carboxylate;

tert-butyl 4-[1-(4-fluorophenyl)-6-[(methanesulfonyl)carbamoyl]-3-(propan-2-yl)-1H-pyrazolo[3,4-b]pyridin-4-yl]piperidine-1-carboxylate; and 3-cyclobutyl-N-(dimethylsulfamoyl)-1-(4-fluorophenyl)-4-{4-[2-(methoxymethyl)morpholin-4-yl]piperidin-1-yl}-1H-pyrazolo[3,4-b]pyridine-6-carboxamide;

3-cyclobutyl-N-(morpholine-4-sulfonyl)-1-phenyl-4-{4-[(pyrrolidin-1-yl)methyl]piperidin-1-yl}-1H-pyrazolo[3,4-b]pyridine-6-carboxamide;

3-cyclobutyl-N-(dimethylsulfamoyl)-1-(4-fluorophenyl)-4-(4-methoxy[1,4'-bipiperidin]-1'-yl)-1H-pyrazolo[3,4-b]pyridine-6-carboxamide;

3-cyclobutyl-N-(dimethylsulfamoyl)-1-(4-fluorophenyl)-4-{4-[4-(propan-2-yl)piperazin-1-yl]piperidin-1-yl}-1H-pyrazolo[3,4-b]pyridine-6-carboxamide;

3-cyclobutyl-N-(morpholine-4-sulfonyl)-4-[4-(morpholin-4-yl)piperidin-1-yl]-1-phenyl-1H-pyrazolo[3,4-b]pyridine-6-carboxamide;

N-(2-amino-2-oxoethanesulfonyl)-3-cyclobutyl-4-[4-(methoxymethyl)piperidin-1-yl]-1-phenyl-1H-pyrazolo[3,4-b]pyridine-6-carboxamide;

3-cyclobutyl-N-(methanesulfonyl)-4-[4-(methoxymethyl)piperidin-1-yl]-1-(2-methoxypyridin-4-yl)-1H-pyrazolo[3,4-b]pyridine-6-carboxamide;

N-(2-acetamidoethanesulfonyl)-3-cyclobutyl-4-[4-(methoxymethyl)piperidin-1-yl]-1-phenyl-1H-pyrazolo[3,4-b]pyridine-6-carboxamide;

3-cyclobutyl-4-[4-(methoxymethyl)piperidin-1-yl]-1-phenyl-N-(pyrrolidine-3-sulfonyl)-1H-pyrazolo[3,4-b]pyridine-6-carboxamide;

3-cyclobutyl-4-[4-(methoxymethyl)piperidin-1-yl]-1-phenyl-N-[4-(pyrrolidin-1-yl)piperidine-1-sulfonyl]-1H-pyrazolo[3,4-b]pyridine-6-carboxamide;

3-cyclobutyl-4-[4-(methoxymethyl)piperidin-1-yl]-N-[(2S)-2-(4-methylpiperazine-1-carbonyl)pyrrolidine-1-sulfonyl]-1-phenyl-1H-pyrazolo[3,4-b]pyridine-6-carboxamide;

3-cyclobutyl-4-[4-(methoxymethyl)piperidin-1-yl]-N-{4-[(2S)-2-(methoxymethyl)pyrrolidin-1-yl]piperidine-1-sulfonyl}-1-phenyl-1H-pyrazolo[3,4-b]pyridine-6-carboxamide;

3-cyclobutyl-4-[4-(methoxymethyl)piperidin-1-yl]-N-[methyl(propyl)sulfamoyl]-1-phenyl-1H-pyrazolo[3,4-b]pyridine-6-carboxamide;

3-cyclobutyl-N-[ethyl(propyl)sulfamoyl]-4-[4-(methoxymethyl)piperidin-1-yl]-1-phenyl-1H-pyrazolo[3,4-b]pyridine-6-carboxamide;

ethyl 4-[({3-cyclobutyl-4-[(methoxymethyl)piperidin-1-yl]-1-phenyl-1H-pyrazolo[3,4-b]pyridine-6-carbonyl}sulfamoyl)amino]piperidine-1-carboxylate;

N-(4-acetyl-1,4-diazepane-1-sulfonyl)-3-cyclobutyl-4-[4-(methoxymethyl)piperidin-1-yl]-1-phenyl-1H-pyrazolo[3,4-b]pyridine-6-carboxamide;

3-cyclobutyl-4-[4-(methoxymethyl)piperidin-1-yl]-N-{4-[(2R)-2-(methoxymethyl)pyrrolidin-1-yl]piperidine-1-sulfonyl}-1-phenyl-1H-pyrazolo[3,4-b]pyridine-6-carboxamide;

3-cyclobutyl-4-[4-(methoxymethyl)piperidin-1-yl]-N-(morpholine-4-sulfonyl)-1-phenyl-1H-pyrazolo[3,4-b]pyridine-6-carboxamide;

3-cyclobutyl-4-[4-(methoxymethyl)piperidin-1-yl]-N-[4-(morpholin-4-yl)piperidine-1-sulfonyl]-1-phenyl-1H-pyrazolo[3,4-b]pyridine-6-carboxamide;

3-cyclobutyl-4-[4-(methoxymethyl)piperidin-1-yl]-N-[4-(4-methylpiperazine-1-carbonyl)piperidine-1-sulfonyl]-1-phenyl-1H-pyrazolo[3,4-b]pyridine-6-carboxamide;

3-cyclobutyl-N-(4-fluoropiperidine-1-sulfonyl)-4-[4-(methoxymethyl)piperidin-1-yl]-1-phenyl-1H-pyrazolo[3,4-b]pyridine-6-carboxamide;

3-cyclobutyl-4-[4-(methoxymethyl)piperidin-1-yl]-N-(4-methylpiperazine-1-sulfonyl)-1-phenyl-1H-pyrazolo[3,4-b]pyridine-6-carboxamide;

3-cyclobutyl-N-(cyclopropanesulfonyl)-4-[4-(methoxymethyl)piperidin-1-yl]-1-phenyl-1H-pyrazolo[3,4-b]pyridine-6-carboxamide;

3-cyclobutyl-N-(dimethylsulfamoyl)-4-[4-(methoxymethyl)piperidin-1-yl]-1-phenyl-1H-pyrazolo[3,4-b]pyridine-6-carboxamide;

3-cyclobutyl-N-(ethanesulfonyl)-4-[4-(methoxymethyl)piperidin-1-yl]-1-phenyl-1H-pyrazolo[3,4-b]pyridine-6-carboxamide;

1-cyclohexyl-N-(methanesulfonyl)-4-{4-[(morpholin-4-yl)methyl]phenyl}-3-[(propan-2-yl)oxy]-1H-pyrazolo[3,4-b]pyridine-6-carboxamide;

1-cyclohexyl-N-(2-methoxyethanesulfonyl)-4-{4-[(morpholin-4-yl)methyl]phenyl}-3-[(propan-2-yl)oxy]-1H-pyrazolo[3,4-b]pyridine-6-carboxamide;

1-cyclohexyl-N-(dimethylsulfamoyl)-4-{4-[(morpholin-4-yl)methyl]phenyl}-3-[(propan-2-yl)oxy]-1H-pyrazolo[3,4-b]pyridine-6-carboxamide;

3-cyclobutyl-1-(4-fluorophenyl)-N-(2-methoxyethanesulfonyl)-4-[4-(morpholin-4-yl)piperidin-1-yl]-1H-pyrazolo[3,4-b]pyridine-6-carboxamide;

3-cyclobutyl-N-(dimethylsulfamoyl)-1-(4-fluorophenyl)-4-[4-(morpholin-4-yl)piperidin-1-yl]-1H-pyrazolo[3,4-b]pyridine-6-carboxamide;

3-cyclobutyl-N-(dimethylsulfamoyl)-1-(4-fluorophenyl)-4-{4-[(morpholin-4-yl)methyl]piperidin-1-yl}-1H-pyrazolo[3,4-b]pyridine-6-carboxamide;

3-cyclobutyl-1-(4-fluorophenyl)-N-(methanesulfonyl)-4-{4-[(morpholin-4-yl)methyl]piperidin-1-yl}-1H-pyrazolo[3,4-b]pyridine-6-carboxamide;

1-(4-fluorophenyl)-N-(methanesulfonyl)-4-[4-(morpholin-4-yl)piperidin-1-yl]-3-(propan-2-yl)-1H-pyrazolo[3,4-b]pyridine-6-carboxamide;

N-(dimethylsulfamoyl)-1-(4-fluorophenyl)-4-[4-(morpholin-4-yl)piperidin-1-yl]-3-(propan-2-yl)-1H-pyrazolo[3,4-b]pyridine-6-carboxamide;

N-(ethanesulfonyl)-1-(4-fluorophenyl)-4-[4-(morpholin-4-yl)piperidin-1-yl]-3-(propan-2-yl)-1H-pyrazolo[3,4-b]pyridine-6-carboxamide;

N-(cyclopropanesulfonyl)-1-(4-fluorophenyl)-4-[4-(morpholin-4-yl)piperidin-1-yl]-3-(propan-2-yl)-1H-pyrazolo[3,4-b]pyridine-6-carboxamide;

3-cyclobutyl-1-(4-fluorophenyl)-N-(2-methoxyethanesulfonyl)-4-{4-[2-(morpholin-4-yl)ethyl]piperidin-1-yl}-1H-pyrazolo[3,4-b]pyridine-6-carboxamide;

3-cyclobutyl-N-(dimethylsulfamoyl)-1-(4-fluorophenyl)-4-{4-[2-(morpholin-4-yl)ethyl]piperidin-1-yl}-1H-pyrazolo[3,4-b]pyridine-6-carboxamide;

3-cyclobutyl-N-[(1,4-dioxan-2-yl)methanesulfonyl]-4-[4-(methoxymethyl)piperidin-1-yl]-1-phenyl-1H-pyrazolo[3,4-b]pyridine-6-carboxamide;

3-cyclobutyl-1-cyclohexyl-N-(methanesulfonyl)-4-[4-(morpholin-4-yl)piperidin-1-yl]-1H-pyrazolo[3,4-b]pyridine-6-carboxamide;

3-cyclobutyl-1-cyclohexyl-N-(2-methoxyethanesulfonyl)-4-[4-(morpholin-4-yl)piperidin-1-yl]-1H-pyrazolo[3,4-b]pyridine-6-carboxamide;

3-cyclobutyl-1-cyclohexyl-N-(dimethylsulfamoyl)-4-[4-(morpholin-4-yl)piperidin-1-yl]-1H-pyrazolo[3,4-b]pyridine-6-carboxamide;

3-cyclobutyl-1-(4-fluorophenyl)-N-(methanesulfonyl)-4-[4-(morpholin-4-yl)piperidin-1-yl]-1H-pyrazolo[3,4-b]pyridine-6-carboxamide;

1-cyclohexyl-N-(methane sulfonyl)-4-[4-(4-methylpiperazine-1-carbonyl)phenyl]-3-[(propan-2-yl)oxy]-1H-pyrazolo[3,4-b]pyridine-6-carboxamide;

1-cyclohexyl-N-(dimethylsulfamoyl)-4-[4-(4-methylpiperazine-1-carbonyl)phenyl]-3-[(propan-2-yl)oxy]-1H-pyrazolo[3,4-b]pyridine-6-carboxamide;

3-cyclobutyl-1-cyclohexyl-N-(dimethylsulfamoyl)-4-{4-[(morpholin-4-yl)methyl]piperidin-1-yl}-1H-pyrazolo[3,4-b]pyridine-6-carboxamide;

3-cyclobutyl-1-cyclohexyl-N-(dimethylsulfamoyl)-4-{4-[2-(morpholin-4-yl)ethyl]piperidin-1-yl}-1H-pyrazolo[3,4-b]pyridine-6-carboxamide;

4-([1,4'-bipiperidin]-1'-yl)-3-cyclobutyl-N-(dimethylsulfamoyl)-1-phenyl-1H-pyrazolo[3,4-b]pyridine-6-carboxamide;

4-([1,4'-bipiperidin]-1'-yl)-3-cyclobutyl-N-(ethanesulfonyl)-1-phenyl-1H-pyrazolo[3,4-b]pyridine-6-carboxamide;

4-([1,4'-bipiperidin]-1'-yl)-3-cyclobutyl-N-(cyclopropanesulfonyl)-1-phenyl-1H-pyrazolo[3,4-b]pyridine-6-carboxamide;

3-cyclobutyl-1-(4-fluorophenyl)-4-[4-(morpholin-4-yl)piperidin-1-yl]-N-(oxolane-3-sulfonyl)-1H-pyrazolo[3,4-b]pyridine-6-carboxamide;

3-cyclobutyl-N-(methanesulfonyl)-4-[4-(methoxymethyl)piperidin-1-yl]-1-(2-methylpyridin-4-yl)-1H-pyrazolo[3,4-b]pyridine-6-carboxamide;

3-cyclobutyl-1-(4-fluorophenyl)-N-(methanesulfonyl)-4-{4-[2-(morpholin-4-yl)ethyl]piperidin-1-yl}-1H-pyrazolo[3,4-b]pyridine-6-carboxamide;

3-cyclobutyl-N-[methyl(propyl)sulfamoyl]-4-[(morpholin-4-yl)piperidin-1-yl]-1-phenyl-1H-pyrazolo[3,4-b]pyridine-6-carboxamide;

ethyl 4-[({3-cyclobutyl-4-[4-(morpholin-4-yl)piperidin-1-yl]-1-phenyl-1H-pyrazolo[3,4-b]pyridine-6-carbonyl}sulfamoyl)amino]piperidine-1-carboxylate;

3-cyclobutyl-N-(4-fluoropiperidine-1-sulfonyl)-4-[4-(morpholin-4-yl)piperidin-1-yl]-1-phenyl-1H-pyrazolo[3,4-b]pyridine-6-carboxamide;

3-cyclobutyl-N-(1-methylcyclopropane-1-sulfonyl)-4-[4-(morpholin-4-yl)piperidin-1-yl]-1-phenyl-1H-pyrazolo[3,4-b]pyridine-6-carboxamide;

3-cyclobutyl-N-(cyclopropanesulfonyl)-4-[4-(morpholin-4-yl)piperidin-1-yl]-1-phenyl-1H-pyrazolo[3,4-b]pyridine-6-carboxamide;

3-cyclobutyl-N-(ethanesulfonyl)-4-[4-(morpholin-4-yl)piperidin-1-yl]-1-phenyl-1H-pyrazolo[3,4-b]pyridine-6-carboxamide;

3-cyclobutyl-N-(2-methoxyethanesulfonyl)-4-[4-(morpholin-4-yl)piperidin-1-yl]-1-phenyl-1H-pyrazolo[3,4-b]pyridine-6-carboxamide;

3-cyclobutyl-N-{4-[(2S)-2-(methoxymethyl)pyrrolidin-1-yl]piperidine-1-sulfonyl}-4-[4-(morpholin-4-yl)piperidin-1-yl]-1-phenyl-1H-pyrazolo[3,4-b]pyridine-6-carboxamide;

3-cyclobutyl-N-(dimethylsulfamoyl)-1-(4-fluorophenyl)-4-{4-[4-(morpholin-4-yl)ethyl]piperidin-1-yl}-1H-pyrazolo[3,4-b]pyridine-6-carboxamide;

1-cyclohexyl-N-(methanesulfonyl)-4-{4-[(4-methylpiperazin-1-yl)methyl]phenyl}-3-[(propan-2-yl)oxy]-1H-pyrazolo[3,4-b]pyridine-6-carboxamide;

1-cyclohexyl-N-(dimethylsulfamoyl)-4-{4-[(4-methylpiperazin-1-yl)methyl]phenyl}-3-[(propan-2-yl)oxy]-1H-pyrazolo[3,4-b]pyridine-6-carboxamide;

1-cyclohexyl-N-(dimethylsulfamoyl)-4-{4-[(piperidin-1-yl)methyl]phenyl}-3-[(propan-2-yl)oxy]-1H-pyrazolo[3,4-b]pyridine-6-carboxamide;

1-cyclohexyl-N-(dimethylsulfamoyl)-3-[(propan-2-yl)oxy]-4-{4-[(pyrrolidin-1-yl)methyl]phenyl}-1H-pyrazolo[3,4-b]pyridine-6-carboxamide;

3-cyclobutyl-1-(4-fluorophenyl)-N-(methanesulfonyl)-4-{4-[1-(morpholin-4-yl)ethyl]piperidin-1-yl}-1H-pyrazolo[3,4-b]pyridine-6-carboxamide;

3-cyclobutyl-N-(ethanesulfonyl)-1-(4-fluorophenyl)-4-{4-[(morpholin-4-yl)ethyl]piperidin-1-yl}-1H-pyrazolo[3,4-b]pyridine-6-carboxamide;

3-cyclobutyl-1-(4-fluorophenyl)-N-(2-methoxyethanesulfonyl)-4-{4-[(morpholin-4-yl)methyl]piperidin-1-yl}-1H-pyrazolo[3,4-b]pyridine-6-carboxamide;

3-cyclobutyl-1-(4-fluorophenyl)-N-(2-hydroxyethanesulfonyl)-4-[4-(morpholin-4-yl)piperidin-1-yl]-1H-pyrazolo[3,4-b]pyridine-6-carboxamide;

N-(chloromethanesulfonyl)-3-cyclobutyl-4-[4-(methoxymethyl)piperidin-1-yl]-1-phenyl-1H-pyrazolo[3,4-b]pyridine-6-carboxamide;

4-([1,4'-bipiperidin]-1'-yl)-3-cyclobutyl-1-(4-fluorophenyl)-N-(methanesulfonyl)-1H-pyrazolo[3,4-b]pyridine-6-carboxamide;

4-([1,4'-bipiperidin]-1'-yl)-3-cyclobutyl-1-(4-fluorophenyl)-N-(oxolane-3-sulfonyl)-1H-pyrazolo[3,4-b]pyridine-6-carboxamide;

3-cyclobutyl-1-(4-fluorophenyl)-4-{4-[4-(morpholin-4-yl)ethyl]piperidin-1-yl}-N-(oxolane-3-sulfonyl)-1H-pyrazolo[3,4-b]pyridine-6-carboxamide;

N-([1,4'-bipiperidine]-1'-sulfonyl)-3-cyclobutyl-4-[4-(morpholin-4-yl)piperidin-1-yl]-1-phenyl-1H-pyrazolo[3,4-b]pyridine-6-carboxamide;

4-([1,4'-bipiperidin]-1'-yl)-3-cyclobutyl-N-[3-(morpholin-4-yl)propane-1-sulfonyl]-1-phenyl-1H-pyrazolo[3,4-b]pyridine-6-carboxamide;

3-cyclobutyl-N-(4-methylpiperazine-1-sulfonyl)-4-[4-(morpholin-4-yl)piperidin-1-yl]-1-phenyl-1H-pyrazolo[3,4-b]pyridine-6-carboxamide;

3-cyclobutyl-N-(dimethylsulfamoyl)-4-[4-(morpholin-4-yl)piperidin-1-yl]-1-phenyl-1H-pyrazolo[3,4-b]pyridine-6-carboxamide;

ethyl 4-{[(3-cyclobutyl-1-phenyl-4-{4-[(pyrrolidin-1-yl)methyl]piperidin-1-yl}-1H-pyrazolo[3,4-b]pyridine-6-carbonyl)sulfamoyl]amino}piperidine-1-carboxylate;

3-cyclobutyl-N-{4-[(2R)-2-(methoxymethyl)pyrrolidin-1-yl]piperidine-1-sulfonyl}-1-phenyl-4-{4-[(pyrrolidin-1-yl)methyl]piperidin-1-yl}-1H-pyrazolo[3,4-b]pyridine-6-carboxamide;

3-cyclobutyl-N-(4-fluoropiperidine-1-sulfonyl)-1-phenyl-4-{4-[(pyrrolidin-1-yl)methyl]piperidin-1-yl}-1H-pyrazolo[3,4-b]pyridine-6-carboxamide;

3-cyclobutyl-N-(4-methylpiperazine-1-sulfonyl)-1-phenyl-4-{4-[(pyrrolidin-1-yl)methyl]piperidin-1-yl}-1H-pyrazolo[3,4-b]pyridine-6-carboxamide;

3-cyclobutyl-N-(1-methylcyclopropane-1-sulfonyl)-1-phenyl-4-{4-[(pyrrolidin-1-yl)methyl]piperidin-1-yl}-1H-pyrazolo[3,4-b]pyridine-6-carboxamide;

3-cyclobutyl-N-(cyclopropanesulfonyl)-1-phenyl-4-{4-[(pyrrolidin-1-yl)methyl]piperidin-1-yl}-1H-pyrazolo[3,4-b]pyridine-6-carboxamide;

3-cyclobutyl-N-(ethanesulfonyl)-1-phenyl-4-{4-[(pyrrolidin-1-yl)methyl]piperidin-1-yl}-1H-pyrazolo[3,4-b]pyridine-6-carboxamide;

3-cyclobutyl-N-(2-methoxyethanesulfonyl)-1-phenyl-4-{4-[(pyrrolidin-1-yl)methyl]piperidin-1-yl}-1H-pyrazolo[3,4-b]pyridine-6-carboxamide;

3-cyclobutyl-N-(2-methylpropane-2-sulfonyl)-1-phenyl-4-{4-[(pyrrolidin-1-yl)methyl]piperidin-1-yl}-1H-pyrazolo[3,4-b]pyridine-6-carboxamide;

3-cyclobutyl-N-(ethanesulfonyl)-1-(4-fluorophenyl)-4-[4-(morpholin-4-yl)piperidin-1-yl]-1H-pyrazolo[3,4-b]pyridine-6-carboxamide;

3-(cyclobutyloxy)-1-cyclohexyl-4-{4-[(morpholin-4-yl)methyl]phenyl}-N-(oxolane-3-sulfonyl)-1H-pyrazolo[3,4-b]pyridine-6-carboxamide;

3-cyclobutyl-1-cyclohexyl-N-(oxolane-3-sulfonyl)-4-[4-(pyridin-4-yl)piperazin-1-yl]-1H-pyrazolo[3,4-b]pyridine-6-carboxamide;

3-cyclobutyl-1-cyclohexyl-N-(dimethylsulfamoyl)-4-[4-(pyridin-4-yl)piperazin-1-yl]-1H-pyrazolo[3,4-b]pyridine-6-carboxamide;

3-cyclobutyl-1-cyclohexyl-N-(ethanesulfonyl)-4-[4-(pyridin-4-yl)piperazin-1-yl]-1H-pyrazolo[3,4-b]pyridine-6-carboxamide;

3-cyclobutyl-1-(4-fluorophenyl)-N-[(2-methoxyethyl)(methyl)sulfamoyl]-4-[4-(morpholin-4-yl)piperidin-1-yl]-1H-pyrazolo[3,4-b]pyridine-6-carboxamide;

4-([1,4'-bipiperidin]-1'-yl)-3-cyclobutyl-N-(dimethylsulfamoyl)-1-(4-fluorophenyl)-1H-pyrazolo[3,4-b]pyridine-6-carboxamide;

3-cyclobutyl-N-(methanesulfonyl)-4-[4-(methoxymethyl)piperidin-1-yl]-1-[2-(oxan-4-yl)pyridin-4-yl]-1H-pyrazolo[3,4-b]pyridine-6-carboxamide;

3-cyclobutyl-N-(methanesulfonyl)-1-(2-methoxypyridin-4-yl)-4-[4-(morpholin-4-yl)piperidin-1-yl]-1H-pyrazolo[3,4-b]pyridine-6-carboxamide;

3-cyclobutyl-1-cyclohexyl-N-(dimethylsulfamoyl)-4-{4-[(morpholin-4-yl)methyl]phenyl}-1H-pyrazolo[3,4-b]pyridine-6-carboxamide;

3-cyclobutyl-1-cyclohexyl-N-(dimethylsulfamoyl)-4-{4-[2-(morpholin-4-yl)ethyl]phenyl}-1H-pyrazolo[3,4-b]pyridine-6-carboxamide;

N-(but-3-yne-1-sulfonyl)-3-cyclobutyl-1-(4-fluorophenyl)-4-[4-(morpholin-4-yl)piperidin-1-yl]-1H-pyrazolo[3,4-b]pyridine-6-carboxamide;

4-([1,4'-bipiperidin]-1'-yl)-3-cyclobutyl-N-(ethanesulfonyl)-1-(4-fluorophenyl)-1H-pyrazolo[3,4-b]pyridine-6-carboxamide;

3-cyclobutyl-N-(dimethyl sulfamoyl)-1-(4-fluorophenyl)-4-{4-[(1R)-1-(morpholin-4-yl)ethyl]piperidin-1-yl}-1H-pyrazolo[3,4-b]pyridine-6-carboxamide;

3-cyclobutyl-N-(dimethylsulfamoyl)-1-(4-fluorophenyl)-4-{4-[(1S)-1-(morpholin-4-yl)ethyl]piperidin-1-yl}-1H-pyrazolo[3,4-b]pyridine-6-carboxamide;

3-(cyclobutyloxy)-1-cyclohexyl-N-(dimethylsulfamoyl)-4-{4-[(morpholin-4-yl)methyl]phenyl}-1H-pyrazolo[3,4-b]pyridine-6-carboxamide;

3-cyclobutyl-1-(4-fluorophenyl)-N-[methyl (propan-2-yl)sulfamoyl]-4-[4-(morpholin-4-yl)piperidin-1-yl]-1H-pyrazolo[3,4-b]pyridine-6-carboxamide;

3-cyclobutyl-N-[ethyl(methyl)sulfamoyl]-1-(4-fluorophenyl)-4-[4-(morpholin-4-yl)piperidin-1-yl]-1H-pyrazolo[3,4-b]pyridine-6-carboxamide;

3-cyclobutyl-1-(4-fluorophenyl)-N-(3-methoxyazetidine-1-sulfonyl)-4-[4-(morpholin-4-yl)piperidin-1-yl]-1H-pyrazolo[3,4-b]pyridine-6-carboxamide;

3-cyclobutyl-1-(4-fluorophenyl)-4-[4-(morpholin-4-yl)piperidin-1-yl]-N-(pyrrolidine-1-sulfonyl)-1H-pyrazolo[3,4-b]pyridine-6-carboxamide;

3-cyclobutyl-1-(4-fluorophenyl)-4-[4-(morpholin-4-yl)piperidin-1-yl]-N-(2,2,2-trifluoroethanesulfonyl)-1H-pyrazolo[3,4-b]pyridine-6-carboxamide;

3-cyclobutyl-1-(4-fluorophenyl)-N-(morpholine-4-sulfonyl)-4-[4-(morpholin-4-yl)piperidin-1-yl]-1H-pyrazolo[3,4-b]pyridine-6-carboxamide;

4-([1,4'-bipiperidin]-1'-yl)-3-cyclobutyl-1-(4-fluorophenyl)-N-(2-methoxyethanesulfonyl)-1H-pyrazolo[3,4-b]pyridine-6-carboxamide;

N-(dimethylsulfamoyl)-1-[2-(morpholin-4-yl)pyridin-4-yl]-4-[(oxan-4-yl)methoxy]-3-(propan-2-yl)-1H-pyrazolo[3,4-b]pyridine-6-carboxamide;

3-cyclobutyl-N-(methanesulfonyl)-4-[4-(morpholin-4-yl)piperidin-1-yl]-1-[2-(oxan-4-yl)pyridin-4-yl]-1H-pyrazolo[3,4-b]pyridine-6-carboxamide;

3-cyclobutyl-1-(4-fluorophenyl)-N-(2-hydroxyethane sulfonyl)-4-{4-[2-(morpholin-4-yl)ethyl]piperidin-1-yl}-1H-pyrazolo[3,4-b]pyridine-6-carboxamide;

methyl 4-(1-{3-cyclobutyl-6-[(dimethylsulfamoyl)carbamoyl]-1-(4-fluorophenyl)-1H-pyrazolo[3,4-b]pyridin-4-yl}piperidin-4-yl)piperazine-1-carboxylate;

4-[4-(4-acetylpiperazin-1-yl)piperidin-1-yl]-3-cyclobutyl-N-(dimethylsulfamoyl)-1-(4-fluorophenyl)-1H-pyrazolo[3,4-b]pyridine-6-carboxamide;

3-cyclobutyl-N-(ethanesulfonyl)-1-(4-fluorophenyl)-4-{4-[(morpholin-4-yl)methyl]piperidin-1-yl}-1H-pyrazolo[3,4-b]pyridine-6-carboxamide;

3-cyclobutyl-1-(4-fluorophenyl)-4-{4-[(morpholin-4-yl)methyl]piperidin-1-yl}-N-(oxolane-3-sulfonyl)-1H-pyrazolo[3,4-b]pyridine-6-carboxamide;

ethyl 4-[1-(4-fluorophenyl)-6-[(methanesulfonyl)carbamoyl]-3-(propan-2-yl)-1H-pyrazolo[3,4-b]pyridin-4-yl]piperidine-1-carboxylate;

ethyl 4-{6-[(dimethylsulfamoyl)carbamoyl]-1-(4-fluorophenyl)-3-(propan-2-yl)-1H-pyrazolo[3,4-b]pyridin-4-yl}piperidine-1-carboxylate;

3-cyclobutyl-N-(dimethylsulfamoyl)-1-(3-methylphenyl)-4-[4-(morpholin-4-yl)piperidin-1-yl]-1H-pyrazolo[3,4-b]pyridine-6-carboxamide;

3-cyclobutyl-N-(dimethylsulfamoyl)-1-(3-methoxyphenyl)-4-[4-(morpholin-4-yl)piperidin-1-yl]-1H-pyrazolo[3,4-b]pyridine-6-carboxamide;

3-cyclobutyl-N-(dimethyl sulfamoyl)-4-[4-(morpholin-4-yl)piperidin-1-yl]-1-[4-(trifluoromethyl)phenyl]-1H-pyrazolo[3,4-b]pyridine-6-carboxamide;

3-cyclobutyl-4-[4-(ethoxymethyl)-4-fluoropiperidin-1-yl]-N-(methanesulfonyl)-1-phenyl-1H-pyrazolo[3,4-b]pyridine-6-carboxamide;

3-cyclobutyl-4-{4-fluoro-4-[(2-methoxyethoxy)methyl]piperidin-1-yl}-N-(methanesulfonyl)-1-phenyl-1H-pyrazolo[3,4-b]pyridine-6-carboxamide;

3-cyclobutyl-4-{3-fluoro-3-[(2-methoxyethoxy)methyl]piperidin-1-yl}-N-(methanesulfonyl)-1-phenyl-1H-pyrazolo[3,4-b]pyridine-6-carboxamide;

3-cyclobutyl-4-[4-fluoro-4-(methoxymethyl)piperidin-1-yl]-N-(methanesulfonyl)-1-phenyl-1H-pyrazolo[3,4-b]pyridine-6-carboxamide;

N-(4-cyanopiperidine-1-sulfonyl)-3-cyclobutyl-1-(4-fluorophenyl)-4-[4-(morpholin-4-yl)piperidin-1-yl]-1H-pyrazolo[3,4-b]pyridine-6-carboxamide;

3-cyclobutyl-1-(4-fluorophenyl)-4-[4-(morpholin-4-yl)piperidin-1-yl]-N-(oxetane-3-sulfonyl)-1H-pyrazolo[3,4-b]pyridine-6-carboxamide;

3-cyclobutyl-N-(cyclopropanesulfonyl)-1-(4-fluorophenyl)-4-[4-(morpholin-4-yl)piperidin-1-yl]-1H-pyrazolo[3,4-b]pyridine-6-carboxamide;

3-cyclobutyl-1-(4-fluorophenyl)-N-(1-methylcyclopropane-1-sulfonyl)-4-[4-(morpholin-4-yl)piperidin-1-yl]-1H-pyrazolo[3,4-b]pyridine-6-carboxamide;

3-cyclobutyl-N-(methanesulfonyl)-1-(3-methylphenyl)-4-[4-(morpholin-4-yl)piperidin-1-yl]-1H-pyrazolo[3,4-b]pyridine-6-carboxamide;

3-cyclobutyl-N-(methanesulfonyl)-4-[4-(morpholin-4-yl)piperidin-1-yl]-1-[4-(trifluoromethyl)phenyl]-1H-pyrazolo[3,4-b]pyridine-6-carboxamide;

3-cyclobutyl-N-(dimethylsulfamoyl)-1-(4-fluoro-3-methylphenyl)-4-[4-(morpholin-4-yl)piperidin-1-yl]-1H-pyrazolo[3,4-b]pyridine-6-carboxamide;

3-cyclobutyl-N-(dimethylsulfamoyl)-1-(3-fluorophenyl)-4-[4-(morpholin-4-yl)piperidin-1-yl]-1H-pyrazolo[3,4-b]pyridine-6-carboxamide;

3-cyclobutyl-N-(dimethylsulfamoyl)-4-[4-(morpholin-4-yl)piperidin-1-yl]-1-[3-(trifluoromethyl)phenyl]-1H-pyrazolo[3,4-b]pyridine-6-carboxamide;

3-cyclobutyl-1-(4-fluoro-3-methylphenyl)-N-(methanesulfonyl)-4-[4-(morpholin-4-yl)piperidin-1-yl]-1H-pyrazolo[3,4-b]pyridine-6-carboxamide;

3-cyclobutyl-1-(3-fluorophenyl)-N-(methanesulfonyl)-4-[4-(morpholin-4-yl)piperidin-1-yl]-1H-pyrazolo[3,4-b]pyridine-6-carboxamide;

3-cyclobutyl-N-(methanesulfonyl)-4-[4-(morpholin-4-yl)piperidin-1-yl]-1-[3-(trifluoromethyl)phenyl]-1H-pyrazolo[3,4-b]pyridine-6-carboxamide;

3-cyclobutyl-1-(4-fluorophenyl)-N-(methylsulfamoyl)-4-[4-(morpholin-4-yl)piperidin-1-yl]-1H-pyrazolo[3,4-b]pyridine-6-carboxamide;

3-cyclobutyl-1-(4-fluorophenyl)-N-(methanesulfonyl)-4-[(4-methylpiperazin-1-yl)methyl]-1H-pyrazolo[3,4-b]pyridine-6-carboxamide;

3-cyclobutyl-1-(4-fluorophenyl)-N-(methanesulfonyl)-4-[(morpholin-4-yl)methyl]-1H-pyrazolo[3,4-b]pyridine-6-carboxamide;

3-cyclobutyl-N-(dimethylsulfamoyl)-1-(4-fluorophenyl)-4-[(morpholin-4-yl)methyl]-1H-pyrazolo[3,4-b]pyridine-6-carboxamide;

3-cyclobutyl-N-(dimethylsulfamoyl)-1-(4-fluorophenyl)-4-{[4-(methoxymethyl)piperidin-1-yl]methyl}-1H-pyrazolo[3,4-b]pyridine-6-carboxamide;

4-(4-cyano[1,4'-bipiperidin]-1'-yl)-3-cyclobutyl-N-(dimethylsulfamoyl)-1-(4-fluorophenyl)-1H-pyrazolo[3,4-b]pyridine-6-carboxamide;

4-[4-cyanoazetidin-1-yl)piperidin-1-yl]-3-cyclobutyl-N-(dimethylsulfamoyl)-1-(4-fluorophenyl)-1H-pyrazolo[3,4-b]pyridine-6-carboxamide;

3-cyclobutyl-N-(dimethylsulfamoyl)-1-(4-fluorophenyl)-4-[4-(3-methoxypyrrolidin-1-yl)piperidin-1-yl]-1H-pyrazolo[3,4-b]pyridine-6-carboxamide;

3-cyclobutyl-N-(dimethylsulfamoyl)-4-(4-fluoro[1,4'-bipiperidin]-1'-yl)-1-(4-fluorophenyl)-1H-pyrazolo[3,4-b]pyridine-6-carboxamide;

3-cyclobutyl-4-(4,4-difluoro[1,4'-bipiperidin]-1'-yl)-N-(dimethylsulfamoyl)-1-(4-fluorophenyl)-1H-pyrazolo[3,4-b]pyridine-6-carboxamide;

4-[4-(2-cyanomorpholin-4-yl)piperidin-1-yl]-3-cyclobutyl-N-(dimethylsulfamoyl)-1-(4-fluorophenyl)-1H-pyrazolo[3,4-b]pyridine-6-carboxamide;

3-cyclobutyl-N-(dimethylsulfamoyl)-1-(4-fluorophenyl)-4-{4-[methyl(oxan-4-yl)amino]piperidin-1-yl}-1H-pyrazolo[3,4-b]pyridine-6-carboxamide;

3-cyclobutyl-N-(dimethylsulfamoyl)-4-[4-(morpholin-4-yl)piperidin-1-yl]-1-{2-[(propan-2-yl)oxy]pyridin-4-yl}-1H-pyrazolo[3,4-b]pyridine-6-carboxamide;

3-cyclobutyl-N-(methanesulfonyl)-4-[4-(morpholin-4-yl)piperidin-1-yl]-1-{2-[(propan-2-yl)oxy]pyridin-4-yl}-1H-pyrazolo[3,4-b]pyridine-6-carboxamide;

3-cyclobutyl-N-(dimethylsulfamoyl)-4-[4-(methoxymethyl)piperidin-1-yl]-1-[2-(oxan-4-yl)pyridin-4-yl]-1H-pyrazolo[3,4-b]pyridine-6-carboxamide;

3-cyclobutyl-N-(dimethylsulfamoyl)-1-(4-fluorophenyl)-4-[4-(2-oxa-5-azabicyclo[2.2.1]heptan-5-yl)piperidin-1-yl]-1H-pyrazolo[3,4-b]pyridine-6-carboxamide;

3-cyclobutyl-N-(dimethylsulfamoyl)-1-(4-fluorophenyl)-4-[3-(morpholin-4-yl)-1-oxa-8-azaspiro[4.5]decan-8-yl]-1H-pyrazolo[3,4-b]pyridine-6-carboxamide;

1-cyclohexyl-N-(dimethylsulfamoyl)-3-[(propan-2-yl)oxy]-4-{4-[4-(propan-2-yl)piperazin-1-yl]phenyl}-1H-pyrazolo[3,4-b]pyridine-6-carboxamide;

3-cyclobutyl-1-cyclohexyl-N-(dimethylsulfamoyl)-4-[4-(2-methylpyridin-4-yl)piperazin-1-yl]-1H-pyrazolo[3,4-b]pyridine-6-carboxamide;

3-cyclobutyl-1-cyclohexyl-4-[6-(4-cyclopropylpiperazin-1-yl)pyridin-3-yl]-N-(dimethylsulfamoyl)-1H-pyrazolo[3,4-b]pyridine-6-carboxamide;

3-cyclobutyl-1-(4-fluorophenyl)-N-(3-fluoropyrrolidine-1-sulfonyl)-4-[4-(morpholin-4-yl)piperidin-1-yl]-1H-pyrazolo[3,4-b]pyridine-6-carboxamide;

3-cyclobutyl-1-(4-fluorophenyl)-N-(3-methoxypyrrolidine-1-sulfonyl)-4-[4-(morpholin-4-yl)piperidin-1-yl]-1H-pyrazolo[3,4-b]pyridine-6-carboxamide;

4-[6-(4-cyanopiperidin-1-yl)pyridin-3-yl]-3-cyclobutyl-N-(dimethylsulfamoyl)-1-phenyl-1H-pyrazolo[3,4-b]pyridine-6-carboxamide;

3-cyclobutyl-1-(4-fluorophenyl)-N-[4-(methoxymethyl)piperidine-1-sulfonyl]-4-[4-(morpholin-4-yl)piperidin-1-yl]-1H-pyrazolo[3,4-b]pyridine-6-carboxamide;

3-cyclobutyl-N-(dimethylsulfamoyl)-1-(4-fluorophenyl)-4-[4-(3-fluoropyrrolidin-1-yl)piperidin-1-yl]-1H-pyrazolo[3,4-b]pyridine-6-carboxamide;

3-cyclobutyl-1-cyclohexyl-N-(dimethylsulfamoyl)-4-{6-[4-(propan-2-yl)piperazin-1-yl]pyridin-3-yl}-1H-pyrazolo[3,4-b]pyridine-6-carboxamide;

3-cyclobutyl-1-cyclohexyl-N-(dimethylsulfamoyl)-4-{4-[1-(morpholin-4-yl)ethyl]phenyl}-1H-pyrazolo[3,4-b]pyridine-6-carboxamide;

1-cyclohexyl-4-{4-[4-(dimethylamino)piperidine-1-carbonyl]phenyl}-N-(methanesulfonyl)-3-[(propan-2-yl)oxy]-1H-pyrazolo[3,4-b]pyridine-6-carboxamide;

1-cyclohexyl-4-{4-[4-(dimethylamino)piperidine-1-carbonyl]phenyl}-N-(2-methoxyethanesulfonyl)-3-[(propan-2-yl)oxy]-1H-pyrazolo[3,4-b]pyridine-6-carboxamide;

1-cyclohexyl-4-{4-[4-(dimethylamino)piperidine-1-carbonyl]phenyl}-N-(dimethylsulfamoyl)-3-[(propan-2-yl)oxy]-1H-pyrazolo[3,4-b]pyridine-6-carboxamide;

3-cyclobutyl-1-cyclohexyl-N-(dimethylsulfamoyl)-4-{4-[4-(propan-2-yl)piperazin-1-yl]phenyl}-1H-pyrazolo[3,4-b]pyridine-6-carboxamide;

3-cyclobutyl-1-(4-fluorophenyl)-N-(methanesulfonyl)-4-(4-methoxy[1,4'-bipiperidin]-1'-yl)-1H-pyrazolo[3,4-b]pyridine-6-carboxamide;

3-cyclobutyl-4-[4-(4-cyclopropylpiperazin-1-yl)piperidin-1-yl]-N-(dimethylsulfamoyl)-1-phenyl-1H-pyrazolo[3,4-b]pyridine-6-carboxamide;

3-cyclobutyl-N-(cyclopropanesulfonyl)-4-[4-(4-cyclopropylpiperazin-1-yl)piperidin-1-yl]-1-phenyl-1H-pyrazolo[3,4-b]pyridine-6-carboxamide;

3-cyclobutyl-1-cyclohexyl-N-(dimethylsulfamoyl)-4-[6-(4-methylpiperazin-1-yl)pyridin-3-yl]-1H-pyrazolo[3,4-b]pyridine-6-carboxamide;

3-cyclobutyl-1-cyclohexyl-N-(dimethylsulfamoyl)-4-{6-[4-(2-methoxyethyl)piperazin-1-yl]pyridin-3-yl}-1H-pyrazolo[3,4-b]pyridine-6-carboxamide;

3-cyclobutyl-1-cyclohexyl-N-(dimethylsulfamoyl)-4-{4-[4-(propan-2-yl)piperazin-1-yl]piperidin-1-yl}-1H-pyrazolo[3,4-b]pyridine-6-carboxamide;

3-cyclobutyl-4-[4-(4-cyclopropylpiperazin-1-yl)piperidin-1-yl]-N-[methyl(propyl)sulfamoyl]-1-phenyl-1H-pyrazolo[3,4-b]pyridine-6-carboxamide;

3-cyclobutyl-4-[4-(4-cyclopropylpiperazin-1-yl)piperidin-1-yl]-N-(morpholine-4-sulfonyl)-1-phenyl-1H-pyrazolo[3,4-b]pyridine-6-carboxamide;

3-cyclobutyl-4-[4-(4-cyclopropylpiperazin-1-yl)piperidin-1-yl]-N-(methanesulfonyl)-1-phenyl-1H-pyrazolo[3,4-b]pyridine-6-carboxamide;

3-cyclobutyl-4-[4-(4-cyclopropylpiperazin-1-yl)piperidin-1-yl]-N-(1-methylcyclopropane-1-sulfonyl)-1-phenyl-1H-pyrazolo[3,4-b]pyridine-6-carboxamide;

3-cyclobutyl-4-[4-(4-cyclopropylpiperazin-1-yl)piperidin-1-yl]-N-(methylsulfamoyl)-1-phenyl-1H-pyrazolo[3,4-b]pyridine-6-carboxamide;

1-cyclohexyl-4-[4-(4-cyclopropylpiperazin-1-yl)phenyl]-N-(dimethylsulfamoyl)-3-[(propan-2-yl)oxy]-1H-pyrazolo[3,4-b]pyridine-6-carboxamide;

3-cyclobutyl-N-(dimethylsulfamoyl)-1-(4-fluorophenyl)-4-{4-[3-(trifluoromethyl)pyrrolidin-1-yl]piperidin-1-yl}-1H-pyrazolo[3,4-b]pyridine-6-carboxamide;

4-[4-(3-cyanopyrrolidin-1-yl)piperidin-1-yl]-3-cyclobutyl-N-(dimethylsulfamoyl)-1-(4-fluorophenyl)-1H-pyrazolo[3,4-b]pyridine-6-carboxamide;

4-(3-cyano[1,4'-bipiperidin]-1'-yl)-3-cyclobutyl-N-(dimethylsulfamoyl)-1-(4-fluorophenyl)-1H-pyrazolo[3,4-b]pyridine-6-carboxamide;

3-cyclobutyl-N-(dimethylsulfamoyl)-4-(3-fluoro[1,4'-bipiperidin]-1'-yl)-1-(4-fluorophenyl)-1H-pyrazolo[3,4-b]pyridine-6-carboxamide;

3-cyclobutyl-1-(4-fluorophenyl)-N-(methanesulfonyl)-4-{4-[3-(trifluoromethyl)pyrrolidin-1-yl]piperidin-1-yl}-1H-pyrazolo[3,4-b]pyridine-6-carboxamide;

4-[4-(3-cyanopyrrolidin-1-yl)piperidin-1-yl]-3-cyclobutyl-1-(4-fluorophenyl)-N-(methanesulfonyl)-1H-pyrazolo[3,4-b]pyridine-6-carboxamide;

4-(3-cyano[1,4'-bipiperidin]-1'-yl)-3-cyclobutyl-1-(4-fluorophenyl)-N-(methanesulfonyl)-1H-pyrazolo[3,4-b]pyridine-6-carboxamide;

3-cyclobutyl-4-(3-fluoro[1,4'-bipiperidin]-1'-yl)-1-(4-fluorophenyl)-N-(methanesulfonyl)-1H-pyrazolo[3,4-b]pyridine-6-carboxamide;

3-cyclobutyl-1-(4-fluorophenyl)-4-[4-(morpholin-4-yl)piperidin-1-yl]-N-(piperidine-1-sulfonyl)-1H-pyrazolo[3,4-b]pyridine-6-carboxamide;

3-cyclobutyl-N-(3-fluoroazetidine-1-sulfonyl)-1-(4-fluorophenyl)-4-[4-(morpholin-4-yl)piperidin-1-yl]-1H-pyrazolo[3,4-b]pyridine-6-carboxamide;

3-cyclobutyl-N-(dimethylsulfamoyl)-1-(4-fluorophenyl)-4-[4-(3-methoxyazetidin-1-yl)piperidin-1-yl]-1H-pyrazolo[3,4-b]pyridine-6-carboxamide;

3-cyclobutyl-N-(dimethylsulfamoyl)-1-(4-fluorophenyl)-4-[3-(trifluoromethyl)[1,4'-bipiperidin]-1'-yl]-1H-pyrazolo[3,4-b]pyridine-6-carboxamide;

3-cyclobutyl-N-(dimethylsulfamoyl)-1-(4-fluorophenyl)-4-(3-methoxy[1,4'-bipiperidin]-1'-yl)-1H-pyrazolo[3,4-b]pyridine-6-carboxamide;

3-cyclobutyl-4-[4-(2,2-dimethylmorpholin-4-yl)piperidin-1-yl]-N-(dimethylsulfamoyl)-1-(4-fluorophenyl)-1H-pyrazolo[3,4-b]pyridine-6-carboxamide;

N-(2-acetamidoethanesulfonyl)-3-cyclobutyl-1-(4-fluorophenyl)-4-[4-(morpholin-4-yl)piperidin-1-yl]-1H-pyrazolo[3,4-b]pyridine-6-carboxamide;

3-cyclobutyl-1-[2-(difluoromethoxy)pyridin-4-yl]-N-(dimethylsulfamoyl)-4-[4-(morpholin-4-yl)piperidin-1-yl]-1H-pyrazolo[3,4-b]pyridine-6-carboxamide;

N-(azetidine-1-sulfonyl)-3-cyclobutyl-1-(4-fluorophenyl)-4-[4-(morpholin-4-yl)piperidin-1-yl]-1H-pyrazolo[3,4-b]pyridine-6-carboxamide;

3-cyclobutyl-1-(4-fluorophenyl)-N-[(2R)-2-(methoxymethyl)pyrrolidine-1-sulfonyl]-4-[4-(morpholin-4-yl)piperidin-1-yl]-1H-pyrazolo[3,4-b]pyridine-6-carboxamide;

3-cyclobutyl-1-(4-fluorophenyl)-4-[4-(morpholin-4-yl)piperidin-1-yl]-N-[(oxan-4-yl)sulfamoyl]-1H-pyrazolo[3,4-b]pyridine-6-carboxamide;

3-cyclobutyl-1-(4-fluorophenyl)-N-[methyl(oxan-4-yl)sulfamoyl]-4-[4-(morpholin-4-yl)piperidin-1-yl]-1H-pyrazolo[3,4-b]pyridine-6-carboxamide;

3-cyclobutyl-N-(3,3-difluoroazetidine-1-sulfonyl)-1-(4-fluorophenyl)-4-[4-(morpholin-4-yl)piperidin-1-yl]-1H-pyrazolo[3,4-b]pyridine-6-carboxamide;

4-[(3S)-4-benzyl-3-methylpiperazin-1-yl]-3-cyclobutyl-1-cyclohexyl-N-(dimethylsulfamoyl)-1H-pyrazolo[3,4-b]pyridine-6-carboxamide;

4-[(3R)-4-benzyl-3-methylpiperazin-1-yl]-3-cyclobutyl-1-cyclohexyl-N-(dimethylsulfamoyl)-1H-pyrazolo[3,4-b]pyridine-6-carboxamide;

3-cyclobutyl-4-[4-(4-cyclopropylpiperazin-1-yl)piperidin-1-yl]-N-(dimethylsulfamoyl)-1-(4-fluorophenyl)-1H-pyrazolo[3,4-b]pyridine-6-carboxamide;

3-cyclobutyl-4-(9-cyclopropyl-3,9-diazaspiro[5.5]undecan-3-yl)-N-(dimethylsulfamoyl)-1-(4-fluorophenyl)-1H-pyrazolo[3,4-b]pyridine-6-carboxamide;

3-cyclobutyl-1-(4-fluorophenyl)-N-(methanesulfonyl)-4-[4-(3-methoxyazetidin-1-yl)piperidin-1-yl]-1H-pyrazolo[3,4-b]pyridine-6-carboxamide;

3-cyclobutyl-1-(4-fluorophenyl)-N-(methanesulfonyl)-4-[3-(trifluoromethyl)[1,4'-bipiperidin]-1'-yl]-1H-pyrazolo[3,4-b]pyridine-6-carboxamide;
3-cyclobutyl-1-(4-fluorophenyl)-N-(methanesulfonyl)-4-(3-methoxy[1,4'-bipiperidin]-1'-yl)-1H-pyrazolo[3,4-b]pyridine-6-carboxamide;
3-cyclobutyl-4-[4-(2,2-dimethylmorpholin-4-yl)piperidin-1-yl]-1-(4-fluorophenyl)-N-(methanesulfonyl)-1H-pyrazolo[3,4-b]pyridine-6-carboxamide;
3-cyclobutyl-N-(dimethylsulfamoyl)-1-(4-fluorophenyl)-4-{4-[(pyrrolidin-1-yl)methyl]piperidin-1-yl}-1H-pyrazolo[3,4-b]pyridine-6-carboxamide;
ethyl 4-(1-{3-cyclobutyl-6-[(dimethylsulfamoyl)carbamoyl]-1-(4-fluorophenyl)-1H-pyrazolo[3,4-b]pyridin-4-yl}piperidin-4-yl)piperazine-1-carboxylate;
3-cyclobutyl-N-(dimethylsulfamoyl)-1-(4-fluorophenyl)-4-{4-[(2-methoxyethyl)(methyl)amino]piperidin-1-yl}-1H-pyrazolo[3,4-b]pyridine-6-carboxamide;
3-cyclobutyl-1-(4-fluorophenyl)-N-(methoxysulfamoyl)-4-[4-(morpholin-4-yl)piperidin-1-yl]-1H-pyrazolo[3,4-b]pyridine-6-carboxamide;
3-cyclobutyl-4-[1-(4,4-difluorocyclohexyl)piperidin-4-yl]-1-(4-fluorophenyl)-N-(methanesulfonyl)-1H-pyrazolo[3,4-b]pyridine-6-carboxamide;
3-cyclobutyl-4-[1-(4,4-difluorocyclohexyl)piperidin-4-yl]-N-(dimethylsulfamoyl)-1-(4-fluorophenyl)-1H-pyrazolo[3,4-b]pyridine-6-carboxamide;
3-cyclobutyl-N-(dimethylsulfamoyl)-1-(4-fluorophenyl)-4-{[4-(morpholin-4-yl)piperidin-1-yl]methyl}-1H-pyrazolo[3,4-b]pyridine-6-carboxamide;
3-cyclobutyl-1-(4-fluorophenyl)-N-(methanesulfonyl)-4-{[4-(morpholin-4-yl)piperidin-1-yl]methyl}-1H-pyrazolo[3,4-b]pyridine-6-carboxamide;
1-cyclohexyl-4-{4-[(4-cyclopropylpiperazin-1-yl)methyl]phenyl}-N-(methanesulfonyl)-3-[(propan-2-yl)oxy]-1H-pyrazolo[3,4-b]pyridine-6-carboxamide;
3-cyclobutyl-N-(dimethylsulfamoyl)-1-(4-fluorophenyl)-4-[1-(propan-2-yl)piperidin-4-yl]-1H-pyrazolo[3,4-b]pyridine-6-carboxamide;
3-cyclobutyl-1-(4-fluorophenyl)-N-(methanesulfonyl)-4-[1-(oxan-4-yl)piperidin-4-yl]-1H-pyrazolo[3,4-b]pyridine-6-carboxamide;
3-cyclobutyl-1-(4-fluorophenyl)-N-(methanesulfonyl)-4-{1-[(oxan-4-yl)methyl]piperidin-4-yl}-1H-pyrazolo[3,4-b]pyridine-6-carboxamide;
3-cyclobutyl-N-(dimethylsulfamoyl)-1-(4-fluorophenyl)-4-{1-[(oxan-4-yl)methyl]piperidin-4-yl}-1H-pyrazolo[3,4-b]pyridine-6-carboxamide;
3-cyclobutyl-4-{1-[(2,5-dimethoxyoxolan-3-yl)methyl]piperidin-4-yl}-1-(4-fluorophenyl)-N-(methanesulfonyl)-1H-pyrazolo[3,4-b]pyridine-6-carboxamide;
3-cyclobutyl-1-(4-fluorophenyl)-N-(methanesulfonyl)-4-[1-(3,3,3-trifluoropropyl)piperidin-4-yl]-1H-pyrazolo[3,4-b]pyridine-6-carboxamide;
3-cyclobutyl-N-(dimethyl sulfamoyl)-1-(4-fluorophenyl)-4-[1-(3,3,3-trifluoropropyl)piperidin-4-yl]-1H-pyrazolo[3,4-b]pyridine-6-carboxamide;
3-cyclobutyl-N-(dimethysulfamoyl)-1-(4-fluorophenyl)-4-(4-hydroxy[1,4'-bipiperidin]-1'-yl)-1H-pyrazolo[3,4-b]pyridine-6-carboxamide;
methyl {3-cyclobutyl-1-(4-fluorophenyl)-4-[4-(morpholin-4-yl)piperidin-1-yl]-1H-pyrazolo[3,4-b]pyridine-6-carbonyl}sulfamate;
3-cyclobutyl-N-(dimethylsulfamoyl)-1-(4-fluorophenyl)-4-{4-[4-(2-methoxyethyl)piperazin-1-yl]piperidin-1-yl}-1H-pyrazolo[3,4-b]pyridine-6-carboxamide;
3-cyclobutyl-1-(4-fluorophenyl)-4-[4-(methoxymethyl)piperidin-1-yl]-N-[3-(morpholin-4-yl)pyrrolidine-1-sulfonyl]-1H-pyrazolo[3,4-b]pyridine-6-carboxamide;
3-cyclobutyl-N-(4-cyclopropylpiperazine-1-sulfonyl)-1-(4-fluorophenyl)-4-[4-(methoxymethyl)piperidin-1-yl]-1H-pyrazolo[3,4-b]pyridine-6-carboxamide;
3-cyclobutyl-1-(4-fluorophenyl)-N-[4-(2-methoxyethyl)piperazine-1-sulfonyl]-4-[4-(methoxymethyl)piperidin-1-yl]-1H-pyrazolo[3,4-b]pyridine-6-carboxamide;
3-cyclobutyl-1-(4-fluorophenyl)-N-(methanesulfonyl)-4-[1-(propan-2-yl)piperidin-4-yl]-1H-pyrazolo[3,4-b]pyridine-6-carboxamide;
3-cyclobutyl-N-(dimethylsulfamoyl)-1-(4-fluorophenyl)-4-[1-(oxan-4-yl)piperidin-4-yl]-1H-pyrazolo[3,4-b]pyridine-6-carboxamide;
3-cyclobutyl-4-[1-(cyclopropylmethyl)piperidin-4-yl]-N-(dimethylsulfamoyl)-1-(4-fluorophenyl)-1H-pyrazolo[3,4-b]pyridine-6-carboxamide;
3-cyclobutyl-N-(dimethylsulfamoyl)-1-(4-fluorophenyl)-4-[9-(oxetan-3-yl)-3,9-diazapiro[5.5]undecan-3-yl]-1H-pyrazolo[3,4-b]pyridine-6-carboxamide;
3-cyclobutyl-N-(dimethylsulfamoyl)-1-(4-fluorophenyl)-4-{4-[4-(oxetan-3-yl)piperazin-1-yl]piperidin-1-yl}-1H-pyrazolo[3,4-b]pyridine-6-carboxamide;
3-cyclobutyl-4-[(1-cyclopropylpiperidin-4-yl)methoxy]-N-(dimethylsulfamoyl)-1-(4-fluorophenyl)-1H-pyrazolo[3,4-b]pyridine-6-carboxamide;
3-cyclobutyl-4-[(1-cyclobutylpiperidin-4-yl)methoxy]-N-(dimethylsulfamoyl)-1-(4-fluorophenyl)-1H-pyrazolo[3,4-b]pyridine-6-carboxamide;
3-cyclobutyl-4-[(1-cyclohexylpiperidin-4-yl)methoxy]-N-(dimethyl sulfamoyl)-1-(4-fluorophenyl)-1H-pyrazolo[3,4-b]pyridine-6-carboxamide;
3-cyclobutyl-N-(dimethylsulfamoyl)-1-(4-fluorophenyl)-4-{[1-(oxan-4-yl)piperidin-4-yl]methoxy}-1H-pyrazolo[3,4-b]pyridine-6-carboxamide;
3-cyclobutyl-4-{1-[(2,5-dimethoxyoxolan-3-yl)methyl]piperidin-4-yl}-N-(dimethylsulfamoyl)-1-(4-fluorophenyl)-1H-pyrazolo[3,4-b]pyridine-6-carboxamide;
3-cyclobutyl-N-(dimethylsulfamoyl)-4-[4-(morpholin-4-yl)piperidin-1-yl]-1-{2-[(propan-2-yl)oxy]pyrimidin-4-yl}-1H-pyrazolo[3,4-b]pyridine-6-carboxamide;
3-cyclobutyl-N-(dimethylsulfamoyl)-1-(2-ethoxypyrimidin-4-yl)-4-[4-(morpholin-4-yl)piperidin-1-yl]-1H-pyrazolo[3,4-b]pyridine-6-carboxamide;
3-cyclobutyl-1-(2,2-difluoro-2H-1,3-benzodioxol-5-yl)-N-(dimethylsulfamoyl)-4-[4-(morpholin-4-yl)piperidin-1-yl]-1H-pyrazolo[3,4-b]pyridine-6-carboxamide;
3-cyclobutyl-1-(4-fluorophenyl)-N-(4-methylpiperazine-1-sulfonyl)-4-[4-(morpholin-4-yl)piperidin-1-yl]-1H-pyrazolo[3,4-b]pyridine-6-carboxamide;
3-cyclobutyl-N-(dimethylsulfamoyl)-1-(4-fluorophenyl)-4-[1-(propan-2-yl)octahydro-5H-pyrrolo[3,2-c]pyridin-5-yl]-1H-pyrazolo[3,4-b]pyridine-6-carboxamide;
3-cyclobutyl-4-(1-cyclobutyloctahydro-5H-pyrrolo[3,2-c]pyridin-5-yl)-N-(dimethylsulfamoyl)-1-(4-fluorophenyl)-1H-pyrazolo[3,4-b]pyridine-6-carboxamide;
3-cyclobutyl-N-(dimethylsulfamoyl)-1-(4-fluorophenyl)-4-[1-(oxetan-3-yl)octahydro-5H-pyrrolo[3,2-c]pyridin-5-yl]-1H-pyrazolo[3,4-b]pyridine-6-carboxamide;
3-cyclobutyl-N-(dimethylsulfamoyl)-1-(4-fluorophenyl)-4-[1-(oxan-4-yl)octahydro-5H-pyrrolo[3,2-c]pyridin-5-yl]-1H-pyrazolo[3,4-b]pyridine-6-carboxamide;
3-cyclobutyl-1-(4-fluorophenyl)-4-(4-methoxy[1,4'-bipiperidin]-1'-yl)-N-(methylsulfamoyl)-1H-pyrazolo[3,4-b]pyridine-6-carboxamide;

3-cyclobutyl-1-(4-fluorophenyl)-4-(4-methoxy[1,4'-bipiperidin]-1'-yl)-N-sulfamoyl-1H-pyrazolo[3,4-b]pyridine-6-carboxamide;

1-cyclohexyl-4-[4-(hexahydropyrrolo[3,4-c]pyrrole-2(1H)-carbonyl)phenyl]-N-(methanesulfonyl)-3-[(propan-2-yl)oxy]-1H-pyrazolo[3,4-b]pyridine-6-carboxamide;

N-(azetidine-1-sulfonyl)-3-cyclobutyl-1-(4-fluorophenyl)-4-(4-methoxy[1,4'-bipiperidin]-1'-yl)-1H-pyrazolo[3,4-b]pyridine-6-carboxamide;

1-cyclohexyl-4-(4-{[3-(dimethylamino)azetidin-1-yl]methyl}phenyl)-N-(methanesulfonyl)-3-[(propan-2-yl)oxy]-1H-pyrazolo[3,4-b]pyridine-6-carboxamide;

1-cyclohexyl-N-(methanesulfonyl)-3-[(propan-2-yl)oxy]-4-(4-{[4-(propan-2-yl)piperazin-1-yl]methyl}phenyl)-1H-pyrazolo[3,4-b]pyridine-6-carboxamide;

1-cyclohexyl-N-(methanesulfonyl)-4-{4-[(4-methoxypiperidin-1-yl)methyl]phenyl}-3-[(propan-2-yl)oxy]-1H-pyrazolo[3,4-b]pyridine-6-carboxamide;

1-cyclohexyl-N-(methanesulfonyl)-4-{4-[(5-methylhexahydropyrrolo[3,4-c]pyrrol-2(1H)-yl)methyl]phenyl}-3-[(propan-2-yl)oxy]-1H-pyrazolo[3,4-b]pyridine-6-carboxamide;

1-cyclohexyl-N-(methanesulfonyl)-4-[4-(5-methylhexahydropyrrolo[3,4-c]pyrrole-2(1H)-carbonyl)phenyl]-3-[(propan-2-yl)oxy]-1H-pyrazolo[3,4-b]pyridine-6-carboxamide;

3-cyclobutyl-1-(4-fluorophenyl)-N-(methylsulfamoyl)-4-{4-[4-(propan-2-yl)piperazin-1-yl]piperidin-1-yl}-1H-pyrazolo[3,4-b]pyridine-6-carboxamide;

4-[4-(4-cyano-1-methylpiperidin-4-yl)phenyl]-1-cyclohexyl-N-(methanesulfonyl)-3-[(propan-2-yl)oxy]-1H-pyrazolo[3,4-b]pyridine-6-carboxamide;

1-cyclohexyl-4-{4-[3-(dimethylamino)azetidine-1-carbonyl]phenyl}-N-(methanesulfonyl)-3-[(propan-2-yl)oxy]-1H-pyrazolo[3,4-b]pyridine-6-carboxamide;

1-cyclohexyl-N-(methanesulfonyl)-4-{4-[(8-methyl-2-oxa-5,8-diazaspiro[3.5]nonan-5-yl)methyl]phenyl}-3-[(propan-2-yl)oxy]-1H-pyrazolo[3,4-b]pyridine-6-carboxamide;

1-cyclohexyl-4-{4-[(4-ethylpiperazin-1-yl)methyl]phenyl}-N-(methanesulfonyl)-3-[(propan-2-yl)oxy]-1H-pyrazolo[3,4-b]pyridine-6-carboxamide;

1-cyclohexyl-4-(4-{[4-(dimethylamino)piperidin-1-yl]methyl}phenyl)-N-(methanesulfonyl)-3-[(propan-2-yl)oxy]-1H-pyrazolo[3,4-b]pyridine-6-carboxamide;

1-(4-fluorophenyl)-N-(methanesulfonyl)-4-(4-methoxy[1,4'-bipiperidin]-1'-yl)-3-[(propan-2-yl)oxy]-1H-pyrazolo[3,4-b]pyridine-6-carboxamide;

3-cyclobutyl-1-(4-fluorophenyl)-N-(3-methoxyazetidine-1-sulfonyl)-4-(4-methoxy[1,4'-bipiperidin]-1'-yl)-1H-pyrazolo[3,4-b]pyridine-6-carboxamide;

3-cyclobutyl-N-(3-fluoroazetidine-1-sulfonyl)-1-(4-fluorophenyl)-4-(4-methoxy[1,4'-bipiperidin]-1'-yl)-1H-pyrazolo[3,4-b]pyridine-6-carboxamide;

3-cyclobutyl-1-(4-fluorophenyl)-4-(4-methoxy[1,4'-bipiperidin]-1'-yl)-N-(morpholine-4-sulfonyl)-1H-pyrazolo[3,4-b]pyridine-6-carboxamide;

3-cyclobutyl-N-(methanesulfonyl)-4-[4-(morpholin-4-yl)cyclohexyl]-1-phenyl-1H-pyrazolo[3,4-b]pyridine-6-carboxamide;

3-cyclobutyl-N-(dimethylsulfamoyl)-4-[4-(morpholin-4-yl)cyclohexyl]-1-phenyl-1H-pyrazolo[3,4-b]pyridine-6-carboxamide;

3-cyclobutyl-4-(4-fluoro[1,4'-bipiperidin]-1'-yl)-1-(4-fluorophenyl)-N-(methylsulfamoyl)-1H-pyrazolo[3,4-b]pyridine-6-carboxamide;

N-(azetidine-1-sulfonyl)-3-cyclobutyl-1-(4-fluorophenyl)-4-{4-[4-(propan-2-yl)piperazin-1-yl]piperidin-1-yl}-1H-pyrazolo[3,4-b]pyridine-6-carboxamide;

3-cyclobutyl-1-[3-(difluoromethoxy)phenyl]-N-(dimethylsulfamoyl)-4-[4-(morpholin-4-yl)piperidin-1-yl]-1H-pyrazolo[3,4-b]pyridine-6-carboxamide;

3-cyclobutyl-1-(4-fluorophenyl)-N-(methanesulfonyl)-N-methyl-4-[4-(morpholin-4-yl)piperidin-1-yl]-1H-pyrazolo[3,4-b]pyridine-6-carboxamide;

3-cyclobutyl-N-(methanesulfonyl)-N-methyl-4-[4-(morpholin-4-yl)piperidin-1-yl]-1-phenyl-1H-pyrazolo[3,4-b]pyridine-6-carboxamide;

3-cyclobutyl-N-(methanesulfonyl)-4-[4-(methoxymethyl)piperidin-1-yl]-N-methyl-1-phenyl-1H-pyrazolo[3,4-b]pyridine-6-carboxamide;

3-cyclobutyl-N-(ethanesulfonyl)-N-methyl-4-[4-(morpholin-4-yl)piperidin-1-yl]-1-phenyl-1H-pyrazolo[3,4-b]pyridine-6-carboxamide;

3-cyclobutyl-N-(ethanesulfonyl)-N-methyl-1-phenyl-4-{4-[(pyrrolidin-1-yl)methyl]piperidin-1-yl}-1H-pyrazolo[3,4-b]pyridine-6-carboxamide;

2-(3-cyclobutyl-1-phenyl-4-{4-[(pyrrolidin-1-yl)methyl]piperidin-1-yl}-1H-pyrazolo[3,4-b]pyridine-6-carbonyl)-6-methyl-1$\lambda^6$,2,6-thiadiazinane-1,1-dione;

2-(3-cyclobutyl-1-phenyl-4-{4-[(pyrrolidin-1-yl)methyl]piperidin-1-yl}-1H-pyrazolo[3,4-b]pyridine-6-carbonyl)-1$\lambda^6$,2-thiazolidine-1,1-dione;

3-cyclobutyl-N-(methanesulfonyl)-N-methyl-1-phenyl-4-{4-[(pyrrolidin-1-yl)methyl]piperidin-1-yl}-1H-pyrazolo[3,4-b]pyridine-6-carboxamide;

2-(3-cyclobutyl-1-phenyl-4-{4-[(pyrrolidin-1-yl)methyl]piperidin-1-yl}-1H-pyrazolo[3,4-b]pyridine-6-carbonyl)-1$\lambda^6$,2-thiazinane-1,1-dione;

2-{3-cyclobutyl-4-[4-(morpholin-4-yl)piperidin-1-yl]-1-phenyl-1H-pyrazolo[3,4-b]pyridine-6-carbonyl}-6-methyl-1$\lambda^6$,2,6-thiadiazinane-1,1-dione;

2-{3-cyclobutyl-4-[4-(morpholin-4-yl)piperidin-1-yl]-1-phenyl-1H-pyrazolo[3,4-b]pyridine-6-carbonyl}-1$\lambda^6$,2-thiazolidine-1,1-dione;

2-{3-cyclobutyl-4-[4-(morpholin-4-yl)piperidin-1-yl]-1-phenyl-1H-pyrazolo[3,4-b]pyridine-6-carbonyl}-1$\lambda^6$,2-thiazinane-1,1-dione;

2-{3-cyclobutyl-4-[4-(methoxymethyl)piperidin-1-yl]-1-phenyl-1H-pyrazolo[3,4-b]pyridine-6-carbonyl}-1$\lambda^6$,2-thiazolidine-1,1-dione;

2-{3-cyclobutyl-4-[4-(methoxymethyl)piperidin-1-yl]-1-phenyl-1H-pyrazolo[3,4-b]pyridine-6-carbonyl}-1$\lambda^6$,2-thiazinane-1,1-dione;

3-cyclobutyl-1-(4-fluorophenyl)-4-[4-(methoxymethyl)piperidin-1-yl]-N-methylsulfamoyl)-1H-pyrazolo[3,4-b]pyridine-6-carboxamide;

3-cyclobutyl-1-(4-fluorophenyl)-N-(2-methoxyethanesulfonyl)-4-[4-(methoxymethyl)piperidin-1-yl]-1H-pyrazolo[3,4-b]pyridine-6-carboxamide;

3-cyclobutyl-1-(4-fluorophenyl)-4-[4-(methoxymethyl)piperidin-1-yl]-N-(morpholine-4-sulfonyl)-1H-pyrazolo[3,4-b]pyridine-6-carboxamide;

3-cyclobutyl-1-(4-fluorophenyl)-N-(3-hydroxypropane-1-sulfonyl)-4-[4-(methoxymethyl)piperidin-1-yl]-1H-pyrazolo[3,4-b]pyridine-6-carboxamide;

ethyl 4-[({3-cyclobutyl-1-(4-fluorophenyl)-4-[4-(methoxymethyl)piperidin-1-yl]-1H-pyrazolo[3,4-b]pyridine-6-carbonyl}sulfamoyl)amino]piperidine-1-carboxylate;

3-cyclobutyl-1-(4-fluorophenyl)-4-[4-(methoxymethyl)piperidin-1-yl]-N-[(oxetan-3-yl)sulfamoyl]-1H-pyrazolo[3,4-b]pyridine-6-carboxamide;

3-cyclobutyl-1-(4-fluorophenyl)-4-[4-(methoxymethyl)piperidin-1-yl]-N-[(oxan-4-yl)sulfamoyl]-1H-pyrazolo[3,4-b]pyridine-6-carboxamide;
3-cyclobutyl-1-(4-fluorophenyl)-4-[4-(methoxymethyl)piperidin-1-yl]-N-[4-(morpholin-4-yl)piperidine-1-sulfonyl]-1H-pyrazolo[3,4-b]pyridine-6-carboxamide;
ethyl 4-{3-cyclobutyl-1-(4-fluorophenyl)-6-[(2-methoxyethanesulfonyl)carbamoyl]-1H-pyrazolo[3,4-b]pyridin-4-yl}piperazine-1-carboxylate;
ethyl 4-{3-cyclobutyl-1-(4-fluorophenyl)-6-[(morpholine-4-sulfonyl)carbamoyl]-1H-pyrazolo[3,4-b]pyridin-4-yl}piperazine-1-carboxylate;
ethyl 4-{3-cyclobutyl-1-(4-fluorophenyl)-6-[(methanesulfonyl)carbamoyl]-1H-pyrazolo[3,4-b]pyridin-4-yl}piperazine-1-carboxylate;
ethyl 4-{3-cyclobutyl-1-(4-fluorophenyl)-6-[(methylsulfamoyl)carbamoyl]-1H-pyrazolo[3,4-b]pyridin-4-yl}piperazine-1-carboxylate;
2-methylpropyl 4-{3-cyclobutyl-1-(4-fluorophenyl)-6-[(methanesulfonyl)carbamoyl]-1H-pyrazolo[3,4-b]pyridin-4-yl}piperazine-1-carboxylate;
2-methylpropyl 4-{3-cyclobutyl-1-(4-fluorophenyl)-6-[(morpholine-4-sulfonyl)carbamoyl]-1H-pyrazolo[3,4-b]pyridin-4-yl}piperazine-1-carboxylate;
2-methylpropyl 4-{3-cyclobutyl-1-(4-fluorophenyl)-6-[(2-methoxyethanesulfonyl)carbamoyl]-1H-pyrazolo[3,4-b]pyridin-4-yl}piperazine-1-carboxylate;
2-methylpropyl 4-{3-cyclobutyl-1-(4-fluorophenyl)-6-[(methylsulfamoyl)carbamoyl]-1H-pyrazolo[3,4-b]pyridin-4-yl}piperazine-1-carboxylate;
3-cyclobutyl-1-(4-fluorophenyl)-4-(9-methyl-3,9-diazaspiro[5.5]undecan-3-yl)-N-(morpholine-4-sulfonyl)-1H-pyrazolo[3,4-b]pyridine-6-carboxamide; and
N-(2-aminopyridine-3-sulfonyl)-3-cyclobutyl-1-(4-fluorophenyl)-4-[4-(methoxymethyl)piperidin-1-yl]-1H-pyrazolo[3,4-b]pyridine-6-carboxamide.
3-methyl-4-[4-(morpholin-4-yl)phenyl]-1-phenyl-1H-pyrazolo[3,4-b]pyridine-6-carboxylic acid; 1-cyclohexyl-4-(4-methoxyphenyl)-3-methyl-1H-pyrazolo[3,4-b]pyridine-6-carboxylic acid;
1-cyclopentyl-4-(4-methoxyphenyl)-3-methyl-1H-pyrazolo[3,4-b]pyridine-6-carboxylic acid;
1-(2-cyanoethyl)-4-(4-methoxyphenyl)-3-methyl-1H-pyrazolo[3,4-b]pyridine-6-carboxylic acid;
4-[4-(morpholin-4-yl)phenyl]-1-phenyl-3-(propan-2-yl)-1H-pyrazolo[3,4-b]pyridine-6-carboxylic acid;
1-(4-fluorophenyl)-3-methyl-4-[4-(morpholin-4-yl)phenyl]-1H-pyrazolo[3,4-b]pyridine-6-carboxylic acid;
3-methyl-4-[4-(morpholin-4-yl)phenyl]-1-[5-(trifluoromethyl)-1H-pyrazol-3-yl]-1H-pyrazolo[3,4-b]pyridine-6-carboxylic acid;
3-methyl-1-phenyl-4-[4-(piperidin-1-yl)phenyl]-1H-pyrazolo[3,4-b]pyridine-6-carboxylic acid;
3-methyl-4-[4-(4-methylpiperazin-1-yl)phenyl]-1-phenyl-1H-pyrazolo[3,4-b]pyridine-6-carboxylic acid;
1-(3,5-difluorophenyl)-3-methyl-4-[4-(morpholin-4-yl)phenyl]-1H-pyrazolo[3,4-b]pyridine-6-carboxylic acid;
1-(3-chlorophenyl)-3-methyl-4-[4-(morpholin-4-yl)phenyl]-1H-pyrazolo[3,4-b]pyridine-6-carboxylic acid;
1-(3-fluorophenyl)-3-methyl-4-[4-(morpholin-4-yl)phenyl]-1H-pyrazolo[3,4-b]pyridine-6-carboxylic acid;
3-methyl-1-(3-methylphenyl)-4-[4-(morpholin-4-yl)phenyl]-1H-pyrazolo[3,4-b]pyridine-6-carboxylic acid;
4-[4-(1,1-dioxo-1$\lambda^6$,4-thiazinan-4-yl)phenyl]-3-methyl-1-phenyl-1H-pyrazolo[3,4-b]pyridine-6-carboxylic acid;
3-methyl-4-[2-(morpholin-4-yl)pyrimidin-5-yl]-1-phenyl-1H-pyrazolo[3,4-b]pyridine-6-carboxylic acid;
3-(ethoxycarbonyl)-4-[4-(morpholin-4-yl)phenyl]-1-phenyl-1H-pyrazolo[3,4-b]pyridine-6-carboxylic acid;
1-cyclohexyl-3-methyl-4-[4-(morpholin-4-yl)phenyl]-1H-pyrazolo[3,4-b]pyridine-6-carboxylic acid;
1-(3-bromophenyl)-3-methyl-4-[4-(morpholin-4-yl)phenyl]-1H-pyrazolo[3,4-b]pyridine-6-carboxylic acid;
3-(hydroxymethyl)-4-[4-(morpholin-4-yl)phenyl]-1-phenyl-1H-pyrazolo[3,4-b]pyridine-6-carboxylic acid;
1-(3-methylphenyl)-4-[4-(morpholin-4-yl)phenyl]-3-(propan-2-yl)-1H-pyrazolo[3,4-b]pyridine-6-carboxylic acid;
1-(3-methoxyphenyl)-3-methyl-4-[4-(morpholin-4-yl)phenyl]-1H-pyrazolo[3,4-b]pyridine-6-carboxylic acid;
3-methyl-4-[4-(morpholin-4-yl)phenyl]-1-[3-(trifluoromethyl)phenyl]-1H-pyrazolo[3,4-b]pyridine-6-carboxylic acid;
3-methyl-4-[4-(morpholin-4-yl)phenyl]-1-(oxan-4-yl)-1H-pyrazolo[3,4-b]pyridine-6-carboxylic acid;
1-phenyl-3-(propan-2-yl)-4-[4-(pyrrolidin-1-yl)phenyl]-1H-pyrazolo[3,4-b]pyridine-6-carboxylic acid;
3-methyl-1-phenyl-4-[4-(pyrrolidin-1-yl)phenyl]-1H-pyrazolo[3,4-b]pyridine-6-carboxylic acid;
4-[2-chloro-4-(morpholin-4-yl)phenyl]-3-methyl-1-phenyl-1H-pyrazolo[3,4-b]pyridine-6-carboxylic acid;
3-methyl-4-[4-(1-methyl-1,2,3,6-tetrahydropyridin-4-yl)phenyl]-1-phenyl-1H-pyrazolo[3,4-b]pyridine-6-carboxylic acid;
4-[4-fluoropyrrolidin-1-yl)phenyl]-3-methyl-1-phenyl-1H-pyrazolo[3,4-b]pyridine-6-carboxylic acid;
4-[4-(4-acetylpiperazin-1-yl)phenyl]-3-methyl-1-phenyl-1H-pyrazolo[3,4-b]pyridine-6-carboxylic acid;
1-(3,5-dimethylphenyl)-3-methyl-4-[4-(morpholin-4-yl)phenyl]-1H-pyrazolo[3,4-b]pyridine-6-carboxylic acid;
3-methyl-4-[4-(morpholin-4-yl)phenyl]-1-[4-(trifluoromethoxy)phenyl]-1H-pyrazolo[3,4-b]pyridine-6-carboxylic acid;
3-methyl-1-[3-(morpholin-4-yl)phenyl]-4-[4-(morpholin-4-yl)phenyl]-1H-pyrazolo[3,4-b]pyridine-6-carboxylic acid;
4-[2-methoxy-4-(morpholin-4-yl)phenyl]-3-methyl-1-phenyl-1H-pyrazolo[3,4-b]pyridine-6-carboxylic acid;
1-cyclopropyl-3-methyl-4-[4-(morpholin-4-yl)phenyl]-1H-pyrazolo[3,4-b]pyridine-6-carboxylic acid;
3-methyl-4-[4-(morpholin-4-yl)phenyl]-1-[3-(trifluoromethoxy)phenyl]-1H-pyrazolo[3,4-b]pyridine-6-carboxylic acid;
1-[3-(dimethylamino)phenyl]-3-methyl-4-[4-(morpholin-4-yl)phenyl]-1H-pyrazolo[3,4-b]pyridine-6-carboxylic acid;
1-(3,4-difluorophenyl)-3-methyl-4-[4-(morpholin-4-yl)phenyl]-1H-pyrazolo[3,4-b]pyridine-6-carboxylic acid;
1-[3-(methanesulfonyl)phenyl]-3-methyl-4-[4-(morpholin-4-yl)phenyl]-1H-pyrazolo[3,4-b]pyridine-6-carboxylic acid;
3-methyl-1-(1-methylpiperidin-4-yl)-4-[4-(morpholin-4-yl)phenyl]-1H-pyrazolo[3,4-b]pyridine-6-carboxylic acid;
3-tert-butyl-4-[4-(morpholin-4-yl)phenyl]-1-phenyl-1H-pyrazolo[3,4-b]pyridine-6-carboxylic acid;
1-(2-chloropyridin-4-yl)-4-[4-(morpholin-4-yl)phenyl]-3-(propan-2-yl)-1H-pyrazolo[3,4-b]pyridine-6-carboxylic acid;
3,5-dimethyl-4-[4-(morpholin-4-yl)phenyl]-1-phenyl-1H-pyrazolo[3,4-b]pyridine-6-carboxylic acid;
4-[4-(morpholin-4-yl)phenyl]-3-(propan-2-yl)-1-[4-(trifluoromethoxy)phenyl]-1H-pyrazolo[3,4-b]pyridine-6-carboxylic acid;
1-(3,5-dichlorophenyl)-3-methyl-4-[4-(morpholin-4-yl)phenyl]-1H-pyrazolo[3,4-b]pyridine-6-carboxylic acid;

3-methyl-4-[4-(morpholin-4-yl)phenyl]-1-(3-sulfamoylphenyl)-1H-pyrazolo[3,4-b]pyridine-6-carboxylic acid;
3-methyl-1-(1-methyl-1H-pyrazol-4-yl)-4-[4-(morpholin-4-yl)phenyl]-1H-pyrazolo[3,4-b]pyridine-6-carboxylic acid;
3-[1-(tert-butoxycarbonyl)azetidin-3-yl]-4-[4-(morpholin-4-yl)phenyl]-1-phenyl-1H-pyrazolo[3,4-b]pyridine-6-carboxylic acid;
4-[4-(morpholin-4-yl)phenyl]-1-phenyl-3-(prop-1-en-2-yl)-1H-pyrazolo[3,4-b]pyridine-6-carboxylic acid;
1-(3-cyanophenyl)-4-[4-(morpholin-4-yl)phenyl]-3-(propan-2-yl)-1H-pyrazolo[3,4-b]pyridine-6-carboxylic acid;
3-methyl-4-[6-(morpholin-4-yl)pyridin-3-yl]-1-phenyl-1H-pyrazolo[3,4-b]pyridine-6-carboxylic acid;
1-(2-methoxypyridin-4-yl)-3-methyl-4-[4-(morpholin-4-yl)phenyl]-1H-pyrazolo[3,4-b]pyridine-6-carboxylic acid;
1-(3-fluoro-5-methoxyphenyl)-3-methyl-4-[4-(morpholin-4-yl)phenyl]-1H-pyrazolo[3,4-b]pyridine-6-carboxylic acid;
4-{4-[4-(methanesulfonyl)piperazin-1-yl]phenyl}-3-methyl-1-phenyl-1H-pyrazolo[3,4-b]pyridine-6-carboxylic acid;
1-cyclohexyl-4-[4-(morpholin-4-yl)phenyl]-3-(propan-2-yl)-1H-pyrazolo[3,4-b]pyridine-6-carboxylic acid;
3-(methylcarbamoyl)-4-[4-(morpholin-4-yl)phenyl]-1-phenyl-1H-pyrazolo[3,4-b]pyridine-6-carboxylic acid;
3-(1-hydroxy-2-methylpropan-2-yl)-4-[4-(morpholin-4-yl)phenyl]-1-phenyl-1H-pyrazolo[3,4-b]pyridine-6-carboxylic acid;
1-(2-fluoropyridin-4-yl)-3-methyl-4-[4-(morpholin-4-yl)phenyl]-1H-pyrazolo[3,4-b]pyridine-6-carboxylic acid;
3-methyl-4-[4-(morpholin-4-yl)phenyl]-1-(2-oxo-1,2-dihydropyridin-4-yl)-1H-pyrazolo[3,4-b]pyridine-6-carboxylic acid;
1-(3-carbamoylphenyl)-3-methyl-4-[4-(morpholin-4-yl)phenyl]-1H-pyrazolo[3,4-b]pyridine-6-carboxylic acid;
4-[4-(4-tert-butylpiperazin-1-yl)phenyl]-3-methyl-1-phenyl-1H-pyrazolo[3,4-b]pyridine-6-carboxylic acid;
1-(6-methoxypyridin-3-yl)-3-methyl-4-[4-(morpholin-4-yl)phenyl]-1H-pyrazolo[3,4-b]pyridine-6-carboxylic acid;
1-cyclohexyl-4-[2-(dimethylamino)pyrimidin-5-yl]-3-(propan-2-yl)-1H-pyrazolo[3,4-b]pyridine-6-carboxylic acid;
3-(2-hydroxypropan-2-yl)-4-[4-(morpholin-4-yl)phenyl]-1-phenyl-1H-pyrazolo[3,4-b]pyridine-6-carboxylic acid;
3-carbamoyl-4-[4-(morpholin-4-yl)phenyl]-1-phenyl-1H-pyrazolo[3,4-b]pyridine-6-carboxylic acid;
1-cyclohexyl-3-methyl-4-[2-(morpholin-4-yl)pyrimidin-5-yl]-1H-pyrazolo[3,4-b]pyridine-6-carboxylic acid;
4-[3-bromo-4-(morpholin-4-yl)phenyl]-3-methyl-1-phenyl-1H-pyrazolo[3,4-b]pyridine-6-carboxylic acid;
1-cyclopentyl-4-[2-(dimethylamino)pyrimidin-5-yl]-3-(propan-2-yl)-1H-pyrazolo[3,4-b]pyridine-6-carboxylic acid;
4-[4-(morpholin-4-yl)phenyl]-1-(oxan-3-yl)-3-(propan-2-yl)-1H-pyrazolo[3,4-b]pyridine-6-carboxylic acid;
1-cyclopentyl-4-[4-(morpholin-4-yl)phenyl]-3-(propan-2-yl)-1H-pyrazolo[3,4-b]pyridine-6-carboxylic acid;
4-{4-[4-(methoxycarbonyl)piperazin-1-yl]phenyl}-3-methyl-1-phenyl-1H-pyrazolo[3,4-b]pyridine-6-carboxylic acid;
1-(1-acetylpiperidin-4-yl)-4-[4-(morpholin-4-yl)phenyl]-3-(propan-2-yl)-1H-pyrazolo[3,4-b]pyridine-6-carboxylic acid;
4-{4-[3-(dimethylamino)azetidin-1-yl]phenyl}-3-methyl-1-phenyl-1H-pyrazolo[3,4-b]pyridine-6-carboxylic acid;
4-[4-(3,3-dimethylazetidin-1-yl)phenyl]-3-methyl-1-phenyl-1H-pyrazolo[3,4-b]pyridine-6-carboxylic acid;
1-cyclohexyl-3-methyl-4-[6-(morpholin-4-yl)pyridin-3-yl]-1H-pyrazolo[3,4-b]pyridine-6-carboxylic acid;
1-cyclohexyl-4-[2-(dimethylamino)pyrimidin-5-yl]-3-methyl-1H-pyrazolo[3,4-b]pyridine-6-carboxylic acid;
3-[1-(tert-butoxycarbonyl)pyrrolidin-2-yl]-4-[4-(morpholin-4-yl)phenyl]-1-phenyl-1H-pyrazolo[3,4-b]pyridine-6-carboxylic acid;
1-cyclopentyl-4-[6-(morpholin-4-yl)pyridin-3-yl]-3-(propan-2-yl)-1H-pyrazolo[3,4-b]pyridine-6-carboxylic acid;
3-(1-acetylazetidin-3-yl)-4-[4-(morpholin-4-yl)phenyl]-1-phenyl-1H-pyrazolo[3,4-b]pyridine-6-carboxylic acid;
4-[2-(morpholin-4-yl)pyrimidin-5-yl]-1-phenyl-3-(propan-2-yl)-1H-pyrazolo[3,4-b]pyridine-6-carboxylic acid;
1-cyclohexyl-4-[2-(morpholin-4-yl)pyrimidin-5-yl]-3-(propan-2-yl)-1H-pyrazolo[3,4-b]pyridine-6-carboxylic acid;
1-cyclohexyl-4-[6-(morpholin-4-yl)pyridin-3-yl]-3-(propan-2-yl)-1H-pyrazolo[3,4-b]pyridine-6-carboxylic acid;
3-methyl-1-phenyl-4-{4-[4-(3,3,3-trifluoropropyl)piperazin-1-yl]phenyl}-1H-pyrazolo[3,4-b]pyridine-6-carboxylic acid;
1-cyclopentyl-4-[6-(dimethylamino)pyridin-3-yl]-3-(propan-2-yl)-1H-pyrazolo[3,4-b]pyridine-6-carboxylic acid;
1-[3-(dimethylamino)phenyl]-4-[2-(morpholin-4-yl)pyrimidin-5-yl]-3-(propan-2-yl)-1H-pyrazolo[3,4-b]pyridine-6-carboxylic acid;
1-[3-(dimethylamino)phenyl]-4-[6-(morpholin-4-yl)pyridin-3-yl]-3-(propan-2-yl)-1H-pyrazolo[3,4-b]pyridine-6-carboxylic acid;
3-[1-(methoxycarbonyl)azetidin-3-yl]-4-[4-(morpholin-4-yl)phenyl]-1-phenyl-1H-pyrazolo[3,4-b]pyridine-6-carboxylic acid;
3-[(dimethylamino)methyl]-4-[4-(morpholin-4-yl)phenyl]-1-phenyl-1H-pyrazolo[3,4-b]pyridine-6-carboxylic acid;
4-[2-(dimethylamino)pyrimidin-5-yl]-1-[3-(morpholin-4-yl)phenyl]-3-(propan-2-yl)-1H-pyrazolo[3,4-b]pyridine-6-carboxylic acid;
4-[6-(dimethylamino)pyridin-3-yl]-1-[3-(morpholin-4-yl)phenyl]-3-(propan-2-yl)-1H-pyrazolo[3,4-b]pyridine-6-carboxylic acid;
1-[3-(dimethylamino)phenyl]-3-methyl-4-[2-(morpholin-4-yl)pyrimidin-5-yl]-1H-pyrazolo[3,4-b]pyridine-6-carboxylic acid;
3-tert-butyl-1-cyclopentyl-4-[2-(dimethylamino)pyrimidin-5-yl]-1H-pyrazolo[3,4-b]pyridine-6-carboxylic acid;
3-(1-hydroxy-2-methylpropan-2-yl)-4-[6-(morpholin-4-yl)pyridin-3-yl]-1-phenyl-1H-pyrazolo[3,4-b]pyridine-6-carboxylic acid;
1-cyclohexyl-4-[6-(dimethylamino)pyridin-3-yl]-3-(propan-2-yl)-1H-pyrazolo[3,4-b]pyridine-6-carboxylic acid;
3-methyl-1-(1-methyl-2-oxo-1,2-dihydropyridin-4-yl)-4-[4-(morpholin-4-yl)phenyl]-1H-pyrazolo[3,4-b]pyridine-6-carboxylic acid;
1-[1-(cyanomethyl)piperidin-4-yl]-4-[4-(morpholin-4-yl)phenyl]-3-(propan-2-yl)-1H-pyrazolo[3,4-b]pyridine-6-carboxylic acid;
4-[4-(cyclobutylamino)phenyl]-3-methyl-1-phenyl-1H-pyrazolo[3,4-b]pyridine-6-carboxylic acid;
4-[4-(3,3-difluoroazetidin-1-yl)phenyl]-3-methyl-1-phenyl-1H-pyrazolo[3,4-b]pyridine-6-carboxylic acid;
4-{4-[4-(cyanomethyl)piperazin-1-yl]phenyl}-3-methyl-1-phenyl-1H-pyrazolo[3,4-b]pyridine-6-carboxylic acid;
1-cyclohexyl-4-[6-(dimethylamino)pyridin-3-yl]-3-methyl-1H-pyrazolo[3,4-b]pyridine-6-carboxylic acid;
3-tert-butyl-1-cyclopentyl-4-[2-(morpholin-4-yl)pyrimidin-5-yl]-1H-pyrazolo[3,4-b]pyridine-6-carboxylic acid;
1-(3-fluorophenyl)-3-methyl-4-[6-(morpholin-4-yl)pyridin-3-yl]-1H-pyrazolo[3,4-b]pyridine-6-carboxylic acid;

3-methyl-4-[6-(morpholin-4-yl)pyridin-3-yl]-1-[3-(trifluoromethyl)phenyl]-1H-pyrazolo[3,4-b]pyridine-6-carboxylic acid;
3-[1-(tert-butoxycarbonyl)pyrrolidin-2-yl]-4-[6-(morpholin-4-yl)pyridin-3-yl]-1-phenyl-1H-pyrazolo[3,4-b]pyridine-6-carboxylic acid;
1-(2,4-difluorophenyl)-3-methyl-4-[6-(morpholin-4-yl)pyridin-3-yl]-1H-pyrazolo[3,4-b]pyridine-6-carboxylic acid;
1-(2,4-difluorophenyl)-3-methyl-4-[4-(morpholin-4-yl)phenyl]-1H-pyrazolo[3,4-b]pyridine-6-carboxylic acid;
1-cyclopentyl-3-methyl-4-[6-(morpholin-4-yl)pyridin-3-yl]-1H-pyrazolo[3,4-b]pyridine-6-carboxylic acid;
4-{4-[4-(2-hydroxyethyl)piperazin-1-yl]phenyl}-3-methyl-1-phenyl-1H-pyrazolo[3,4-b]pyridine-6-carboxylic acid;
4-[4-(4,4-difluoropiperidin-1-yl)phenyl]-3-methyl-1-phenyl-1H-pyrazolo[3,4-b]pyridine-6-carboxylic acid;
4-[4-(4-cyanopiperidin-1-yl)phenyl]-3-methyl-1-phenyl-1H-pyrazolo[3,4-b]pyridine-6-carboxylic acid;
3-methyl-4-{4-[methyl(oxan-4-yl)amino]phenyl}-1-phenyl-1H-pyrazolo[3,4-b]pyridine-6-carboxylic acid;
4-[4-(3,3-difluoropyrrolidin-1-yl)phenyl]-3-methyl-1-phenyl-1H-pyrazolo[3,4-b]pyridine-6-carboxylic acid;
3-methyl-4-{4-[(oxetan-3-yl)amino]phenyl}-1-phenyl-1H-pyrazolo[3,4-b]pyridine-6-carboxylic acid;
3-(3-methyloxetan-3-yl)-4-[4-(morpholin-4-yl)phenyl]-1-phenyl-1H-pyrazolo[3,4-b]pyridine-6-carboxylic acid;
4-[4-(2,6-dimethylmorpholin-4-yl)phenyl]-3-methyl-1-phenyl-1H-pyrazolo[3,4-b]pyridine-6-carboxylic acid;
4-{4-[cyclobutyl(methyl)amino]phenyl}-3-methyl-1-phenyl-1H-pyrazolo[3,4-b]pyridine-6-carboxylic acid;
4-{4-[(3R,4R)-3,4-dihydroxypyrrolidin-1-yl]phenyl}-3-methyl-1-phenyl-1H-pyrazolo[3,4-b]pyridine-6-carboxylic acid;
4-[4-(morpholin-4-yl)phenyl]-3-(propan-2-yl)-1-[1-(2,2,2-trifluoroethyl)piperidin-4-yl]-1H-pyrazolo[3,4-b]pyridine-6-carboxylic acid;
3-methyl-4-(morpholin-4-yl)-1-phenyl-1H-pyrazolo[3,4-b]pyridine-6-carboxylic acid;
4-[4-(2,2-dimethylmorpholin-4-yl)phenyl]-3-methyl-1-phenyl-1H-pyrazolo[3,4-b]pyridine-6-carboxylic acid;
4-[4-(morpholin-4-yl)phenyl]-1-(oxolan-3-yl)-3-(propan-2-yl)-1H-pyrazolo[3,4-b]pyridine-6-carboxylic acid;
1-[3-(morpholin-4-yl)phenyl]-4-[4-(morpholin-4-yl)phenyl]-3-(propan-2-yl)-1H-pyrazolo[3,4-b]pyridine-6-carboxylic acid;
3-(methoxymethyl)-4-[4-(morpholin-4-yl)phenyl]-1-phenyl-1H-pyrazolo[3,4-b]pyridine-6-carboxylic acid;
3-methyl-1-phenyl-4-(piperidin-1-yl)-1H-pyrazolo[3,4-b]pyridine-6-carboxylic acid;
4-[4-(3-hydroxyazetidin-1-yl)phenyl]-3-methyl-1-phenyl-1H-pyrazolo[3,4-b]pyridine-6-carboxylic acid;
4-[4-(3-fluoroazetidin-1-yl)phenyl]-3-methyl-1-phenyl-1H-pyrazolo[3,4-b]pyridine-6-carboxylic acid;
3-methyl-4-[4-(2-oxa-6-azaspiro[3.3]heptan-6-yl)phenyl]-1-phenyl-1H-pyrazolo[3,4-b]pyridine-6-carboxylic acid;
3-methyl-4-{4-[(1S,4S)-2-oxa-5-azabicyclo[2.2.1]heptan-5-yl]phenyl}-1-phenyl-1H-pyrazolo[3,4-b]pyridine-6-carboxylic acid;
4-(3,6-dihydro-2H-pyran-4-yl)-3-methyl-1-phenyl-1H-pyrazolo[3,4-b]pyridine-6-carboxylic acid;
3-(1-methylcyclopropyl)-4-[4-(morpholin-4-yl)phenyl]-1-phenyl-1H-pyrazolo[3,4-b]pyridine-6-carboxylic acid;
3-cyclobutyl-4-[4-(morpholin-4-yl)phenyl]-1-phenyl-1H-pyrazolo[3,4-b]pyridine-6-carboxylic acid;
3-tert-butyl-1-cyclohexyl-4-[4-(dimethylamino)phenyl]-1H-pyrazolo[3,4-b]pyridine-6-carboxylic acid;
4-(4-acetylpiperazin-1-yl)-3-methyl-1-phenyl-1H-pyrazolo[3,4-b]pyridine-6-carboxylic acid;
4-{4-[2-(hydroxymethyl)morpholin-4-yl]phenyl}-3-methyl-1-phenyl-1H-pyrazolo[3,4-b]pyridine-6-carboxylic acid;
3-methyl-4-[4-(8-oxa-3-azabicyclo[3.2.1]octan-3-yl)phenyl]-1-phenyl-1H-pyrazolo[3,4-b]pyridine-6-carboxylic acid;
4-[4-(azetidin-1-yl)phenyl]-3-methyl-1-phenyl-1H-pyrazolo[3,4-b]pyridine-6-carboxylic acid;
4-[4-(cyanomethyl)piperazin-1-yl]-3-methyl-1-phenyl-1H-pyrazolo[3,4-b]pyridine-6-carboxylic acid;
4-(4-hydroxypiperidin-1-yl)-3-methyl-1-phenyl-1H-pyrazolo[3,4-b]pyridine-6-carboxylic acid;
4-(1-acetylpiperidin-4-yl)-3-methyl-1-phenyl-1H-pyrazolo[3,4-b]pyridine-6-carboxylic acid;
4-[1-(cyanomethyl)piperidin-4-yl]-3-methyl-1-phenyl-1H-pyrazolo[3,4-b]pyridine-6-carboxylic acid;
3-methyl-4-{4-[methyl(oxetan-3-yl)amino]phenyl}-1-phenyl-1H-pyrazolo[3,4-b]pyridine-6-carboxylic acid;
1-[1-(cyanomethyl)pyrrolidin-3-yl]-4-[4-(morpholin-4-yl)phenyl]-3-(propan-2-yl)-1H-pyrazolo[3,4-b]pyridine-6-carboxylic acid;
1-[1-(methoxycarbonyl)pyrrolidin-3-yl]-4-[4-(morpholin-4-yl)phenyl]-3-(propan-2-yl)-1H-pyrazolo[3,4-b]pyridine-6-carboxylic acid;
4-(4-methoxypiperidin-1-yl)-3-methyl-1-phenyl-1H-pyrazolo[3,4-b]pyridine-6-carboxylic acid;
4-[4-(4-hydroxypiperidin-1-yl)phenyl]-3-methyl-1-phenyl-1H-pyrazolo[3,4-b]pyridine-6-carboxylic acid;
3-methyl-4-{4-[(oxan-4-yl)amino]phenyl}-1-phenyl-1H-pyrazolo[3,4-b]pyridine-6-carboxylic acid;
4-[4-(methanesulfonyl)piperazin-1-yl]-3-methyl-1-phenyl-1H-pyrazolo[3,4-b]pyridine-6-carboxylic acid;
3-tert-butyl-1-cyclohexyl-4-[2-(dimethylamino)pyrimidin-5-yl]-1H-pyrazolo[3,4-b]pyridine-6-carboxylic acid;
3-[1-(cyanomethyl)azetidin-3-yl]-4-[4-(morpholin-4-yl)phenyl]-1-phenyl-1H-pyrazolo[3,4-b]pyridine-6-carboxylic acid;
3-tert-butyl-1-cyclohexyl-4-[2-(morpholin-4-yl)pyrimidin-5-yl]-1H-pyrazolo[3,4-b]pyridine-6-carboxylic acid;
3-methyl-4-(2-oxopiperidin-1-yl)-1-phenyl-1H-pyrazolo[3,4-b]pyridine-6-carboxylic acid;
1-[3-(azetidin-1-yl)phenyl]-4-[4-(morpholin-4-yl)phenyl]-3-(propan-2-yl)-1H-pyrazolo[3,4-b]pyridine-6-carboxylic acid;
4-(cyclohexylmethoxy)-3-methyl-1-phenyl-1H-pyrazolo[3,4-b]pyridine-6-carboxylic acid;
4-[4-(3-hydroxypyrrolidin-1-yl)phenyl]-3-methyl-1-phenyl-1H-pyrazolo[3,4-b]pyridine-6-carboxylic acid;
3-methyl-4-[4-(2-oxa-7-azaspiro[3.5]nonan-7-yl)phenyl]-1-phenyl-1H-pyrazolo[3,4-b]pyridine-6-carboxylic acid;
4-{4-[(3S)-3-cyanopyrrolidin-1-yl]phenyl}-3-methyl-1-phenyl-1H-pyrazolo[3,4-b]pyridine-6-carboxylic acid;
4-[4-(3-acetamidopyrrolidin-1-yl)phenyl]-3-methyl-1-phenyl-1H-pyrazolo[3,4-b]pyridine-6-carboxylic acid;
4-[4-(morpholin-4-yl)phenyl]-3-(propan-2-yl)-1-[3-(pyrrolidin-1-yl)phenyl]-1H-pyrazolo[3,4-b]pyridine-6-carboxylic acid; 3-methyl-1-phenyl-4-(piperidine-1-carbonyl)-1H-pyrazolo[3,4-b]pyridine-6-carboxylic acid;
1-(4,4-difluorocyclohexyl)-4-[4-(morpholin-4-yl)phenyl]-3-(propan-2-yl)-1H-pyrazolo[3,4-b]pyridine-6-carboxylic acid;
1-[3-(3,3-dimethylazetidin-1-yl)phenyl]-4-[4-(morpholin-4-yl)phenyl]-3-(propan-2-yl)-1H-pyrazolo[3,4-b]pyridine-6-carboxylic acid;

4-[4-(morpholin-4-yl)phenyl]-3-(propan-2-yl)-1-[1-(2,2,2-trifluoroethyl)piperidin-3-yl]-1H-pyrazolo[3,4-b]pyridine-6-carboxylic acid;

1-(3-methylphenyl)-4-(piperidin-1-yl)-3-(propan-2-yl)-1H-pyrazolo[3,4-b]pyridine-6-carboxylic acid;

1-[(1R,3R)-3-(benzyloxy)cyclohexyl]-4-[4-(morpholin-4-yl)phenyl]-3-(propan-2-yl)-1H-pyrazolo[3,4-b]pyridine-6-carboxylic acid;

1-[3-(3-methoxyazetidin-1-yl)phenyl]-4-[4-(morpholin-4-yl)phenyl]-3-(propan-2-yl)-1H-pyrazolo[3,4-b]pyridine-6-carboxylic acid;

1-[3-(3-fluoropyrrolidin-1-yl)phenyl]-4-[4-(morpholin-4-yl)phenyl]-3-(propan-2-yl)-1H-pyrazolo[3,4-b]pyridine-6-carboxylic acid;

1-cyclohexyl-4-[2-(dimethylamino)pyrimidin-5-yl]-3-[1-(methoxycarbonyl)azetidin-3-yl]-1H-pyrazolo[3,4-b]pyridine-6-carboxylic acid;

1-[3-(3-fluoroazetidin-1-yl)phenyl]-4-[4-(morpholin-4-yl)phenyl]-3-(propan-2-yl)-1H-pyrazolo[3,4-b]pyridine-6-carboxylic acid;

3-methyl-4-{6-[methyl(oxan-4-yl)amino]pyridin-3-yl}-1-phenyl-1H-pyrazolo[3,4-b]pyridine-6-carboxylic acid;

1-cyclohexyl-4-{6-[methyl(oxan-4-yl)amino]pyridin-3-yl}-3-(propan-2-yl)-1H-pyrazolo[3,4-b]pyridine-6-carboxylic acid;

1-cyclohexyl-4-{6[(2-methoxyethyl)(methyl)amino]pyridin-3-yl}-3-(propan-2-yl)-1H-pyrazolo[3,4-b]pyridine-6-carboxylic acid;

4-(4-acetamidophenyl)-1-cyclohexyl-3-(propan-2-yl)-1H-pyrazolo[3,4-b]pyridine-6-carboxylic acid;

1-{3-[(2-methoxyethyl)(methyl)amino]phenyl}-4-[4-(morpholin-4-yl)phenyl]-3-(propan-2-yl)-1H-pyrazolo[3,4-b]pyridine-6-carboxylic acid;

1-(3-methylphenyl)-3-(propan-2-yl)-4-(pyrrolidin-1-yl)-1H-pyrazolo[3,4-b]pyridine-6-carboxylic acid;

4-(3-fluoroazetidin-1-yl)-1-(3-methylphenyl)-3-(propan-2-yl)-1H-pyrazolo[3,4-b]pyridine-6-carboxylic acid;

4-[6-(4-cyanopiperidin-1-yl)pyridin-3-yl]-1-(3-methylphenyl)-3-(propan-2-yl)-1H-pyrazolo[3,4-b]pyridine-6-carboxylic acid;

4-[4-(4-cyanopiperidin-1-yl)phenyl]-1-[3-(dimethylamino)phenyl]-3-(propan-2-yl)-1H-pyrazolo[3,4-b]pyridine-6-carboxylic acid;

4-[6-(4-cyanopiperidin-1-yl)pyridin-3-yl]-1-[3-(dimethylamino)phenyl]-3-(propan-2-yl)-1H-pyrazolo[3,4-b]pyridine-6-carboxylic acid;

4-[6-(4-cyanopiperidin-1-yl)pyridin-3-yl]-1-[3-(morpholin-4-yl)phenyl]-3-(propan-2-yl)-1H-pyrazolo[3,4-b]pyridine-6-carboxylic acid;

4-{6-[(2-methoxyethyl)(methyl)amino]pyridin-3-yl}-1-[(morpholin-4-yl)phenyl]-3-(propan-2-yl)-1H-pyrazolo[3,4-b]pyridine-6-carboxylic acid;

4-[6-(4-cyanopiperidin-1-yl)pyridin-3-yl]-1-cyclohexyl-3-(propan-2-yl)-1H-pyrazolo[3,4-b]pyridine-6-carboxylic acid;

1-cyclohexyl-4-[6-(3,3-difluoropyrrolidin-1-yl)pyridin-3-yl]-3-(propan-2-yl)-1H-pyrazolo[3,4-b]pyridine-6-carboxylic acid;

4-[6-(4-cyanopiperidin-1-yl)pyridin-3-yl]-3-cyclobutyl-1-phenyl-1H-pyrazolo[3,4-b]pyridine-6-carboxylic acid;

3-cyclobutyl-4-{6-[methyl(oxan-4-yl)amino]pyridin-3-yl}-1-phenyl-1H-pyrazolo[3,4-b]pyridine-6-carboxylic acid;

1-cyclohexyl-4-{4-[(2-methoxyethyl)(methyl)amino]phenyl}-3-(propan-2-yl)-1H-pyrazolo[3,4-b]pyridine-6-carboxylic acid;

4-[4-(4-cyanopiperidin-1-yl)phenyl]-1-cyclohexyl-3-(propan-2-yl)-1H-pyrazolo[3,4-b]pyridine-6-carboxylic acid;

4-[4-(morpholin-4-yl)phenyl]-3-(oxolan-2-yl)-1-phenyl-1H-pyrazolo[3,4-b]pyridine-6-carboxylic acid;

4-{6-[methyl(oxan-4-yl)amino]pyridin-3-yl}-1-[3-(morpholin-4-yl)phenyl]-3-(propan-2-yl)-1H-pyrazolo[3,4-b]pyridine-6-carboxylic acid;

4-{4-[(2-methoxyethyl)(methyl)amino]phenyl}-1-[3-(morpholin-4-yl)phenyl]-3-(propan-2-yl)-1H-pyrazolo[3,4-b]pyridine-6-carboxylic acid;

1-[3-(dimethylamino)phenyl]-4-{6-[methyl(oxan-4-yl)amino]pyridin-3-yl}-3-(propan-2-yl)-1H-pyrazolo[3,4-b]pyridine-6-carboxylic acid;

4-(3-methoxypiperidin-1-yl)-1-(3-methylphenyl)-3-(propan-2-yl)-1H-pyrazolo[3,4-b]pyridine-6-carboxylic acid;

4-(4-cyanopiperidin-1-yl)-1-(3-methylphenyl)-3-(propan-2-yl)-1H-pyrazolo[3,4-b]pyridine-6-carboxylic acid;

4-(4-methoxypiperidin-1-yl)-1-(3-methylphenyl)-3-(propan-2-yl)-1H-pyrazolo[3,4-b]pyridine-6-carboxylic acid;

1-cyclohexyl-3-cyclopropyl-4-[6-(dimethylamino)pyridin-3-yl]-1H-pyrazolo[3,4-b]pyridine-6-carboxylic acid;

rac-1-[(1R,3R)-3-hydroxycyclohexyl]-4-[4-(morpholin-4-yl)phenyl]-3-(propan-2-yl)-1H-pyrazolo[3,4-b]pyridine-6-carboxylic acid;

rac-1-[(1R,3S)-3-hydroxycyclohexyl]-4-[4-(morpholin-4-yl)phenyl]-3-(propan-2-yl)-1H-pyrazolo[3,4-b]pyridine-6-carboxylic acid;

1-cyclohexyl-4-[6-(2,6-dimethylmorpholin-4-yl)pyridin-3-yl]-3-(propan-2-yl)-1H-pyrazolo[3,4-b]pyridine-6-carboxylic acid;

1-cyclohexyl-4-[6-(2,2-dimethylmorpholin-4-yl)pyridin-3-yl]-3-(propan-2-yl)-1H-pyrazolo[3,4-b]pyridine-6-carboxylic acid;

4-[4-(3-hydroxypiperidin-1-yl)phenyl]-3-methyl-1-phenyl-1H-pyrazolo[3,4-b]pyridine-6-carboxylic acid;

4-[2-(4-cyanopiperidin-1-yl)pyrimidin-5-yl]-1-[3-(dimethylamino)phenyl]-3-(propan-2-yl)-1H-pyrazolo[3,4-b]pyridine-6-carboxylic acid;

1-[3-(dimethylamino)phenyl]-4-{2-[methyl(oxan-4-yl)amino]pyrimidin-5-yl}-3-(propan-2-yl)-1H-pyrazolo[3,4-b]pyridine-6-carboxylic acid;

4-[4-(morpholin-4-yl)phenyl]-1-[2-(morpholin-4-yl)pyridin-4-yl]-3-(propan-2-yl)-1H-pyrazolo[3,4-b]pyridine-6-carboxylic acid;

1-(3-methylphenyl)-4-(2-oxa-7-azaspiro[3.5]nonan-7-yl)-3-(propan-2-yl)-1H-pyrazolo[3,4-b]pyridine-6-carboxylic acid;

4-[6-(4-cyano-4-methylpiperidin-1-yl)pyridin-3-yl]-1-cyclohexyl-3-(propan-2-yl)-1H-pyrazolo[3,4-b]pyridine-6-carboxylic acid;

4-[2-(4-cyanopiperidin-1-yl)pyrimidin-5-yl]-1-[3-(morpholin-4-yl)phenyl]-3-(propan-2-yl)-1H-pyrazolo[3,4-b]pyridine-6-carboxylic acid;

1-[(1R,3S)-3-methoxycyclohexyl]-4-[4-(morpholin-4-yl)phenyl]-3-(propan-2-yl)-1H-pyrazolo[3,4-b]pyridine-6-carboxylic acid;

4-[4-(4-cyanopiperidin-1-yl)phenyl]-1-[3-(morpholin-4-yl)phenyl]-3-(propan-2-yl)-1H-pyrazolo[3,4-b]pyridine-6-carboxylic acid;

1-[3-(dimethylamino)phenyl]-4-{4-[methyl(oxan-4-yl)amino]phenyl}-3-(propan-2-yl)-1H-pyrazolo[3,4-b]pyridine-6-carboxylic acid;

4-{4-[methyl(oxan-4-yl)amino]phenyl}-1-[3-(morpholin-4-yl)phenyl]-3-(propan-2-yl)-1H-pyrazolo[3,4-b]pyridine-6-carboxylic acid;

4-[(2-methoxyethyl)(methyl)amino]-1-(3-methylphenyl)-3-(propan-2-yl)-1H-pyrazolo[3,4-b]pyridine-6-carboxylic acid;

4-(4,4-difluoropiperidin-1-yl)-1-(3-methylphenyl)-3-(propan-2-yl)-1H-pyrazolo[3,4-b]pyridine-6-carboxylic acid;

4-[4-(morpholin-4-yl)phenyl]-1-[5-(morpholin-4-yl)pyridin-3-yl]-3-(propan-2-yl)-1H-pyrazolo[3,4-b]pyridine-6-carboxylic acid;

4-(3-methoxyazetidin-1-yl)-1-(3-methylphenyl)-3-(propan-2-yl)-1H-pyrazolo[3,4-b]pyridine-6-carboxylic acid;

4-[4-(hydroxymethyl)piperidin-1-yl]-1-(3-methylphenyl)-3-(propan-2-yl)-1H-pyrazolo[3,4-b]pyridine-6-carboxylic acid;

1-[(1R,3R)-3-methoxycyclohexyl]-4-[4-(morpholin-4-yl)phenyl]-3-(propan-2-yl)-1H-pyrazolo[3,4-b]pyridine-6-carboxylic acid;

1-(3-methylphenyl)-3-(propan-2-yl)-4-[3-(trifluoromethyl)pyrrolidin-1-yl]-1H-pyrazolo[3,4-b]pyridine-6-carboxylic acid;

4-[5-(tert-butoxycarbonyl)hexahydropyrrolo[3,4-c]pyrrol-2(1H)-yl]-1-(3-methylphenyl)-3-(propan-2-yl)-1H-pyrazolo[3,4-b]pyridine-6-carboxylic acid;

4-{4-[3-(dimethylamino)pyrrolidin-1-yl]phenyl}-3-methyl-1-phenyl-1H-pyrazolo[3,4-b]pyridine-6-carboxylic acid;

4-(3-cyanopyrrolidin-1-yl)-1-(3-methylphenyl)-3-(propan-2-yl)-1H-pyrazolo[3,4-b]pyridine-6-carboxylic acid;

4-[4-(4-cyanopiperidin-1-yl)phenyl]-3-cyclobutyl-1-cyclohexyl-1H-pyrazolo[3,4-b]pyridine-6-carboxylic acid;

4-[6-(4-cyanopiperidin-1-yl)pyridin-3-yl]-3-cyclobutyl-1-cyclohexyl-1H-pyrazolo[3,4-b]pyridine-6-carboxylic acid;

4-[4-(4-cyanopiperidin-1-yl)phenyl]-3-(propan-2-yl)-1-[3-(pyrrolidin-1-yl)phenyl]-1H-pyrazolo[3,4-b]pyridine-6-carboxylic acid;

4-[4-(4-cyanopiperidin-1-yl)pyridin-3-yl]-3-(propan-2-yl)-1-[3-(pyrrolidin-1-yl)phenyl]-1H-pyrazolo[3,4-b]pyridine-6-carboxylic acid;

1-cyclohexyl-4-[6-(3-fluoropiperidin-1-yl)pyridin-3-yl]-3-(propan-2-yl)-1H-pyrazolo[3,4-b]pyridine-6-carboxylic acid;

1-cyclohexyl-4-[6-(3-methoxypyrrolidin-1-yl)pyridin-3-yl]-3-(propan-2-yl)-1H-pyrazolo[3,4-b]pyridine-6-carboxylic acid;

1-[3-(3-hydroxyazetidin-1-yl)phenyl]-4-[4-(morpholin-4-yl)phenyl]-3-(propan-2-yl)-1H-pyrazolo[3,4-b]pyridine-6-carboxylic acid;

4-[5-(cyanomethyl)hexahydropyrrolo[3,4-c]pyrrol-2(1H)-yl]-1-(3-methylphenyl)-3-(propan-2-yl)-1H-pyrazolo[3,4-b]pyridine-6-carboxylic acid;

4-[4-(methoxymethyl)piperidin-1-yl]-1-(3-methylphenyl)-3-(propan-2-yl)-1H-pyrazolo[3,4-b]pyridine-6-carboxylic acid;

4-[4-(2-methoxyethyl)piperidin-1-yl]-1-(3-methylphenyl)-3-(propan-2-yl)-1H-pyrazolo[3,4-b]pyridine-6-carboxylic acid;

1-(4-chloropyridin-2-yl)-4-[4-(morpholin-4-yl)phenyl]-3-(propan-2-yl)-1H-pyrazolo[3,4-b]pyridine-6-carboxylic acid;

4-{2-[(2-methoxyethyl)(methyl)amino]pyrimidin-5-yl}-1-[3-(morpholin-4-yl)phenyl]-3-(propan-2-yl)-1H-pyrazolo[3,4-b]pyridine-6-carboxylic acid;

4-{2-[methyl(oxan-4-yl)amino]pyrimidin-5-yl}-1-[3-(morpholin-4-yl)phenyl]-3-(propan-2-yl)-1H-pyrazolo[3,4-b]pyridine-6-carboxylic acid;

4-{4-[4-(cyanomethyl)piperazin-1-yl]phenyl}-1-(3-methoxyphenyl)-3-methyl-1H-pyrazolo[3,4-b]pyridine-6-carboxylic acid;

4-(5-acetylhexahydropyrrolo[3,4-c]pyrrol-2(1H)-yl)-1-(3-methylphenyl)-3-(propan-2-yl)-1H-pyrazolo[3,4-b]pyridine-6-carboxylic acid;

4-[1-(tert-butoxycarbonyl)octahydro-5H-pyrrolo[3,2-c]pyridin-5-yl]-1-(3-methylphenyl)-3-(propan-2-yl)-1H-pyrazolo[3,4-b]pyridine-6-carboxylic acid;

4-[2-(4-cyanopiperidin-1-yl)pyrimidin-5-yl]-1-cyclohexyl-3-(propan-2-yl)-1H-pyrazolo[3,4-b]pyridine-6-carboxylic acid;

1-cyclohexyl-4-{2-[methyl(oxan-4-yl)amino]pyrimidin-5-yl}-3-(propan-2-yl)-1H-pyrazolo[3,4-b]pyridine-6-carboxylic acid;

1-cyclohexyl-4-{2-[(2-methoxyethyl)(methyl)amino]pyrimidin-5-yl}-3-(propan-2-yl)-1H-pyrazolo[3,4-b]pyridine-6-carboxylic acid;

4-{4-[(2-methoxyethyl)(methyl)amino]phenyl}-3-(propan-2-yl)-1-[3-(pyrrolidin-1-yl)phenyl]-1H-pyrazolo[3,4-b]pyridine-6-carboxylic acid;

1-[3-(azetidin-1-yl)phenyl]-4-{6-[(2-methoxyethyl)(methyl)amino]pyridin-3-yl}-3-(propan-2-yl)-1H-pyrazolo[3,4-b]pyridine-6-carboxylic acid;

1-[3-(azetidin-1-yl)phenyl]-4-{4-[methyl(oxan-4-yl)amino]phenyl}-3-(propan-2-yl)-1H-pyrazolo[3,4-b]pyridine-6-carboxylic acid;

4-[4-(morpholin-4-yl)phenyl]-1-[4-(morpholin-4-yl)pyridin-2-yl]-3-(propan-2-yl)-1H-pyrazolo[3,4-b]pyridine-6-carboxylic acid;

1-(3-fluorophenyl)-4-[4-(morpholin-4-yl)phenyl]-3-(propan-2-yl)-1H-pyrazolo[3,4-b]pyridine-6-carboxylic acid;

1-(3,4-difluorophenyl)-4-[4-(morpholin-4-yl)phenyl]-3-(propan-2-yl)-1H-pyrazolo[3,4-b]pyridine-6-carboxylic acid;

4-[4-(morpholin-4-yl)phenyl]-1-[6-(morpholin-4-yl)pyridin-2-yl]-3-(propan-2-yl)-1H-pyrazolo[3,4-b]pyridine-6-carboxylic acid;

1-(3,5-difluorophenyl)-4-{4-[methyl(oxan-4-yl)amino]phenyl}-3-(propan-2-yl)-1H-pyrazolo[3,4-b]pyridine-6-carboxylic acid;

1-(3,5-difluorophenyl)-4-{6-[methyl(oxan-4-yl)amino]pyridin-3-yl}-3-(propan-2-yl)-1H-pyrazolo[3,4-b]pyridine-6-carboxylic acid;

4-[4-(4-cyanopiperidin-1-yl)phenyl]-3-cyclobutyl-1-[3-(pyrrolidin-1-yl)phenyl]-1H-pyrazolo[3,4-b]pyridine-6-carboxylic acid;

4-[6-(4-cyanopiperidin-1-yl)pyridin-3-yl]-3-cyclobutyl-1-[3-(pyrrolidin-1-yl)phenyl]-1H-pyrazolo[3,4-b]pyridine-6-carboxylic acid;

4-{4-[methyl(oxan-4-yl)amino]phenyl}-3-(propan-2-yl)-1-[3-(pyrrolidin-1-yl)phenyl]-1H-pyrazolo[3,4-b]pyridine-6-carboxylic acid;

4-{6-[methyl(oxan-4-yl)amino]pyridin-3-yl}-3-(propan-2-yl)-1-[3-(pyrrolidin-1-yl)phenyl]-1H-pyrazolo[3,4-b]pyridine-6-carboxylic acid;

3-cyclobutyl-4-{4-[methyl(oxan-4-yl)amino]phenyl}-1-[3-(pyrrolidin-1-yl)phenyl]-1H-pyrazolo[3,4-b]pyridine-6-carboxylic acid;

3-cyclobutyl-4-{6-[methyl(oxan-4-yl)amino]pyridin-3-yl}-1-[3-(pyrrolidin-1-yl)phenyl]-1H-pyrazolo[3,4-b]pyridine-6-carboxylic acid;

4-{6-[(2-methoxyethyl)(methyl)amino]pyridin-3-yl}-3-(propan-2-yl)-1-[3-(pyrrolidin-1-yl)phenyl]-1H-pyrazolo[3,4-b]pyridine-6-carboxylic acid;

1-cyclohexyl-4-{4-[methyl(oxan-4-yl)amino]phenyl}-3-(propan-2-yl)-1H-pyrazolo[3,4-b]pyridine-6-carboxylic acid;

4-(1-acetyloctahydro-5H-pyrrolo[3,2-c]pyridin-5-yl)-1-(3-methylphenyl)-3-(propan-2-yl)-1H-pyrazolo[3,4-b]pyridine-6-carboxylic acid;

4-[1-(cyanomethyl)octahydro-5H-pyrrolo[3,2-c]pyridin-5-yl]-1-(3-methylphenyl)-3-(propan-2-yl)-1H-pyrazolo[3,4-b]pyridine-6-carboxylic acid;

4-[4-(methanesulfonyl)piperidin-1-yl]-1-(3-methylphenyl)-3-(propan-2-yl)-1H-pyrazolo[3,4-b]pyridine-6-carboxylic acid;

1-(3-methylphenyl)-4-(7-oxa-2-azaspiro[3.5]nonan-2-yl)-3-(propan-2-yl)-1H-pyrazolo[3,4-b]pyridine-6-carboxylic acid;

4-[2-(4-cyanopiperidin-1-yl)pyrimidin-5-yl]-3-(propan-2-yl)-1-[3-(pyrrolidin-1-yl)phenyl]-1H-pyrazolo[3,4-b]pyridine-6-carboxylic acid;

4-[6-(4-cyanopiperidin-1-yl)pyridin-3-yl]-3-(propan-2-yl)-1-[3-(trifluoromethyl)phenyl]-1H-pyrazolo[3,4-b]pyridine-6-carboxylic acid;

4-[4-(4-cyanopiperidin-1-yl)phenyl]-3-(propan-2-yl)-1-[3-(trifluoromethyl)phenyl]-1H-pyrazolo[3,4-b]pyridine-6-carboxylic acid;

1-(3-methylphenyl)-4-(8-oxa-2-azaspiro[4.5]decan-2-yl)-3-(propan-2-yl)-1H-pyrazolo[3,4-b]pyridine-6-carboxylic acid;

4-(4-cyanopiperidin-1-yl)-1-cyclohexyl-3-(propan-2-yl)-1H-pyrazolo[3,4-b]pyridine-6-carboxylic acid;

1-cyclohexyl-4-(4-methoxypiperidin-1-yl)-3-(propan-2-yl)-1H-pyrazolo[3,4-b]pyridine-6-carboxylic acid;

1-cyclohexyl-4-(piperidin-1-yl)-3-(propan-2-yl)-1H-pyrazolo[3,4-b]pyridine-6-carboxylic acid;

1-cyclohexyl-4-[4-(hydroxymethyl)piperidin-1-yl]-3-(propan-2-yl)-1H-pyrazolo[3,4-b]pyridine-6-carboxylic acid;

1-[6-(dimethylamino)pyridin-2-yl]-4-[4-(morpholin-4-yl)phenyl]-3-(propan-2-yl)-1H-pyrazolo[3,4-b]pyridine-6-carboxylic acid;

1-(3,5-difluorophenyl)-4-[4-(morpholin-4-yl)phenyl]-3-(propan-2-yl)-1H-pyrazolo[3,4-b]pyridine-6-carboxylic acid;

4-[4-(morpholin-4-yl)phenyl]-3-(propan-2-yl)-1-[3-(trifluoromethoxy)phenyl]-1H-pyrazolo[3,4-b]pyridine-6-carboxylic acid;

1-[3-(dimethylamino)phenyl]-3-(propan-2-yl)-4-[3-(trifluoromethyl)pyrrolidin-1-yl]-1H-pyrazolo[3,4-b]pyridine-6-carboxylic acid;

4-(1,1-difluoro-5-azaspiro[2.4]heptan-5-yl)-1-(3-methylphenyl)-3-(propan-2-yl)-1H-pyrazolo[3,4-b]pyridine-6-carboxylic acid;

4-[3-(methanesulfonyl)pyrrolidin-1-yl]-1-(3-methylphenyl)-3-(propan-2-yl)-1H-pyrazolo[3,4-b]pyridine-6-carboxylic acid;

4-(2-azaspiro[3.3]heptan-2-yl)-1-(3-methylphenyl)-3-(propan-2-yl)-1H-pyrazolo[3,4-b]pyridine-6-carboxylic acid;

1-(3-methylphenyl)-4-(5-oxa-2-azaspiro[3.5]nonan-2-yl)-3-(propan-2-yl)-1H-pyrazolo[3,4-b]pyridine-6-carboxylic acid;

4-{6-[bis(2-methoxyethyl)amino]pyridin-3-yl}-1-cyclohexyl-3-(propan-2-yl)-1H-pyrazolo[3,4-b]pyridine-6-carboxylic acid;

1-cyclohexyl-4-{6-[methyl(oxolan-3-yl)amino]pyridin-3-yl}-3-(propan-2-yl)-1H-pyrazolo[3,4-b]pyridine-6-carboxylic acid;

3-cyclobutyl-4-{2-[methyl(oxan-4-yl)amino]pyrimidin-5-yl}-1-[3-(pyrrolidin-1-yl)phenyl]-1H-pyrazolo[3,4-b]pyridine-6-carboxylic acid;

1-(3,4-difluorophenyl)-4-{4-[methyl(oxan-4-yl)amino]phenyl}-3-(propan-2-yl)-1H-pyrazolo[3,4-b]pyridine-6-carboxylic acid;

4-[6-(4-cyanopiperidin-1-yl)pyridin-3-yl]-1-(3,4-difluorophenyl)-3-(propan-2-yl)-1H-pyrazolo[3,4-b]pyridine-6-carboxylic acid;

1-(4-fluorophenyl)-4-{2-[methyl(oxan-4-yl)amino]pyrimidin-5-yl}-3-(propan-2-yl)-1H-pyrazolo[3,4-b]pyridine-6-carboxylic acid;

4-{2-[methyl(oxan-4-yl)amino]pyrimidin-5-yl}-3-(propan-2-yl)-1-[3-(trifluoromethyl)phenyl]-1H-pyrazolo[3,4-b]pyridine-6-carboxylic acid;

4-[4-(4-cyanopiperidin-1-yl)phenyl]-1-(3,5-difluorophenyl)-3-(propan-2-yl)-1H-pyrazolo[3,4-b]pyridine-6-carboxylic acid;

1-(3-fluorophenyl)-4-{6-[methyl(oxan-4-yl)amino]pyridin-3-yl}-3-(propan-2-yl)-1H-pyrazolo[3,4-b]pyridine-6-carboxylic acid;

1-(3-fluorophenyl)-4-{4-[methyl(oxan-4-yl)amino]phenyl}-3-(propan-2-yl)-1H-pyrazolo[3,4-b]pyridine-6-carboxylic acid;

4-[6-(4-cyanopiperidin-1-yl)pyridin-3-yl]-1-(3-fluorophenyl)-3-(propan-2-yl)-1H-pyrazolo[3,4-b]pyridine-6-carboxylic acid;

4-[4-(4-cyanopiperidin-1-yl)phenyl]-1-(3-fluorophenyl)-3-(propan-2-yl)-1H-pyrazolo[3,4-b]pyridine-6-carboxylic acid;

4-{6-[methyl(oxan-4-yl)amino]pyridin-3-yl}-3-(propan-2-yl)-1-[3-(trifluoromethyl)phenyl]-1H-pyrazolo[3,4-b]pyridine-6-carboxylic acid;

3-methyl-4-(4-methyl-3-oxo-1-oxa-4,9-diazaspiro[5.5]undecan-9-yl)-1-phenyl-1H-pyrazolo[3,4-b]pyridine-6-carboxylic acid;

4-[3-(methoxymethyl)-3-methylazetidin-1-yl]-3-methyl-1-phenyl-1H-pyrazolo[3,4-b]pyridine-6-carboxylic acid;

3-methyl-4-(3-oxohexahydroimidazo[1,5-a]pyrazin-2(3H)-yl)-1-phenyl-1H-pyrazolo[3,4-b]pyridine-6-carboxylic acid;

4-[4-(methoxymethyl)piperidin-1-yl]-3-methyl-1-phenyl-1H-pyrazolo[3,4-b]pyridine-6-carboxylic acid;

4-(4-acetamidopiperidin-1-yl)-3-methyl-1-phenyl-1H-pyrazolo[3,4-b]pyridine-6-carboxylic acid;

3-methyl-4-(7-oxa-2-azaspiro[3.5]nonan-2-yl)-1-phenyl-1H-pyrazolo[3,4-b]pyridine-6-carboxylic acid;

4-[3-(methoxymethyl)azetidin-1-yl]-3-methyl-1-phenyl-1H-pyrazolo[3,4-b]pyridine-6-carboxylic acid;

4-[(3R)-3-methoxypyrrolidin-1-yl]-3-methyl-1-phenyl-1H-pyrazolo[3,4-b]pyridine-6-carboxylic acid;

4-[(3S)-3-methoxypyrrolidin-1-yl]-3-methyl-1-phenyl-1H-pyrazolo[3,4-b]pyridine-6-carboxylic acid;

4-(4-fluoropiperidin-1-yl)-3-methyl-1-phenyl-1H-pyrazolo[3,4-b]pyridine-6-carboxylic acid;

4-[(3R)-3-fluoropyrrolidin-1-yl]-3-methyl-1-phenyl-1H-pyrazolo[3,4-b]pyridine-6-carboxylic acid;

4-(3,3-difluoropyrrolidin-1-yl)-3-methyl-1-phenyl-1H-pyrazolo[3,4-b]pyridine-6-carboxylic acid;

4-[(3S)-3-fluoropyrrolidin-1-yl]-3-methyl-1-phenyl-1H-pyrazolo[3,4-b]pyridine-6-carboxylic acid;

3-methyl-4-(3-oxotetrahydro-3H-[1,3]oxazolo[3,4-a]pyrazin-7(1H)-yl)-1-phenyl-1H-pyrazolo[3,4-b]pyridine-6-carboxylic acid;

3-methyl-4-[3-(morpholin-4-yl)azetidin-1-yl]-1-phenyl-1H-pyrazolo[3,4-b]pyridine-6-carboxylic acid;

4-{4-[(methanesulfonyl)amino]piperidin-1-yl}-3-methyl-1-phenyl-1H-pyrazolo[3,4-b]pyridine-6-carboxylic acid;

4-(3-azabicyclo[3.1.0]hexan-3-yl)-3-methyl-1-phenyl-1H-pyrazolo[3,4-b]pyridine-6-carboxylic acid;

3-methyl-1-phenyl-4-[4-(pyrrolidine-1-carbonyl)piperidin-1-yl]-1H-pyrazolo[3,4-b]pyridine-6-carboxylic acid;

3-methyl-4-(6-oxa-2-azaspiro[3.4]octan-2-yl)-1-phenyl-1H-pyrazolo[3,4-b]pyridine-6-carboxylic acid;

4-(2-azaspiro[3.4]octan-2-yl)-3-methyl-1-phenyl-1H-pyrazolo[3,4-b]pyridine-6-carboxylic acid;

3-methyl-4-(6-oxa-2-azaspiro[3.5]nonan-2-yl)-1-phenyl-1H-pyrazolo[3,4-b]pyridine-6-carboxylic acid;
4-(2-azaspiro[3.5]nonan-2-yl)-3-methyl-1-phenyl-1H-pyrazolo[3,4-b]pyridine-6-carboxylic acid;
4-(5-azaspiro[2.5]octan-5-yl)-3-methyl-1-phenyl-1H-pyrazolo[3,4-b]pyridine-6-carboxylic acid;
3-methyl-4-(1-oxa-7-azaspiro[4.4]nonan-7-yl)-1-phenyl-1H-pyrazolo[3,4-b]pyridine-6-carboxylic acid;
3-methyl-4-(5-oxa-2-azaspiro[3.5]nonan-2-yl)-1-phenyl-1H-pyrazolo[3,4-b]pyridine-6-carboxylic acid;
3-methyl-4-(6-oxo-2,7-diazaspiro[4.4]nonan-2-yl)-1-phenyl-1H-pyrazolo[3,4-b]pyridine-6-carboxylic acid;
4-{4-[(1S)-2-(dimethylamino)-1-fluoroethyl]piperidin-1-yl}-3-methyl-1-phenyl-1H-pyrazolo[3,4-b]pyridine-6-carboxylic acid;
3-methyl-4-(1,4-oxazepan-4-yl)-1-phenyl-1H-pyrazolo[3,4-b]pyridine-6-carboxylic acid;
1-(3-fluorophenyl)-4-{2-[methyl(oxan-4-yl)amino]pyrimidin-5-yl}-3-(propan-2-yl)-1H-pyrazolo[3,4-b]pyridine-6-carboxylic acid;
1-(3,5-difluorophenyl)-4-{2-[methyl(oxan-4-yl)amino]pyrimidin-5-yl}-3-(propan-2-yl)-1H-pyrazolo[3,4-b]pyridine-6-carboxylic acid;
4-[4-(2-methoxyethoxy)piperidin-1-yl]-3-methyl-1-phenyl-1H-pyrazolo[3,4-b]pyridine-6-carboxylic acid;
4-[4-(dimethylcarbamoyl)piperidin-1-yl]-3-methyl-1-phenyl-1H-pyrazolo[3,4-b]pyridine-6-carboxylic acid;
4-[4-(methanesulfonyl)-1,4-diazepan-1-yl]-3-methyl-1-phenyl-1H-pyrazolo[3,4-b]pyridine-6-carboxylic acid;
4-[4-(3-methoxypropyl)piperazin-1-yl]-3-methyl-1-phenyl-1H-pyrazolo[3,4-b]pyridine-6-carboxylic acid;
3-methyl-4-[4-(morpholine-4-carbonyl)piperazin-1-yl]-1-phenyl-1H-pyrazolo[3,4-b]pyridine-6-carboxylic acid;
4-{4-[2-(dimethylamino)-2-oxoethyl]piperazin-1-yl}-3-methyl-1-phenyl-1H-pyrazolo[3,4-b]pyridine-6-carboxylic acid;
3-methyl-4-[4-(morpholin-4-yl)piperidin-1-yl]-1-phenyl-1H-pyrazolo[3,4-b]pyridine-6-carboxylic acid;
4-[2-(4-cyanopiperidin-1-yl)pyrimidin-5-yl]-1-(2,4-difluorophenyl)-3-(propan-2-yl)-1H-pyrazolo[3,4-b]pyridine-6-carboxylic acid;
4-[6-(4-cyanopiperidin-1-yl)pyridin-3-yl]-1-(2,4-difluorophenyl)-3-(propan-2-yl)-1H-pyrazolo[3,4-b]pyridine-6-carboxylic acid;
4-[4-(4-cyanopiperidin-1-yl)phenyl]-1-(2,4-difluorophenyl)-3-(propan-2-yl)-1H-pyrazolo[3,4-b]pyridine-6-carboxylic acid;
1-[3-(dimethylamino)phenyl]-4-(piperidin-1-yl)-3-(propan-2-yl)-1H-pyrazolo[3,4-b]pyridine-6-carboxylic acid;
4-(4-cyanopiperidin-1-yl)-1-[3-(dimethylamino)phenyl]-3-(propan-2-yl)-1H-pyrazolo[3,4-b]pyridine-6-carboxylic acid;
1-[3-(dimethylamino)phenyl]-4-(4-methoxypiperidin-1-yl)-3-(propan-2-yl)-1H-pyrazolo[3,4-b]pyridine-6-carboxylic acid;
1-[3-(dimethylamino)phenyl]-4-[4-(hydroxymethyl)piperidin-1-yl]-3-(propan-2-yl)-1H-pyrazolo[3,4-b]pyridine-6-carboxylic acid;
3-(1-methylcyclobutyl)-4-[4-(morpholin-4-yl)phenyl]-1-phenyl-1H-pyrazolo[3,4-b]pyridine-6-carboxylic acid;
4-{[cis-3-(1,1-dioxo-1λ⁶,4-thiazinan-4-yl)cyclobutyl]oxy}-3-methyl-1-phenyl-1H-pyrazolo[3,4-b]pyridine-6-carboxylic acid;
4-[2-(1,1-dioxo-1λ⁶,4-thiazinan-4-yl)ethoxy]-3-methyl-1-phenyl-1H-pyrazolo[3,4-b]pyridine-6-carboxylic acid;
4-[(2S)-2-fluoro-2-(oxan-4-yl)ethoxy]-3-methyl-1-phenyl-1H-pyrazolo[3,4-b]pyridine-6-carboxylic acid;
4-[(2R)-2-fluoro-2-(oxan-4-yl)ethoxy]-3-methyl-1-phenyl-1H-pyrazolo[3,4-b]pyridine-6-carboxylic acid;
3-methyl-4-{[(3S)-1-methylpyrrolidin-3-yl]oxy}-1-phenyl-1H-pyrazolo[3,4-b]pyridine-6-carboxylic acid;
3-methyl-4-{[(3R)-1-methylpyrrolidin-3-yl]oxy}-1-phenyl-1H-pyrazolo[3,4-b]pyridine-6-carboxylic acid;
3-methyl-4-[(1-methylpiperidin-4-yl)oxy]-1-phenyl-1H-pyrazolo[3,4-b]pyridine-6-carboxylic acid;
4-{[cis-3-(dimethylamino)cyclobutyl]oxy}-3-methyl-1-phenyl-1H-pyrazolo[3,4-b]pyridine-6-carboxylic acid;
3-methyl-4-[(oxetan-3-yl)oxy]-1-phenyl-1H-pyrazolo[3,4-b]pyridine-6-carboxylic acid;
3-methyl-1-phenyl-4-[2-(pyrrolidin-1-yl)ethoxy]-1H-pyrazolo[3,4-b]pyridine-6-carboxylic acid;
3-methyl-4-{[(3R)-1-methylpiperidin-3-yl]oxy}-1-phenyl-1H-pyrazolo[3,4-b]pyridine-6-carboxylic acid;
3-methyl-4-[(2-oxaspiro[3.3]heptan-6-yl)oxy]-1-phenyl-1H-pyrazolo[3,4-b]pyridine-6-carboxylic acid;
3-methyl-1-phenyl-4-{[trans-3-(piperidin-1-yl)cyclobutyl]oxy}-1H-pyrazolo[3,4-b]pyridine-6-carboxylic acid;
3-methyl-1-phenyl-4-{[cis-3-(piperidin-1-yl)cyclobutyl]oxy}-1H-pyrazolo[3,4-b]pyridine-6-carboxylic acid;
4-[2-(3,3-difluorocyclobutyl)ethoxy]-3-methyl-1-phenyl-1H-pyrazolo[3,4-b]pyridine-6-carboxylic acid;
4-[4-(fluoromethyl)piperidin-1-yl]-1-(3-methylphenyl)-3-(propan-2-yl)-1H-pyrazolo[3,4-b]pyridine-6-carboxylic acid;
3-cyclobutyl-1-(3-fluorophenyl)-4-[4-(morpholin-4-yl)phenyl]-1H-pyrazolo[3,4-b]pyridine-6-carboxylic acid;
3-cyclobutyl-1-(3,4-difluorophenyl)-4-[4-(morpholin-4-yl)phenyl]-1H-pyrazolo[3,4-b]pyridine-6-carboxylic acid;
1-cyclohexyl-4-(1-methyl-1H-pyrrol-3-yl)-3-(propan-2-yl)-1H-pyrazolo[3,4-b]pyridine-6-carboxylic acid;
1-cyclohexyl-4-(1,3-dimethyl-1H-pyrazol-4-yl)-3-(propan-2-yl)-1H-pyrazolo[3,4-b]pyridine-6-carboxylic acid;
3-cyclobutyl-1-(3,5-difluorophenyl)-4-[4-(morpholin-4-yl)phenyl]-1H-pyrazolo[3,4-b]pyridine-6-carboxylic acid;
3-cyclobutyl-4-[4-(morpholin-4-yl)phenyl]-1-[3-(trifluoromethyl)phenyl]-1H-pyrazolo[3,4-b]pyridine-6-carboxylic acid;
3-cyclobutyl-1-(3-fluoro-4-methylphenyl)-4-[4-(morpholin-4-yl)phenyl]-1H-pyrazolo[3,4-b]pyridine-6-carboxylic acid;
3-cyclobutyl-4-[4-(morpholin-4-yl)phenyl]-1-[4-(trifluoromethyl)phenyl]-1H-pyrazolo[3,4-b]pyridine-6-carboxylic acid;
3-cyclobutyl-1-[4-(dimethylamino)phenyl]-4-[4-(morpholin-4-yl)phenyl]-1H-pyrazolo[3,4-b]pyridine-6-carboxylic acid;
3-cyclobutyl-4-(4-methoxypiperidin-1-yl)-1-phenyl-1H-pyrazolo[3,4-b]pyridine-6-carboxylic acid;
4-(3-methyl-2-oxo-1-oxa-3,8-diazaspiro[4.5]decan-8-yl)-1-(3-methylphenyl)-3-(propan-2-yl)-1H-pyrazolo[3,4-b]pyridine-6-carboxylic acid;
4-(3-azaspiro[5.5]undecan-3-yl)-1-(3-methylphenyl)-3-(propan-2-yl)-1H-pyrazolo[3,4-b]pyridine-6-carboxylic acid;
1-cyclohexyl-3-(propan-2-yl)-4-[1-(propan-2-yl)-1H-pyrazol-4-yl]-1H-pyrazolo[3,4-b]pyridine-6-carboxylic acid;
1-cyclohexyl-4-(1-methyl-1H-pyrrol-2-yl)-3-(propan-2-yl)-1H-pyrazolo[3,4-b]pyridine-6-carboxylic acid;
1-cyclohexyl-3-(propan-2-yl)-4-(1H-pyrazol-4-yl)-1H-pyrazolo[3,4-b]pyridine-6-carboxylic acid;
1-cyclohexyl-4-(1-oxo-2,3-dihydro-1H-isoindol-5-yl)-3-(propan-2-yl)-1H-pyrazolo[3,4-b]pyridine-6-carboxylic acid;

4-[6-(4-cyanopiperidin-1-yl)pyridin-3-yl]-1-(oxan-3-yl)-3-(propan-2-yl)-1H-pyrazolo[3,4-b]pyridine-6-carboxylic acid;
4-[2-(3-cyanopiperidin-1-yl)pyrimidin-5-yl]-1-cyclohexyl-3-(propan-2-yl)-1H-pyrazolo[3,4-b]pyridine-6-carboxylic acid;
3-cyclobutyl-4-{4-[2-oxo-2-(pyrrolidin-1-yl)ethoxy]piperidin-1-yl}-1-phenyl-1H-pyrazolo[3,4-b]pyridine-6-carboxylic acid;
1-[3-(dimethylamino)phenyl]-4-[4-(methoxymethyl)piperidin-1-yl]-3-(propan-2-yl)-1H-pyrazolo[3,4-b]pyridine-6-carboxylic acid;
4-[6-(4-cyanopiperidin-1-yl)pyridin-3-yl]-3-(propan-2-yl)-1-[2-(pyrrolidin-1-yl)pyridin-4-yl]-1H-pyrazolo[3,4-b]pyridine-6-carboxylic acid;
1-cyclohexyl-4-(1-methyl-1H-pyrazol-5-yl)-3-(propan-2-yl)-1H-pyrazolo[3,4-b]pyridine-6-carboxylic acid;
4-[1-(tert-butoxycarbonyl)-1,2,3,6-tetrahydropyrin-4-yl]-1-cyclohexyl-3-(propan-2-yl)-1H-pyrazolo[3,4-b]pyridine-6-carboxylic acid;
3-cyclobutyl-1-phenyl-4-{4-[(propan-2-yl)oxy]piperidin-1-yl}-1H-pyrazolo[3,4-b]pyridine-6-carboxylic acid;
3-cyclobutyl-4-[3-(methoxymethyl)piperidin-1-yl]-1-phenyl-1H-pyrazolo[3,4-b]pyridine-6-carboxylic acid;
4-(2-{[1-(tert-butoxycarbonyl)piperidin-4-yl](methyl)amino}pyrimidin-5-yl)-1-cyclohexyl-3-(propan-2-yl)-1H-pyrazolo[3,4-b]pyridine-6-carboxylic acid;
3-methyl-4-[(3-methyloxetan-3-yl)methoxy]-1-phenyl-1H-pyrazolo[3,4-b]pyridine-6-carboxylic acid;
4-[(4-methoxycyclohexyl)oxy]-3-methyl-1-phenyl-1H-pyrazolo[3,4-b]pyridine-6-carboxylic acid;
4-[2-fluoro-2-(oxan-4-yl)ethoxy]-3-methyl-1-phenyl-1H-pyrazolo[3,4-b]pyridine-6-carboxylic acid;
4-[(3-fluoro-1-methylpyrrolidin-3-yl)methoxy]-3-methyl-1-phenyl-1H-pyrazolo[3,4-b]pyridine-6-carboxylic acid;
4-[(2S)-2-fluoro-2-(1-methylpiperidin-4-yl)ethoxy]-3-methyl-1-phenyl-1H-pyrazolo[3,4-b]pyridine-6-carboxylic acid;
4-[(2R)-2-fluoro-2-(1-methylpiperidin-4-yl)ethoxy]-3-methyl-1-phenyl-1H-pyrazolo[3,4-b]pyridine-6-carboxylic acid;
4-{[3-fluoro-1-(oxetan-3-yl)piperidin-3-yl]methoxy}-3-methyl-1-phenyl-1H-pyrazolo[3,4-b]pyridine-6-carboxylic acid;
4-[(3,3-difluorocyclopentyl)methoxy]-3-methyl-1-phenyl-1H-pyrazolo[3,4-b]pyridine-6-carboxylic acid;
3-methyl-4-[2-oxo-2-(piperidin-1-yl)ethoxy]-1-phenyl-1H-pyrazolo[3,4-b]pyridine-6-carboxylic acid;
4-{[1-(methanesulfonyl)cyclobutyl]methoxy}-3-methyl-1-phenyl-1H-pyrazolo[3,4-b]pyridine-6-carboxylic acid;
4-{2-[cyclopropyl(2-methylpropyl)amino]ethoxy}-3-methyl-1-phenyl-1H-pyrazolo[3,4-b]pyridine-6-carboxylic acid;
4-[(3,3-difluoro-1-methylcyclobutyl)methoxy]-3-methyl-1-phenyl-1H-pyrazolo[3,4-b]pyridine-6-carboxylic acid;
4-{[1-(fluoromethyl)cyclopropyl]methoxy}-3-methyl-1-phenyl-1H-pyrazolo[3,4-b]pyridine-6-carboxylic acid;
4-{[1-(2-methoxyethyl)cyclopropyl]methoxy}-3-methyl-1-phenyl-1H-pyrazolo[3,4-b]pyridine-6-carboxylic acid;
4-[(2,2-difluorocyclopentyl)methoxy]-3-methyl-1-phenyl-1H-pyrazolo[3,4-b]pyridine-6-carboxylic acid;
4-[4-(morpholin-4-yl)phenyl]-1-phenyl-3-[(propan-2-yl)oxy]-1H-pyrazolo[3,4-b]pyridine-6-carboxylic acid;
1-(4-fluorophenyl)-4-[4-(methoxymethyl)piperidin-1-yl]-3-(propan-2-yl)-1H-pyrazolo[3,4-b]pyridine-6-carboxylic acid;
4-[4-(4-cyanopiperidin-1-yl)phenyl]-3-(propan-2-yl)-1-[2-(pyrrolidin-1-yl)pyridin-4-yl]-1H-pyrazolo[3,4-b]pyridine-6-carboxylic acid;
1-(4-fluorophenyl)-4-(4-methoxypiperidin-1-yl)-3-(propan-2-yl)-1H-pyrazolo[3,4-b]pyridine-6-carboxylic acid;
1-(4-fluorophenyl)-4-[4-(hydroxymethyl)piperidin-1-yl]-3-(propan-2-yl)-1H-pyrazolo[3,4-b]pyridine-6-carboxylic acid;
4-(4-butoxypiperidin-1-yl)-1-(4-fluorophenyl)-3-(propan-2-yl)-1H-pyrazolo[3,4-b]pyridine-6-carboxylic acid;
1-(4-fluorophenyl)-4-[4-(2-methylpropoxy)piperidin-1-yl]-3-(propan-2-yl)-1H-pyrazolo[3,4-b]pyridine-6-carboxylic acid;
1-(4-fluorophenyl)-4-(4-methoxy-4-methylpiperidin-1-yl)-3-(propan-2-yl)-1H-pyrazolo[3,4-b]pyridine-6-carboxylic acid;
1-(4-fluorophenyl)-4-(1-oxa-7-azaspiro[3.5]nonan-7-yl)-3-(propan-2-yl)-1H-pyrazolo[3,4-b]pyridine-6-carboxylic acid;
4-[3-(difluoromethyl)piperidin-1-yl]-1-(4-fluorophenyl)-3-(propan-2-yl)-1H-pyrazolo[3,4-b]pyridine-6-carboxylic acid;
1-(4-fluorophenyl)-4-(6-oxa-2-azaspiro[3.5]nonan-2-yl)-3-(propan-2-yl)-1H-pyrazolo[3,4-b]pyridine-6-carboxylic acid;
1-(4-fluorophenyl)-4-(1-oxa-8-azaspiro[4.5]decan-8-yl)-3-(propan-2-yl)-1H-pyrazolo[3,4-b]pyridine-6-carboxylic acid;
1-cyclohexyl-3-(propan-2-yl)-4-(2,2,6,6-tetramethyl-3,6-dihydro-2H-pyran-4-yl)-1H-pyrazolo[3,4-b]pyridine-6-carboxylic acid;
3-cyclobutyl-4-[4-(2-methoxyethyl)piperidin-1-yl]-1-phenyl-1H-pyrazolo[3,4-b]pyridine-6-carboxylic acid;
4-(2-azaspiro[3.4]octan-2-yl)-3-cyclobutyl-1-phenyl-1H-pyrazolo[3,4-b]pyridine-6-carboxylic acid;
3-cyclobutyl-4-[4-(methoxymethyl)piperidin-1-yl]-1-phenyl-1H-pyrazolo[3,4-b]pyridine-6-carboxylic acid;
4-(3-azabicyclo[3.1.0]hexan-3-yl)-3-cyclobutyl-1-phenyl-1H-pyrazolo[3,4-b]pyridine-6-carboxylic acid;
3-cyclobutyl-4-(cyclohexylmethoxy)-1-phenyl-1H-pyrazolo[3,4-b]pyridine-6-carboxylic acid;
3-cyclobutyl-1-phenyl-4-(piperidin-1-yl)-1H-pyrazolo[3,4-b]pyridine-6-carboxylic acid;
4-(2-azaspiro[3.5]nonan-2-yl)-3-cyclobutyl-1-phenyl-1H-pyrazolo[3,4-b]pyridine-6-carboxylic acid;
4-(4-cyanopiperidin-1-yl)-3-cyclobutyl-1-phenyl-1H-pyrazolo[3,4-b]pyridine-6-carboxylic acid;
3-cyclobutyl-4-[4-(methanesulfonyl)piperidin-1-yl]-1-phenyl-1H-pyrazolo[3,4-b]pyridine-6-carboxylic acid;
4-(4-methoxypiperidin-1-yl)-3-(propan-2-yl)-1-[2-(pyrrolidin-1-yl)pyridin-4-yl]-1H-pyrazolo[3,4-b]pyridine-6-carboxylic acid;
4-[6-(4-cyanopiperidin-1-yl)pyridin-3-yl]-3-cyclobutyl-1-[2-(pyrrolidin-1-yl)pyridin-4-yl]-1H-pyrazolo[3,4-b]pyridine-6-carboxylic acid;
3-cyclobutyl-4-[2-(oxan-4-yl)ethoxy]-1-phenyl-1H-pyrazolo[3,4-b]pyridine-6-carboxylic acid;
3-cyclobutyl-4-[(2S)-2-fluoro-2-(oxan-4-yl)ethoxy]-1-phenyl-1H-pyrazolo[3,4-b]pyridine-6-carboxylic acid;
4-[6-(4-cyanopiperidin-1-yl)pyridin-3-yl]-3-cyclobutyl-1-[2-(morpholin-4-yl)pyridin-4-yl]-1H-pyrazolo[3,4-b]pyridine-6-carboxylic acid;
3-cyclobutyl-4-[(oxan-4-yl)methoxy]-1-phenyl-1H-pyrazolo[3,4-b]pyridine-6-carboxylic acid;
3-cyclobutyl-4-[3-(methoxymethyl)azetidin-1-yl]-1-phenyl-1H-pyrazolo[3,4-b]pyridine-6-carboxylic acid;

4-(5-azaspiro[2.5]octan-5-yl)-3-cyclobutyl-1-phenyl-1H-pyrazolo[3,4-b]pyridine-6-carboxylic acid;

4-[6-(4-cyanopiperidin-1-yl)pyridin-3-yl]-3-(3,3-difluorocyclobutyl)-1-phenyl-1H-pyrazolo[3,4-b]pyridine-6-carboxylic acid;

4-[6-(4-cyanopiperidin-1-yl)pyridin-3-yl]-3-(cis-3-methoxycyclobutyl)-1-phenyl-1H-pyrazolo[3,4-b]pyridine-6-carboxylic acid;

3-cyclobutyl-4-[(2-methoxyethyl)(methyl)amino]-1-phenyl-1H-pyrazolo[3,4-b]pyridine-6-carboxylic acid;

3-cyclobutyl-4-(1,1-difluoro-5-azaspiro[2.4]heptan-5-yl)-1-phenyl-1H-pyrazolo[3,4-b]pyridine-6-carboxylic acid;

3-cyclobutyl-4-(5-oxa-2-azaspiro[3.5]nonan-2-yl)-1-phenyl-1H-pyrazolo[3,4-b]pyridine-6-carboxylic acid;

3-cyclobutyl-4-(7-oxa-2-azaspiro[3.5]nonan-2-yl)-1-phenyl-1H-pyrazolo[3,4-b]pyridine-6-carboxylic acid;

4-(2-azaspiro[3.3]heptan-2-yl)-3-cyclobutyl-1-phenyl-1H-pyrazolo[3,4-b]pyridine-6-carboxylic acid;

4-{4-[(benzyloxy)methyl]piperidin-1-yl}-3-cyclobutyl-1-phenyl-1H-pyrazolo[3,4-b]pyridine-6-carboxylic acid;

3-cyclobutyl-4-[(cis-4-methoxycyclohexyl)oxy]-1-phenyl-1H-pyrazolo[3,4-b]pyridine-6-carboxylic acid;

3-cyclobutyl-4-[(trans-4-methoxycyclohexyl)oxy]-1-phenyl-1H-pyrazolo[3,4-b]pyridine-6-carboxylic acid;

4-[6-(4-cyanopiperidin-1-yl)pyridin-3-yl]-3-(3,3-dimethylcyclobutyl)-1-phenyl-1H-pyrazolo[3,4-b]pyridine-6-carboxylic acid;

1-cyclohexyl-4-[4-(methoxymethyl)piperidin-1-yl]-3-(propan-2-yl)-1H-pyrazolo[3,4-b]pyridine-6-carboxylic acid;

4-[6-(4-cyanopiperidin-1-yl)pyridin-3-yl]-3-(cis-3-fluorocyclobutyl)-1-phenyl-1H-pyrazolo[3,4-b]pyridine-6-carboxylic acid;

4-[6-(4-cyanopiperidin-1-yl)pyridin-3-yl]-3-(trans-3-fluorocyclobutyl)-1-phenyl-1H-pyrazolo[3,4-b]pyridine-6-carboxylic acid;

3-cyclobutyl-4-[(2R)-2-fluoro-2-(oxan-4-yl)ethoxy]-1-phenyl-1H-pyrazolo[3,4-b]pyridine-6-carboxylic acid;

3-cyclobutyl-4-[(3,3-difluorocyclopentyl)methoxy]-1-phenyl-1H-pyrazolo[3,4-b]pyridine-6-carboxylic acid;

3-cyclobutyl-4-[2-(1,1-dioxo-1$\lambda^6$,4-thiazinan-4-yl)ethoxy]-1-phenyl-1H-pyrazolo[3,4-b]pyridine-6-carboxylic acid;

4-[6-(4-cyanopiperidin-1-yl)pyridin-3-yl]-1-[2-(morpholin-4-yl)pyridin-4-yl]-3-(propan-2-yl)-1H-pyrazolo[3,4-b]pyridine-6-carboxylic acid;

1-(4-fluorophenyl)-4-[4-(2-methoxypropan-2-yl)piperidin-1-yl]-3-(propan-2-yl)-1H-pyrazolo[3,4-b]pyridine-6-carboxylic acid;

4-[(cis-3-tert-butoxycyclobutyl)(methyl)amino]-3-cyclobutyl-1-phenyl-1H-pyrazolo[3,4-b]pyridine-6-carboxylic acid;

3-cyclobutyl-4-(3-methylazetidin-1-yl)-1-phenyl-1H-pyrazolo[3,4-b]pyridine-6-carboxylic acid;

3-cyclobutyl-4-(3,3-difluoropyrrolidin-1-yl)-1-phenyl-1H-pyrazolo[3,4-b]pyridine-6-carboxylic acid;

3-cyclobutyl-1-phenyl-4-[3-(trifluoromethyl)pyrrolidin-1-yl]-1H-pyrazolo[3,4-b]pyridine-6-carboxylic acid;

3-cyclobutyl-1-phenyl-4-[4-(pyrrolidin-1-yl)piperidin-1-yl]-1H-pyrazolo[3,4-b]pyridine-6-carboxylic acid;

3-cyclobutyl-4-(4-fluoropiperidin-1-yl)-1-phenyl-1H-pyrazolo[3,4-b]pyridine-6-carboxylic acid;

3-cyclobutyl-4-[(3R,4R)-3,4-dihydroxypyrrolidin-1-yl]-1-phenyl-1H-pyrazolo[3,4-b]pyridine-6-carboxylic acid;

3-cyclobutyl-4-[(3S,4S)-3,4-dihydroxypyrrolidin-1-yl]-1-phenyl-1H-pyrazolo[3,4-b]pyridine-6-carboxylic acid;

3-cyclobutyl-4-{4-[2-(dimethylamino)ethyl]piperidin-1-yl}-1-phenyl-1H-pyrazolo[3,4-b]pyridine-6-carboxylic acid;

3-cyclobutyl-4-{4-[2-(diethylamino)ethyl]piperidin-1-yl}-1-phenyl-1H-pyrazolo[3,4-b]pyridine-6-carboxylic acid;

3-cyclobutyl-4-[4-(cyclopropylmethyl)piperazin-1-yl]-1-phenyl-1H-pyrazolo[3,4-b]pyridine-6-carboxylic acid;

3-cyclobutyl-4-(4-cyclobutylpiperazin-1-yl)-1-phenyl-1H-pyrazolo[3,4-b]pyridine-6-carboxylic acid;

3-cyclobutyl-4-(3-fluoro-3-methylazetidin-1-yl)-1-phenyl-1H-pyrazolo[3,4-b]pyridine-6-carboxylic acid;

4-(8-azaspiro[4.5]decan-8-yl)-3-cyclobutyl-1-phenyl-1H-pyrazolo[3,4-b]pyridine-6-carboxylic acid;

3-cyclobutyl-4-(3,3-difluoro-1-oxa-8-azaspiro[4.5]decan-8-yl)-1-phenyl-1H-pyrazolo[3,4-b]pyridine-6-carboxylic acid;

3-cyclobutyl-4-(1'-methyl[4,4'-bipiperidin]-1-yl)-1-phenyl-1H-pyrazolo[3,4-b]pyridine-6-carboxylic acid;

3-cyclobutyl-4-{4-[(1R)-2-(dimethylamino)-1-fluoroethyl]piperidin-1-yl}-1-phenyl-1H-pyrazolo[3,4-b]pyridine-6-carboxylic acid;

3-cyclobutyl-4-{4-[(1S)-2-(dimethylamino)-1-fluoroethyl]piperidin-1-yl}-1-phenyl-1H-pyrazolo[3,4-b]pyridine-6-carboxylic acid;

3-cyclobutyl-4-{4-[(1S)-1-fluoro-2-hydroxyethyl]piperidin-1-yl}-1-phenyl-1H-pyrazolo[3,4-b]pyridine-6-carboxylic acid;

3-cyclobutyl-4-{4-[(1R)-1-fluoro-2-hydroxyethyl]piperidin-1-yl}-1-phenyl-1H-pyrazolo[3,4-b]pyridine-6-carboxylic acid;

3-cyclobutyl-4-{4-fluoro-4-[(2-methoxyethoxy)methyl]piperidin-1-yl}-1-phenyl-1H-pyrazolo[3,4-b]pyridine-6-carboxylic acid;

3-cyclobutyl-4-[3-(ethoxymethyl)-3-fluoropiperidin-1-yl]-1-phenyl-1H-pyrazolo[3,4-b]pyridine-6-carboxylic acid;

3-cyclobutyl-4-[4-(ethoxymethyl)-4-fluoropiperidin-1-yl]-1-phenyl-1H-pyrazolo[3,4-b]pyridine-6-carboxylic acid;

3-cyclobutyl-4-{3-fluoro-3-[(2-methoxyethoxy)methyl]piperidin-1-yl}-1-phenyl-1H-pyrazolo[3,4-b]pyridine-6-carboxylic acid;

3-cyclobutyl-4-[4-fluoro-4-(methoxymethyl)piperidin-1-yl]-1-phenyl-1H-pyrazolo[3,4-b]pyridine-6-carboxylic acid;

3-cyclobutyl-4-[(3R,4R)-3-fluoro-4-hydroxypiperidin-1-yl]-1-phenyl-1H-pyrazolo[3,4-b]pyridine-6-carboxylic acid;

3-cyclobutyl-4-[(3R,4R)-4-fluoro-3-hydroxypiperidin-1-yl]-1-phenyl-1H-pyrazolo[3,4-b]pyridine-6-carboxylic acid;

3-cyclobutyl-1-phenyl-4-[3-(piperidin-1-yl)azetidin-1-yl]-1H-pyrazolo[3,4-b]pyridine-6-carboxylic acid;

3-cyclobutyl-4-[(3R)-3-(methanesulfonyl)pyrrolidin-1-yl]-1-phenyl-1H-pyrazolo[3,4-b]pyridine-6-carboxylic acid;

3-cyclobutyl-4-(3-methoxypiperidin-1-yl)-1-phenyl-1H-pyrazolo[3,4-b]pyridine-6-carboxylic acid;

3-cyclobutyl-4-[4-oxo-1-(propan-2-yl)-1,3,8-triazaspiro[4.5]decan-8-yl]-1-phenyl-1H-pyrazolo[3,4-b]pyridine-6-carboxylic acid;

3-cyclobutyl-1-phenyl-4-[4-(2,2,2-trifluoroethyl)piperazin-1-yl]-1H-pyrazolo[3,4-b]pyridine-6-carboxylic acid;

3-cyclobutyl-4-[4-(3-hydroxypropyl)piperazin-1-yl]-1-phenyl-1H-pyrazolo[3,4-b]pyridine-6-carboxylic acid;

3-cyclobutyl-4-{4-[2-oxo-2-(pyrrolidin-1-yl)ethyl]piperazin-1-yl}-1-phenyl-1H-pyrazolo[3,4-b]pyridine-6-carboxylic acid;

4-(azepan-1-yl)-3-cyclobutyl-1-phenyl-1H-pyrazolo[3,4-b]pyridine-6-carboxylic acid;

3-cyclobutyl-4-{4-[2-(morpholin-4-yl)-2-oxoethyl]piperazin-1-yl}-1-phenyl-1H-pyrazolo[3,4-b]pyridine-6-carboxylic acid;

3-cyclobutyl-4-[(7R,8aS)-7-hydroxyhexahydropyrrolo[1,2-a]pyrazin-2(1H)-yl]-1-phenyl-1H-pyrazolo[3,4-b]pyridine-6-carboxylic acid;

3-cyclobutyl-4-[(3,3-difluoro-1-methylcyclobutyl)methoxy]-1-phenyl-1H-pyrazolo[3,4-b]pyridine-6-carboxylic acid;

3-cyclobutyl-4-[2-(3,3-difluorocyclobutyl)ethoxy]-1-phenyl-1H-pyrazolo[3,4-b]pyridine-6-carboxylic acid;

3-cyclobutyl-4-{2-[(oxetan-3-yl)(propan-2-yl)amino]ethoxy}-1-phenyl-1H-pyrazolo[3,4-b]pyridine-6-carboxylic acid;

4-[(1-acetyl-4-fluoropiperidin-4-yl)methoxy]-3-cyclobutyl-1-phenyl-1H-pyrazolo[3,4-b]pyridine-6-carboxylic acid;

3-cyclobutyl-4-{[(2S)-oxolan-2-yl]methoxy}-1-phenyl-1H-pyrazolo[3,4-b]pyridine-6-carboxylic acid;

3-cyclobutyl-4-[2-(3-methoxyazetidin-1-yl)-2-oxoethoxy]-1-phenyl-1H-pyrazolo[3,4-b]pyridine-6-carboxylic acid;

3-cyclobutyl-4-[(2R)-2-fluoro-2-(1-methylpiperidin-4-yl)ethoxy]-1-phenyl-1H-pyrazolo[3,4-b]pyridine-6-carboxylic acid;

3-cyclobutyl-4-{2-[(oxetan-3-yl)oxy]ethoxy}-1-phenyl-1H-pyrazolo[3,4-b]pyridine-6-carboxylic acid;

3-cyclobutyl-4-{2-[1-(2-methoxyethyl)cyclopropyl]ethoxy}-1-phenyl-1H-pyrazolo[3,4-b]pyridine-6-carboxylic acid;

3-cyclobutyl-4-{[1-(2-methoxyethyl)cyclopropyl]methoxy}-1-phenyl-1H-pyrazolo[3,4-b]pyridine-6-carboxylic acid;

3-cyclobutyl-4-[(2,2-difluorocyclopentyl)methoxy]-1-phenyl-1H-pyrazolo[3,4-b]pyridine-6-carboxylic acid;

3-cyclobutyl-4-[3-(morpholin-4-yl)propoxy]-1-phenyl-1H-pyrazolo[3,4-b]pyridine-6-carboxylic acid;

3-cyclobutyl-4-[2-(1,3-dioxan-2-yl)ethoxy]-1-phenyl-1H-pyrazolo[3,4-b]pyridine-6-carboxylic acid;

3-cyclobutyl-4-(3-fluoropropoxy)-1-phenyl-1H-pyrazolo[3,4-b]pyridine-6-carboxylic acid;

3-cyclobutyl-4-[(3-methyloxetan-3-yl)methoxy]-1-phenyl-1H-pyrazolo[3,4-b]pyridine-6-carboxylic acid;

3-cyclobutyl-4-[(1,3-dimethoxypropan-2-yl)oxy]-1-phenyl-1H-pyrazolo[3,4-b]pyridine-6-carboxylic acid;

3-cyclobutyl-4-{[cis-3-(dimethylamino)cyclobutyl]oxy}-1-phenyl-1H-pyrazolo[3,4-b]pyridine-6-carboxylic acid;

3-cyclobutyl-4-[(2-methyl-1,3-dioxan-5-yl)oxy]-1-phenyl-1H-pyrazolo[3,4-b]pyridine-6-carboxylic acid;

3-cyclobutyl-4-{[(3S)-1-methylpiperidin-3-yl]oxy}-1-phenyl-1H-pyrazolo[3,4-b]pyridine-6-carboxylic acid;

3-cyclobutyl-4-[(2-oxaspiro[3.3]heptan-6-yl)oxy]-1-phenyl-1H-pyrazolo[3,4-b]pyridine-6-carboxylic acid;

3-cyclobutyl-4-{[(3R)-1-methylpiperidin-3-yl]oxy}-1-phenyl-1H-pyrazolo[3,4-b]pyridine-6-carboxylic acid;

3-[(1-acetylazetidin-3-yl)oxy]-4-[4-(morpholin-4-yl)phenyl]-1-phenyl-1H-pyrazolo[3,4-b]pyridine-6-carboxylic acid;

3-cyclobutyl-4-[4-(1-methoxyethyl)piperidin-1-yl]-1-phenyl-1H-pyrazolo[3,4-b]pyridine-6-carboxylic acid;

3-cyclobutyl-1-phenyl-4-[4-(1,1,1-trifluoro-2-methoxypropan-2-yl)piperidin-1-yl]-1H-pyrazolo[3,4-b]pyridine-6-carboxylic acid;

3-cyclobutyl-4-[3-(diethylcarbamoyl)piperidin-1-yl]-1-phenyl-1H-pyrazolo[3,4-b]pyridine-6-carboxylic acid;

3-cyclobutyl-4-(4-hydroxypiperidin-1-yl)-1-phenyl-1H-pyrazolo[3,4-b]pyridine-6-carboxylic acid;

3-cyclobutyl-4-{4-[2-(1,4-dimethyl-6-oxo-1,6-dihydropyrimidin-5-yl)ethyl]piperazin-1-yl}-1-phenyl-1H-pyrazolo[3,4-b]pyridine-6-carboxylic acid;

3-cyclobutyl-4-[(4aS,7aR)-4-methyl-3-oxohexahydropyrrolo[3,4-b][1,4]oxazin-6(2H)-yl]-1-phenyl-1H-pyrazolo[3,4-b]pyridine-6-carboxylic acid;

3-cyclobutyl-4-(3-oxopiperazin-1-yl)-1-phenyl-1H-pyrazolo[3,4-b]pyridine-6-carboxylic acid;

3-cyclobutyl-4-[(5aS,8aS)-2-oxooctahydropyrrolo[3,4-b]azepin-7(1H)-yl]-1-phenyl-1H-pyrazolo[3,4-b]pyridine-6-carboxylic acid;

3-cyclobutyl-4-[(2R)-4,4-difluoro-2-(hydroxymethyl)pyrrolidin-1-yl]-1-phenyl-1H-pyrazolo[3,4-b]pyridine-6-carboxylic acid;

3-cyclobutyl-4-[(2S,4S)-4-fluoro-2-(hydroxymethyl)pyrrolidin-1-yl]-1-phenyl-1H-pyrazolo[3,4-b]pyridine-6-carboxylic acid;

3-cyclobutyl-4-[3-fluoro-3-(methoxymethyl)pyrrolidin-1-yl]-1-phenyl-1H-pyrazolo[3,4-b]pyridine-6-carboxylic acid;

3-cyclobutyl-4-[(3R,4S)-3-fluoro-4-hydroxypiperidin-1-yl]-1-phenyl-1H-pyrazolo[3,4-b]pyridine-6-carboxylic acid;

3-cyclobutyl-4-[3-(ethoxymethyl)-3-fluoropyrrolidin-1-yl]-1-phenyl-1H-pyrazolo[3,4-b]pyridine-6-carboxylic acid;

3-cyclobutyl-4-[3-(hydroxymethyl)-3-methylazetidin-1-yl]-1-phenyl-1H-pyrazolo[3,4-b]pyridine-6-carboxylic acid;

3-cyclobutyl-4-[(3S)-3-methoxypyrrolidin-1-yl]-1-phenyl-1H-pyrazolo[3,4-b]pyridine-6-carboxylic acid;

3-cyclobutyl-4-[3-(2,2-difluoroethoxy)azetidin-1-yl]-1-phenyl-1H-pyrazolo[3,4-b]pyridine-6-carboxylic acid;

3-cyclobutyl-4-[(2R,4S)-4-fluoro-2-(hydroxymethyl)pyrrolidin-1-yl]-1-phenyl-1H-pyrazolo[3,4-b]pyridine-6-carboxylic acid;

3-cyclobutyl-4-[(7S,8aS)-7-fluorohexahydropyrrolo[1,2-a]pyrazin-2(1H)-yl]-1-phenyl-1H-pyrazolo[3,4-b]pyridine-6-carboxylic acid;

3-cyclobutyl-4-[(4aS,7aS)-4-methyl-3-oxohexahydropyrrolo[3,4-b][1,4]oxazin-6(2H)-yl]-1-phenyl-1H-pyrazolo[3,4-b]pyridine-6-carboxylic acid;

3-cyclobutyl-4-[4-fluoro-4-(hydroxymethyl)piperidin-1-yl]-1-phenyl-1H-pyrazolo[3,4-b]pyridine-6-carboxylic acid;

3-cyclobutyl-4-(1-oxa-7-azaspiro[4.4]nonan-7-yl)-1-phenyl-1H-pyrazolo[3,4-b]pyridine-6-carboxylic acid;

3-cyclobutyl-4-{4-[(methanesulfonyl)amino]piperidin-1-yl}-1-phenyl-1H-pyrazolo[3,4-b]pyridine-6-carboxylic acid;

3-cyclobutyl-4-[4-(1-fluoro-2-hydroxyethyl)piperidin-1-yl]-1-phenyl-1H-pyrazolo[3,4-b]pyridine-6-carboxylic acid;

3-cyclobutyl-4-[3-(methoxymethyl)-3-methylazetidin-1-yl]-1-phenyl-1H-pyrazolo[3,4-b]pyridine-6-carboxylic acid;

3-cyclobutyl-4-[(3R)-3-methoxypyrrolidin-1-yl]-1-phenyl-1H-pyrazolo[3,4-b]pyridine-6-carboxylic acid;

3-cyclobutyl-4-[4-(methanesulfonyl)piperazin-1-yl]-1-phenyl-1H-pyrazolo[3,4-b]pyridine-6-carboxylic acid;

4-{6-[bis(2-methoxyethyl)amino]pyridin-3-yl}-1-[2-(morpholin-4-yl)pyridin-4-yl]-3-(propan-2-yl)-1H-pyrazolo[3,4-b]pyridine-6-carboxylic acid;

4-[4-(methoxymethyl)piperidin-1-yl]-1-[2-(morpholin-4-yl)pyridin-4-yl]-3-(propan-2-yl)-1H-pyrazolo[3,4-b]pyridine-6-carboxylic acid;

3-cyclobutyl-4-[4-methoxy-4-(methoxymethyl)piperidin-1-yl]-1-phenyl-1H-pyrazolo[3,4-b]pyridine-6-carboxylic acid;

3-cyclobutyl-4-[(3S)-3-fluoropyrrolidin-1-yl]-1-phenyl-1H-pyrazolo[3,4-b]pyridine-6-carboxylic acid;

3-cyclobutyl-4-(3,3-difluoroazetidin-1-yl)-1-phenyl-1H-pyrazolo[3,4-b]pyridine-6-carboxylic acid;

3-cyclobutyl-4-[3-(2-oxo-1,3-oxazolidin-3-yl)azetidin-1-yl]-1-phenyl-1H-pyrazolo[3,4-b]pyridine-6-carboxylic acid;
3-cyclobutyl-4-(3-ethyl-3-fluoroazetidin-1-yl)-1-phenyl-1H-pyrazolo[3,4-b]pyridine-6-carboxylic acid;
3-cyclobutyl-4-[2-(hydroxymethyl)morpholin-4-yl]-1-phenyl-1H-pyrazolo[3,4-b]pyridine-6-carboxylic acid;
3-cyclobutyl-4-{3-fluoro-3-[(2-methoxyethoxy)methyl]pyrrolidin-1-yl}-1-phenyl-1H-pyrazolo[3,4-b]pyridine-6-carboxylic acid;
3-cyclobutyl-4-[(cis-3-hydroxycyclobutyl)(methyl)amino]-1-phenyl-1H-pyrazolo[3,4-b]pyridine-6-carboxylic acid;
3-cyclobutyl-4-(6-oxa-2-azaspiro[3.4]octan-2-yl)-1-phenyl-1H-pyrazolo[3,4-b]pyridine-6-carboxylic acid;
3-cyclobutyl-4-[(3R,4S)-4-fluoro-3-hydroxypiperidin-1-yl]-1-phenyl-1H-pyrazolo[3,4-b]pyridine-6-carboxylic acid;
3-cyclobutyl-4-(3-hydroxy-3-methylazetidin-1-yl)-1-phenyl-1H-pyrazolo[3,4-b]pyridine-6-carboxylic acid;
3-cyclobutyl-4-(6-oxo-2,7-diazaspiro[4.4]nonan-2-yl)-1-phenyl-1H-pyrazolo[3,4-b]pyridine-6-carboxylic acid;
3-cyclobutyl-4-[(2S)-4,4-difluoro-2-(hydroxymethyl)pyrrolidin-1-yl]-1-phenyl-1H-pyrazolo[3,4-b]pyridine-6-carboxylic acid;
3-cyclobutyl-4-[4-(ethoxycarbonyl)piperazin-1-yl]-1-phenyl-1H-pyrazolo[3,4-b]pyridine-6-carboxylic acid;
3-cyclobutyl-4-{4-[2-(cyclohexylamino)-2-oxoethyl]piperazin-1-yl}-1-phenyl-1H-pyrazolo[3,4-b]pyridine-6-carboxylic acid;
3-cyclobutyl-4-[(3R)-3-fluoropyrrolidin-1-yl]-1-phenyl-1H-pyrazolo[3,4-b]pyridine-6-carboxylic acid;
3-cyclobutyl-4-(3-methoxyazetidin-1-yl)-1-phenyl-1H-pyrazolo[3,4-b]pyridine-6-carboxylic acid;
3-cyclobutyl-4-(2-hydroxy-7-azaspiro[3.5]nonan-7-yl)-1-phenyl-1H-pyrazolo[3,4-b]pyridine-6-carboxylic acid;
3-cyclobutyl-4-[(3R)-3-(hydroxymethyl)piperidin-1-yl]-1-phenyl-1H-pyrazolo[3,4-b]pyridine-6-carboxylic acid;
3-cyclobutyl-4-(1,4-oxazepan-4-yl)-1-phenyl-1H-pyrazolo[3,4-b]pyridine-6-carboxylic acid;
3-cyclobutyl-4-[4-hydroxy-4-(2-hydroxyethyl)piperidin-1-yl]-1-phenyl-1H-pyrazolo[3,4-b]pyridine-6-carboxylic acid;
1-(cyclobutylmethyl)-4-[4-(methoxymethyl)piperidin-1-yl]-3-(propan-2-yl)-1H-pyrazolo[3,4-b]pyridine-6-carboxylic acid;
4-[4-(methoxymethyl)piperidin-1-yl]-1-(2-methylpropyl)-3-(propan-2-yl)-1H-pyrazolo[3,4-b]pyridine-6-carboxylic acid;
rac-4-[(3aR,7aS)-1-(tert-butoxycarbonyl)octahydro-5H-pyrrolo[3,2-c]pyridin-5-yl]-3-cyclobutyl-1-phenyl-1H-pyrazolo[3,4-b]pyridine-6-carboxylic acid;
4-[6-(4-cyanopiperidin-1-yl)pyridin-3-yl]-1-phenyl-3-[(pyrrolidin-3-yl)oxy]-1H-pyrazolo[3,4-b]pyridine-6-carboxylic acid;
4-[6-(4-cyanopiperidin-1-yl)pyridin-3-yl]-3-(trans-3-methylcyclobutyl)-1-phenyl-1H-pyrazolo[3,4-b]pyridine-6-carboxylic acid;
3-{[1-(tert-butoxycarbonyl)pyrrolidin-3-yl]oxy}-4-[6-(4-cyanopiperidin-1-yl)pyridin-3-yl]-1-phenyl-1H-pyrazolo[3,4-b]pyridine-6-carboxylic acid;
3-{[1-(tert-butoxycarbonyl)piperidin-4-yl]oxy}-4-[6-(4-cyanopiperidin-1-yl)pyridin-3-yl]-1-phenyl-1H-pyrazolo[3,4-b]pyridine-6-carboxylic acid;
3-cyclobutyl-4-{methyl[(oxan-4-yl)methyl]amino}-1-phenyl-1H-pyrazolo[3,4-b]pyridine-6-carboxylic acid;
3-cyclobutyl-1-phenyl-4-[4-(2-propoxyethyl)piperazin-1-yl]-1H-pyrazolo[3,4-b]pyridine-6-carboxylic acid;
3-cyclobutyl-1-phenyl-4-{2-[(piperidin-1-yl)methyl]morpholin-4-yl}-1H-pyrazolo[3,4-b]pyridine-6-carboxylic acid;
3-cyclobutyl-1-phenyl-4-{4-[(pyrrolidin-1-yl)methyl]piperidin-1-yl}-1H-pyrazolo[3,4-b]pyridine-6-carboxylic acid;
3-cyclobutyl-4-{4-[3-(morpholin-4-yl)propyl]piperazin-1-yl}-1-phenyl-1H-pyrazolo[3,4-b]pyridine-6-carboxylic acid;
3-cyclobutyl-4-{4-[2-(dimethylamino)-2-oxoethyl]piperazin-1-yl}-1-phenyl-1H-pyrazolo[3,4-b]pyridine-6-carboxylic acid;
3-cyclobutyl-4-[4-(morpholin-4-yl)piperidin-1-yl]-1-phenyl-1H-pyrazolo[3,4-b]pyridine-6-carboxylic acid;
4-[4-(2-cyanoethyl)piperazin-1-yl]-3-cyclobutyl-1-phenyl-1H-pyrazolo[3,4-b]pyridine-6-carboxylic acid;
3-cyclobutyl-4-{2-[(dimethylamino)methyl]morpholin-4-yl}-1-phenyl-1H-pyrazolo[3,4-b]pyridine-6-carboxylic acid;
3-cyclobutyl-4-(4-methylpiperazin-1-yl)-1-phenyl-1H-pyrazolo[3,4-b]pyridine-6-carboxylic acid;
3-cyclobutyl-4-(methyl{[1-(2-methylpropyl)piperidin-4-yl]methyl}amino)-1-phenyl-1H-pyrazolo[3,4-b]pyridine-6-carboxylic acid;
3-cyclobutyl-4-{methyl[2-(morpholin-4-yl)ethyl]amino}-1-phenyl-1H-pyrazolo[3,4-b]pyridine-6-carboxylic acid;
3-cyclobutyl-4-[4-(2-ethoxyethyl)piperazin-1-yl]-1-phenyl-1H-pyrazolo[3,4-b]pyridine-6-carboxylic acid;
3-cyclobutyl-4-[(3R)-3-(dimethylamino)pyrrolidin-1-yl]-1-phenyl-1H-pyrazolo[3,4-b]pyridine-6-carboxylic acid;
3-cyclobutyl-4-[(3S)-3-(dimethylamino)pyrrolidin-1-yl]-1-phenyl-1H-pyrazolo[3,4-b]pyridine-6-carboxylic acid;
3-cyclobutyl-4-{4-[2-(methylamino)-2-oxoethyl]piperazin-1-yl}-1-phenyl-1H-pyrazolo[3,4-b]pyridine-6-carboxylic acid;
3-cyclobutyl-4-{4-[(morpholin-4-yl)acetyl]piperazin-1-yl}-1-phenyl-1H-pyrazolo[3,4-b]pyridine-6-carboxylic acid;
3-cyclobutyl-4-[4-(2-methoxyethyl)piperazin-1-yl]-1-phenyl-1H-pyrazolo[3,4-b]pyridine-6-carboxylic acid;
3-cyclobutyl-4-{4-[(oxolan-2-yl)methyl]-1,4-diazepan-1-yl}-1-phenyl-1H-pyrazolo[3,4-b]pyridine-6-carboxylic acid;
3-cyclobutyl-1-phenyl-4-{3-[(propan-2-yl)oxy]azetidin-1-yl}-1H-pyrazolo[3,4-b]pyridine-6-carboxylic acid;
3-cyclobutyl-1-phenyl-4-{4-[2-(pyrrolidin-1-yl)ethyl]piperidin-1-yl}-1H-pyrazolo[3,4-b]pyridine-6-carboxylic acid;
3-cyclobutyl-4-{4-[2-(morpholin-4-yl)ethyl]piperidin-1-yl}-1-phenyl-1H-pyrazolo[3,4-b]pyridine-6-carboxylic acid;
4-([1,4'-bipiperidin]-1'-yl)-3-cyclobutyl-1-phenyl-1H-pyrazolo[3,4-b]pyridine-6-carboxylic acid;
3-cyclobutyl-4-[(3R)-3-(morpholin-4-yl)pyrrolidin-1-yl]-1-phenyl-1H-pyrazolo[3,4-b]pyridine-6-carboxylic acid;
3-cyclobutyl-4-[(4,4-difluorocyclohexyl)oxy]-1-phenyl-1H-pyrazolo[3,4-b]pyridine-6-carboxylic acid;
3-cyclobutyl-4-[(oxan-4-yl)oxy]-1-phenyl-1H-pyrazolo[3,4-b]pyridine-6-carboxylic acid;
3-cyclobutyl-4-{[(1S,2S)-2-methoxycyclohexyl]oxy}-1-phenyl-1H-pyrazolo[3,4-b]pyridine-6-carboxylic acid;
3-cyclobutyl-4-[(3-ethyloxetan-3-yl)methoxy]-1-phenyl-1H-pyrazolo[3,4-b]pyridine-6-carboxylic acid;
3-cyclobutyl-4-{[(3R)-oxolan-3-yl]oxy}-1-phenyl-1H-pyrazolo[3,4-b]pyridine-6-carboxylic acid;
3-cyclobutyl-4-{[(3S)-oxolan-3-yl]oxy}-1-phenyl-1H-pyrazolo[3,4-b]pyridine-6-carboxylic acid;

3-cyclobutyl-4-methoxy-1-phenyl-1H-pyrazolo[3,4-b]pyridine-6-carboxylic acid;

3-cyclobutyl-4-(cyclobutyloxy)-1-phenyl-1H-pyrazolo[3,4-b]pyridine-6-carboxylic acid;

3-cyclobutyl-4-[2-(2-methoxyethoxy)ethoxy]-1-phenyl-1H-pyrazolo[3,4-b]pyridine-6-carboxylic acid;

4-[(3aR,7aS)-1-acetyloctahydro-5H-pyrrolo[3,2-c]pyridin-5-yl]-3-cyclobutyl-1-phenyl-1H-pyrazolo[3,4-b]pyridine-6-carboxylic acid;

4-[(3aS,7aR)-1-acetyloctahydro-5H-pyrrolo[3,2-c]pyridin-5-yl]-3-cyclobutyl-1-phenyl-1H-pyrazolo[3,4-b]pyridine-6-carboxylic acid;

4-[4-(methoxymethyl)piperidin-1-yl]-1-[2-(morpholin-4-yl)pyrimidin-4-yl]-3-(propan-2-yl)-1H-pyrazolo[3,4-b]pyridine-6-carboxylic acid;

3-cyclobutyl-4-{[(oxan-4-yl)methyl]amino}-1-phenyl-1H-pyrazolo[3,4-b]pyridine-6-carboxylic acid;

4-[6-(4-cyanopiperidin-1-yl)pyridin-3-yl]-3-[(oxolan-3-yl)oxy]-1-phenyl-1H-pyrazolo[3,4-b]pyridine-6-carboxylic acid;

4-[6-(4-cyanopiperidin-1-yl)pyridin-3-yl]-3-[(oxetan-3-yl)oxy]-1-phenyl-1H-pyrazolo[3,4-b]pyridine-6-carboxylic acid;

3-cyclobutyl-4-{methyl[(1-methylpiperidin-3-yl)methyl]amino}-1-phenyl-1H-pyrazolo[3,4-b]pyridine-6-carboxylic acid;

3-cyclobutyl-4-(4,4-difluoropiperidin-1-yl)-1-phenyl-1H-pyrazolo[3,4-b]pyridine-6-carboxylic acid;

3-cyclobutyl-4-[3-fluoro-3-(methoxymethyl)piperidin-1-yl]-1-phenyl-1H-pyrazolo[3,4-b]pyridine-6-carboxylic acid;

3-cyclobutyl-1-phenyl-4-[2-(trifluoromethyl)morpholin-4-yl]-1H-pyrazolo[3,4-b]pyridine-6-carboxylic acid;

3-cyclobutyl-4-(cyclopentyloxy)-1-phenyl-1H-pyrazolo[3,4-b]pyridine-6-carboxylic acid;

4-{[cis-3-(azetidin-1-yl)cyclobutyl]oxy}-3-cyclobutyl-1-phenyl-1H-pyrazolo[3,4-b]pyridine-6-carboxylic acid;

3-cyclobutyl-4-[(1-cyclohexylazetidin-3-yl)oxy]-1-phenyl-1H-pyrazolo[3,4-b]pyridine-6-carboxylic acid;

3-cyclobutyl-4-[(3,3-difluorocyclobutyl)methoxy]-1-phenyl-1H-pyrazolo[3,4-b]pyridine-6-carboxylic acid;

3-cyclobutyl-4-[(1-methylazetidin-3-yl)oxy]-1-phenyl-1H-pyrazolo[3,4-b]pyridine-6-carboxylic acid;

1-[3-(dimethylamino)phenyl]-4-[(oxan-4-yl)methoxy]-3-(propan-2-yl)-1H-pyrazolo[3,4-b]pyridine-6-carboxylic acid;

1-cyclohexyl-4-[(oxan-4-yl)methoxy]-3-(propan-2-yl)-1H-pyrazolo[3,4-b]pyridine-6-carboxylic acid;

1-(4-fluorophenyl)-4-[2-(oxan-4-yl)ethoxy]-3-(propan-2-yl)-1H-pyrazolo[3,4-b]pyridine-6-carboxylic acid;

3-cyclobutyl-4-[4-(2-methoxypropan-2-yl)piperidin-1-yl]-1-phenyl-1H-pyrazolo[3,4-b]pyridine-6-carboxylic acid;

4-[3-(dimethylamino)propoxy]-1-(4-fluorophenyl)-3-(propan-2-yl)-1H-pyrazolo[3,4-b]pyridine-6-carboxylic acid;

1-(4-fluorophenyl)-4-[3-(morpholin-4-yl)propoxy]-3-(propan-2-yl)-1H-pyrazolo[3,4-b]pyridine-6-carboxylic acid;

1-(4-fluorophenyl)-4-[(3-methyloxetan-3-yl)methoxy]-3-(propan-2-yl)-1H-pyrazolo[3,4-b]pyridine-6-carboxylic acid;

1-(4-fluorophenyl)-4-[(oxolan-2-yl)methoxy]-3-(propan-2-yl)-1H-pyrazolo[3,4-b]pyridine-6-carboxylic acid;

rac-3-cyclobutyl-1-phenyl-4-[(3aR,7aS)-1-{[(propan-2-yl)oxy]carbonyl}octahydro-5H-pyrrolo[3,2-c]pyridin-5-yl]-1H-pyrazolo[3,4-b]pyridine-6-carboxylic acid;

3-cyclobutyl-4-[4-(dimethylamino)butoxy]-1-phenyl-1H-pyrazolo[3,4-b]pyridine-6-carboxylic acid;

4-[(1-acetylpiperidin-4-yl)oxy]-3-cyclobutyl-1-phenyl-1H-pyrazolo[3,4-b]pyridine-6-carboxylic acid;

3-cyclobutyl-1-phenyl-4-(2,2,2-trifluoroethoxy)-1H-pyrazolo[3,4-b]pyridine-6-carboxylic acid;

3-cyclobutyl-4-{2-[2-(dimethylamino)ethoxy]ethoxy}-1-phenyl-1H-pyrazolo[3,4-b]pyridine-6-carboxylic acid;

3-cyclobutyl-4-{[(2S)-1-(dimethylamino)propan-2-yl]oxy}-1-phenyl-1H-pyrazolo[3,4-b]pyridine-6-carboxylic acid;

3-cyclobutyl-4-[(4,4-difluorocyclohexyl)methoxy]-1-phenyl-1H-pyrazolo[3,4-b]pyridine-6-carboxylic acid;

3-cyclobutyl-4-{[(2R)-5-oxopyrrolidin-2-yl]methoxy}-1-phenyl-1H-pyrazolo[3,4-b]pyridine-6-carboxylic acid;

3-cyclobutyl-4-{[(4R)-2,2-dimethyl-1,3-dioxolan-4-yl]methoxy}-1-phenyl-1H-pyrazolo[3,4-b]pyridine-6-carboxylic acid;

3-cyclobutyl-4-{[(3S)-6-oxopiperidin-3-yl]oxy}-1-phenyl-1H-pyrazolo[3,4-b]pyridine-6-carboxylic acid;

3-cyclobutyl-4-[(5-ethyl-1,3-dioxan-5-yl)methoxy]-1-phenyl-1H-pyrazolo[3,4-b]pyridine-6-carboxylic acid;

3-cyclobutyl-4-{[(3-endo)-8-methyl-8-azabicyclo[3.2.1]octan-3-yl]oxy}-1-phenyl-1H-pyrazolo[3,4-b]pyridine-6-carboxylic acid;

3-cyclobutyl-4-[(5-methyl-1,3-dioxan-5-yl)methoxy]-1-phenyl-1H-pyrazolo[3,4-b]pyridine-6-carboxylic acid;

3-cyclobutyl-4-[2-(1,4-dioxa-8-azaspiro[4.5]decan-8-yl)ethoxy]-1-phenyl-1H-pyrazolo[3,4-b]pyridine-6-carboxylic acid;

3-cyclobutyl-4-[3-(diethylamino)propoxy]-1-phenyl-1H-pyrazolo[3,4-b]pyridine-6-carboxylic acid;

3-cyclobutyl-4-{2-[cyclohexyl(oxetan-3-yl)amino]ethoxy}-1-phenyl-1H-pyrazolo[3,4-b]pyridine-6-carboxylic acid;

3-cyclobutyl-4-{[4-fluoro-1-(methanesulfonyl)piperidin-4-yl]methoxy}-1-phenyl-1H-pyrazolo[3,4-b]pyridine-6-carboxylic acid;

3-cyclobutyl-4-{[4-(methanesulfonyl)oxan-4-yl]methoxy}-1-phenyl-1H-pyrazolo[3,4-b]pyridine-6-carboxylic acid;

3-cyclobutyl-1-phenyl-4-[2-(pyrrolidin-1-yl)ethoxy]-1H-pyrazolo[3,4-b]pyridine-6-carboxylic acid;

3-cyclobutyl-4-[2-(methanesulfonyl)-2-methylpropoxy]-1-phenyl-1H-pyrazolo[3,4-b]pyridine-6-carboxylic acid;

3-cyclobutyl-4-[(1-methylcyclopropyl)methoxy]-1-phenyl-1H-pyrazolo[3,4-b]pyridine-6-carboxylic acid;

3-cyclobutyl-4-[2-(1-methylcyclopropyl)ethoxy]-1-phenyl-1H-pyrazolo[3,4-b]pyridine-6-carboxylic acid;

3-cyclobutyl-4-{[1-(methanesulfonyl)cyclobutyl]methoxy}-1-phenyl-1H-pyrazolo[3,4-b]pyridine-6-carboxylic acid;

3-cyclobutyl-4-(2-cyclohexylethoxy)-1-phenyl-1H-pyrazolo[3,4-b]pyridine-6-carboxylic acid;

3-cyclobutyl-4-[3-(4-methylpiperazin-1-yl)propoxy]-1-phenyl-1H-pyrazolo[3,4-b]pyridine-6-carboxylic acid;

3-cyclobutyl-4-[3-(dimethylamino)propoxy]-1-phenyl-1H-pyrazolo[3,4-b]pyridine-6-carboxylic acid;

3-cyclobutyl-4-[3-(dimethylamino)-2,2-dimethylpropoxy]-1-phenyl-1H-pyrazolo[3,4-b]pyridine-6-carboxylic acid;

3-cyclobutyl-4-[2-(dimethylamino)ethoxy]-1-phenyl-1H-pyrazolo[3,4-b]pyridine-6-carboxylic acid;

4-{[1,3-bis(dimethylamino)propan-2-yl]oxy}-3-cyclobutyl-1-phenyl-1H-pyrazolo[3,4-b]pyridine-6-carboxylic acid;

3-cyclobutyl-1-phenyl-4-[2-(piperidin-1-yl)ethoxy]-1H-pyrazolo[3,4-b]pyridine-6-carboxylic acid;

3-cyclobutyl-4-[2-(2-oxoimidazolidin-1-yl)ethoxy]-1-phenyl-1H-pyrazolo[3,4-b]pyridine-6-carboxylic acid;

4-{[1,3-bis(morpholin-4-yl)propan-2-yl]oxy}-3-cyclobutyl-1-phenyl-1H-pyrazolo[3,4-b]pyridine-6-carboxylic acid;

3-cyclobutyl-1-phenyl-4-[3-(piperidin-1-yl)propoxy]-1H-pyrazolo[3,4-b]pyridine-6-carboxylic acid;
4-[2-(azepan-1-yl)ethoxy]-3-cyclobutyl-1-phenyl-1H-pyrazolo[3,4-b]pyridine-6-carboxylic acid;
3-cyclobutyl-4-[2-(4-methyl-1,4-diazepan-1-yl)ethoxy]-1-phenyl-1H-pyrazolo[3,4-b]pyridine-6-carboxylic acid;
3-cyclobutyl-4-{[(2s,4r)-5-methyl-5-azaspiro[3.4]octan-2-yl]oxy}-1-phenyl-1H-pyrazolo[3,4-b]pyridine-6-carboxylic acid;
3-cyclobutyl-4-[(1-{3-[(diethylamino)methyl]oxetan-3-yl}azetidin-3-yl)oxy]-1-phenyl-1H-pyrazolo[3,4-b]pyridine-6-carboxylic acid;
3-cyclobutyl-1-phenyl-4-{[1-(propan-2-yl)piperidin-4-yl]oxy}-1H-pyrazolo[3,4-b]pyridine-6-carboxylic acid;
3-cyclobutyl-4-(cycloheptyloxy)-1-phenyl-1H-pyrazolo[3,4-b]pyridine-6-carboxylic acid;
3-cyclobutyl-4-(cyclooctyloxy)-1-phenyl-1H-pyrazolo[3,4-b]pyridine-6-carboxylic acid;
3-cyclobutyl-4-{[(3R)-1-methylpyrrolidin-3-yl]oxy}-1-phenyl-1H-pyrazolo[3,4-b]pyridine-6-carboxylic acid;
3-cyclobutyl-4-{[(3)-1-methylpyrrolidin-3-yl]oxy}-1-phenyl-1H-pyrazolo[3,4-b]pyridine-6-carboxylic acid;
4-[(3,3-difluoro-1-methylcyclobutyl)methoxy]-1-(4-fluorophenyl)-3-(propan-2-yl)-1H-pyrazolo[3,4-b]pyridine-6-carboxylic acid;
1-(4-fluorophenyl)-4-[3-(piperidin-1-yl)propoxy]-3-(propan-2-yl)-1H-pyrazolo[3,4-b]pyridine-6-carboxylic acid;
4-[(1,3-dimethoxypropan-2-yl)oxy]-1-(4-fluorophenyl)-3-(propan-2-yl)-1H-pyrazolo[3,4-b]pyridine-6-carboxylic acid;
3-cyclobutyl-4-({[(2S)-oxolan-2-yl]methyl}amino)-1-phenyl-1H-pyrazolo[3,4-b]pyridine-6-carboxylic acid;
1-(4-fluorophenyl)-4-[4-(2-hydroxypropan-2-yl)piperidin-1-yl]-3-(propan-2-yl)-1H-pyrazolo[3,4-b]pyridine-6-carboxylic acid;
3-cyclobutyl-1-(4-fluorophenyl)-4-[4-(methoxymethyl)piperidin-1-yl]-1H-pyrazolo[3,4-b]pyridine-6-carboxylic acid;
3-cyclobutyl-1-(4-fluorophenyl)-4-[(oxan-4-yl)methoxy]-1H-pyrazolo[3,4-b]pyridine-6-carboxylic acid;
3-cyclobutyl-4-[4-(2-hydroxypropan-2-yl)piperidin-1-yl]-1-phenyl-1H-pyrazolo[3,4-b]pyridine-6-carboxylic acid;
4-[4-(dimethylamino)piperidin-1-yl]-1-(4-fluorophenyl)-3-(propan-2-yl)-1H-pyrazolo[3,4-b]pyridine-6-carboxylic acid;
1-(4-fluorophenyl)-4-(1'-methyl[4,4'-bipiperidin]-1-yl)-3-(propan-2-yl)-1H-pyrazolo[3,4-b]pyridine-6-carboxylic acid;
4-[(1-acetylpiperidin-4-yl)methoxy]-1-(4-fluorophenyl)-3-(propan-2-yl)-1H-pyrazolo[3,4-b]pyridine-6-carboxylic acid;
1-(4-fluorophenyl)-4-{[1-(methoxycarbonyl)piperidin-4-yl]methoxy}-3-(propan-2-yl)-1H-pyrazolo[3,4-b]pyridine-6-carboxylic acid;
1-(4-fluorophenyl)-4-[(oxane-4-carbonyl)amino]-3-(propan-2-yl)-1H-pyrazolo[3,4-b]pyridine-6-carboxylic acid;
4-[4-(cyanomethyl)-4-hydroxypiperidin-1-yl]-3-cyclobutyl-1-phenyl-1H-pyrazolo[3,4-b]pyridine-6-carboxylic acid;
4-[4-(ethoxymethyl)-4-fluoropiperidin-1-yl]-1-(4-fluorophenyl)-3-(propan-2-yl)-1H-pyrazolo[3,4-b]pyridine-6-carboxylic acid;
4-{4-fluoro-4-[(2-methoxyethoxy)methyl]piperidin-1-yl}-1-(4-fluorophenyl)-3-(propan-2-yl)-1H-pyrazolo[3,4-b]pyridine-6-carboxylic acid;
4-[(3R,4R)-3-fluoro-4-hydroxypiperidin-1-yl]-1-(4-fluorophenyl)-3-(propan-2-yl)-1H-pyrazolo[3,4-b]pyridine-6-carboxylic acid;
4-[4-fluoro-4-(methoxymethyl)piperidin-1-yl]-1-(4-fluorophenyl)-3-(propan-2-yl)-1H-pyrazolo[3,4-b]pyridine-6-carboxylic acid;
4-{3-fluoro-3-[(2-methoxyethoxy)methyl]piperidin-1-yl}-1-(4-fluorophenyl)-3-(propan-2-yl)-1H-pyrazolo[3,4-b]pyridine-6-carboxylic acid;
4-[(3S)-3-{[(tert-butoxycarbonyl)amino]methyl}pyrrolidin-1-yl]-3-cyclobutyl-1-phenyl-1H-pyrazolo[3,4-b]pyridine-6-carboxylic acid;
4-[(3R)-3-{[(tert-butoxycarbonyl)amino]methyl}pyrrolidin-1-yl]-3-cyclobutyl-1-phenyl-1H-pyrazolo[3,4-b]pyridine-6-carboxylic acid;
3-cyclobutyl-4-(1,1-dioxo-1$\lambda^6$,4-thiazinan-4-yl)-1-phenyl-1H-pyrazolo[3,4-b]pyridine-6-carboxylic acid;
4-[(3R)-3-{[(tert-butoxycarbonyl)(methyl)amino]methyl}pyrrolidin-1-yl]-3-cyclobutyl-1-phenyl-1H-pyrazolo[3,4-b]pyridine-6-carboxylic acid;
4-[(3S)-3-{[(tert-butoxycarbonyl)(methyl)amino]methyl}pyrrolidin-1-yl]-3-cyclobutyl-1-phenyl-1H-pyrazolo[3,4-b]pyridine-6-carboxylic acid;
3-cyclobutyl-4-{(3S)-3-[(methylamino)methyl]pyrrolidin-1-yl}-1-phenyl-1H-pyrazolo[3,4-b]pyridine-6-carboxylic acid;
1-(2,6-dimethylpyridin-4-yl)-4-[4-(methoxymethyl)piperidin-1-yl]-3-(propan-2-yl)-1H-pyrazolo[3,4-b]pyridine-6-carboxylic acid;
3-cyclobutyl-4-[4-(methoxymethyl)piperidin-1-yl]-1-(2-methoxypyridin-4-yl)-1H-pyrazolo[3,4-b]pyridine-6-carboxylic acid;
3-cyclobutyl-1-(4-fluorophenyl)-4-[4-(morpholin-4-yl)piperidin-1-yl]-1H-pyrazolo[3,4-b]pyridine-6-carboxylic acid;
3-cyclobutyl-1-phenyl-4-[3-(pyrrolidin-1-yl)azetidin-1-yl]-1H-pyrazolo[3,4-b]pyridine-6-carboxylic acid;
3-cyclobutyl-4-{4-[(oxolan-2-yl)methyl]piperazin-1-yl}-1-phenyl-1H-pyrazolo[3,4-b]pyridine-6-carboxylic acid;
3-cyclobutyl-4-[4-(1-methoxypropan-2-yl)piperazin-1-yl]-1-phenyl-1H-pyrazolo[3,4-b]pyridine-6-carboxylic acid;
3-cyclobutyl-4-{4-[1-(morpholin-4-yl)ethyl]piperidin-1-yl}-1-phenyl-1H-pyrazolo[3,4-b]pyridine-6-carboxylic acid;
3-cyclobutyl-4-{4-[(1,3-dioxolan-2-yl)methyl]piperazin-1-yl}-1-phenyl-1H-pyrazolo[3,4-b]pyridine-6-carboxylic acid;
3-cyclobutyl-4-[4-(2-methoxyethoxy)piperidin-1-yl]-1-phenyl-1H-pyrazolo[3,4-b]pyridine-6-carboxylic acid;
3-cyclobutyl-1-phenyl-4-{4-[(piperidin-1-yl)methyl]piperidin-1-yl}-1H-pyrazolo[3,4-b]pyridine-6-carboxylic acid;
3-cyclobutyl-4-{4-[2-(4-methylpiperidin-1-yl)ethyl]piperidin-1-yl}-1-phenyl-1H-pyrazolo[3,4-b]pyridine-6-carboxylic acid;
3-cyclobutyl-4-[4-(2,6-dimethylmorpholin-4-yl)piperidin-1-yl]-1-phenyl-1H-pyrazolo[3,4-b]pyridine-6-carboxylic acid;
3-cyclobutyl-4-[4-(diethylamino)piperidin-1-yl]-1-phenyl-1H-pyrazolo[3,4-b]pyridine-6-carboxylic acid;
3-cyclobutyl-4-[{3-[cyclohexyl(methyl)amino]propyl}(methyl)amino]-1-phenyl-1H-pyrazolo[3,4-b]pyridine-6-carboxylic acid;
3-cyclobutyl-1-phenyl-4-[4-(propan-2-yl)-1,4-diazepan-1-yl]-1H-pyrazolo[3,4-b]pyridine-6-carboxylic acid;
3-cyclobutyl-4-[(3aR,6aS)-5-(2-methylpropyl)hexahydropyrrolo[3,4-c]pyrrol-2(1H)-yl]-1-phenyl-1H-pyrazolo[3,4-b]pyridine-6-carboxylic acid;
4-([1,4'-bipiperidin]-1'-yl)-3-cyclobutyl-1-(4-fluorophenyl)-1H-pyrazolo[3,4-b]pyridine-6-carboxylic acid;

3-cyclobutyl-4-{4-[4-(2-methoxyethyl)piperazin-1-yl]piperidin-1-yl}-1-phenyl-1H-pyrazolo[3,4-b]pyridine-6-carboxylic acid;
3-cyclobutyl-4-{4-[2-(4-methylpiperazin-1-yl)ethyl]piperidin-1-yl}-1-phenyl-1H-pyrazolo[3,4-b]pyridine-6-carboxylic acid;
3-cyclobutyl-4-[4-(ethoxyacetyl)piperazin-1-yl]-1-phenyl-1H-pyrazolo[3,4-b]pyridine-6-carboxylic acid;
3-cyclobutyl-4-[(3R)-3-(2-oxopyrrolidin-1-yl)piperidin-1-yl]-1-phenyl-1H-pyrazolo[3,4-b]pyridine-6-carboxylic acid;
3-cyclobutyl-4-(4'-methyl[1,4'-bipiperidin]-1'-yl)-1-phenyl-1H-pyrazolo[3,4-b]pyridine-6-carboxylic acid;
3-cyclobutyl-4-(9-methyl-3,9-diazaspiro[5.5]undecan-3-yl)-1-phenyl-1H-pyrazolo[3,4-b]pyridine-6-carboxylic acid;
3-cyclobutyl-4-(1,4-dioxa-8-azaspiro[4.5]decan-8-yl)-1-phenyl-1H-pyrazolo[3,4-b]pyridine-6-carboxylic acid;
3-cyclobutyl-4-{4-[(2-methylpropoxy)carbonyl]piperazin-1-yl}-1-phenyl-1H-pyrazolo[3,4-b]pyridine-6-carboxylic acid;
3-cyclobutyl-4-(4-methyl-1,4-diazepan-1-yl)-1-phenyl-1H-pyrazolo[3,4-b]pyridine-6-carboxylic acid;
4-(4-acetylpiperazin-1-yl)-3-cyclobutyl-1-phenyl-1H-pyrazolo[3,4-b]pyridine-6-carboxylic acid;
3-cyclobutyl-4-[4-(3-methoxypropyl)piperazin-1-yl]-1-phenyl-1H-pyrazolo[3,4-b]pyridine-6-carboxylic acid;
3-cyclobutyl-4-(4-cyclopentyl-1,4-diazepan-1-yl)-1-phenyl-1H-pyrazolo[3,4-b]pyridine-6-carboxylic acid;
3-cyclobutyl-4-[(3R)-3-hydroxypiperidin-1-yl]-1-phenyl-1H-pyrazolo[3,4-b]pyridine-6-carboxylic acid;
3-cyclobutyl-1-phenyl-4-(4-propylpiperazin-1-yl)-1H-pyrazolo[3,4-b]pyridine-6-carboxylic acid;
3-cyclobutyl-4-[4-(dimethylcarbamoyl)piperazin-1-yl]-1-phenyl-1H-pyrazolo[3,4-b]pyridine-6-carboxylic acid;
3-cyclobutyl-4-[3-(morpholin-4-yl)azetidin-1-yl]-1-phenyl-1H-pyrazolo[3,4-b]pyridine-6-carboxylic acid;
4-(4-butyl-1,4-diazepan-1-yl)-3-cyclobutyl-1-phenyl-1H-pyrazolo[3,4-b]pyridine-6-carboxylic acid;
3-cyclobutyl-4-[3-(morpholine-4-carbonyl)[1,4'-bipiperidin]-1'-yl]-1-phenyl-1H-pyrazolo[3,4-b]pyridine-6-carboxylic acid;
3-cyclobutyl-1-phenyl-4-(4-propyl-1,4-diazepan-1-yl)-1H-pyrazolo[3,4-b]pyridine-6-carboxylic acid;
3-cyclobutyl-4-(1,4-dioxa-7-azaspiro[4.4]nonan-7-yl)-1-phenyl-1H-pyrazolo[3,4-b]pyridine-6-carboxylic acid;
3-cyclobutyl-4-{4-[2-(2-hydroxyethoxy)ethyl]piperazin-1-yl}-1-phenyl-1H-pyrazolo[3,4-b]pyridine-6-carboxylic acid;
3-cyclobutyl-1-phenyl-4-[(3R)-3-(piperidin-1-yl)pyrrolidin-1-yl]-1H-pyrazolo[3,4-b]pyridine-6-carboxylic acid;
4-(7-cyano-5-oxa-2-azaspiro[3.4]octan-2-yl)-3-cyclobutyl-1-phenyl-1H-pyrazolo[3,4-b]pyridine-6-carboxylic acid;
3-cyclobutyl-4-{4-[3-(4-methyl-1,4-diazepan-1-yl)-3-oxopropyl]piperazin-1-yl}-1-phenyl-1H-pyrazolo[3,4-b]pyridine-6-carboxylic acid;
3-cyclobutyl-4-[4-(dimethylcarbamoyl)-4-(2-oxopyrrolidin-1-yl)piperidin-1-yl]-1-phenyl-1H-pyrazolo[3,4-b]pyridine-6-carboxylic acid;
3-cyclobutyl-4-[4-(cyclohexylmethyl)piperidin-1-yl]-1-phenyl-1H-pyrazolo[3,4-b]pyridine-6-carboxylic acid;
3-cyclobutyl-4-(6-oxa-2-azaspiro[3.5]nonan-2-yl)-1-phenyl-1H-pyrazolo[3,4-b]pyridine-6-carboxylic acid;
3-cyclobutyl-4-[(8aR)-hexahydropyrrolo[1,2-a]pyrazin-2(1H)-yl]-1-phenyl-1H-pyrazolo[3,4-b]pyridine-6-carboxylic acid;
3-cyclobutyl-4-[4-(2-hydroxyethyl)piperazin-1-yl]-1-phenyl-1H-pyrazolo[3,4-b]pyridine-6-carboxylic acid;
3-cyclobutyl-4-[3-(4-methylmorpholin-2-yl)azetidin-1-yl]-1-phenyl-1H-pyrazolo[3,4-b]pyridine-6-carboxylic acid;
3-cyclobutyl-4-(3-{4-[methyl(oxetan-3-yl)amino]piperidin-1-yl}azetidin-1-yl)-1-phenyl-1H-pyrazolo[3,4-b]pyridine-6-carboxylic acid;
3-cyclobutyl-4-{3-[4-(morpholin-4-yl)piperidin-1-yl]azetidin-1-yl}-1-phenyl-1H-pyrazolo[3,4-b]pyridine-6-carboxylic acid;
3-cyclobutyl-4-{4-[1-(2-ethoxyethyl)piperidin-4-yl]piperazin-1-yl}-1-phenyl-1H-pyrazolo[3,4-b]pyridine-6-carboxylic acid;
3-cyclobutyl-4-{4-[1-(2-hydroxypropyl)piperidin-4-yl]piperazin-1-yl}-1-phenyl-1H-pyrazolo[3,4-b]pyridine-6-carboxylic acid;
3-cyclobutyl-4-{4-[3-(dimethylamino)propyl]piperazin-1-yl}-1-phenyl-1H-pyrazolo[3,4-b]pyridine-6-carboxylic acid;
3-cyclobutyl-4-{4-[4-(2-ethoxyethyl)piperazin-1-yl]piperidin-1-yl}-1-phenyl-1H-pyrazolo[3,4-b]pyridine-6-carboxylic acid;
3-cyclobutyl-1-phenyl-4-{4-[2-(piperidin-1-yl)ethoxy]piperidin-1-yl}-1H-pyrazolo[3,4-b]pyridine-6-carboxylic acid;
3-cyclobutyl-4-{4-[3-(diethylamino)propyl]piperidin-1-yl}-1-phenyl-1H-pyrazolo[3,4-b]pyridine-6-carboxylic acid;
3-cyclobutyl-1-phenyl-4-{4-[3-(piperidin-1-yl)propyl]piperidin-1-yl}-1H-pyrazolo[3,4-b]pyridine-6-carboxylic acid;
3-cyclobutyl-1-phenyl-4-{4-[3-(pyrrolidin-1-yl)propyl]piperidin-1-yl}-1H-pyrazolo[3,4-b]pyridine-6-carboxylic acid;
3-cyclobutyl-4-{4-[ethyl(oxetan-3-yl)amino]piperidin-1-yl}-1-phenyl-1H-pyrazolo[3,4-b]pyridine-6-carboxylic acid;
3-cyclobutyl-4-{4-[methyl(oxetan-3-yl)amino]piperidin-1-yl}-1-phenyl-1H-pyrazolo[3,4-b]pyridine-6-carboxylic acid;
3-cyclobutyl-4-[1'-(oxetan-3-yl)[4,4'-bipiperidin]-1-yl]-1-phenyl-1H-pyrazolo[3,4-b]pyridine-6-carboxylic acid;
3-cyclobutyl-4-[4-(dimethylamino)piperidin-1-yl]-1-phenyl-1H-pyrazolo[3,4-b]pyridine-6-carboxylic acid;
3-cyclobutyl-4-[4-(4-cyclopropylpiperazin-1-yl)piperidin-1-yl]-1-phenyl-1H-pyrazolo[3,4-b]pyridine-6-carboxylic acid;
3-cyclobutyl-4-[4-(4-methylpiperazine-1-carbonyl)piperidin-1-yl]-1-phenyl-1H-pyrazolo[3,4-b]pyridine-6-carboxylic acid;
1-(4-fluorophenyl)-4-[3-(4-methylmorpholin-2-yl)azetidin-1-yl]-3-(propan-2-yl)-1H-pyrazolo[3,4-b]pyridine-6-carboxylic acid;
4-{4-[1-(2-ethoxyethyl)piperidin-4-yl]piperazin-1-yl}-1-(4-fluorophenyl)-3-(propan-2-yl)-1H-pyrazolo[3,4-b]pyridine-6-carboxylic acid;
1-(4-fluorophenyl)-4-{4-[1-(2-hydroxypropyl)piperidin-4-yl]piperazin-1-yl}-3-(propan-2-yl)-1H-pyrazolo[3,4-b]pyridine-6-carboxylic acid;
4-[4(1-cyclopropylpiperidin-4-yl)piperazin-1-yl]-1-(4-fluorophenyl)-3-(propan-2-yl)-1H-pyrazolo[3,4-b]pyridine-6-carboxylic acid;
1-(4-fluorophenyl)-4-{4-[4-(oxetan-3-yl)piperazin-1-yl]piperidin-1-yl}-3-(propan-2-yl)-1H-pyrazolo[3,4-b]pyridine-6-carboxylic acid;
4-{4-[4-(2-ethoxyethyl)piperazin-1-yl]piperidin-1-yl}-1-(4-fluorophenyl)-3-(propan-2-yl)-1H-pyrazolo[3,4-b]pyridine-6-carboxylic acid;

1-(4-fluorophenyl)-4-{4-[4-(2-methoxyethyl)piperazin-1-yl]piperidin-1-yl}-3-(propan-2-yl)-1H-pyrazolo[3,4-b]pyridine-6-carboxylic acid;

4-{4-[3-(diethylamino)propyl]piperidin-1-yl}-1-(4-fluorophenyl)-3-(propan-2-yl)-1H-pyrazolo[3,4-b]pyridine-6-carboxylic acid;

1-(4-fluorophenyl)-4-{4-[3-(piperidin-1-yl)propyl]piperidin-1-yl}-3-(propan-2-yl)-1H-pyrazolo[3,4-b]pyridine-6-carboxylic acid;

1-(4-fluorophenyl)-3-(propan-2-yl)-4-{4-[3-(pyrrolidin-1-yl)propyl]piperidin-1-yl}-1H-pyrazolo[3,4-b]pyridine-6-carboxylic acid;

4-{4-[ethyl(oxetan-3-yl)amino]piperidin-1-yl}-1-(4-fluorophenyl)-3-(propan-2-yl)-1H-pyrazolo[3,4-b]pyridine-6-carboxylic acid;

1-(4-fluorophenyl)-4-{4-[methyl(oxetan-3-yl)amino]piperidin-1-yl}-3-(propan-2-yl)-1H-pyrazolo[3,4-b]pyridine-6-carboxylic acid;

1-(4-fluorophenyl)-4-[1'-(oxetan-3-yl)[4,4'-bipiperidin]-1-yl]-3-(propan-2-yl)-1H-pyrazolo[3,4-b]pyridine-6-carboxylic acid;

1-(4-fluorophenyl)-4-[4-(4-methylpiperazin-1-yl)piperidin-1-yl]-3-(propan-2-yl)-1H-pyrazolo[3,4-b]pyridine-6-carboxylic acid;

4-[4(4-cyclopropylpiperazin-1-yl)piperidin-1-yl]-1-(4-fluorophenyl)-3-(propan-2-yl)-1H-pyrazolo[3,4-b]pyridine-6-carboxylic acid;

1-(4-fluorophenyl)-4-[4-(4-methylpiperazine-1-carbonyl)piperidin-1-yl]-3-(propan-2-yl)-1H-pyrazolo[3,4-b]pyridine-6-carboxylic acid;

1-(4-fluorophenyl)-4-[4-(morpholin-4-yl)piperidin-1-yl]-3-(propan-2-yl)-1H-pyrazolo[3,4-b]pyridine-6-carboxylic acid;

3-cyclobutyl-4-[4-(4-methylpiperazin-1-yl)piperidin-1-yl]-1-phenyl-1H-pyrazolo[3,4-b]pyridine-6-carboxylic acid;

1-(4-fluorophenyl)-4-(3-{4-[methyl(oxetan-3-yl)amino]piperidin-1-yl}azetidin-1-yl)-3-(propan-2-yl)-1H-pyrazolo[3,4-b]pyridine-6-carboxylic acid;

1-(4-fluorophenyl)-4-{3-[4-(morpholin-4-yl)piperidin-1-yl]azetidin-1-yl}-3-(propan-2-yl)-1H-pyrazolo[3,4-b]pyridine-6-carboxylic acid;

4-{4-[3-(dimethylamino)propyl]piperazin-1-yl}-1-(4-fluorophenyl)-3-(propan-2-yl)-1H-pyrazolo[3,4-b]pyridine-6-carboxylic acid;

1-(4-fluorophenyl)-4-[4-methyl-4-(4-methylpiperazin-1-yl)piperidin-1-yl]-3-(propan-2-yl)-1H-pyrazolo[3,4-b]pyridine-6-carboxylic acid;

1-(4-fluorophenyl)-4-{4-[2-(piperidin-1-yl)ethoxy]piperidin-1-yl}-3-(propan-2-yl)-1H-pyrazolo[3,4-b]pyridine-6-carboxylic acid;

1-(4-fluorophenyl)-5-methyl-4-[4-(morpholin-4-yl)piperidin-1-yl]-3-(propan-2-yl)-1H-pyrazolo[3,4-b]pyridine-6-carboxylic acid;

1-cyclohexyl-4-[4-(4-methylpiperazine-1-carbonyl)phenyl]-3-[(propan-2-yl)oxy]-1H-pyrazolo[3,4-b]pyridine-6-carboxylic acid;

1-(4-fluorophenyl)-4-[3-(morpholin-4-yl)azetidin-1-yl]-3-(propan-2-yl)-1H-pyrazolo[3,4-b]pyridine-6-carboxylic acid;

1-(4-fluorophenyl)-3-(propan-2-yl)-4-(4-propyl-1,4-diazepan-1-yl)-1H-pyrazolo[3,4-b]pyridine-6-carboxylic acid;

4-(4-cyclobutyl-1,4-diazepan-1-yl)-1-(4-fluorophenyl)-3-(propan-2-yl)-1H-pyrazolo[3,4-b]pyridine-6-carboxylic acid;

4-(4-butyl-1,4-diazepan-1-yl)-1-(4-fluorophenyl)-3-(propan-2-yl)-1H-pyrazolo[3,4-b]pyridine-6-carboxylic acid;

1-(4-fluorophenyl)-4-(4-methyl-1,4-diazepan-1-yl)-3-(propan-2-yl)-1H-pyrazolo[3,4-b]pyridine-6-carboxylic acid;

1-(4-fluorophenyl)-4-[(8aR)-hexahydropyrrolo[1,2-a]pyrazin-2(1H)-yl]-3-(propan-2-yl)-1H-pyrazolo[3,4-b]pyridine-6-carboxylic acid;

4-(4-acetylpiperazin-1-yl)-1-(4-fluorophenyl)-3-(propan-2-yl)-1H-pyrazolo[3,4-b]pyridine-6-carboxylic acid;

4-(4-ethylpiperazin-1-yl)-1-(4-fluorophenyl)-3-(propan-2-yl)-1H-pyrazolo[3,4-b]pyridine-6-carboxylic acid;

1-(4-fluorophenyl)-4-[4-(2-hydroxyethyl)piperazin-1-yl]-3-(propan-2-yl)-1H-pyrazolo[3,4-b]pyridine-6-carboxylic acid;

4-[4-(dimethylcarbamoyl)piperazin-1-yl]-1-(4-fluorophenyl)-3-(propan-2-yl)-1H-pyrazolo[3,4-b]pyridine-6-carboxylic acid;

4-[4-(ethoxyacetyl)piperazin-1-yl]-1-(4-fluorophenyl)-3-(propan-2-yl)-1H-pyrazolo[3,4-b]pyridine-6-carboxylic acid;

1-(4-fluorophenyl)-4-[4-(3-methoxypropyl)piperazin-1-yl]-3-(propan-2-yl)-1H-pyrazolo[3,4-b]pyridine-6-carboxylic acid;

1-(4-fluorophenyl)-3-(propan-2-yl)-4-(4-propylpiperazin-1-yl)-1H-pyrazolo[3,4-b]pyridine-6-carboxylic acid;

1-(4-fluorophenyl)-4-{4-[2-(2-hydroxyethoxy)ethyl]piperazin-1-yl}-3-(propan-2-yl)-1H-pyrazolo[3,4-b]pyridine-6-carboxylic acid;

1-(4-fluorophenyl)-4-{4-[3-(4-methyl-1,4-diazepan-1-yl)-3-oxopropyl]piperazin-1-yl}-3-(propan-2-yl)-1H-pyrazolo[3,4-b]pyridine-6-carboxylic acid;

4-[4-(cyclohexylmethyl)piperidin-1-yl]-1-(4-fluorophenyl)-3-(propan-2-yl)-1H-pyrazolo[3,4-b]pyridine-6-carboxylic acid;

1-(4-fluorophenyl)-4-(9-methyl-3,9-diazaspiro[5.5]undecan-3-yl)-3-(propan-2-yl)-1H-pyrazolo[3,4-b]pyridine-6-carboxylic acid;

4-(1,4-dioxa-8-azaspiro[4.5]decan-8-yl)-1-(4-fluorophenyl)-3-(propan-2-yl)-1H-pyrazolo[3,4-b]pyridine-6-carboxylic acid;

1-(4-fluorophenyl)-4-[(3R)-3-hydroxypiperidin-1-yl]-3-(propan-2-yl)-1H-pyrazolo[3,4-b]pyridine-6-carboxylic acid;

1-(4-fluorophenyl)-4-(4'-methyl[1,4'-bipiperidin]-1'-yl)-3-(propan-2-yl)-1H-pyrazolo[3,4-b]pyridine-6-carboxylic acid;

1-(4-fluorophenyl)-4-{4-[2-(4-methylpiperazin-1-yl)ethyl]piperidin-1-yl}-3-(propan-2-yl)-1H-pyrazolo[3,4-b]pyridine-6-carboxylic acid;

1-(4-fluorophenyl)-4-[(3R)-3-(piperidin-1-yl)pyrrolidin-1-yl]-3-(propan-2-yl)-1H-pyrazolo[3,4-b]pyridine-6-carboxylic acid;

4-[4-(diethylamino)piperidin-1-yl]-1-(4-fluorophenyl)-3-(propan-2-yl)-1H-pyrazolo[3,4-b]pyridine-6-carboxylic acid;

4-(4-tert-butylpiperazin-1-yl)-1-(4-fluorophenyl)-3-(propan-2-yl)-1H-pyrazolo[3,4-b]pyridine-6-carboxylic acid;

1-(4-fluorophenyl)-3-(propan-2-yl)-4-{4-[1-(pyrrolidin-1-yl)ethyl]piperidin-1-yl}-1H-pyrazolo[3,4-b]pyridine-6-carboxylic acid;

1-(4-fluorophenyl)-4-{4-[(piperidin-1-yl)methyl]piperidin-1-yl}-3-(propan-2-yl)-1H-pyrazolo[3,4-b]pyridine-6-carboxylic acid;

1-(4-fluorophenyl)-4-{4-[(1-methylpiperidin-3-yl)methyl]piperazin-1-yl}-3-(propan-2-yl)-1H-pyrazolo[3,4-b]pyridine-6-carboxylic acid;

1-(4-fluorophenyl)-4-{4-[(oxolan-2-yl)methyl]piperazin-1-yl}-3-(propan-2-yl)-1H-pyrazolo[3,4-b]pyridine-6-carboxylic acid;

1-(4-fluorophenyl)-4-[4-(1-methoxypropan-2-yl)piperazin-1-yl]-3-(propan-2-yl)-1H-pyrazolo[3,4-b]pyridine-6-carboxylic acid;

1-(4-fluorophenyl)-3-(propan-2-yl)-4-[3-(pyrrolidin-1-yl)azetidin-1-yl]-1H-pyrazolo[3,4-b]pyridine-6-carboxylic acid;

1-(4-fluorophenyl)-3-(propan-2-yl)-4-[4-(propan-2-yl)-1,4-diazepan-1-yl]-1H-pyrazolo[3,4-b]pyridine-6-carboxylic acid;

1-(4-fluorophenyl)-4-[(3aR,6aS)-5-(2-methylpropyl)hexahydropyrrolo[3,4-c]pyrrol-2(1H)-yl]-3-(propan-2-yl)-1H-pyrazolo[3,4-b]pyridine-6-carboxylic acid;

4-(4-ethyl-1,4-diazepan-1-yl)-1-(4-fluorophenyl)-3-(propan-2-yl)-1H-pyrazolo[3,4-b]pyridine-6-carboxylic acid;

1-(4-fluorophenyl)-4-(4-hydroxy-4-{[methyl(propan-2-yl)amino]methyl}piperidin-1-yl)-3-(propan-2-yl)-1H-pyrazolo[3,4-b]pyridine-6-carboxylic acid;

1-(4-fluorophenyl)-4-{4-[methyl(propan-2-yl)amino]piperidin-1-yl}-3-(propan-2-yl)-1H-pyrazolo[3,4-b]pyridine-6-carboxylic acid;

4-{4-[2-(diethylamino)ethyl]piperazin-1-yl}-1-(4-fluorophenyl)-3-(propan-2-yl)-1H-pyrazolo[3,4-b]pyridine-6-carboxylic acid;

1-(4-fluorophenyl)-4-[4-(1-methylpiperidin-4-yl)piperazin-1-yl]-3-(propan-2-yl)-1H-pyrazolo[3,4-b]pyridine-6-carboxylic acid;

3-cyclobutyl-4-(4-{[(3R)-3-(methoxymethyl)pyrrolidin-1-yl]methyl}piperidin-1-yl)-1-phenyl-1H-pyrazolo[3,4-b]pyridine-6-carboxylic acid;

3-cyclobutyl-4-(4-{[(3R)-3-methoxypyrrolidin-1-yl]methyl}piperidin-1-yl)-1-phenyl-1H-pyrazolo[3,4-b]pyridine-6-carboxylic acid;

3-cyclobutyl-4-(4-{[(3S)-3-(methoxymethyl)pyrrolidin-1-yl]methyl}piperidin-1-yl)-1-phenyl-1H-pyrazolo[3,4-b]pyridine-6-carboxylic acid;

3-cyclobutyl-1-(4-fluorophenyl)-4-{4-[1-(morpholin-4-yl)ethyl]piperidin-1-yl}-1H-pyrazolo[3,4-b]pyridine-6-carboxylic acid;

3-cyclobutyl-1-cyclohexyl-4-{4-[(morpholin-4-yl)methyl]piperidin-1-yl}-1H-pyrazolo[3,4-b]pyridine-6-carboxylic acid;

3-cyclobutyl-1-cyclohexyl-4-{4-[2-(morpholin-4-yl)ethyl]piperidin-1-yl}-1H-pyrazolo[3,4-b]pyridine-6-carboxylic acid;

3-(cyclobutyloxy)-1-cyclohexyl-4-{4-[(morpholin-4-yl)methyl]phenyl}-1H-pyrazolo[3,4-b]pyridine-6-carboxylic acid;

3-cyclobutyl-1-cyclohexyl-4-[4-(pyridin-4-yl)piperazin-1-yl]-1H-pyrazolo[3,4-b]pyridine-6-carboxylic acid;

3-cyclobutyl-1-(4-fluorophenyl)-4-{4-[2-(morpholin-4-yl)ethyl]piperidin-1-yl}-1H-pyrazolo[3,4-b]pyridine-6-carboxylic acid;

1-(4-fluorophenyl)-3-(propan-2-yl)-4-{4-[(pyrrolidin-1-yl)methyl]piperidin-1-yl}-1H-pyrazolo[3,4-b]pyridine-6-carboxylic acid;

3-cyclobutyl-1-phenyl-4-{4-[1-(pyrrolidin-1-yl)ethyl]piperidin-1-yl}-1H-pyrazolo[3,4-b]pyridine-6-carboxylic acid;

3-cyclobutyl-4-(3-oxo-2,8-diazaspiro[4.5]decan-2-yl)-1-phenyl-1H-pyrazolo[3,4-b]pyridine-6-carboxylic acid;

1-(4-fluorophenyl)-4-{4-[(2-methylpropoxy)carbonyl]piperazin-1-yl}-3-(propan-2-yl)-1H-pyrazolo[3,4-b]pyridine-6-carboxylic acid;

3-cyclobutyl-1-(2-methoxypyridin-4-yl)-4-[4-(morpholin-4-yl)piperidin-1-yl]-1H-pyrazolo[3,4-b]pyridine-6-carboxylic acid;

3-cyclobutyl-4-[4-(methoxymethyl)piperidin-1-yl]-1-[2-(oxan-4-yl)pyridin-4-yl]-1H-pyrazolo[3,4-b]pyridine-6-carboxylic acid;

3-cyclobutyl-1-phenyl-4-[4-(propan-2-yl)piperazin-1-yl]-1H-pyrazolo[3,4-b]pyridine-6-carboxylic acid;

3-cyclobutyl-4-[4-(morpholin-4-yl)piperidin-1-yl]-1-[2-(oxan-4-yl)pyridin-4-yl]-1H-pyrazolo[3,4-b]pyridine-6-carboxylic acid;

3-cyclobutyl-1-(3-methylphenyl)-4-[4-(morpholin-4-yl)piperidin-1-yl]-1H-pyrazolo[3,4-b]pyridine-6-carboxylic acid;

3-cyclobutyl-1-(4-fluorophenyl)-4-{4-[(morpholin-4-yl)methyl]piperidin-1-yl}-1H-pyrazolo[3,4-b]pyridine-6-carboxylic acid;

3-cyclobutyl-1-(3-methoxyphenyl)-4-[4-(morpholin-4-yl)piperidin-1-yl]-1H-pyrazolo[3,4-b]pyridine-6-carboxylic acid;

3-cyclobutyl-4-[4-(morpholin-4-yl)piperidin-1-yl]-1-[4-(trifluoromethyl)phenyl]-1H-pyrazolo[3,4-b]pyridine-6-carboxylic acid;

3-cyclobutyl-1-(4-fluoro-3-methylphenyl)-4-[4-(morpholin-4-yl)piperidin-1-yl]-1H-pyrazolo[3,4-b]pyridine-6-carboxylic acid;

3-cyclobutyl-1-(3-fluorophenyl)-4-[4-(morpholin-4-yl)piperidin-1-yl]-1H-pyrazolo[3,4-b]pyridine-6-carboxylic acid;

3-cyclobutyl-4-[4-(morpholin-4-yl)piperidin-1-yl]-1-[3-(trifluoromethyl)phenyl]-1H-pyrazolo[3,4-b]pyridine-6-carboxylic acid;

3-cyclobutyl-4-{4-[(3-fluoroazetidin-1-yl)methyl]piperidin-1-yl}-1-phenyl-1H-pyrazolo[3,4-b]pyridine-6-carboxylic acid;

3-cyclobutyl-4-{4-[(3,3-difluoropyrrolidin-1-yl)methyl]piperidin-1-yl}-1-phenyl-1H-pyrazolo[3,4-b]pyridine-6-carboxylic acid;

3-cyclobutyl-4-{4-[(3-methoxyazetidin-1-yl)methyl]piperidin-1-yl}-1-phenyl-1H-pyrazolo[3,4-b]pyridine-6-carboxylic acid;

3-cyclobutyl-4-{4-[(3,3-difluoropiperidin-1-yl)methyl]piperidin-1-yl}-1-phenyl-1H-pyrazolo[3,4-b]pyridine-6-carboxylic acid;

3-cyclobutyl-4-(4-{[3-(methoxymethyl)azetidin-1-yl]methyl}piperidin-1-yl)-1-phenyl-1H-pyrazolo[3,4-b]pyridine-6-carboxylic acid;

3-cyclobutyl-4-(4-{[(3R)-3-fluoropyrrolidin-1-yl]methyl}piperidin-1-yl)-1-phenyl-1H-pyrazolo[3,4-b]pyridine-6-carboxylic acid;

3-cyclobutyl-4-(4-{[(3S)-3-fluoropyrrolidin-1-yl]methyl}piperidin-1-yl)-1-phenyl-1H-pyrazolo[3,4-b]pyridine-6-carboxylic acid;

3-cyclobutyl-4-{4-[(1,4-oxazepan-4-yl)methyl]piperidin-1-yl}-1-phenyl-1H-pyrazolo[3,4-b]pyridine-6-carboxylic acid;

3-cyclobutyl-4-(4-{[3-(2,2-difluoroethoxy)azetidin-1-yl]methyl}piperidin-1-yl)-1-phenyl-1H-pyrazolo[3,4-b]pyridine-6-carboxylic acid;

3-cyclobutyl-4-{4-[(6-oxa-2-azaspiro[3.5]nonan-2-yl)methyl]piperidin-1-yl}-1-phenyl-1H-pyrazolo[3,4-b]pyridine-6-carboxylic acid;

3-cyclobutyl-4-{4-[(6-oxa-2-azaspiro[3.4]octan-2-yl)methyl]piperidin-1-yl}-1-phenyl-1H-pyrazolo[3,4-b]pyridine-6-carboxylic acid;

3-cyclobutyl-4-(4-{[(7S,8aS)-7-fluorohexahydropyrrolo[1,2-a]pyrazin-2(1H)-yl]methyl}piperidin-1-yl)-1-phenyl-1H-pyrazolo[3,4-b]pyridine-6-carboxylic acid;

3-cyclobutyl-4-{4-[(4-formyl-1,4-diazepan-1-yl)methyl]piperidin-1-yl}-1-phenyl-1H-pyrazolo[3,4-b]pyridine-6-carboxylic acid;

3-cyclobutyl-4-{4-[(2-oxa-7-azaspiro[3.5]nonan-7-yl)methyl]piperidin-1-yl}-1-phenyl-1H-pyrazolo[3,4-b]pyridine-6-carboxylic acid;

3-cyclobutyl-4-{4-[(4-methoxypiperidin-1-yl)methyl]piperidin-1-yl}-1-phenyl-1H-pyrazolo[3,4-b]pyridine-6-carboxylic acid;

3-cyclobutyl-4-{4-[(2-oxa-6-azaspiro[3.4]octan-6-yl)methyl]piperidin-1-yl}-1-phenyl-1H-pyrazolo[3,4-b]pyridine-6-carboxylic acid;

3-cyclobutyl-4-{4-[(4-formylpiperazin-1-yl)methyl]piperidin-1-yl}-1-phenyl-1H-pyrazolo[3,4-b]pyridine-6-carboxylic acid;

4-{4-[(3-azabicyclo[3.1.0]hexan-3-yl)methyl]piperidin-1-yl}-3-cyclobutyl-1-phenyl-1H-pyrazolo[3,4-b]pyridine-6-carboxylic acid;

3-cyclobutyl-4-{4-[(5-methyl-6-oxo-2-oxa-5,8-diazaspiro[3.5]nonan-8-yl)methyl]piperidin-1-yl}-1-phenyl-1H-pyrazolo[3,4-b]pyridine-6-carboxylic acid;

3-cyclobutyl-1-(4-fluorophenyl)-4-[4-(3-fluoropyrrolidin-1-yl)piperidin-1-yl]-1H-pyrazolo[3,4-b]pyridine-6-carboxylic acid;

4-[4-(3-cyanoazetidin-1-yl)piperidin-1-yl]-3-cyclobutyl-1-(4-fluorophenyl)-1H-pyrazolo[3,4-b]pyridine-6-carboxylic acid;

3-cyclobutyl-1-(4-fluorophenyl)-4-[4-(3-methoxypyrrolidin-1-yl)piperidin-1-yl]-1H-pyrazolo[3,4-b]pyridine-6-carboxylic acid;

3-cyclobutyl-4-(4-fluoro[1,4'-bipiperidin]-1'-yl)-1-(4-fluorophenyl)-1H-pyrazolo[3,4-b]pyridine-6-carboxylic acid;

3-cyclobutyl-4-(4,4-difluoro[1,4'-bipiperidin]-1'-yl)-1-(4-fluorophenyl)-1H-pyrazolo[3,4-b]pyridine-6-carboxylic acid;

4-[4-(2-cyanomorpholin-4-yl)piperidin-1-yl]-3-cyclobutyl-1-(4-fluorophenyl)-1H-pyrazolo[3,4-b]pyridine-6-carboxylic acid;

3-cyclobutyl-1-(4-fluorophenyl)-4-[4-(2-oxa-5-azabicyclo[2.2.1]heptan-5-yl)piperidin-1-yl]-1H-pyrazolo[3,4-b]pyridine-6-carboxylic acid;

3-cyclobutyl-1-(4-fluorophenyl)-4-{4-[2-(methoxymethyl)morpholin-4-yl]piperidin-1-yl}-1H-pyrazolo[3,4-b]pyridine-6-carboxylic acid;

3-cyclobutyl-1-(4-fluorophenyl)-4-{4-[methyl(oxan-4-yl)amino]piperidin-1-yl}-1H-pyrazolo[3,4-b]pyridine-6-carboxylic acid;

3-cyclobutyl-4-[4-(morpholin-4-yl)piperidin-1-yl]-1-{2-[(propan-2-yl)oxy]pyridin-4-yl}-1H-pyrazolo[3,4-b]pyridine-6-carboxylic acid;

1-[2-(benzyloxy)pyridin-4-yl]-3-cyclobutyl-4-[4-(morpholin-4-yl)piperidin-1-yl]-1H-pyrazolo[3,4-b]pyridine-6-carboxylic acid;

3-cyclobutyl-1-(4-fluorophenyl)-4-[(morpholin-4-yl)methyl]-1H-pyrazolo[3,4-b]pyridine-6-carboxylic acid;

3-cyclobutyl-1-(4-fluorophenyl)-4-[(4-methylpiperazin-1-yl)methyl]-1H-pyrazolo[3,4-b]pyridine-6-carboxylic acid;

3-cyclobutyl-1-(4-fluorophenyl)-4-{[4-(methoxymethyl)piperidin-1-yl]methyl}-1H-pyrazolo[3,4-b]pyridine-6-carboxylic acid;

4-(4-cyano[1,4'-bipiperidin]-1'-yl)-3-cyclobutyl-1-(4-fluorophenyl)-1H-pyrazolo[3,4-b]pyridine-6-carboxylic acid;

1-cyclohexyl-4-{4-[4-(dimethylamino)piperidine-1-carbonyl]phenyl}-3-[(propan-2-yl)oxy]-1H-pyrazolo[3,4-b]pyridine-6-carboxylic acid;

3-cyclobutyl-1-(4-fluorophenyl)-4-[3-(pyrrolidin-1-yl)-1-oxa-8-azaspiro[4.5]decan-8-yl]-1H-pyrazolo[3,4-b]pyridine-6-carboxylic acid;

1-cyclohexyl-3-[(propan-2-yl)oxy]-4-{4-[4-(propan-2-yl)piperazin-1-yl]phenyl}-1H-pyrazolo[3,4-b]pyridine-6-carboxylic acid;

3-cyclobutyl-1-cyclohexyl-4-[4-(2-methylpyridin-4-yl)piperazin-1-yl]-1H-pyrazolo[3,4-b]pyridine-6-carboxylic acid;

3-cyclobutyl-1-cyclohexyl-4-{6-[4-(propan-2-yl)piperazin-1-yl]pyridin-3-yl}-1H-pyrazolo[3,4-b]pyridine-6-carboxylic acid;

3-cyclobutyl-1-cyclohexyl-4-{4-[1-(morpholin-4-yl)ethyl]phenyl}-1H-pyrazolo[3,4-b]pyridine-6-carboxylic acid;

3-cyclobutyl-1-cyclohexyl-4-{4-[4-(propan-2-yl)piperazin-1-yl]phenyl}-1H-pyrazolo[3,4-b]pyridine-6-carboxylic acid;

3-cyclobutyl-1-cyclohexyl-4-[6-(4-cyclopropylpiperazin-1-yl)pyridin-3-yl]-1H-pyrazolo[3,4-b]pyridine-6-carboxylic acid;

3-cyclobutyl-1-(4-fluorophenyl)-4-{4-[3-(trifluoromethyl)pyrrolidin-1-yl]piperidin-1-yl}-1H-pyrazolo[3,4-b]pyridine-6-carboxylic acid;

4-[4-(3-cyanopyrrolidin-1-yl)piperidin-1-yl]-3-cyclobutyl-1-(4-fluorophenyl)-1H-pyrazolo[3,4-b]pyridine-6-carboxylic acid;

4-(3-cyano[1,4'-bipiperidin]-1'-yl)-3-cyclobutyl-1-(4-fluorophenyl)-1H-pyrazolo[3,4-b]pyridine-6-carboxylic acid;

3-cyclobutyl-4-(3-fluoro[1,4'-bipiperidin]-1'-yl)-1-(4-fluorophenyl)-1H-pyrazolo[3,4-b]pyridine-6-carboxylic acid;

3-cyclobutyl-1-(4-fluorophenyl)-4-[4-(3-methoxyazetidin-1-yl)piperidin-1-yl]-1H-pyrazolo[3,4-b]pyridine-6-carboxylic acid;

3-cyclobutyl-1-(4-fluorophenyl)-4-[3-(trifluoromethyl)[1,4'-bipiperidin]-1'-yl]-1H-pyrazolo[3,4-b]pyridine-6-carboxylic acid;

3-cyclobutyl-1-(4-fluorophenyl)-4-(3-methoxy[1,4'-bipiperidin]-1'-yl)-1H-pyrazolo[3,4-b]pyridine-6-carboxylic acid;

3-cyclobutyl-4-[4-(2,2-dimethylmorpholin-4-yl)piperidin-1-yl]-1-(4-fluorophenyl)-1H-pyrazolo[3,4-b]pyridine-6-carboxylic acid;

3-cyclobutyl-1-cyclohexyl-4-[6-(4-methylpiperazin-1-yl)pyridin-3-yl]-1H-pyrazolo[3,4-b]pyridine-6-carboxylic acid;

3-cyclobutyl-1-cyclohexyl-4-{6-[4-(2-methoxyethyl)piperazin-1-yl]pyridin-3-yl}-1H-pyrazolo[3,4-b]pyridine-6-carboxylic acid;

3-cyclobutyl-1-(4-fluorophenyl)-4-{4-[4-(propan-2-yl)piperazin-1-yl]piperidin-1-yl}-1H-pyrazolo[3,4-b]pyridine-6-carboxylic acid;

3-cyclobutyl-1-cyclohexyl-4-{4-[4-(propan-2-yl)piperazin-1-yl]piperidin-1-yl}-1H-pyrazolo[3,4-b]pyridine-6-carboxylic acid;

4-[(3S)-4-benzyl-3-methylpiperazin-1-yl]-3-cyclobutyl-1-cyclohexyl-1H-pyrazolo[3,4-b]pyridine-6-carboxylic acid;

4-[(3R)-4-benzyl-3-methylpiperazin-1-yl]-3-cyclobutyl-1-cyclohexyl-1H-pyrazolo[3,4-b]pyridine-6-carboxylic acid;

1-cyclohexyl-4-[4-(4-methylpiperazin-1-yl)phenyl]-3-[(propan-2-yl)oxy]-1H-pyrazolo[3,4-b]pyridine-6-carboxylic acid;

1-cyclohexyl-4-{4-[(4-cyclopropylpiperazin-1-yl)methyl]phenyl}-3-[(propan-2-yl)oxy]-1H-pyrazolo[3,4-b]pyridine-6-carboxylic acid;

3-cyclobutyl-1-(2-hydroxypyridin-4-yl)-4-[4-(morpholin-4-yl)piperidin-1-yl]-1H-pyrazolo[3,4-b]pyridine-6-carboxylic acid;

3-cyclobutyl-4-[4-(4-cyclopropylpiperazin-1-yl)piperidin-1-yl]-1-(4-fluorophenyl)-1H-pyrazolo[3,4-b]pyridine-6-carboxylic acid;

3-cyclobutyl-4-(9-cyclopropyl-3,9-diazaspiro[5.5]undecan-3-yl)-1-(4-fluorophenyl)-1H-pyrazolo[3,4-b]pyridine-6-carboxylic acid;

3-cyclobutyl-1-(4-fluorophenyl)-4-{4-[(pyrrolidin-1-yl)methyl]piperidin-1-yl}-1H-pyrazolo[3,4-b]pyridine-6-carboxylic acid;

3-cyclobutyl-1-[2-(difluoromethoxy)pyridin-4-yl]-4-[4-(morpholin-4-yl)piperidin-1-yl]-1H-pyrazolo[3,4-b]pyridine-6-carboxylic acid;

3-cyclobutyl-1-(4-fluorophenyl)-4-[9-(propan-2-yl)-3,9-diazaspiro[5.5]undecan-3-yl]-1H-pyrazolo[3,4-b]pyridine-6-carboxylic acid 3-cyclobutyl-4-{4-[4-(ethoxycarbonyl)piperazin-1-yl]piperidin-1-yl}-1-(4-fluorophenyl)-1H-pyrazolo[3,4-b]pyridine-6-carboxylic acid;

3-cyclobutyl-1-(4-fluorophenyl)-4-(4-methoxy[1,4'-bipiperidin]-1'-yl)-1H-pyrazolo[3,4-b]pyridine-6-carboxylic acid;

3-cyclobutyl-1-(4-fluorophenyl)-4-{[4-(morpholin-4-yl)piperidin-1-yl]methyl}-1H-pyrazolo[3,4-b]pyridine-6-carboxylic acid;

3-cyclobutyl-4-(9-cyclobutyl-3,9-diazaspiro[5.5]undecan-3-yl)-1-(4-fluorophenyl)-1H-pyrazolo[3,4-b]pyridine-6-carboxylic acid;

3-cyclobutyl-1-(4-fluorophenyl)-4-{4-[(2-methoxyethyl)(methyl)amino]piperidin-1-yl}-1H-pyrazolo[3,4-b]pyridine-6-carboxylic acid;

3-cyclobutyl-1-(4-fluorophenyl)-4-{4-[4-(2-methoxyethyl)piperazin-1-yl]piperidin-1-yl}-1H-pyrazolo[3,4-b]pyridine-6-carboxylic acid;

3-cyclobutyl-1-(4-fluorophenyl)-4-[9-(2-methoxyethyl)-3,9-diazaspiro[5.5]undecan-3-yl]-1H-pyrazolo[3,4-b]pyridine-6-carboxylic acid;

3-cyclobutyl-1-(4-fluorophenyl)-4-(4-hydroxy[1,4'-bipiperidin]-1'-yl)-1H-pyrazolo[3,4-b]pyridine-6-carboxylic acid;

3-cyclobutyl-1-(4-fluorophenyl)-4-{4-[4-(oxetan-3-yl)piperazin-1-yl]piperidin-1-yl}-1H-pyrazolo[3,4-b]pyridine-6-carboxylic acid;

3-cyclobutyl-1-(4-fluorophenyl)-4-[1-(propan-2-yl)octahydro-5H-pyrrolo[3,2-c]pyridin-5-yl]-1H-pyrazolo[3,4-b]pyridine-6-carboxylic acid;

3-cyclobutyl-4-(1-cyclobutyloctahydro-5H-pyrrolo[3,2-c]pyridin-5-yl)-1-(4-fluorophenyl)-1H-pyrazolo[3,4-b]pyridine-6-carboxylic acid;

3-cyclobutyl-1-(4-fluorophenyl)-4-[1-(oxetan-3-yl)octahydro-5H-pyrrolo[3,2-c]pyridin-5-yl]-1H-pyrazolo[3,4-b]pyridine-6-carboxylic acid;

3-cyclobutyl-1-(4-fluorophenyl)-4-[1-(oxan-4-yl)octahydro-5H-pyrrolo[3,2-c]pyridin-5-yl]-1H-pyrazolo[3,4-b]pyridine-6-carboxylic acid;

3-cyclobutyl-1-(4-fluorophenyl)-4-[9-(oxetan-3-yl)-3,9-diazaspiro[5.5]undecan-3-yl]-1H-pyrazolo[3,4-b]pyridine-6-carboxylic acid;

3-cyclobutyl-1-(3,5-difluorophenyl)-4-[4-(morpholin-4-yl)piperidin-1-yl]-1H-pyrazolo[3,4-b]pyridine-6-carboxylic acid;

3-cyclobutyl-1-(2,2-difluoro-2H-1,3-benzodioxol-5-yl)-4-[4-(morpholin-4-yl)piperidin-1-yl]-1H-pyrazolo[3,4-b]pyridine-6-carboxylic acid;

3-cyclobutyl-1-(3,4-difluorophenyl)-4-[4-(morpholin-4-yl)piperidin-1-yl]-1H-pyrazolo[3,4-b]pyridine-6-carboxylic acid;

3-cyclobutyl-1-(4-fluoro-3-methoxyphenyl)-4-[4-(morpholin-4-yl)piperidin-1-yl]-1H-pyrazolo[3,4-b]pyridine-6-carboxylic acid;

3-cyclobutyl-4-[4-(morpholin-4-yl)piperidin-1-yl]-1-[4-(trifluoromethoxy)phenyl]-1H-pyrazolo[3,4-b]pyridine-6-carboxylic acid;

3-cyclobutyl-1-[3-(difluoromethoxy)phenyl]-4-[4-(morpholin-4-yl)piperidin-1-yl]-1H-pyrazolo[3,4-b]pyridine-6-carboxylic acid;

1-(bicyclo[4.2.0]octa-1,3,5-trien-3-yl)-3-cyclobutyl-4-[4-(morpholin-4-yl)piperidin-1-yl]-1H-pyrazolo[3,4-b]pyridine-6-carboxylic acid;

3-cyclobutyl-1-(3-fluoro-4-methoxyphenyl)-4-[4-(morpholin-4-yl)piperidin-1-yl]-1H-pyrazolo[3,4-b]pyridine-6-carboxylic acid;

3-cyclobutyl-1-(3-fluoro-5-methoxyphenyl)-4-[4-(morpholin-4-yl)piperidin-1-yl]-1H-pyrazolo[3,4-b]pyridine-6-carboxylic acid;

3-cyclobutyl-1-[4-(difluoromethoxy)phenyl]-4-[4-(morpholin-4-yl)piperidin-1-yl]-1H-pyrazolo[3,4-b]pyridine-6-carboxylic acid;

3-cyclobutyl-1-[3-(1,1-difluoroethyl)phenyl]-4-[4-(morpholin-4-yl)piperidin-1-yl]-1H-pyrazolo[3,4-b]pyridine-6-carboxylic acid;

3-cyclobutyl-1-(2,5-difluorophenyl)-4-[4-(morpholin-4-yl)piperidin-1-yl]-1H-pyrazolo[3,4-b]pyridine-6-carboxylic acid;

3-cyclobutyl-1-[6-(2-fluoroethoxy)pyridin-3-yl]-4-[4-(morpholin-4-yl)piperidin-1-yl]-1H-pyrazolo[3,4-b]pyridine-6-carboxylic acid;

3-cyclobutyl-4-[4-(morpholin-4-yl)piperidin-1-yl]-1-{2-[(oxan-4-yl)oxy]pyridin-4-yl}-1H-pyrazolo[3,4-b]pyridine-6-carboxylic acid;

3-cyclobutyl-4-[4-(morpholin-4-yl)piperidin-1-yl]-1-{2-[(oxan-4-yl)methoxy]pyridin-4-yl}-1H-pyrazolo[3,4-b]pyridine-6-carboxylic acid;

3-cyclobutyl-1-(2,4-difluorophenyl)-4-[4-(morpholin-4-yl)piperidin-1-yl]-1H-pyrazolo[3,4-b]pyridine-6-carboxylic acid;

3-cyclobutyl-1-(2,2-difluoro-2H-1,3-benzodioxol-4-yl)-4-[4-(morpholin-4-yl)piperidin-1-yl]-1H-pyrazolo[3,4-b]pyridine-6-carboxylic acid;

4-(4-cyanophenyl)-1-cyclohexyl-3-[(propan-2-yl)oxy]-1H-pyrazolo[3,4-b]pyridine-6-carboxylic acid;

3-cyclobutyl-4-[4-(morpholin-4-yl)piperidin-1-yl]-1-{6-[(propan-2-yl)oxy]pyridin-2-yl}-1H-pyrazolo[3,4-b]pyridine-6-carboxylic acid;

1-(4-fluorophenyl)-3-hydroxy-4-(4-methoxy[1,4'-bipiperidin]-1'-yl)-1H-pyrazolo[3,4-b]pyridine-6-carboxylic acid;

1-(4-fluorophenyl)-4-(4-methoxy[1,4'-bipiperidin]-1'-yl)-3-[(propan-2-yl)oxy]-1H-pyrazolo[3,4-b]pyridine-6-carboxylic acid;

1-cyclohexyl-4-(4-{[3-(dimethylamino)azetidin-1-yl]methyl}phenyl)-3-[(propan-2-yl)oxy]-1H-pyrazolo[3,4-b]pyridine-6-carboxylic acid;

3-cyclobutyl-1-(4-fluorophenyl)-4-(9-methyl-3,9-diazaspiro[5.5]undecan-3-yl)-1H-pyrazolo[3,4-b]pyridine-6-carboxylic acid;

3-cyclobutyl-4-[4-(ethoxycarbonyl)piperazin-1-yl]-1-(4-fluorophenyl)-1H-pyrazolo[3,4-b]pyridine-6-carboxylic acid; and 3-cyclobutyl-1-(4-fluorophenyl)-4-{4-[(2-methylpropoxy) carbonyl]piperazin-1-yl}-1H-pyrazolo[3,4-b]pyridine-6-carboxylic acid.

Pharmaceutical Compositions

In its second aspect, the present invention relates to a pharmaceutical composition for treating cystic fibrosis comprising a first corrector agent and a pharmaceutically acceptable carrier, wherein the first corrector agent is a corrector agent described herein and above.

In some embodiments, the composition of the present invention further comprises a potentiator agent. The potentiator agent can be any compound that is capable of increasing the gating activity of CFTR in a membrane of a cell.

Non-limiting examples of the potentiator includes Ivacaftor (VX-770), N-(3-carbamoyl-5,5,7,7-tetramethyl-4,7-dihydro-5H-thieno[2,3-c]pyran-2-yl)-1H-pyrazole-5-carboxamide, the compounds disclosed in WO2005120497, WO2008147952, WO2009076593, WO2010048573, WO2006002421, WO2008147952, WO2011072241, WO2011113894, WO2013038373, WO2013038378, WO2013038381, WO2013038386, and WO2013038390; and U.S. application Ser. Nos. 14/271,080, 14/451,619 and 62/169,881, and the compounds selected from the list below:

2-(2-fluorobenzamido)-5,5,7,7-tetramethyl-5,7-dihydro-4H-thieno[2,3-c]pyran-3-carboxamide;

2-(2-hydroxybenzamido)-5,5,7,7-tetramethyl-5,7-dihydro-4H-thieno[2,3-c]pyran-3-carboxamide 2-(1-hydroxycyclopropanecarboxamido)-5,5,7,7-tetramethyl-5,7-dihydro-4H-thieno[2,3-c]pyran-3-carboxamide;

5,5,7,7-tetramethyl-2-(2-(trifluoromethyl)benzamido)-5,7-dihydro-4H-thieno[2,3-c]pyran-3-carboxamide;

2-(2-hydroxy-2-methylpropanamido)-5,5,7,7-tetramethyl-5,7-dihydro-4H-thieno[2,3-c]pyran-3-carboxamide;

2-(1-(hydroxymethyl)cyclopropanecarboxamido)-5,5,7,7-tetramethyl-5,7-dihydro-4H-thieno[2,3-c]pyran-3-carboxamide;

2-(3-hydroxy-2,2-dimethylpropanamido)-5,5,7,7-tetramethyl-5,7-dihydro-4H-thieno[2,3-c]pyran-3-carboxamide;

N-(3-carbamoyl-5,5,7,7-tetramethyl-5,7-dihydro-4H-thieno[2,3-c]pyran-2-yl)-5-methyl-1H-pyrazole-3-carboxamide;

N-(3-carbamoyl-5,5,7,7-tetramethyl-5,7-dihydro-4H-thieno[2,3-c]pyran-2-yl)-5-cyclopropyl-1H-pyrazole-3-carboxamide;

N-(3-carbamoyl-5,5,7,7-tetramethyl-5,7-dihydro-4H-thieno[2,3-c]pyran-2-yl)-5-isopropyl-1H-pyrazole-3-carboxamide;

N-(3-carbamoyl-5,5,7,7-tetramethyl-5,7-dihydro-4H-thieno[2,3-c]pyran-2-yl)-5-(trifluoromethyl)-1H-pyrazole-3-carboxamide;

5-tert-butyl-N-(3-carbamoyl-5,5,7,7-tetramethyl-5,7-dihydro-4H-thieno[2,3-c]pyran-2-yl)-1H-pyrazole-3-carboxamide;

N-(3-carbamoyl-5,5,7,7-tetramethyl-5,7-dihydro-4H-thieno[2,3-c]pyran-2-yl)-5-ethyl-1H-pyrazole-3-carboxamide;

N-(3-carbamoyl-5,5,7,7-tetramethyl-5,7-dihydro-4H-thieno[2,3-c]pyran-2-yl)-3-ethyl-4-methyl-1H-pyrazole-5-carboxamide;

2-(2-hydroxypropanamido)-5,5,7,7-tetramethyl-5,7-dihydro-4H-thieno[2,3-c]pyran-3-carboxamide;

N-(3-carbamoyl-5,5,7,7-tetramethyl-5,7-dihydro-4H-thieno[2,3-c]pyran-2-yl)-4-chloro-1H-pyrazole-3-carboxamide;

N-(3-carbamoyl-5,5,7,7-tetramethyl-5,7-dihydro-4H-thieno[2,3-c]pyran-2-yl)-1,4,6,7-tetrahydropyrano[4,3-c]pyrazole-3-carboxamide;

4-bromo-N-(3-carbamoyl-5,5,7,7-tetramethyl-5,7-dihydro-4H-thieno[2,3-c]pyran-2-yl)-1H-pyrazole-3-carboxamide;

N-(3-carbamoyl-5,5,7,7-tetramethyl-5,7-dihydro-4H-thieno[2,3-c]pyran-2-yl)-4-chloro-5-methyl-1H-pyrazole-3-carboxamide;

N-(3-carbamoyl-5,5,7,7-tetramethyl-5,7-dihydro-4H-thieno[2,3-c]pyran-2-yl)-4-methyl-1H-pyrazole-3-carboxamide;

2-(2-hydroxy-3,3-dimethylbutanamido)-5,5,7,7-tetramethyl-5,7-dihydro-4H-thieno[2,3-c]pyran-3-carboxamide;

2-[(2-hydroxy-4-methyl-pentanoyl)amino]-5,5,7,7-tetramethyl-4H-thieno[2,3-c]pyran-3-carboxamide;

5-(2-methoxy-ethoxy)-1H-pyrazole-3-carboxylic acid (3-carbamoyl-5,5,7,7-tetramethyl-4,7-dihydro-5H-thieno[2,3-c]pyran-2-yl)-amide;

N-(3-carbamoyl-5,5,7,7-tetramethyl-4H-thieno[2,3-c]pyran-2-yl)-4-(3-methoxypropyl)-1H-pyrazole-3-carboxamide;

N-(3-carbamoyl-5,5,7,7-tetramethyl-4H-thieno[2,3-c]pyran-2-yl)-4-(2-ethoxyethyl)-1H-pyrazole-3-carboxamide;

2-[[(2S)-2-hydroxy-3,3-dimethyl-butanoyl]amino]-5,5,7,7-tetramethyl-4H-thieno[2,3-c]pyran-3-carboxamide;

2-[[(2R)-2-hydroxy-3,3-dimethyl-butanoyl]amino]-5,5,7,7-tetramethyl-4H-thieno[2,3-c]pyran-3-carboxamide;

2-[(2-hydroxy-2,3,3-trimethyl-butanoyl)amino]-5,5,7,7-tetramethyl-4H-thieno[2,3-c]pyran-3-carboxamide;

[5-[(3-carbamoyl-5,5,7,7-tetramethyl-4H-thieno[2,3-c]pyran-2-yl)carbamoyl]pyrazol-1-yl]methyl dihydrogen phosphate;

[3-[(3-carbamoyl-5,5,7,7-tetramethyl-4H-thieno[2,3-c]pyran-2-yl)carbamoyl]pyrazol-1-yl]methyl dihydrogen phosphate;

N-(3-carbamoyl-5,5,7,7-tetramethyl-4H-thieno[2,3-c]pyran-2-yl)-4-(1,4-dioxan-2-yl)-1H-pyrazole-3-carboxamide;

5,5,7,7-tetramethyl-2-[[(2S)-3,3,3-trifluoro-2-hydroxy-2-methyl-propanoyl]amino]-4H-thieno[2,3-c]pyran-3-carboxamide;

2-[[(2S)-2-hydroxypropanoyl]amino]-5,5,7,7-tetramethyl-4H-thieno[2,3-c]pyran-3-carboxamide;

3-amino-N-(2-hydroxy-2-methylpropyl)-5-{[4-(trifluoromethoxy)phenyl]sulfonyl}pyridine-2-carboxamide;

3-amino-N-[(4-hydroxy-1-methylpiperidin-4-yl)methyl]-5-{[4-(trifluoromethoxy)phenyl]sulfonyl}pyridine-2-carboxamide;

3-amino-N-(3-hydroxy-2,2-dimethylpropyl)-5-{[4-(trifluoromethoxy)phenyl]sulfonyl}pyridine-2-carboxamide;

3-amino-5-[(4-fluorophenyl)sulfonyl]-N-[(1-hydroxycyclopropyl)methyl]pyridine-2-carboxamide;

3-amino-5-[(4-fluorophenyl)sulfonyl]-N-[(2R)-3,3,3-trifluoro-2-hydroxypropyl]pyridine-2-carboxamide;

3-amino-5-[(3-fluorophenyl)sulfonyl]-N-(2-hydroxy-2-methylpropyl)pyridine-2-carboxamide;

3-amino-N-[2-(cyclopropylamino)-2-oxoethyl]-5-{[4-(trifluoromethoxy)phenyl]sulfonyl}pyridine-2-carboxamide;

(3-amino-5-{[4-(trifluoromethoxy)phenyl]sulfonyl}pyridin-2-yl)(azetidin-1-yl)methanone;

(3-amino-5-{[4-(trifluoromethoxy)phenyl]sulfonyl}pyridin-2-yl)[3-(hydroxymethyl)azetidin-1-yl]methanone;

(3-amino-5-{[4-(trifluoromethoxy)phenyl]sulfonyl}pyridin-2-yl)(3-fluoroazetidin-1-yl)methanone;

3-amino-N-[(2R)-2-hydroxy-3-methoxypropyl]-5-{[4-(trifluoromethyl)phenyl]sulfonyl}pyridine-2-carboxamide;

(3-amino-5-{[2-fluoro-4-(trifluoromethoxy)phenyl]
sulfonyl}pyridin-2-yl)(3-hydroxyazetidin-1-yl)metha-
none;
(3-amino-5-{[2-(trifluoromethoxy)phenyl]
sulfonyl}pyridin-2-yl)(3,3-difluoroazetidin-1-yl)metha-
none;
rac-3-amino-N-[(3R,4S)-4-hydroxytetrahydro-2H-pyran-3-
yl]-5-{[2-(trifluoromethoxy)phenyl]sulfonyl}pyridine-2-
carboxamide;
3-amino-5-[(4,4-difluoropiperidin-1-yl)sulfonyl]-N-(3,3,3-
trifluoro-2-hydroxypropyl)pyridine-2-carboxamide;
(3-amino-5-{[2-(trifluoromethoxy)phenyl]
sulfonyl}pyridin-2-yl)[3-hydroxy-3-(trifluoromethyl)
azetidin-1-yl]methanone;
3-amino-N-(2-hydroxy-4-methylpentyl)-5-{[4-(trifluo-
romethoxy)phenyl]sulfonyl}pyridine-2-carboxamide;
(3-amino-5-{[4-(trifluoromethyl)phenyl]sulfonyl}pyridin-
2-yl)(3-hydroxy-3-methylazetidin-1-yl)methanone;
3-amino-N-(3,3,3-trifluoro-2-hydroxypropyl)-5-{[4-(trif-
luoromethyl)piperidin-1-yl]sulfonyl}pyridine-2-carbox-
amide;
3-amino-N-[2-hydroxy-1-(4-methoxyphenyl)ethyl]-5-{[4-
(trifluoromethoxy)phenyl]sulfonyl}pyridine-2-carbox-
amide;
3-amino-5-[(3,3-difluoroazetidin-1-yl)sulfonyl]-N-(3,3,3-
trifluoro-2-hydroxypropyl)pyridine-2-carboxamide;
3-amino-5-{[2-fluoro-4-(trifluoromethyl)phenyl]sulfonyl}-
N-[(2S)-2-hydroxypropyl]pyridine-2-carboxamide;
3-amino-5-{[2-fluoro-4-(trifluoromethyl)phenyl]sulfonyl}-
N-[(2R)-2-hydroxy-3-methoxypropyl]pyridine-2-carbox-
amide;
3-amino-N-[2-oxo-2-(propan-2-ylamino)ethyl]-5-{[4-(trif-
luoromethyl)phenyl]sulfonyl}pyridine-2-carboxamide;
(3-amino-5-{[4-(trifluoromethyl)phenyl]sulfonyl}pyridin-
2-yl)[3-hydroxy-3-(trifluoromethyl)azetidin-1-yl]metha-
none;
3-amino-5-{[2-fluoro-4-(trifluoromethyl)phenyl]sulfonyl}-
N-[(3R)-tetrahydrofuran-3-ylmethyl]pyridine-2-carbox-
amide;
(3-amino-5-{[2-fluoro-4-(trifluoromethyl)phenyl]
sulfonyl}pyridin-2-yl)[3-hydroxy-3-(trifluoromethyl)
azetidin-1-yl]methanone;
3-amino-5-{[2-fluoro-4-(trifluoromethyl)phenyl]sulfonyl}-
N-[(3S)-tetrahydrofuran-3-ylmethyl]pyridine-2-carbox-
amide;
3-amino-5-{[2-fluoro-4-(trifluoromethoxy)phenyl]sulfo-
nyl}-N-[(3S)-tetrahydrofuran-3-ylmethyl]pyridine-2-car-
boxamide;
3-amino-N-[2-hydroxy-3-(2,2,2-trifluoroethoxy)propyl]-5-
{[4-(trifluoromethyl)phenyl]sulfonyl}pyridine-2-carbox-
amide;
3-amino-N-(3-tert-butoxy-2-hydroxypropyl)-5-{[2-fluoro-
4-(trifluoromethyl)phenyl]sulfonyl}pyridine-2-carbox-
amide;
[3-amino-5-(phenylsulfonyl)pyridin-2-yl][3-hydroxy-3-(tri-
fluoromethyl)azetidin-1-yl]methanone; and
{3-amino-5-[(3-fluorophenyl)sulfonyl]pyridin-2-yl}[3-hy-
droxy-3-(trifluoromethyl)azetidin-1-yl]methanone.

In some embodiments, the composition of the present invention further comprises a second corrector agent, wherein the second corrector agent works through different correction mechanisms as the first corrector agent.

In some embodiments, the second corrector binds to different regions of a CFTR protein as compared to a first corrector agent which is described herein in this application.

In some embodiments, the second corrector stabilizes at least one of biogenic intermediates selected from a group consisting of CFTR375, CFTR380, CFTR430, CFTR653, CFTR837 and CFTR837-1480 during the biosynthesis of the CFTR protein.

Non-limiting examples of the second correctors include Lumacaftor (VX-809), 1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661), VX-983, GLPG2222, GLPG2665, GLPG2851, VX-152, VX-440, FDL169, FDL304, FD2052160, and FD2035659. Examples of correctors are also disclosed in U.S. application Ser. Nos. 14/925,649, 14/926,727 and 15/205,512. and compounds selected from the list below:

3-[(2R,4R)-4-({[1-(2,2-difluoro-1,3-benzodioxol-5-yl)cy-
clopropyl]carbonyl}amino)-7-methoxy-3,4-dihydro-2H-
chromen-2-yl]benzoic acid;
3-[(2R,4R)-4-({[1-(2,2-difluoro-1,3-benzodioxol-5-yl)cy-
clopropyl]carbonyl}amino)-3,4-dihydro-2H-chromen-2-
yl]benzoic acid;
3-[(2R,4R)-4-({[1-(2,2-difluoro-1,3-benzodioxol-5-yl)cy-
clopropyl]carbonyl}amino)-6-methyl-3,4-dihydro-2H-
chromen-2-yl]benzoic acid;
3-[(2R,4R)-4-({[1-(2,2-difluoro-1,3-benzodioxol-5-yl)cy-
clopropyl]carbonyl}amino)-7-methyl-3,4-dihydro-2H-
chromen-2-yl]benzoic acid;
3-[(2R,4R)-4-({[1-(2,2-difluoro-1,3-benzodioxol-5-yl)cy-
clopropyl]carbonyl}amino)-6-methoxy-3,4-dihydro-2H-
chromen-2-yl]benzoic acid;
3-[(2R,4R)-4-({[1-(2,2-difluoro-1,3-benzodioxol-5-yl)cy-
clopropyl]carbonyl}amino)-7-(difluoromethoxy)-3,4-di-
hydro-2H-chromen-2-yl]cyclohexanecarboxylic acid;
3-[(2R,4R)-4-({[1-(2,2-difluoro-1,3-benzodioxol-5-yl)cy-
clopropyl]carbonyl}amino)-7-(difluoromethoxy)-3,4-di-
hydro-2H-chromen-2-yl]benzoic acid;
3-[(2R,4R)-4-({[1-(2,2-difluoro-1,3-benzodioxol-5-yl)cy-
clopropyl]carbonyl}amino)-7-methoxy-3,4-dihydro-2H-
chromen-2-yl]cyclohexanecarboxylic acid;
3-[(2R,4R)-4-({[1-(2,2-difluoro-1,3-benzodioxol-5-yl)cy-
clopropyl]carbonyl}amino)-7-fluoro-3,4-dihydro-2H-
chromen-2-yl]benzoic acid;
3-[(2R,4R)-4-({[1-(2,2-difluoro-1,3-benzodioxol-5-yl)cy-
clopropyl]carbonyl}amino)-7-methyl-3,4-dihydro-2H-
chromen-2-yl]benzoyl}amino)-1-methylcyclopentan-
ecarboxylic acid;
3-[(2R,4R)-4-({[1-(2,2-difluoro-1,3-benzodioxol-5-yl)cy-
clopropyl]carbonyl}amino)-7-methyl-3,4-dihydro-2H-
chromen-2-yl]-N-[(2R)-2,3-dihydroxypropyl]benzamide;
3-[(2R,4R)-4-({[1-(2,2-difluoro-1,3-benzodioxol-5-yl)cy-
clopropyl]carbonyl}amino)-7-(2-methoxyethoxy)-3,4-di-
hydro-2H-chromen-2-yl]benzoic acid;
3-[(2R,4R)-7-(benzyloxy)-4-({[1-(2,2-difluoro-1,3-benzo-
dioxol-5-yl)cyclopropyl]carbonyl}amino)-3,4-dihydro-
2H-chromen-2-yl]benzoic acid;
3-[(2R,4R)-4-({[1-(2,2-difluoro-1,3-benzodioxol-5-yl)cy-
clopropyl]carbonyl}amino)-7-(2-fluoroethoxy)-3,4-di-
hydro-2H-chromen-2-yl]benzoic acid;
3-[(2R,4R)-4-({[1-(2,2-difluoro-1,3-benzodioxol-5-yl)cy-
clopropyl]carbonyl}amino)-7-(trifluoromethyl)-3,4-di-
hydro-2H-chromen-2-yl]benzoic acid;
3-[(2R,4R)-4-({[1-(2,2-difluoro-1,3-benzodioxol-5-yl)cy-
clopropyl]carbonyl}amino)-7-(trifluoromethyl)-3,4-di-
hydro-2H-chromen-2-yl]cyclohexanecarboxylic acid;
4-[(2R,4R)-4-({[1-(2,2-difluoro-1,3-benzodioxol-5-yl)cy-
clopropyl]carbonyl}amino)-7-methoxy-3,4-dihydro-2H-
chromen-2-yl]benzoic acid;

3-[(2R,4R)-4-({[1-(2,2-difluoro-1,3-benzodioxol-5-yl)cyclopropyl]carbonyl}amino)-8-fluoro-3,4-dihydro-2H-chromen-2-yl]benzoic acid;

4-[(2R,4R)-4-({[1-(2,2-difluoro-1,3-benzodioxol-5-yl)cyclopropyl]carbonyl}amino)-3,4-dihydro-2H-chromen-2-yl]benzoic acid;

4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;

rac-3-[(2R,4S)-4-({[1-(2,2-difluoro-1,3-benzodioxol-5-yl)cyclopropyl]carbonyl}amino)tetrahydro-2H-pyran-2-yl]benzoic acid;

rac-4-[(2R,4S)-4-({[1-(2,2-difluoro-1,3-benzodioxol-5-yl)cyclopropyl]carbonyl}amino)tetrahydro-2H-pyran-2-yl]benzoic acid;

3-[(2S,4R)-4-({[1-(2,2-difluoro-1,3-benzodioxol-5-yl)cyclopropyl]carbonyl}amino)tetrahydro-2H-pyran-2-yl]benzoic acid;

3-[(2R,4S)-4-({[1-(2,2-difluoro-1,3-benzodioxol-5-yl)cyclopropyl]carbonyl}amino)tetrahydro-2H-pyran-2-yl]benzoic acid;

rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;

3-[(2S,4R,6R)-4-({[1-(2,2-difluoro-1,3-benzodioxol-5-yl)cyclopropyl]carbonyl}amino)-6-phenyltetrahydro-2H-pyran-2-yl]benzoic acid;

3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid; and 4-[(2R,4S)-4-({[1-(2,2-difluoro-1,3-benzodioxol-5-yl)cyclopropyl]carbonyl}amino)tetrahydro-2H-pyran-2-yl]benzoic acid.

When employed as a pharmaceutical, a corrector agent of the invention is typically administered in the form of a pharmaceutical composition. Such compositions can be prepared in a manner well known in the pharmaceutical art and comprise a therapeutically effective amount of a compound, or a pharmaceutically acceptable salt thereof together with a pharmaceutically acceptable carrier. The phrase "pharmaceutical composition" refers to a composition suitable for administration in medical or veterinary use.

The pharmaceutical compositions that comprise a corrector agent of the present invention, alone or in combination with further therapeutically active ingredient, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which may serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants may also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous diluents, solvents, or vehicles include water, ethanol, polyols (such as glycerol, propylene glycol, polyethylene glycol and the like), vegetable oils (such as olive oil), injectable organic esters (such as ethyl oleate), and suitable mixtures thereof. Proper fluidity may be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

In some cases, in order to prolong the effect of the drug, it may be desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release may be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations may be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In certain embodiments, solid dosage forms may contain from 1% to 95% (w/w) of a compound of formula (I) or (I-a-i). In certain embodiments, the compound of formula (I) or (I-a-i), or pharmaceutically acceptable salts thereof, may be present in the solid dosage form in a range of from 5% to 70% (w/w). In such solid dosage forms, the active compound may be mixed with at least one inert, pharmaceutically acceptable carrier, such as sodium citrate or dicalcium phosphate and/or a), fillers or extenders such as starches, lactose, sucrose, glucose, mannitol, and silicic acid; b) binders such as carboxymethylcellulose, alginates, gelatin, polyvinylpyrrolidone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form may be a capsule, tablet, cachet, or lozenge itself, or it may be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition may, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician may evaluate factors such as the circulating plasma levels of the compound, compound toxicities, and/or the progression of the disease, etc.

For administration, compounds may be administered at a rate determined by factors that may include, but are not limited to, the $LD_{50}$ of the compound, the pharmacokinetic profile of the compound, contraindicated drugs, and the side-effects of the compound at various concentrations, as applied to the mass and overall health of the subject. Administration may be accomplished via single or divided doses.

The compounds utilized in the pharmaceutical method of the invention may be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds may also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols, and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which may be prepared by mixing the compounds with suitable non-irritating carriers or carriers such as cocoa butter, polyethylene glycol, or a suppository wax which are solid at room temperature but liquid at body temperature and therefore melt in the rectum or vaginal cavity and release the active compound.

Compounds may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes may be used. The present compositions in liposome form may contain, in addition to a compound of the invention, stabilizers, preservatives, excipients, and the like. Examples of lipids include, but are not limited to, natural and synthetic phospholipids, and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments, and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

A compound of the invention may also be administered in sustained release forms or from sustained release drug delivery systems.

Methods of Treating Cystic Fibrosis

In its third aspect, the present invention is directed to methods of treating cystic fibrosis in a subject or patient by using the corrector agents or pharmaceutical compositions described herein and above.

In some embodiments, the method of the present invention comprises the step of administering to the patient an effective amount of a first corrector agent, wherein the first corrector agent is an agent of the present invention as described herein.

The term "administering" refers to the method of contacting a compound with a subject. Thus, the compounds may be administered by injection, that is, intravenously, intramuscularly, intracutaneously, subcutaneously, intraduodenally, parentally, or intraperitoneally. Also, the compounds described herein may be administered by inhalation, for example, intranasally. Additionally, the compounds may be administered transdermally, topically, via implantation, transdermally, topically, and via implantation. In certain embodiments, the compounds and compositions thereof may be delivered orally. The compounds may also be delivered rectally, bucally, intravaginally, ocularly, or by insufflation. CFTR-modulated disorders and conditions may be treated prophylactically, acutely, and chronically using compounds and compositions thereof, depending on the nature of the disorder or condition. Typically, the host or subject in each of these methods is human, although other mammals may also benefit from the administration of compounds and compositions thereof as set forth hereinabove.

In some embodiments, the present corrector agent is administered as the sole active agent. In some embodiments, the present corrector is co-administered with other therapeutic agents.

In some embodiments, the first corrector agent is co-administered with an effective amount of a second corrector agent, wherein the second corrector agent works through a different correction mechanisms as the first corrector agent.

In some embodiments, the second corrector stabilizes at least one of biogenic intermediates selected from a group consisting of CFTR375, CFTR380, CFTR430, CFTR653, CFTR837 and CFTR837-1480 during the biosynthesis of the CFTR protein. Examples of the second corrector agents are described above.

In some embodiments, the first corrector is co-administered with a potentiator. Examples of the potentiators are described above.

The term "co-administered" means the administration of two or more different therapeutic agents to a subject in a single pharmaceutical composition or in separate pharmaceutical compositions. Thus co-administration involves administration at the same time of a single pharmaceutical composition comprising two or more therapeutic agents or administration of two or more different compositions to the same subject at the same or different times.

In some embodiments, the method of the present invention additional comprises the step of administering a therapeutically effective amount of one or more additional therapeutic agents to treat a CFTR mediated disease, where examples of the therapeutic agents include, but are not limited to antibiotics (for example, aminoglycosides, colistin, aztreonam, ciprofloxacin, and azithromycin), expectorants (for example, hypertonic saline, acetylcysteine, dornase alfa, and denufosol), pancreatic enzyme supplements (for example, pancreatin, and pancrelipase), CFTR potentiators, and CFTR correctors.

Methods of Screening Candidate Correctors

In its fourth aspect, the present invention relates to a method of screening for a candidate corrector agent for cystic fibrosis. comprising the steps of i) contacting a test agent with a cell expressing at least one of the CFTR biogenic intermediates selected from group consisting of CFTR380, CFTR837 and CFTR837-1480 and a CFTR protein, ii) measuring the accumulation of the CFTR biogenic intermediate and the CFTR protein, iii) comparing the accumulation of the CFTR biogenic intermediate and the CFTR protein in the cell with the accumulation of the CFTR biogenic intermediate and the CFTR protein in a cell that is not contacted with the test agent, wherein the test agent is a candidate corrector agent if the accumulation of the CFTR biogenic intermediate in the cell contacted with the test agent is no greater than the accumulation of said CFTR biogenic intermediate in the cell not contacted with the test agent, and if the accumulation of the CFTR protein in the cell contacted with the test agent is greater than the accumulation of the CFTR protein in the cell not contacted with the test agent. In a particular embodiment of the method, one or more biogenic intermediates are tested. More specifically the method steps are repeated using a different biogenic intermediate. In a particular embodiment the test agent is a candidate corrector agent if the accumulation of one or more of the CFTR biogenic intermediates in the cell contacted with the test agent is no greater than the accumulation of said CFTR biogenic intermediates in the cell not contacted with the test agent, and if the accumulation of the CFTR protein in the cell contacted with the test agent is greater than the accumulation of the CFTR protein in the cell not contacted with the test agent One can measure and compare the accumulation of the CFTR intermediates or the CFTR protein using any technology known in the art, including, but not limited to, the methods illustrated in Examples below.

This invention also is directed to kits for screening a corrector candidate. The kit comprises a cell expressing one or more CFTR biogenic intermediates selected from group consisting of CFTR380, CFTR837 and CFTR837-1480 and a CFTR protein. The kit may further comprise a test agent.

EXAMPLES

To localize the region in CFTR and stage of CFTR folding on which the compounds of interest act to correct a mutant CFTR misfolding, immunolochemistry and pulse-chase studies are used to monitor the impact of the compounds on the accumulation of a set of CFTR and F508-CFTR fragments.

However, it should be understood that the foregoing detailed description and accompanying examples are merely illustrative and are not to be taken as limitations upon the scope of the invention, which is defined solely by the appended claims and their equivalents. Various changes and modifications to the described embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

Fragment Analysis

In order to define the region of CFTR whose conformation is modulated by compounds or corrector agents of interest, a fragment analysis assay was employed. The fragment analysis assay is described in detail in several publications including Grove et al. 2009, Caldwell et al. 2011 and Ren et al. 2013, both of which are incorporated herein by reference in their entirety.

Plasmids, Antibodies, and Reagents.

CFTR expression plasmids pcDNA3.1(+)-CFTR and pcDNA3.1(+)ΔF508-CFTR have been described elsewhere (Meacham et al., 2001; Younger et al., 2006). CFTR constructs representing CF diseasecausing point mutants or truncated biogenic intermediates were made using the QuikChange protocol. The CFTR antibody used in this study was MM13-4 (N-terminal tail epitope).

Cell Culture and Transfection.

HEK293 cells from the American Type Culture Collection (Manassas, Va.) were maintained in DMEM (Gibco, Grand Island, N.Y.) supplemented with 1% fetal bovine serum (Thermoscientific, Waltham, Mass.) and antibiotics (100 U/ml penicillin and 100 µg/ml streptomycin; Gibco) at 37° C. in an atmosphere of 5% CO2. Cell transfections were performed using Effectene reagent (Qiagen, Valencia, Calif.). The empty pcDNA3.1(+) vector was used to ensure equal microgram quantities of DNA were used in all transfection reactions.

Analysis of CFTR Biogenic Intermediates.

The fragments of CFTR were expressed in HEK293 cells and the compounds were added to the cells to stimulate F508-CFTR function. After 18 hours incubation the steady state level of the fragments of CFTR were determined by western blot. Changes in steady-state levels of a specific CFTR fragment caused by the compounds were compared side by side on the same gels. Changes in CFTR steady-state levels caused by the compounds were quantitated relative to loaded controls via densitometry and blotted as bar graphs.

Results

As described in the above-mentioned publications, the assay has demonstrated that VX-809 acts on MSD1 region of a CFTR in the absence of NBD1 to indirectly suppress folding defects causes by deletion of F508 from NBD1. This assay has also demonstrated that different from VX-809, Corr-4a has little effect on stability of MSD1 (CFTR 380), but can stabilize MSD2 and NBD2 (CFTR 837-1480). In contrast, VX-809 promotes accumulation of MSD1, but has not effect on CFTR 837-1480 (MSD2 and NBD2).

CFTR380X

To test whether the compounds alert the protein conformation of MSD1 and result in a more stable folded form, CFTR 380 fragment was transiently expressed in HEK293 cells and the cells were treated with 5 uM VX-809, 5 uM Corr-4a and 3 uM compound A for 18 hours. The Western blot assay with anti-CFTR showed (FIG. 1) that different from VX-089 but similar to Corr-4a, Compound A (3-cyclobutyl-4-[4-(morpholin-4-yl)phenyl]-1-phenyl-1H-pyrazolo[3,4-b]pyridine-6-carboxylic acid) did not increase CFTR380 accumulation, indicating that compound A does not stabilize MSD1 domain of CFTR.

CFTR837X and CFTR873-1480

Figure 2:
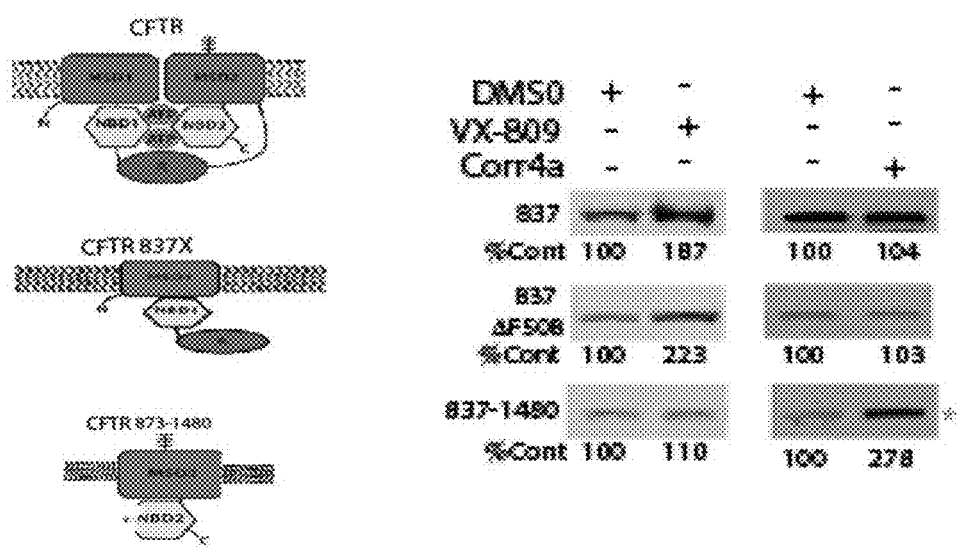
FIG. 2 is a western blot showing the effect of VX-809 and Corr-4a on the accumulation of CFTR837X and CFTR873-1480.

Fragments CFTR837X and CFTR873-1480 were used to test whether the compound A alters C-terminal regions of CFTR that include MSD2 and NBD2. As shown in FIG. 2, Corr-4a treatment did not affect accumulation of the stable N-terminal fragment CFTR 837X which is truncated after the R-domain, nor did it enhance the accumulation of the F508 deleted form of CFTR837X, but increased accumulation of CFTR 837-1480. In contrast, VX-809 did not increase accumulation of CFTR 837-1480 alone, but it did increase accumulation of CFTR 837.

Figure 3:
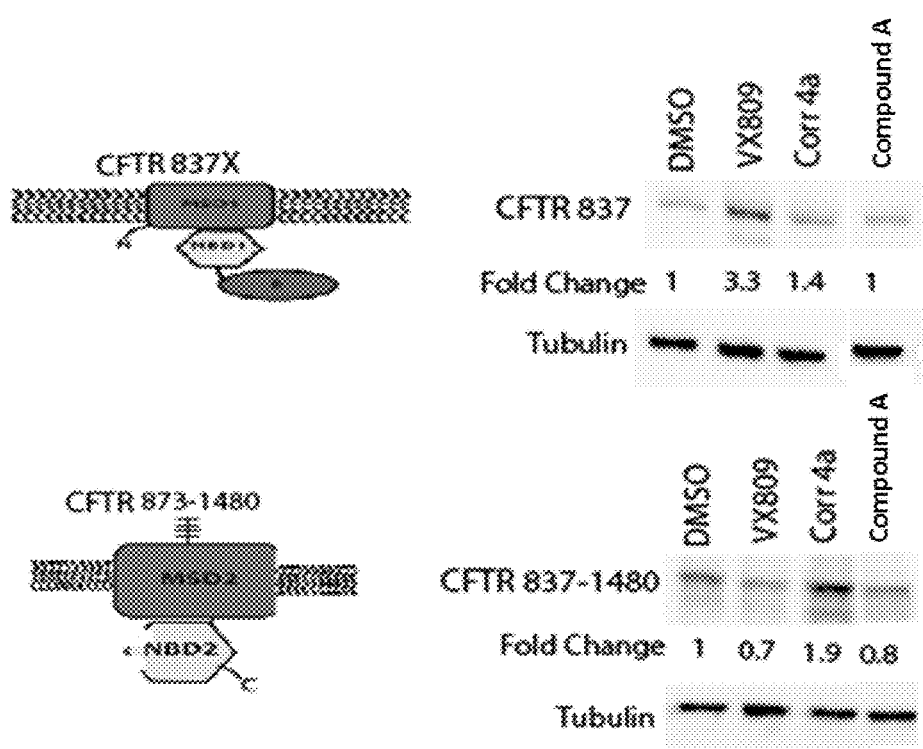
FIG. 3 is a western blot showing the effect of VX-809, Corr-4a and Compound A on the accumulation of CFTR837X and CFTR873-1480.

As shown in FIG. 3, Compound A, different from VX-809 or Corr-4a, had no effect on or slightly reduced the accumulation of CFTR837X and CFTR837-1480, indicating Compound A does not enhance the stability of C-terminal regions of CFTR alone.

CFTR1172X

Figure 4:
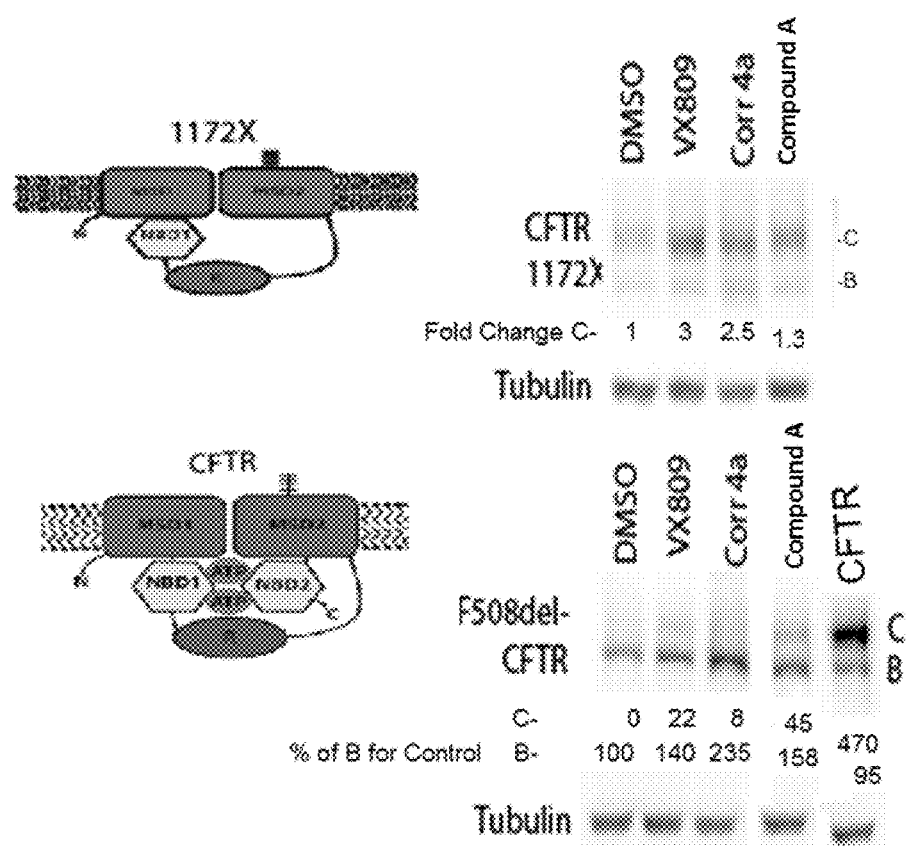
FIG. 4 is a western blot showing the effect of VX-809, Corr-4a and Compound A on the accumulation of CFTR1172X and F508del-CFTR.

The CFTR 1172X fragment, which lacks NBD2, is able to fold into a conformation that can escape the ERQC system, become maturely glycosylated and traffic to the plasma membrane. As shown in FIG. 4, an increase in the accumulation of both the B- and C-forms of CFTR 1172X was observed in the presence of Corr-4a. The immature and maturely glycosylated forms of CFTR are designated as B- and C-bands, respectively. In contrast to what was observed with shorter fragments, Corr-4a increased the accumulation of the B-form of the F508 deleted form of CFTR, but was ineffective at promoting the folding of the F508 deleted CFTR. VX-809 had similar impact on CFTR1172X and F808del-CFTR.

Figure 5:
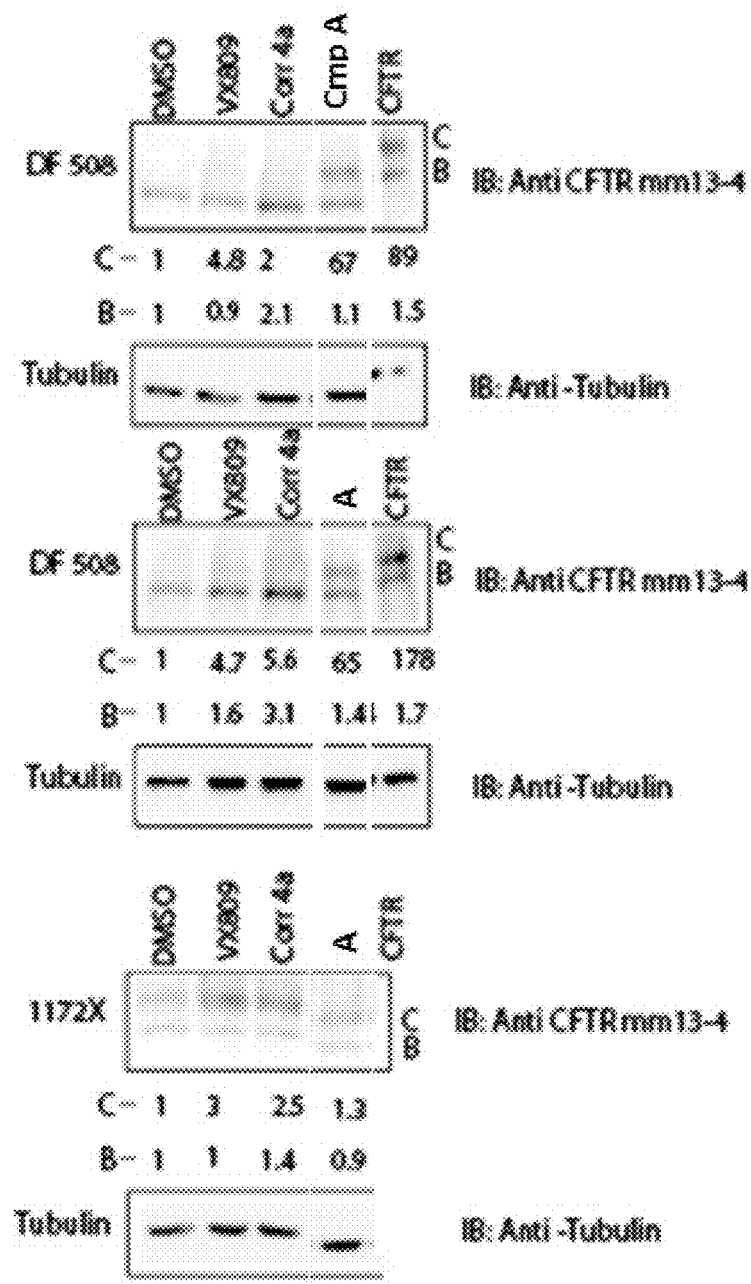
FIG. 5 is a western blot showing the effect of VX-809, Corr-4a and Compound A on the accumulation of F508del-CFTR and CFTR1172X.

Different from Corr-4a, Compound A had a little or no effect on accumulation of CFTR1172X fragment (FIG. 4 and FIG. 5), but Compound A significantly increased the accumulation of C-form F508del-CFTR, indicating that Compound A corrects F508-del-CFTR when the protein is fully synthesized.

Figure 6:
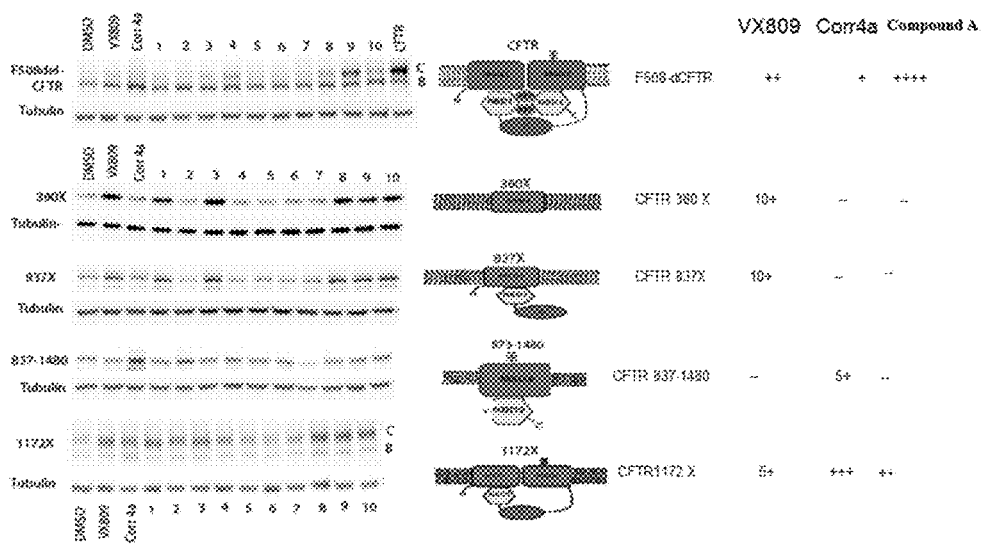
FIG. 6 is a western blot showing the effect of VX-809, Corr-4a and Compound A on the accumulation of CFTR, CFTR380X, CFTR837X, CFTR873-1480 and CFTR1172X.

FIG. 6 summaries the fragment assay on VX-809, Corr-4a and Compound A. It appears that the correction mechanism of Compound A is different from that of VX-809 and Corr-4a. Specifically, Compound A does not stabilize N-terminal MSD1, MSD1-NBD1 or MSD2-NBD2 during the CFTR biosynthesis. Not until after the CFTR protein is fully synthesized, Compound A is capable of promoting the folding and stability of the CFTR protein.

Pulse-chase Analysis

Time-of-addition experiments. The combinatorial effects of compounds on F508del-CFTR trafficking (ER vs. Golgi Complex), and the conformation of individual domains NBD1 and NBD2 was investigated after different time points. F508del CFTR was expressed in HEK293T cells for 24 h. After 20 minutes starvation, cells were pulsed with 35S-Met/Cys for 15 min followed by a 2 hour chase. Radiolabelled lysate was treated with 25 µg/ml proteinase K for 15 minutes on ice. Protease resistant NBD1 and NBD2 fragment were immunoprecipitated using Mr Pink or 596 antibodies, respectively. Compounds were added during the 24 hours, together with starvation/pulse or only during the chase experiment.

Figure 7:
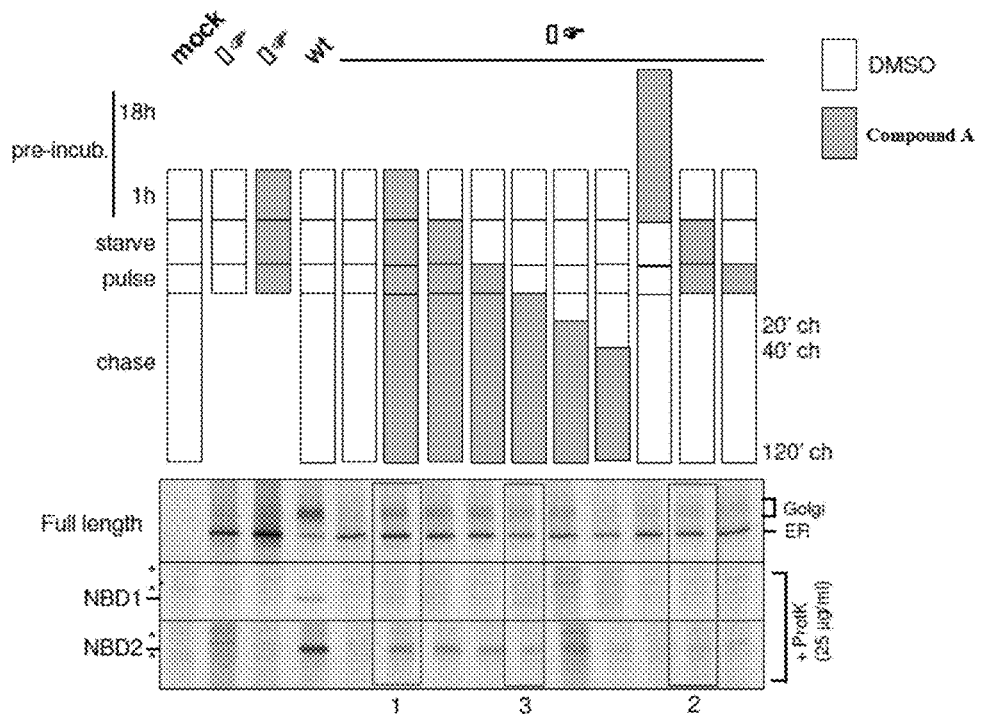
FIG. 7 is a time-of-addition assay showing different mode-of-action of VX-809 and Compound A.
Figure 8:
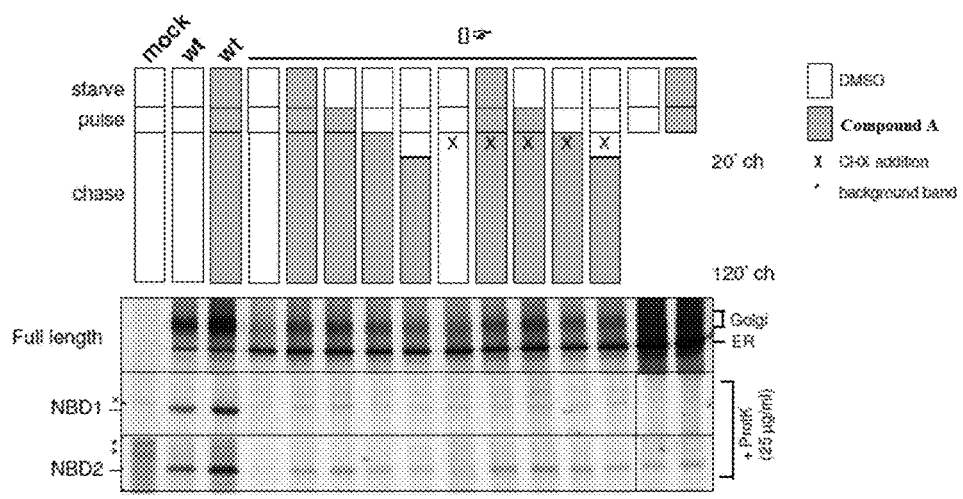
FIG. 8 is a pulse-chase assay showing Compound A action on translation inhibition after pulse and suggesting Compound A improves folding/stability of newly synthesized wild type CFTR.

As shown in FIGS. 7 and 8, the pulse-chase assay showed that Compound A did not stabilize NBD1 or NBD2, but enhanced the stability of full length CFTR protein when the protein was newly synthesized in ER and prior to reaching to Golgi for post-translational modifications.

Combination Effect of Correctors and Potentiators

Figure 9:
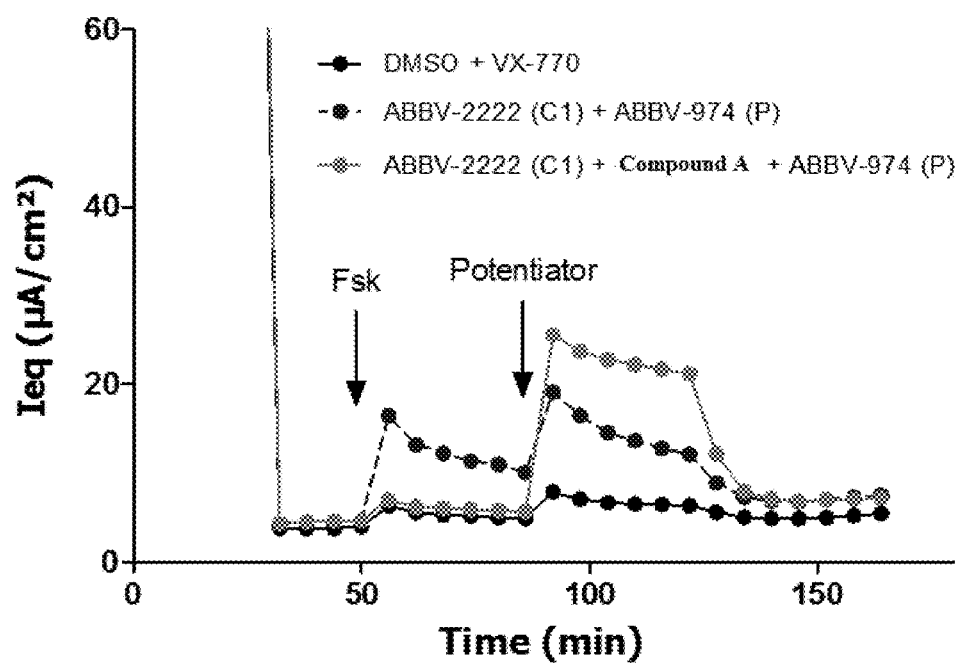
FIG. 9 is a forskolin plus equivalent short-circuit current assay showing the combination effect of correctors and potentiators on activity of CF proteins.

Forskolin plus equivalent short-circuit current trace was measured to determine the combination effect of a potentiator (P) N-(3-carbamoyl-5,5,7,7-tetramethyl-5,7-dihydro-4H-thieno[2,3-c]pyran-2-yl)-1H-pyrazole-5-carboxamide, a type I corrector (C1) 4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid and Compound A on the channel activity and functional responses of a CFTR protein. As shown in FIG. 9, the combination significantly increased the activity of CFTR protein in a cell.

Measuring CFTR Cell Surface Expression of CFTR-ΔF508 in the Presence of a Corrector Agent The PathHunter® U2OS CFTR-ΔF508 cell assay measures the expression of CFTR-ΔF508 at the plasma membrane. CFTR-ΔF508 has a folding defect leading to absence of protein at the plasma membrane. This assay is used to evaluate the capacity of compounds to increase the expression of CFTR-ΔF508 at the plasma membrane. The CFTR-ΔF508 is tagged with a ProLink peptide which can complement with plasma membrane expressed EA-MEM acceptor protein. When both Pro-Link and EA-MEM acceptor are in close proximity i.e. both located at the plasma membrane, a functional enzyme is formed of which the activity can be measured. The amount of CFTR-ΔF508 that can be rescued to the plasma membrane is correlated with the amount of functional enzyme that can be measured.

There are several ways to measure the capacity of compounds to rescue CFTR-ΔF508 to the plasma membrane; either compounds are evaluated on their own and the impact on plasma membrane levels is measured or compounds are evaluated in combination with a co-corrector i.e. a compound that rescues CFTR-ΔF508 to the plasma membrane but rescue can be enhanced by addition of compounds due to complementary mode of action.

Activity of Compounds in Combination with Co-Corrector

For this purpose PathHunter® U2OS CFTR-ΔF508 cells (DiscoveRx; custom made were cultured in AssayComplete™U2OS Cell Culture medium (DiscoveRx; 92-0018GK3) as per manufacturer's instructions. For compound testing, cells were seeded in white 384 well plates (Greiner; 781080) at five thousand cells/well in 25 μl AssayComplete™ Cell Plating 5 Reagent (DiscoveRx; 93-0563R5A) and incubated overnight at 37° C., 5% $CO_2$. On day two, 5 μL of test compounds diluted in Cell Plating 5 Reagent were added to the cells with a final DMSO concentration of 0.1%. In order to measure synergy with a co-corrector, 3 μM of co-corrector was added along with test compounds. All cell plates contained 3 μM co-corrector and DMSO as positive and negative controls respectively. Cells were incubated with compounds for twenty to twenty-four hours at 37° C., 5% $CO_2$. On day three, plates were placed at room temperature for thirty minutes and then 15 μL of substrate (PathHunter® Flash Detection Kit, DiscoveRx; 93-0247) was added per well. After one hour of incubation at room temperature in the dark, luminescence signal was measured on a plate reader (Envision, Perkin Elmer). Raw data were normalized to percentage activity values using the equation: 100×(Sample−Negative control)/(Positive control−Negative Control).

Activity of Compounds for Their Intrinsic Corrector Capacity

For this purpose PathHunter® U2OS CFTR-ΔF508 cells (DiscoveRx; custom made) were cultured in AssayComplete™ U2OS Cell Culture medium (DiscoveRx; 92-0018GK3) as per manufacturer's instructions. For compound testing, cells were seeded in white 384 well plates (Greiner; 781080) at five thousand cells/well in 25 μL AssayComplete™ Cell Plating 5 Reagent (DiscoveRx; 93-0563R5A) and incubated overnight at 37° C., 5% $CO_2$. On day two, 5 μL of test compounds diluted in Cell Plating 5 Reagent were added to the cells with a final DMSO concentration of 0.1%. All cell plates contained DMSO as positive and negative controls respectively. Cells were incubated with compounds for twenty to twenty-four hours at 37° C., 5% $CO_2$. On day three, plates were placed at room temperature for thirty minutes and then 15 μL of substrate (PathHunter® Flash Detection Kit, DiscoveRx; 93-0247) was added per well. After one hour of incubation at room temperature in the dark, luminescence signal was measured on a plate reader (Envision, Perkin Elmer). Raw data were normalized to percentage activity values using the equation: 100×(Sample−Negative control)/(Positive control−Negative Control).

Cell surface expression in the presence of the test compounds on their own or in combination of a type I corrector showed activities of at least 75% of type I corrector on their own or of at least 300% of type I corrector when combined with another type I corrector.

Measuring CFTR Cell Surface Levels using HRP-Tagged ΔF508-CFTR Expressing CFBE Cells in the Presence of a Corrector Agent The HRP-tagged ΔF508-CFTR cell assay measures the expression of CFTR-ΔF508 at the plasma membrane. CFTR-ΔF508 has a folding defect leading to absence of protein at the plasma membrane. This assay is used to evaluate the capacity of compounds to increase the expression of CFTR-ΔF508 at the plasma membrane. The CFTR-ΔF508 is tagged with HRP (Horse radish Peroxidase enzyme) within the ECL4 (Extracellular loop 4) of CFTR (Phuan, P.-W. et al. Mol. Pharmacol. 86,42-51, 2014). When HRP-tagged ΔF508-CFTR is present at the plasma membrane, the HRP enzyme activity can be measured. The amount of CFTR-ΔF508 that can be rescued to the plasma membrane is correlated with the amount of functional enzyme that can be measured.

There are several ways to measure the capacity of compounds to rescue CFTR-ΔF508 to the plasma membrane; either compounds are evaluated on their own and the impact on plasma membrane levels is measured or compounds are evaluated in combination with a co-corrector i.e. a compound that rescues CFTR-ΔF508 to the plasma membrane but rescue can be enhanced by addition of compounds due to complementary mode of action.

Activity of Compounds in Combination with a Co-Corrector

For this purpose Doxycycline-inducible ΔF508-CFTR-HRP expressing CFBE4lo− cells (obtained from Gergely Lukacs, McGill University) were maintained in MEM (Gibco; 31095) supplemented with 10% fetal bovine serum (Hyclone; SV30160.03) under puromycin (3 μg/ml) and G418 selection (0.2 mg/ml). For compound testing, cells were seeded at 4000 cells/well in white 384 well plates (Greiner; 781080) in 50 μL medium containing 0.5 μg/ml doxycycline and incubated for 68 hours at 37° C., 5% $CO_2$. On day four, 10 μl test compounds diluted in PBS were added to the plates at a final DMSO concentration of 0.1%. In order to measure compound synergy with a co-corrector, 3 μM co-corrector was added along with test compounds. All compound plates contained negative controls (DMSO) and positive controls (3 μM co-corrector). Cell plates were incubated at 33° C., 5% $CO_2$ for 20 hours. On day five, the cells were washed five times with phosphate-buffered saline, and HRP activity was assayed by the addition of 50 μL/well of HRP substrate (SuperSignal West Pico Chemiluminescent Substrate, Thermo Scientific; 34080). After incubation for 15 minutes in the dark, chemiluminescence was measured using a plate reader (EnVision, Perkin Elmer). Raw data were normalized to percentage activity values using the equation: 100×(Sample−Negative control)/(Positive control−Negative Control).

Activity of Compounds for Their Intrinsic Corrector Capacity

For this purpose Doxycycline-inducible ΔF508-CFTR-HRP expressing CFBE4lo− cells (obtained from Gergely Lukacs, McGill University) were maintained in MEM (Gibco; 31095) supplemented with 10% fetal bovine serum (Hyclone; SV30160.03) under puromycin (3 μg/ml) and G418 selection (0.2 mg/ml). For compound testing, cells were seeded at 4000 cells/well in white 384 well plates (Greiner; 781080) in 50 μL medium containing 0.5 μg/ml doxycycline and incubated for 68 hours at 37° C., 5% $CO_2$. On day four, 10 μl test compounds diluted in PBS were added to the plates at a final DMSO concentration of 0.1%. All compound plates contained negative controls (DMSO) and positive controls (3 μM co-corrector). Cell plates were incubated at 33° C., 5% $CO_2$ for 20 hours. On day five, the cells were washed five times with phosphate-buffered saline, and HRP activity was assayed by the addition of 50 μL/well of HRP substrate (SuperSignal West Pico Chemiluminescent Substrate, Thermo Scientific; 34080). After incubation for 15 minutes in the dark, chemiluminescence was measured using a plate reader (EnVision, Perkin Elmer). Raw data were normalized to percentage activity values using the equation: 100×(Sample−Negative control)/(Positive control−Negative Control).

Cell surface expression in the presence of the test compounds alone or in combination with a type I corrector demonstrated activities of at least 75% of type I corrector alone or of at least 300% of type I corrector when combined with another type I corrector.

YFP-Halide Influx Assay

YFP-Halide Influx Assay for the CFTR-ΔF508 Mutation and Suppressor mutants (I539T or G550E)

The YFP halide influx assay measures the functionality of the Cystic Fibrosis Transmembrane Conductance regulator (CFTR) channels in the cystic fibrosis bronchial epithelium cell line CFBE4lo−. The fluorescence of the yellow fluorescent protein (YFP) variant YFP H148Q, I152L or variant YFP H148Q, I152L & F47L is substantially quenched by iodine, a halide that is efficiently transported by CFTR. The assay is thus used to evaluate the effect of corrector compounds on CFTR channel function by measuring the extent of YFP signal quenching. (Galietta et al. American Journal of Physiology—Cell Physiology Vol. 281 no. 5, C1734-C1742, 2001; Nagai et al., Nat Biotechnol. 2002 January; 20(1):87-90.)

For this purpose, HEK293 cells are transfected with plasmid DNA containing F508del CFTR, F508del/I539T CFTR or F508del/G550E CFTR and seeded in 96 well plates (70,000 HEK cells/well). The next day, cells are treated with test compounds.

Cells are treated with test compounds for 24 h at 37° C. to allow trafficking of corrected CFTR to the membrane.

The next day the CFTR channels are activated by treatment with the cAMP inducer forskolin (10.67 μM) and potentiator GLPG1837 (0.5 μM) in 1×D-PBS (from Gibco, Cat n#14090-091) for 20 minutes prior to addition of an I⁻ solution (137 mM NaI, 2.7 mM KI, 1.76 mM $KH_2PO_4$, 10.1 mM $Na_2HPO_4$, 5 mM glucose). The I⁻ induced quenching of fluorescence is recorded immediately after injection of for 7 seconds. The capacity of a compound to increase number of channels, and therefore overall halide influx is directly correlated with the decrease in fluorescence, and is expressed as (1−(fluorescence after 7 seconds (F)/fluorescence before injection (F0))) and an $EC_{50}$ can be derived from a (1-F/F0) vs compound concentration plot.

YFP-Halide Influx Assay for the CFTR-WT

For this purpose, HEK293 cells are transfected with plasmid DNA containing WT CFTR and seeded in 96 well plates (70,000 HEK cells/well). Two days after transfection, cells are treated with test compounds.

The CFTR channels are activated by treatment with the cAMP inducer forskolin (10.67 μM) and a dose response of test compounds in 1×D-PBS (from Gibco, Cat n#14090-091) for 20 minutes prior to addition of an F solution (137 mM NaI, 2.7 mM KI, 1.76 mM $KH_2PO_4$, 10.1 mM $Na_2HPO_4$, 5 mM glucose). The I⁻ induced quenching of fluorescence is recorded immediately after injection of for 7 seconds. The impact of a compound on the channel functionality can be measured by looking at the effect on fluorescence, and is expressed as (1-(fluorescence after 7 seconds (F)/fluorescence before injection (F0))) and an $EC_{50}$ can be derived from a (1−F/F0) vs compound concentration plot.

TABLE

| | YFP-halide influx assay results for example agents | | | | | |
|---|---|---|---|---|---|---|
| Compound | YHA I539T Average perc inh/act | YHA G550E IEC IC50/ EC50 (nM) | YHA WT CFTR Average perc inh/act | IEC IC50/ EC50 (nM) | Average perc inh/act | IEC IC50/ EC50 (nM) |
| 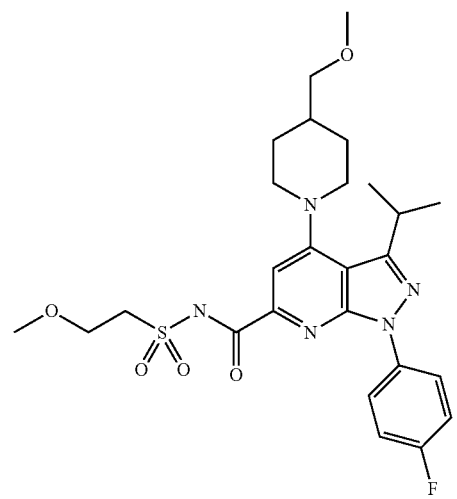 [SMILES: COCCS(=O)(=O)NC(=O)c1cc(N2CCC(COC)CC2)c2c(C(C)C)nn(-c3ccc(F)cc3)c2n1] | 105 | 102 | 64.1 | 40 | 88.2 | 103 |

TABLE-continued

YFP-halide influx assay results for example agents

| Compound | YHA I539T Average perc inh/act | YHA G550E IEC IC50/EC50 (nM) | YHA WT CFTR Average perc inh/act | IEC IC50/EC50 (nM) | Average perc inh/act | IEC IC50/EC50 (nM) |
|---|---|---|---|---|---|---|
| [structure] | 119 | 417 | 38.3 | >6670 | 83.1 | 104 |
| [structure] | 116 | 496 | 51.9 | 3250 | 88.5 | 138 |

Patch Clamp Assay

Calu-3 cells are maintained at 37° C. and 5% $CO_2$ in MEM supplemented with 10% FBS. For manual electrophysiology (EP) experiments, the cells were dissociated and plated on glass cover slips at a density of 50K cells/ml, one day prior to the experiment.

Whole-cell patch-clamp experiments were carried out by manual electrophysiological methods utilizing Axon™ pClamp 10 and MultiClamp Commander Software, the Multiclamp 700B amplifier, and DigiData 1440A interface (Molecular Devices, Sunnyvale, Calif.). Fire-polished borosilicate glass electrodes had resistances from 1-2.5 MOhm when filled with internal solution. Solutions were continuously superfused via a gravity driven system. Extracellular solution consisted of (in mM): 145 NaCl, 1 $CaCl_2$, 10 CsCl, 2 $MgCl_2$, 10 HEPES, pH 7.3 w/NaOH. Intracellular solution consisted of (in mM): 113 Cs-aspartate, 10 CsCl, 10 NaCl, 10 EGTA, 10 HEPES, 2 MgATP, pH 7.2 with CsOH.

Compounds were prepared as 10 mM stocks in 100% DMSO and were then serial diluted in DMSO and brought up to testing concentrations in extracellular solution yielding final DMSO concentrations of 0.1%. Control solutions contained the same final DMSO concentration as the compound solutions. Cells were voltage clamped at a holding potential of −40 mV. One every 5 seconds, the voltage was stepped briefly to −90 mV and then ramped to +20 mV over 220 ms. Current measured at −90 mV and +20 mV was plotted vs time.

Measuring Direct Binding to CFTR Using TruBind™ Back Scattering Interferometry Technology (BSI)

Backscattering interferometry (BSI) uses light interaction with a microfluidic channel to measure temporal changes in refractive index (RI) that result from changes in target shape and solvation when molecular complexes form.

The TruBind BSI System employs an optical train comprised of a coherent light source (HeNe laser), a microfluidic interferometric channel (object) and a CMOS array (detector). Upon coherent-laser illumination of a microfluidic channel, a highly modulated fringe pattern is produced perpendicular to the channel. Its bright and dark features shift position with changes in the RI of the sample and monitoring this shift forms the basis of BSI. This information can be used to perform label free equilibrium $K_d$ measurements in complex biological matrices To measure the direct binding of small molecules with CFTR, the interaction between small molecules and membrane fragments derived from HEK293 cells over-expressing WT CFTR was investigated on the TruBind BSI System.

HEK293 containing WT CFTR and HEK293 control membrane fractions were prepared as follows. HEK293 were transiently transfected with WT CFTR or left untreated, washed with PBS and collected in cold PBS supplemented with protease inhibitor cocktail (PIC). Cells were centrifuged and resuspended in homogenisation buffer (15 mM Tris-HCl pH 7.5, 2 mM $MgCl_2$, 0.3 mM EDTA, 1 mM EGTA+protease inhibitors). Membranes were prepared with a douncer (Wheaton, at least 10 stokes). Membrane fragments were collected by centrifugation (40000 g for 30 min) and resuspended in storage buffer (50 mM Tris-HCl pH 7.5, 1 mM EDTA, 10% glycerol+protease inhibitors), sonicated to remove all clots and stored in aliquots of 100 μg (total protein amount) at −80° C.

For compound testing HEK293 WT CFTR or HEK293 membrane fractions, at final concentration of 10 μg/mL in 50 mM Tris-HCl pH 7.5, 1 mM EDTA with 1.2% DMSO were mixed 1/1 with a serial dilution of the compound, starting from 10 μM, in 50 mM Tris-HCl pH 7.5, 1 mM EDTA with 1.2% DMSO. Mixtures were incubated at room temperature for 4 hours before being run on the BSI instrument. Samples were measured in quadruplicate in dual channel mode which allows the simultaneous measurement of specific, WT CFTR membranes (assay), as well as unspecific, control membranes (reference). For each assay the reference data is subtracted, point by point, from the assay data and plotted as fringe shift in units of radions. Each compound was run to have at least two successful experiments with good reproducibility. Success was defined as having a binding signal with a $R^2>0.7$. The final data is exported to Graphpad Prism and fit with a one-site binding equation to determine a Kd for the assay. The data obtained using the method demonstrates clearly that the test compound as defined in the present claims directly bind to CFTR with low $K_d$.

| Compound | Kd (nM) | $R^2$ |
|---|---|---|
| (a reference compound) | 9655 ± 3314 | 0.79 |

-continued

| Compound | Kd (nM) | $R^2$ |
|---|---|---|
|  | 20.2 ± 4.8 | 0.72 |

TECC Assay in Primary Bronchial Epithelial Cells

The TECC (Tranepithelial Clamp Circuit, EP-design) assay measures the functionality of the cystic fibrosis Transmembrane Conductance regulator (CFTR) by measuring the short circuit current ($I_{SC}$) generated over the basolateral and apical membrane of lung epithelial cells. In TECC the transepithelial potential PD and transepithelial resistance ($R_t$) are measured in an open circuit and transformed to $I_{SC}$ using Ohm's law. 24 wells can be measured simultaneously allowing a higher throughput compared to using chambers.

For this purpose, bronchial epithelial cells isolated from CF patients homozygous for the CFTR ΔF508 mutation (hAEC-CF, Epithelix, Geneva, Switzerland; McGill University, Montreal, Qc; Asterand, Detroit, Mich.; University of North Carolina, Chapel Hill, N.C.) are plated on type IV collagen-coated Transwell supports (Costar). Human airway epithelia are generated by provision of an airliquid interface for 21 days to form well-differentiated polarized cultures that resemble in vivo pseudo-stratified ciliated epithelium (Fulcher et al., 2005). The differentiated cells are treated with test corrector compounds for 24 hours basolaterally to allow sufficient expression of properly folded CFTR protein on the membrane.

For electrophysiological recording, the human airway epithelia are mounted in the TECC heating plate and kept at 37° C. The epithelia are bathed in a NaCl-Ringer solution (120 mM NaCl, 25 mM $NaHCO_3$, 1.2 mM $CaCl_2$, 1.2 mM $MgCl_2$, 0.8 mM $KH_2PO_4$, 0.8 mM $K_2HPO_4$, pH 7.4, 5 mM glucose) on both the basolateral and apical sides. Test compounds are re-added to the recording solution prior to measurement. Apical amiloride is used to inhibit the endogenous ENaC currents while forkolin is applied on both apical and basolateral side to stimulate CFTR. CFTR activity is measured by addition of forskolin followed by addition of a potentiator, GLPG1837, on both sides. Measurements are done during a 20 minute timeframe with recordings every 2 minutes. The increase in $I_{SC}$ is used as a measure for the increased CFTR activity. $EC_{50}$ values can be generated by measuring impact of different concentrations of compound on $I_{SC}$ on primary cells, for this purpose each transwell is treated with a different compound concentration for 24 hours. Inh-172, an inhibitor specific for CFTR, is used to test the specificity of the tested compounds. The agents disclosed herein that are pre-incubated with cells for at least 24 hours do hardly show an increase in current when forskolin stimulus is applied to the cells, a strong increase in current is measured when a potentiator is added to the cells resulted in a high total increase in CFTR channel activity as compared to control cells.

Limited Proteolysis of CFTR

To investigate the mode-of-action of the agents disclosed herein on newly protein, HEK293T cells transiently expressing WT CFTR or CFTR mutants are pulse labelled for 15 min with 35S-Methionine/Cysteine and chased for 0 h (early folding events) and 2 h (late folding events). Compound (3 uM) was present during the entire pulse chase protocol; during the starvation to deplete for methionine and cysteine (20 min prior pulse labelling), during the actual pulse labeling (15 min), until the indicated chase time.

After the pulse chase procedure the radiolabeled cells were lysed in MNT buffer (20 mM MES, 150 mM NaCl, 50 mM Tris-Cl, pH 7,5) +1% Triton X100 without protease inhibitors. To probe the folding of individual CFTR domains, limited proteolysis was performed (25 ug/ml Proteinase K) on the radiolabeled lysate for 15 min on ice, stopped proteolysis by adding 2.5 mM final concentration PMSF, spin down the proteolysed lysate for 10 min rpm max at 4° C., and set up the supernatant for immunoprecipitation to isolate protease resistant domain fragments. For the experiments performed on compound the domain folding of NBD1 (polyclonal anti-NBD1, Mr. Pink) and NBD2 (monoclonal anti-NBD2, 596) was analyzed.

Addition of the compound never restored NBD1 domain folding of newly synthesized F508del-CFTR in the assay, despite rescue of F508del-CFTR trafficking to the Golgi complex (increased band C).

We claim:

1. A method of using a corrector agent for the treatment of Cystic Fibrosis, comprising the step of administering to the patient an effective amount of a corrector agent wherein the corrector agent is capable of stabilizing a newly synthesized Cystic fibrosis transmembrane conductance regulator (CFTR) protein, wherein the corrector agent is a compound of formula (I) or a pharmaceutically acceptable salt thereof,

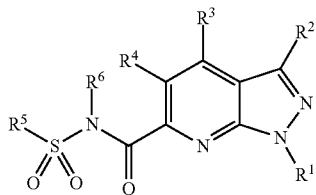

(I)

wherein $R^1$ is $G^{1A}$, $C_1$-$C_6$ haloalkyl, or $C_1$-$C_6$ alkyl; wherein the $C_1$-$C_6$ haloalkyl and the $C_1$-$C_6$ alkyl are each optionally substituted with one $G^{1A}$;

$G^{1A}$, at each occurrence, is independently phenyl, 5-6 membered monocyclic heteroaryl, 4-7 membered monocyclic heterocycle, 5-11 membered fused bicyclic heterocycle, or $C_3$-$C_6$ monocyclic cycloalkyl; wherein each $G^{1A}$ is optionally substituted with 1, 2, 3, or 4 substituents independently selected from the group consisting of $R^{1a}$ and $G^{1B}$;

$G^{1B}$, at each occurrence, is independently 4-7 membered monocyclic heterocycle which is optionally substituted with 1, 2, 3, or 4 independently selected $R^{1b}$ groups;

$R^2$ is hydrogen, $C_2$-$C_4$ alkenyl, $C_1$-$C_6$ alkyl, $C_1$-$C_6$ haloalkyl, —$OR^{2xa}$, —$N(R^{2xa})(R^{2xb})$, or $G^{2A}$;

$R^{2xa}$, at each occurrence, is independently $C_1$-$C_6$ alkyl, $C_1$-$C_6$ haloalkyl, or $G^{2B}$;

$R^{2xb}$ is hydrogen, $C_1$-$C_3$ alkyl, or $C_1$-$C_3$ haloalkyl;

$G^{2A}$ and $G^{2B}$ are each independently a 4-7 membered monocyclic heterocycle or a $C_3$-$C_6$ monocyclic cycloalkyl; wherein $G^{2A}$ and $G^{2B}$ are each optionally substituted with 1, 2, or 3 independently selected $R^{2a}$ groups;

$R^3$ is $G^{3A}$, -$G^{3B}$-$L^1$-$G^{3C}$, -$G^{3B}$-$L^3$-$G^{3C}$-$G^{3E}$, —($C_1$-$C_6$ alkylenyl)-$G^{3D}$, —$OR^{3a}$, or —$N(R^{3a})(R^{3b})$;

$R^{3a}$, at each occurrence, is independently $G^{3D}$, $C_1$-$C_6$ haloalkyl, or $C_1$-$C_6$ alkyl; wherein the $C_1$-$C_6$ haloalkyl and the $C_1$-$C_6$ alkyl are each optionally substituted with one or two substituents independently selected from the group consisting of $G^{3D}$, —$OR^{3a}$, and —$N(R^{3xb})_2$;

$R^{3xa}$ and $R^{3xb}$, at each occurrence, are each independently hydrogen, $C_1$-$C_6$ haloalkyl, $C_1$-$C_6$ alkyl, or $G^{3D}$;

$R^{3b}$ is hydrogen, $C_1$-$C_6$ alkyl, or $C_1$-$C_6$ haloalkyl;

$L^1$ is a bond, $C_1$-$C_6$ alkylenyl, ($C_1$-$C_6$ alkylenyl)$_r$-$L^2$-($C_1$-$C_6$ alkylenyl)$_s$, or O—($C_1$-$C_6$ alkylenyl)-C(O), wherein the left end of the $L^1$ moiety is attached to $G^{3B}$;

$L^2$ is O, $N(R^x)$, C(O), $N(R^x)C(O)$, or $C(O)N(R^x)$; wherein each $R^x$ is independently hydrogen, $C_1$-$C_6$ alkyl, or $C_1$-$C_6$ haloalkyl;

$L^3$ is a bond or $C_1$-$C_6$ alkylenyl;

r is 0 or 1;

s is 0 or 1;

$G^{3A}$, $G^{3B}$, and $G^{3C}$ and each independently $C_3$-$C_1$ cycloalkyl, phenyl, 5-6 membered monocyclic heteroaryl, or 4-11 membered heterocycle; wherein $G^{3A}$, $G^{3B}$, and $G^{3C}$ are each optionally substituted with 1, 2, 3, or 4 independently selected $R^e$ groups;

$G^{3D}$, at each occurrence, is independently $C_3$-$C_8$ monocyclic cycloalkyl, 4-7 membered monocyclic heterocycle, a 5-11 membered fused bicyclic heterocycle, or a 5-11 membered spiro heterocycle; wherein each $G^{3D}$ is optionally substituted with 1, 2, 3, or 4 substituents independently selected from the group consisting of $R^e$ and $G^{3E}$;

$G^{3E}$, at each occurrence, is independently $C_3$-$C_8$ monocyclic cycloalkyl or 4-7 membered monocyclic heterocycle; wherein each $G^{3E}$ is optionally substituted with 1, 2, 3, or 4 independently selected $R^e$ groups;

$R^4$ is hydrogen, $C_1$-$C_3$ alkyl, or $C_1$-$C_3$ haloalkyl;

$R^5$ is $C_1$-$C_6$ alkyl, $C_2$-$C_6$ alkenyl, $C_2$-$C_6$ alkynyl, $C_1$-$C_6$ haloalkyl, —$N(R^{5ax})(R^{5bx})$, —$OR^{5dx}$, or $G^{5A}$;

wherein the $C_1$-$C_6$ alkyl and the $C_1$-$C_6$ haloalkyl are each optionally substituted with one or two substituents independently selected from the group consisting of $G^{5A}$, —CN, —$N_3$, —$OR^{5ax}$, —$S(O)_2R^{5ax}$, —$S(O)_2N(R^{5ax})(R^{5bx})$, —$N(R^{5ax})(R^{5bx})$, —$N(R^{5bx})S(O)_2R^{5cx}$, —$N(R^{5bx})C(O)R^{5cx}$, —$N(R^{5bx})C(O)N(R^{5ax})(R^{5bx})$, —$N(R^{5bx})C(O)OR^{5cx}$, —$C(O)R^{5ax}$, —$C(O)OR^{5ax}$, —$C(O)N(R^{5bx})S(O)_2R^{5cx}$, and —$C(O)N(R^{5ax})(R^{5bx})$;

$R^{5ax}$ and $R^{5bx}$, at each occurrence, are each independently hydrogen, $C_1$-$C_6$ alkyl, $C_1$-$C_6$ haloalkyl, —$OR^{5ex}$, —($C_1$-$C_6$ alkylenyl)-$OR^{5ex}$, $G^{5A}$, or —($C_1$-$C_6$ alkylenyl)-$G^{5A}$;

$R^{5cx}$, at each occurrence, is independently $C_1$-$C_6$ alkyl, $C_1$-$C_6$ haloalkyl, $G^{5A}$, or —($C_1$-$C_6$ alkylenyl)-$G^{5A}$;

$R^{5dx}$ is $C_1$-$C_6$ alkyl, or $C_1$-$C_6$ haloalkyl;

$R^{5x}$ is hydrogen, $C_1$-$C_6$ alkyl, or $C_1$-$C_6$ haloalkyl;

$G^{5A}$, at each occurrence, is independently $C_3$-$C_{11}$ cycloalkyl, phenyl, 5-6 membered monocyclic heteroaryl, or 4-11 membered heterocycle; wherein each $G^{5A}$ is optionally substituted with 1, 2, 3, or 4 independently selected $R^{5a}$ groups;

$R^{5a}$, at each occurrence, is independently $C_1$-$C_6$ alkyl, $C_2$-$C_6$ alkenyl, $C_2$-$C_6$ alkynyl, halogen, $C_1$-$C_6$ haloalkyl, oxo, $G^{5B}$, —CN, $NO_2$, —$OR^b$, —$OC(O)R^c$, —$OC(O)N(R^d)_2$, —$SR^b$, —$S(O)_2R^b$, —$S(O)_2N(R^d)_2$, —$C(O)R^b$, —$C(O)OR^b$, —$C(O) N(R^d)_2$, —$C(O)N(R^d)S(O)_2R^c$, —$N(R^d)_2$, —$N(R^d)C(O)R^c$, —$N(R^d)S(O)_2R^c$, —$N(R^d)C(O)O(R^b)$, —$N(R^d)C(O)N(R^d)_2$, —$N(R^d)S(O)_2N(R^d)_2$, —($C_1$-$C_6$ alkylenyl)-CN, —($C_1$-$C_6$ alkylenyl)-$G^{5B}$, —($C_1$-$C_6$ alkylenyl)-$OR^b$, —($C_1$-$C_6$ alkylenyl)-OC(O)R, —($C_1$-$C_6$ alkylenyl)-OC(O)N$(R^d)_2$, —($C_1$-$C_6$ alkylenyl)-$SR^b$, —($C_1$-$C_6$ alkylenyl)-$S(O)_2R^b$, —($C_1$-$C_6$ alkylenyl)-$S(O)_2N(R^d)_2$, —($C_1$-$C_6$ alkylenyl)-$C(O)R^b$, —($C_1$-$C_6$ alkylenyl)-$C(O)OR^b$, —($C_1$-$C_6$ alkylenyl)-$C(O)N(R^d)_2$, —($C_1$-$C_6$ alkylenyl)-C(O)N$(R^d)$S (O)$_2$R$^c$, —(C$_1$-C$_6$ alkylenyl)-N(R$^d$)$_2$, —(C$_1$-C$_6$ alkylenyl)-N(R$^d$)C(O)R$^c$, —(C$_1$-C$_6$ alkylenyl)-N(R$^d$)S(O)$_2$R, —(C$_1$-C$_6$ alkylenyl)-N(R$^d$)C(O)O(R$^e$), —(C$_1$-C$_6$ alkylenyl)-N(R$^d$)C(O)N(R$^d$)$_2$, or —(C$_1$-C$_6$ alkylenyl)-N(R$^d$)S(O)$_2$N(R$^d$)$_2$;

R$^b$ and R$^d$, at each occurrence, are each independently hydrogen, C$_1$-C$_6$ alkyl, C$_1$-C$_6$ haloalkyl, alkoxyalkyl, G$^{5B}$, or —(C$_1$-C$_6$ alkylenyl)-G$^{5B}$;

R$^c$, at each occurrence, is independently C$_1$-C$_6$ alkyl, C$_1$-C$_6$ haloalkyl, alkoxyalkyl, G$^{5B}$, or —(C$_1$-C$_6$ alkylenyl)-G$^{5B}$;

G$^{5B}$, at each occurrence, is independently C$_3$-C$_6$ monocyclic cycloalkyl, phenyl, 5-6 membered monocyclic heteroaryl, or 4-7 membered monocyclic heterocycle; wherein each G$^{5B}$ is optionally substituted with 1, 2, 3, or 4 independently selected R$^{5b}$ groups;

R$^e$, at each occurrence, is independently C$_2$-C$_6$ alkenyl, C$_2$-C$_6$ alkynyl, C$_1$-C$_6$ alkyl, C$_1$-C$_6$ haloalkyl, halogen, oxo, —CN, —N$_3$, NO$_2$, —OR$^f$, —OC(O)R$^g$, —OC(O)NR$^f$R$^h$, —SR$^f$, —S(O)$_2$R$^f$, —S(O)$_2$NR$^f$R$^h$, —C(O)R$^f$, —C(O)OR$^f$, —C(O)NR$^f$R$^h$, —C(O)N(R$^h$)S(O)$_2$R$^f$, —N(R$^f$)$_2$, —N(R$^h$)C(O)R$^h$, —N(R$^h$)S(O)$_2$R$^g$, —N(R$^h$)C(O)O(R$^g$), —N(R$^h$)C(O)NR$^f$R$^h$, or —N(R$^h$)S(O)$_2$NR$^f$R$^h$; wherein the C$_1$-C$_6$ haloalkyl and the C$_1$-C$_6$ alkyl are each optionally substituted with 1 or 2 substituents independently selected from the group consisting of —CN, NO$_2$, —OR$^f$, —OC(O)R$^g$OC(OC(O)NR$^f$R$^h$, —SR$^f$, —S(O)$_2$R$^f$, —S(O)$_2$NR$^f$R$^h$, —C(O)R$^f$, —C(O)OR$^f$, —C(O)NR$^f$R$^h$, —C(O)N(R$^h$)S(O)$_2$R$^f$, —N(R$^f$)$_2$, —N(R$^h$)C(O)R$^g$, —N(R$^h$)S(O)$_2$R$^g$, —N(R$^h$)C(O)O(R$^g$), —N(R$^h$)C(O)NR$^f$R$^h$, and —N(R$^h$)S(O)$_2$NR$^f$R$^h$;

R$^f$, at each occurrence, is independently hydrogen, C$_1$-C$_6$ alkyl, C$_2$-C$_6$ alkenyl, C$_2$-C$_6$ alkynyl, C$_1$-C$_6$ haloalkyl, —(C$_1$-C$_6$ alkylenyl)-CN, —(C$_1$-C$_6$ alkylenyl)-OR$^m$, —(C$_1$-C$_6$ alkylenyl)-OC(O)R$^n$, —(C$_1$-C$_6$ alkylenyl)-OC(O)N(R$^m$)$_2$, —(C$_1$-C$_6$ alkylenyl)-SR$^m$, —(C$_1$-C$_6$ alkylenyl)-S(O)$_2$R$^n$, —(C$_1$-C$_6$ alkylenyl)-S(O)$_2$N(R$^m$)$_2$, —(C$_1$-C$_6$ alkylenyl)-C(O)R$^m$, —(C$_1$-C$_6$ alkylenyl)-C(O)OR$^m$, —(C$_1$-C$_6$ alkylenyl)-C(O)N(R$^m$)$_2$, —(C$_1$-C$_6$ alkylenyl)-C(O)N(R$^m$)S(O)$_2$R$^n$, —(C$_1$-C$_6$ alkylenyl)-N(R$^m$)$_2$, —(C$_1$-C$_6$ alkylenyl)-N(R$^m$)C(O)R$^n$, —(C$_1$-C$_6$ alkylenyl)-N(R$^m$)S(O)$_2$R$^n$, —(C$_1$-C$_6$ alkylenyl)-N(R$^m$)C(O)O(R$^n$), —(C$_1$-C$_6$ alkylenyl)-N(R$^m$)C(O)N(R$^m$)$_2$, or —(C$_1$-C$_6$ alkylenyl)-N(R$^m$)S(O)$_2$N(R$^m$)$_2$;

R$^g$, at each occurrence, is independently C$_1$-C$_6$ alkyl, C$_2$-C$_6$ alkenyl, C$_2$-C$_6$ alkynyl, C$_1$-C$_6$ haloalkyl, —(C$_1$-C$_6$ alkylenyl)-CN, —(C$_1$-C$_6$ alkylenyl)-OR$^m$, —(C$_1$-C$_6$ alkylenyl)-OC(O)R$^n$, —(C$_1$-C$_6$ alkylenyl)-OC(O)N(R$^m$)$_2$, —(C$_1$-C$_6$ alkylenyl)-SR$^m$, —(C$_1$-C$_6$ alkylenyl)-S(O)$_2$R$^n$, —(C$_1$-C$_6$ alkylenyl)-S(O)$_2$N(R$^m$)$_2$, —(C$_1$-C$_6$ alkylenyl)-C(O)R$^m$, —(C$_1$-C$_6$ alkylenyl)-C(O)OR$^m$, —(C$_1$-C$_6$ alkylenyl)-C(O)N(R$^m$)$_2$, —(C$_1$-C$_6$ alkylenyl)-C(O)N(R$^m$)S(O)$_2$R$^n$, —(C$_1$-C$_6$ alkylenyl)-N(R$^m$)$_2$, —(C$_1$-C$_6$ alkylenyl)-N(R$^m$)C(O)R$^n$, —(C$_1$-C$_6$ alkylenyl)-N(R$^m$)S(O)$_2$R$^n$, —(C$_1$-C$_6$ alkylenyl)-N(R$^m$)C(O)O(R$^n$), —(C$_1$-C$_6$ alkylenyl)-N(R$^m$)C(O)N(R$^m$)$_2$, or —(C$_1$-C$_6$ alkylenyl)-N(R$^m$)S(O)$_2$N(R$^m$)$_2$;

R$^h$, at each occurrence, is independently hydrogen, C$_1$-C$_6$ alkyl, C$_1$-C$_6$ haloalkyl, or —(C$_1$-C$_6$ alkylenyl)-OR$^m$;

R$^{1a}$, R$^{1b}$, R$^{2a}$, and R$^{5b}$, at each occurrence, are each independently C$_1$-C$_6$ alkyl, C$_2$-C$_6$ alkenyl, C$_2$-C$_6$ alkynyl, halogen, C$_1$-C$_6$ haloalkyl, oxo, —CN, NO$_2$, —OR$^m$, —OC(O)R$^n$, —OC(O)N(R$^m$)$_2$, —SR$^m$, —S(O)$_2$R$^n$, —S(O)$_2$N(R$^m$)$_2$, —C(O)R$^m$, —C(O)OR$^m$, —C(O)O(benzyl), —C(O)N(R$^m$)$_2$, —C(O)N(R$^m$)S(O)$_2$R$^n$, —N(R$^m$)$_2$, —N(R$^m$)(alkoxyalkyl), —N(alkoxyalkyl)$_2$, —N(R$^m$)C(O)R$^n$, —N(R$^m$)S(O)$_2$R$^n$, —N(R$^m$)C(O)O(R$^n$), —N(R$^m$)C(O)N(R$^m$)$_2$, —N(R$^m$)S(O)$_2$N(R$^m$)$_2$, —(C$_1$-C$_6$ alkylenyl)-CN, —(C$_1$-C$_6$ alkylenyl)-OR$^m$, —(C$_1$-C$_6$ alkylenyl)-OC(O)R$^n$, —(C$_1$-C$_6$ alkylenyl)-OC(O)N(R$^m$)$_2$, —(C$_1$-C$_6$ alkylenyl)-SR$^m$, —(C$_1$-C$_6$ alkylenyl)-S(O)$_2$R$^m$, —(C$_1$-C$_6$ alkylenyl)-S(O)$_2$N(R$^m$)$_2$, —(C$_1$-C$_6$ alkylenyl)-C(O)R$^m$, —(C$_1$-C$_6$ alkylenyl)-C(O)OR$^m$, —(C$_1$-C$_6$ alkylenyl)-C(O)N(R$^m$)$_2$, —(C$_1$-C$_6$ alkylenyl)-C(O)N(R$^m$)S(O)$_2$R$^n$, —(C$_1$-C$_6$ alkylenyl)-N(R$^m$)$_2$, —(C$_1$-C$_6$ alkylenyl)-N(R$^m$)C(O)R$^n$, —(C$_1$-C$_6$ alkylenyl)-N(R$^m$)S(O)$_2$R$^n$, —(C$_1$-C$_6$ alkylenyl)-N(R$^m$)C(O)O(R$^n$), —(C$_1$-C$_6$ alkylenyl)-N(R$^m$)C(O)N(R$^m$)$_2$, or —(C$_1$-C$_6$ alkylenyl)-N(R$^m$)S(O)$_2$N(R$^m$)$_2$;

R$^m$, at each occurrence, is independently hydrogen, C$_1$-C$_6$ alkyl, or C$_1$-C$_6$ haloalkyl;

R$^n$, at each occurrence, is independently C$_1$-C$_6$ alkyl or C$_1$-C$_6$ haloalkyl;

R$^6$ is hydrogen, C$_1$-C$_6$ alkyl, or C$_1$-C$_6$ haloalkyl; or

R$^5$ and R$^6$ together form a C$_1$-C$_6$ alkylenyl or —N(R$^z$)—(C$_1$-C$_6$ alkylenyl)- wherein the N(R$^z$) is attached to the S(O)$_2$ moiety of formula (I); and R$^z$ is hydrogen, C$_1$-C$_6$ alkyl, or C$_1$-C$_6$ haloalkyl.

2. The method of claim 1, wherein the CFTR protein is a mutant CFTR protein.

3. The method of claim 1, wherein the CFTR protein is a wild-type CFTR protein.

4. The method of claim 1, wherein the CFTR protein comprises a mutation selected from a group consisting of Class II, Class III, Class IV, Class V and Class VI mutations.

5. The method of claim 1, wherein the CFTR comprises a Class I mutation or Class III mutation.

6. The method of claim 5, wherein the CFTR comprises a CFTRΔF508 mutation.

7. The method of claim 1, wherein said CFTR comprises a CFTRΔF508 mutation and the plasma membrane levels of said CFTR in the presence of said agent are at least 300% of the level obtainable with a type I corrector with said CFTR protein.

8. The method of claim 7, wherein said level is measured in a Cell Surface Expression assay.

9. The method of claim 1, wherein the CFTR comprises a CFTRΔF508 mutation and activity of said CFTR protein in the presence of said agent in combination with type I corrector and potentiator are at least 50% of the level of wild-type CFTR in healthy cells.

10. The method of claim 1, wherein said corrector agent directly binds to CFTR protein.

11. The method of claim 10, wherein said binding is measured using patch clamp and Back scattering technology.

12. The method of claim 1, wherein the CFTR protein is synthesized in full length and prior to post-translational modifications.

13. The method of claim 12, wherein the post-translation modification is glycosylation or ubiquitination in Golgi complex.

14. The method of claim 1, wherein the CFTR protein comprises MSD1, NBD1, MSD2, NBD2 and R domains.

15. The method of claim 1, wherein the CFTR protein comprises NBD1 domain, wherein said domain comprises a CFTRΔF508 mutation.

16. The method of claim 15, whereby said NBD1 domain is not produced in a correctly folded form in the presence of said agent.

17. The method of claim 1, wherein the CFTR protein comprises a sequence identical to or at least 90% identical to SEQ ID NO: 1.

18. The method of claim 1, wherein the corrector agent does not stabilize biogenic intermediate CFTR380, CFTR837 or CFTR837-1480 during the biosynthesis of the CFTR protein.

19. The method of claim 1, wherein the corrector agent is capable of stabilizing the CFTR protein by at least about 15%.

20. The method of claim 1, wherein the corrector agent is capable of stabilizing CFTRΔF508 mutation containing CFTR protein by at least 15% compared to wild-type CFTR levels in healthy cells.

21. The method of claim 1, wherein the corrector agent reduces the channel activity of the CFTR protein.

22. The method of claim 1, wherein the corrector agent decreases the CFTR channel gating activity.

23. The method of claim 1, wherein the corrector agent decreases the CFTR channel gating activity by at least 25%.

24. The method of claim 1, wherein the corrector agent decreases the CFTR channel gating activity in a dose dependent manner.

25. The method of claim 22, wherein the corrector agent decreases the CFTR channel gating activity and said activity is reversed in the presence of a potentiator agent.

26. The method of claim 1, wherein the corrector agent reduces the forkolin dependent CFTR channel activity by at least 25%.

27. A pharmaceutical composition for treating cystic fibrosis comprising a first corrector agent and a pharmaceutically acceptable carrier, wherein the first corrector agent is an agent of claim 1.

28. The composition of claim 27, wherein the composition further comprises a potentiator agent.

29. The composition of claim 27, wherein the composition further comprises a second corrector agent, wherein the second corrector agent works through a different correction mechanisms as the first corrector agent.

30. The composition of claim 29, wherein the second corrector stabilizes at least one of biogenic intermediates selected from a group consisting of CFTR375, CFTR380, CFTR430, CFTR653, CFTR837 and CFTR837-1480 during the biosynthesis of the CFTR protein.

31. The method of claim 1, wherein the corrector agent is co-administered with an effective amount of a second corrector agent, wherein the second corrector agent works through a different correction mechanism as compared to the first corrector agent.

32. The method of claim 31, wherein the second corrector stabilizes at least one of biogenic intermediates selected from a group consisting of CFTR375, CFTR380, CFTR430, CFTR653, CFTR837 and CFTR837-1480 during the biosynthesis of the CFTR protein.

33. The method of claim 1, wherein the corrector agent is co-administered with an effective amount of a potentiator agent.

\* \* \* \* \*